United States Patent
Olmsted et al.

(10) Patent No.: US 6,783,939 B2
(45) Date of Patent: Aug. 31, 2004

(54) ALPHAVIRUS VECTORS AND VIROSOMES WITH MODIFIED HIV GENES FOR USE IN VACCINES

(75) Inventors: Robert Olmsted, Chapel Hill, NC (US); Paula Keith, Holly Springs, NC (US); Sergey Dryga, Chapel Hill, NC (US); Ian Caley, Durham, NC (US); Maureen Maughan, Durham, NC (US); Robert Johnston, Chapel Hill, NC (US); Nancy Davis, Chapel Hill, NC (US); Ronald Swanstrom, Chapel HIll, NC (US)

(73) Assignees: Alphavax, Inc., Research Triangle Park, NC (US); University of North Carolina at Chapel Hill, Chapel Hill, NC (US)

( * ) Notice: Subject to any disclaimer, the term of this patent is extended or adjusted under 35 U.S.C. 154(b) by 94 days.

(21) Appl. No.: 09/991,258

(22) Filed: Nov. 16, 2001

(65) Prior Publication Data

US 2002/0141975 A1 Oct. 3, 2002

Related U.S. Application Data

(63) Continuation-in-part of application No. 09/902,537, filed on Jul. 9, 2001, now abandoned.
(60) Provisional application No. 60/216,995, filed on Jul. 7, 2000.

(51) Int. Cl.[7] ............................ C12Q 1/68; C12P 21/04; C12N 5/16; C07H 21/02; A61K 39/00
(52) U.S. Cl. ..................... 435/6; 435/5; 435/69.7; 435/339.1; 435/320.1; 536/23.1; 536/23.72; 424/192.1; 424/208.1
(58) Field of Search .................. 435/6, 5, 69.7, 435/339.1, 320.1; 536/23.1, 23.72; 424/192.1, 208.1

(56) References Cited

U.S. PATENT DOCUMENTS

| | | | |
|---|---|---|---|
| 5,185,440 A | 2/1993 | Davis et al. | 536/237.2 |
| 5,505,947 A | 4/1996 | Johnston et al. | 424/218.1 |

(List continued on next page.)

FOREIGN PATENT DOCUMENTS

| | | |
|---|---|---|
| WO | WO 00/39302 | 7/2000 |
| WO | WO 02/04493 | 1/2002 |

OTHER PUBLICATIONS

Betts et al. Cross–Clade Human Immunodeficiency Virus (HIV)–Specific Cytotoxic T–Lymphocyte Responses in HIV–Infected Zambians. *J. Virol.* 71(11):8908–8911 (1997).

(List continued on next page.)

*Primary Examiner*—Hankyel T. Park
(74) *Attorney, Agent, or Firm*—Myers Bigel Sibley & Sajovec, P.A.

(57) ABSTRACT

The present invention provides methods and compositions comprising a population of alphavirus replicon particles comprising two or more isolated nucleic acids selected from 1) an isolated nucleic acid encoding an env gene product or an immunogenic fragment thereof of a human immunodeficiency virus, 2) an isolated nucleic acid encoding a gag gene product or an immunogenic fragment thereof of a human immunodeficiency virus, wherein the gag gene product or immunogenic fragment thereof is modified to inhibit formation of virus-like particles containing the gag gene product or the immunogenic fragment thereof and their release from a cell, and 3) an isolated nucleic acid encoding a pol gene product or an immunogenic fragment thereof of a human immunodeficiency virus, wherein the pol gene product or immunogenic fragment thereof is modified to inhibit protease, integrase, RNase H and/or reverse transcriptase activity, and wherein the nucleic acids are each contained within a separate alphavirus replicon particle.

25 Claims, 15 Drawing Sheets

U.S. PATENT DOCUMENTS

| | | | |
|---|---|---|---|
| 5,639,650 A | 6/1997 | Johnston et al. | 435/236 |
| 5,643,576 A | 7/1997 | Johnston et al. | 424/199.1 |
| 5,739,026 A | 4/1998 | Garoff et al. | 435/240.2 |
| 5,766,602 A | 6/1998 | Xiong et al. | 424/218.1 |
| 5,789,245 A | 8/1998 | Dubensky, Jr. et al. | 435/320.1 |
| 5,792,462 A | 8/1998 | Johnston et al. | 424/199.1 |
| 5,811,407 A | 9/1998 | Johnston et al. | 514/44 |
| 5,814,482 A | 9/1998 | Dubensky, Jr. et al. | 435/69.3 |
| 5,843,723 A | 12/1998 | Dubensky, Jr. et al. | 435/69.3 |
| 6,008,035 A | 12/1999 | Johnston et al. | 435/235.1 |
| 6,015,686 A | 1/2000 | Dubensky, Jr. et al. | 435/69.1 |
| 6,015,694 A | 1/2000 | Dubensky, Jr. et al. | 435/69.3 |
| 6,146,874 A | 11/2000 | Zolotukhin et al. | 435/235.1 |
| 6,156,558 A | 12/2000 | Johnston et al. | 435/235.1 |
| 6,190,666 B1 | 2/2001 | Garoff et al. | 424/208.1 |
| 6,224,879 B1 | 5/2001 | Sjöberg et al. | 424/218.1 |
| 6,242,259 B1 | 6/2001 | Polo et al. | 435/456 |
| 6,261,570 B1 | 7/2001 | Parker et al. | 424/205.1 |
| 6,329,201 B1 | 12/2001 | Polo et al. | 435/320.1 |
| 6,342,372 B1 | 1/2002 | Dubensky, Jr. et al. | 435/69.1 |
| 6,376,236 B1 | 4/2002 | Dubensky, Jr. et al. | 435/320.1 |
| 6,391,632 B1 | 5/2002 | Dubensky, Jr. et al. | 435/325 |
| 6,426,196 B1 | 7/2002 | Dubensky, Jr. et al. | 435/69.1 |

OTHER PUBLICATIONS

Caley et al. Humoral, Mucosal, and Cellular Immunity in Response to a Human Immunodeficiency Virus Type 1 Immunogen Expressed by a Venezuelan Equine Encephalitis Virus Vaccine Vector. *J. Virol.* 71(4):3031–3038 (1997).

Davis et al. In Vitro Synthesis of Infectious Venezuelan Equine Encephalitis Virus RNA from a cDNA Clone: Analysis of a Viable Delection Mutant. *Virology* 171:189–204 (1989).

Davis et al. In Vitro Synthesis of Infectious Venezuelan Equine Encephalitis Virus RNA from a cDNA Clone: Analysis of a Viable Delection Mutant and Mutations Affecting Virulence. *Vaccines* 90:109–113 (1990).

Davis et al. Attenuating Mutations in the E2 Glycoprotein Gene of Venezuelan Equine Encephalitis Virus: Construction of Single and Multiple Mutants in a Full–Length cDNA Clone. *Virology* 183:20–31 (1991).

Davis et al. Attenuated Mutants of Venezuelan Equine Encephalitis Virus Containing Lethal Mutations in the PE2 Cleavage Signal Combined with a Second–Site Suppressor Mutation in E1. *Virology* 212:102–110 (1995).

Davis et al. A Viral Vaccine That Expresses Foreign Genes in Lymph Nodes and Protects against Mucosal Challenge. *J. Virol.* 70(6):3781–3787 (1996).

Davis et al. Immunization against influenza with attenuated Venezuelan equine encephlitis virus vectors. In: *Options for the Control of Influenza III.* L. E. Brown and A. W. Hampson, eds. Elsevier, Amsterdam pp. 803–809 (1996).

Davis et al. Vaccination of Macaques against Pathogenic Simian Immunodeficiency Virus with Venezuelan Equine Encephalitis Virus Replicon Particles. *J. Virol.* 74(1):371–378 (2000).

Grieder et al. Specific Restrictions in the Progression of Venezuelan Equine Encephalitis Virus–Induced Disease Resulting from Single Amino Acid Changes in the Glycoproteins. *Virology* 206:994–1006 (1995).

Hevey et al. Marburg virus vaccines: comparing classical and new approaches. *Vaccine* 20:586–593 (2002).

Hirsch et al. Patterns of Viral Replication Correlate with Outcome in Simian Immunodeficiency Virus (SIV)–Infected Macaques: Effect of Prior Immunization with a Trivalent SIV Vaccine in Modified Vaccinia Virus Ankara. *J. Virol.* 70(6):3741–3752 (1996).

Johnston and Smith. Selection for Accelerated Penetration in Cell Culture Coselects for Attenuated Mutants of Venezuelan Equine Encephalitis Virus. *Virology* 162:437–443 (1988).

Johnston and Peters. Alphaviruses. *Fields Virology*, 3rd ed., Lippincott–Raven Publishers, Philadelphia, Chapt. 28 pp. 843–898 (1996).

Kinney et al. The Full–Length Nucleotide Sequences of the Virulent Trinidad Donkey Strain of Venezuelan Equine Encephalitis Virus and Its Attenuated Vaccine Derivative, Strain TC–83. *Virology* 170:19–30 (1989).

Kinney et al. Attenuation of Venezuelan Equine Encephalitis Virus Strain TC–83 Is Encoded by the 5'–Noncoding Region and the E2 Envelope Glycoprotein. *J. Virol.* 67(3):1296–1277 (1993).

Paredes et al. Three–dimensional structure of a membrane–containing virus. *Proc. Natl. Acad. Sci. USA* 90:9095–9099 (1993).

Pushko et al. Replicon–Helper Systems from Attenuated Venezuelan Equine Encephalitis Virus: Expression of Heterologous Genes in Vitro and Immunization against Heterologous Pathogens in Vivo. *Virology* 239:389–401 (1997).

Schlesinger and Schlesinger. Togaviridae: The Viruses and Their Replication. *Fields Virology*, 3rd. edition. (Fields et al., ed) Lipincott–Raven Publishers, Philadelphia (1996).

Strauss and Strauss. The Alphaviruses: Gene Expression, Replication, and Evolution. *Microbiol. Rev.* 58(3):491–562 (1994).

Strauss and Strauss. Alphavirus proteinases. *Virology* 1:347–356 (1990).

Barouch et al. "Augmentation of immune responses to HIV–1 and simian immunodeficiency virus DNA vaccines by IL–2/Ig plasmid administration in rhesus monkeys" *PNAS*, 97(8):4192–4197, Apr. 2000.

Sykes and Johnston "Genetic Live Vaccines Mimic the Antigenicity But Not Pathogenicity of Live Viruses" *Dna and Cell Biology*, 18(7):521–531, 1999.

Feyzi et al. "Structural Requirement of Heparan Sulfate for Interaction with Herpes Simplex Virus Type 1 Virions and Isolated Glycoprotein C*" *The Journal of Biological Chemistry*, 272(40):24850–24857, Oct. 1997.

Suomalainen et al. "Spike Protein–Nucleocapsid Interactions Drive the Budding of Alphaviruses" *Journal of Virology*, 66(8):4737–4747, Aug. 1992.

Smerdou and Liljeström "Two–Helper RNA System for Production of Recombinant Semliki Forest Virus Particles" *Journal of Virology*, 73(2):1092–1098, Feb. 1999.

Caley et al., "Venezuelan Equine Encephalitis Virus Vectors Expressing HIV–1 Proteins: Vector Design Strategies for Improved Vaccine Efficacy," *Vaccine*, 17 3124–3135 (1999).

Li et al., "Production of Infectious Recombinant Moloney Murine Leukemia Virus Particles in BHK Cells Using Semliki Forest Virus–Derived RNA Expression Vectors," *Proc. Natl. Acad. Sci. USA*, 93 11658–11663 (Oct. 1996).

FIG. 12

ALPHAVIRUS VECTORS AND VIROSOMES WITH MODIFIED HIV GENES FOR USE IN VACCINES

This application is a continuation-in-part of and claims priority to, U.S. application Ser. No. 09/902,537, filed Jul. 9, 2001 (abandoned), which claims priority to provisional application Ser. No. 60/216,995, filed Jul. 7, 2000, which applications are incorporated by reference herein in their entirety.

BACKGROUND OF THE INVENTION

1. Field of the Invention

The present invention relates to vaccines using viral antigens, and in particular, to vaccines for the treatment and prevention of human immunodeficiency virus (HIV) infection. The vaccines of this invention comprise alphavirus RNA replicon systems which contain nucleic acid sequence encoding antigens for eliciting an immune response to HIV.

2. Background

The successful control of the AIDS epidemic will require an effective vaccine for human immunodeficiency virus type 1 (HIV) that significantly reduces or prevents the spread of infection. Currently, several viral vector systems as well as naked DNA are at various stages of pre-clinical and clinical evaluation as candidate HIV vaccines. Recombinant poxviruses are the most widely studied virus vectors and are furthest along in clinical development (e.g., ALVAC).

The alphavirus-based replicon particle systems, such as the ones described in U.S. Pat. No. 5,792,462 and herein referred to as "VRPs," have multiple distinct properties that make them attractive as an HIV vaccine delivery technology. These properties include: natural targeting to and expression in lymphoid tissues (an optimal site for induction of an immune response); high antigen expression levels, e.g., up to 20% of total cell protein; induction of balanced humoral, cellular, and mucosal immune responses; sustained efficacy over multiple simultaneous or sequential inoculations of the vector; and a high margin of safety.

Venezuelan equine encephalitis virus (VEE) is a member of the Alphaviruses group, which also includes the prototype Sindbis virus (SIN) and Semliki Forest virus (SFV), and is comprised of enveloped viruses containing plus-stranded RNA genomes within icosahedral capsids (Strauss, 1994). Alphavirus genomes are: approximately 11.5 kb long, capped, polyadenylated, and infectious under appropriate transfection conditions. The nucleocapsid is composed of 240 molecules of the capsid protein arranged as a T=4 icosahedron, and is surrounded by a lipoprotein envelope (Paredes et al., 1993). Protruding from the virion surface are 80 glycoprotein spikes, each of which is a trimer of virally encoded E1 and E2 glycoprotein heterodimers. The virions contain no host proteins.

Alphaviruses share replication strategies and genomic organization. The complete replicative cycle of alphaviruses occurs in the cytoplasm of infected cells. Expression from the alphavirus genome is segregated into two regions. The four enzymatic nonstructural proteins (nsP1–nsP4) are synthesized from the 5' two-thirds of the genome-length RNA and are required for RNA replication. Immediately following infection, the nsPs are produced by translation of parental genomes and catalyze the synthesis of a full-length negative-sense copy of the genome. This serves as a template for the synthesis of progeny plus-stranded genomes. The negative-sense copy of the genome also serves as the template for the synthesis of subgenomic mRNA at approximately 10-fold molar excess relative to genomic RNA in infected cells (Schlesinger and Schlesinger, 1990). Synthesis of subgenomic 26S mRNA is initiated from the highly active internal 26S mRNA promoter, which is functional only on the negative-sense RNA. The subgenomic mRNA corresponds to the 3' one-third of the genome and encodes the alphavirus structural proteins.

Full-length, infectious cDNA clones of the RNA genome of VEE Davis et al., 1989) have been constructed, a panel of mutations which strongly attenuate the virus have been identified (Johnston and Smith, 1988; Davis et al., 1990), and various constellations of these attenuating mutations have been inserted into the clones to generate several live attenuated VEE vaccine candidates (Davis et al., 1991; 1995b; Grieder et al., 1995). The resulting vaccine candidates are avirulent and provide complete protection against lethal virus challenge in rodents, horses and nonhuman primates.

The alphavirus VRPs are propagation defective, single cycle vectors that contain a self-amplifying alphavirus RNA (replicon RNA) in which the structural protein genes of the virus are replaced by a heterologous antigen gene to be expressed. Alphavirus VRPs are typically made in cultured cells, referred to as packaging cells. Following introduction into mammalian cells, the replicon RNA is packaged into VRP by supplying the structural proteins in "trans," i.e., the cells are co-transfected with both replicon RNA and one or more separate helper RNAs which together encode the full complement of alphavirus structural proteins. Importantly, only the replicon RNA is packaged into VRP, as the helper RNA(s) lack the cis-acting packaging sequence required for encapsidation. Thus, the VRPs are defective, in that they can only infect target cells in culture or in vivo, where they express the heterologous antigen gene to high level, but they lack critical portions of the VEE genome (i.e., the VEE structural protein genes) necessary to produce virus particles which could spread to other cells.

Delivery of the replicon RNA into target cells (for vaccination) is facilitated by the VRP following infection of the target cells. In the cytoplasm of the target cell, the replicon RNA is first translated to produce the viral replicase proteins necessary to initiate self-amplification and expression. The heterologous antigen gene is encoded by a subgenomic mRNA, abundantly transcribed from the replicon RNA, leading to high level expression of the heterologous antigen gene product. Since the VEE structural protein genes are not encoded by the replicon RNA delivered to the target cell, progeny virion particles are not assembled, thus limiting the replication to a single cycle within the infected target cell. Experimental VRP vaccines have been successful in vaccinating rodents against influenza virus, Lassa fever virus and Marburg virus (Pushko et al., 1997; Hevey et al., 1998). In nonhuman primates, VRP vaccines have demonstrated complete efficacy against lethal Marburg virus challenge (Hevey et al., 1998), shown partial but significant protection against SIV infection and disease (Davis et al., 2000) and induced an anti-HA response at a level consistent with protection of humans against influenza virus infection.

The alphavirus based replicon vector systems, and in particular the VEE-based systems, present several advantages in vaccination, including safety and high immunogenicity/efficacy. VEE is unique among the alphaviruses in that a live attenuated IND VEE vaccine, TC-83, (Kinney et al., 1989; Kinney et al., 1993) has been inoculated into approximately 8,000 humans. This allows direct safety and efficacy comparisons between human, nonhuman primate and rodent responses to the same VEE derivative. A large body of experience strongly suggests that the animal models generally reflect the human susceptibility and disease course, except that mice are far more susceptible to lethal VEE disease than humans or nonhuman primates. Furthermore, the VEE replicon vectors express high levels of the gene of interest in cell culture, and in vivo expression is targeted to lymphoid tissues, reflecting the natural tropism mediated by the VEE glycoproteins. Cells in the draining lymph node of VRP-inoculated mice contain detectable amounts of the desired gene product within hours of inoculation. This expression continues for up to five days.

To date, VRP vector vaccines have been used in over 2000 rodents and in 94 macaques at doses up to $5 \times 10^8$ i.u., with no indication of any clinical manifestations.

In work reported by Pushko et al. (1997), individual mice were immunized sequentially with Lassa virus N-VRP and influenza virus HA-VRP. Groups of mice, which received two inoculations of $3 \times 10^4$ or $3 \times 10^6$ i.u. of Lassa N-VRP followed by two inoculations of $2 \times 10^5$ i.u. of HA-VRP, all responded with serum antibodies to both antigens. The level of anti-influenza antibody induced in these sequentially inoculated mice was equivalent to a control group, which received two inoculations of buffer followed by two inoculations of $2 \times 10^5$ i.u. of HA-VRP. All HA-VRP immunized mice were completely protected against influenza virus challenge. Furthermore, sequential immunization of mice with two inoculations of N-VRP prior to two inoculations of HA-VRP induced an immune response to both HA and N equivalent to immunization with either VRP construct alone. Primary and booster immunization with a VRP preparation expressing an immunogen from one pathogen did not interfere with the development of a protective response to subsequent primary immunization and boosting with VRP expressing an immunogen from a second pathogen, thus showing that the VRP-based system can be used to induce immunity to a variety of pathogens in the same individual over time.

Four macaques were inoculated subcutaneously at week 0 with $10^5$ i.u. each of SIV-gp160-VRP (env) and SIV MA/CA-VRP (gag), boosted by the same route at week 7 with $10^7$ i.u. of each VRP vaccine, and intravenously at weeks 12 and 20 with $5 \times 10^8$ i.u. of each VRP. Two control animals were inoculated with equivalent doses of HA-VRP (haemagglutinin, a glycoprotein from influenza virus), and two with the vehicle only. The four SIV-VRPs immunized monkeys received subcutaneously an additional dose of $2 \times 10^7$ i.u. of gp140-VRP at week 41, followed by a final boost of $2 \times 10^7$ i.u. each of gp140-VRP and MA/CA-VRP at week 49. Four weeks after the final immunization, all eight macaques were challenged intravenously with the pathogenic virus, SIVsmE660.

After these inoculations, three of four test macaques had measurable CTL-specific killing directed against both SIV gag and env, all four had gp160 IgG antibody by ELISA, and the three animals which harbored SIV-specific CTL also showed neutralizing antibody to SIVsmH-4.

Four of four vaccinated animals were protected against disease for at least 16 months following intravenous challenge with the pathogenic SIV swarm, while the two vehicle controls required euthanasia at week 10 and week 11, post challenge. In two of the vaccinees, plasma virus levels were below the limit of detection by branched chain DNA assay. At 64 weeks post challenge, all four vaccinated animals showed no clinical signs of disease. One animal remained vDNA negative at 64 weeks.

The results of this highly pathogenic challenge demonstrated that the immune response induced by vaccination with SIV-VRP was effective in preventing early mortality and increasing the ability to suppress challenge virus replication. The ability to control SIV replication and reduce viral load to undetectable levels was closely correlated with the strongest measurable antibody and cellular immune responses.

While these results are encouraging, the level of protection obtained would not be acceptable for a human vaccine against HIV infection. Thus, there remains a need for a robust, effective and safe vaccine against HIV infection in humans. Development of a HIV vaccine comprising the complete, or immunogenic fragments of the, gag gene (Gag-VRP), an immunogenic portion of the pol gene (Pol-VRP), and the complete, or immunogenic fragments of the, env gene (Env-VRP), would increase the diversity of available CTL epitopes substantially and thus address this need.

SUMMARY OF THE INVENTION

The present invention provides a composition comprising two or more isolated nucleic acids selected from the group consisting of an isolated nucleic acid encoding an env gene product or an immunogenic fragment thereof of a human immunodeficiency virus, an isolated nucleic acid encoding a gag gene product or an immunogenic fragment thereof of a human immunodeficiency virus, wherein the gag gene product or immunogenic fragment thereof is modified to inhibit formation of virus-like particles by the gag gene product or the immunogenic fragment thereof and their release from a cell, and an isolated nucleic acid encoding a pol gene product or an immunogenic fragment thereof of a human immunodeficiency virus, wherein the pol gene product or immunogenic fragment thereof is modified to inhibit reverse transcriptase activity.

Also provided is a composition comprising a population of alphavirus replicon particles comprising two or more isolated nucleic acids selected from the group consisting of 1) an isolated nucleic acid encoding an env gene product or an immunogenic fragment thereof of a human immunodeficiency virus, 2) an isolated nucleic acid encoding a gag gene product or an immunogenic fragment thereof of a human immunodeficiency virus, wherein the gag gene product or immunogenic fragment thereof is modified to inhibit formation of virus-like particles by the gag gene product or the immunogenic fragment thereof and their release from a cell, and 3) an isolated nucleic acid encoding a pol gene product or an immunogenic fragment thereof of a human immunodeficiency virus, wherein the pol gene product or immunogenic fragment thereof is modified to remove protease, integrase and RNase H regions and to inhibit reverse transcriptase activity, and wherein the nucleic acids are each contained within a separate alphavirus replicon particle.

In addition, the present invention provides a composition comprising a population of alphavirus replicon particles comprising two or more isolated nucleic acids selected from the group consisting of 1) an isolated nucleic acid encoding an env gene product or an immunogenic fragment thereof of a human immunodeficiency virus, 2) an isolated nucleic acid encoding a gag gene product or an immunogenic fragment thereof of a human immunodeficiency virus, wherein the gag gene product or immunogenic fragment thereof is modified to inhibit formation of virus-like particles containing the gag gene product or the immunogenic fragment thereof and their release from a cell, and 3) an isolated nucleic acid encoding a pol gene product or an immunogenic fragment thereof of a human immunodeficiency virus, wherein the pol gene product or immunogenic fragment thereof is modified to inhibit reverse transcriptase activity, and wherein the nucleic acids are each contained within a separate alphavirus replicon particle, and further wherein the alphavirus replicon particles comprise a replicon RNA or at least one structural protein which comprises one or more attenuating mutations.

10. A method of making a population of alphavirus replicon particles of this invention is provided herein, comprising;

A) (a) providing a first helper cell for producing a first population of infectious, replication defective alphavirus particles, comprising in an alphavirus-permissive cell:
  (i) an alphavirus replicon RNA, wherein the replicon RNA comprises an alphavirus packaging signal and a nucleic acid encoding an env gene product or an immunogenic fragment thereof of a human immunodeficiency virus, and wherein the replicon RNA lacks sequences encoding alphavirus structural proteins;
  (ii) a first helper RNA separate from said replicon RNA, said first helper RNA encoding at least one alphavirus structural protein and furthermore not encoding at least one other alphavirus structural protein; and
  (iii) one or more additional helper RNA(s) separate from said replicon RNA and separate from said first helper RNA, said additional helper RNA(s) encoding at least one other alphavirus structural protein not encoded by said first helper RNA;
and with at least one of said helper RNAs lacking an alphavirus packaging signal;
wherein the combined expression of the alphavirus replicon RNA and the helper RNAs produces an assembled alphavirus particle which is able to infect a cell, and is unable to complete viral replication, and further wherein the first population contains no detectable replication-competent alphavirus particles as determined by passage on permissive cells in culture;
(b) producing the alphavirus particles in the helper cell; and
(c) collecting the alphavirus particles from the helper cells;

B) (a) providing a second helper cell for producing a second population of infectious, replication defective alphavirus particles, comprising in an alphavirus-permissive cell:
  (i) an alphavirus replicon RNA, wherein the replicon RNA comprises an alphavirus packaging signal and a nucleic acid encoding a gag gene product or an immunogenic fragment thereof of a human immunodeficiency virus, wherein the gag gene product or immunogenic fragment thereof is modified to inhibit formation of virus-like particles containing the gag gene product or the immunogenic fragment thereof and their release from a cell, and wherein the replicon RNA lacks sequences encoding alphavirus structural proteins;
  (ii) a first helper RNA separate from said replicon RNA, said first helper RNA encoding at least one alphavirus structural protein and furthermore not encoding at least one other alphavirus structural protein; and
  (iii) one or more additional helper RNA(s) separate from said replicon RNA and separate from said first helper RNA, said additional helper RNA(s) encoding at least one other alphavirus structural protein not encoded by said first helper RNA;
and with at least one of said helper RNAs lacking an alphavirus packaging signal;
wherein the combined expression of the alphavirus replicon RNA and the helper RNAs produces an assembled alphavirus particle which is able to infect a cell, and is unable to complete viral replication, and further wherein the second population contains no detectable replication-competent alphavirus particles as determined by passage on permissive cells in culture;
(b) producing the alphavirus particles in the helper cell; and
(c) collecting the alphavirus particles from the helper cells;

C) (a) providing a third helper cell for producing a third population of infectious, replication defective alphavirus particles, comprising in an alphavirus-permissive cell:
  (i) an alphavirus replicon RNA, wherein the replicon RNA comprises an alphavirus packaging signal and a nucleic acid encoding a pol gene product or an immunogenic fragment thereof of a human immunodeficiency virus, wherein the pol gene product or immunogenic fragment thereof is modified to inhibit reverse transcriptase activity, and wherein the replicon RNA lacks sequences encoding alphavirus structural proteins;
  (ii) a first helper RNA separate from said replicon RNA, said first helper RNA encoding at least one alphavirus structural protein and furthermore not encoding at least one other alphavirus structural protein; and
  (iii) one or more additional helper RNA(s) separate from said replicon RNA and separate from said first helper RNA, said additional helper RNA(s) encoding at least one other alphavirus structural protein not encoded by said first helper RNA;
and with at least one of said helper RNAs lacking an alphavirus packaging signal;
wherein the combined expression of the alphavirus replicon RNA and the helper RNAs produces an assembled alphavirus particle which is able to infect a cell, and is unable to complete viral replication, and further wherein the third population contains no detectable replication-competent alphavirus particles as determined by passage on permissive cells in culture;
(b) producing the alphavirus particles in the helper cell; and
(c) collecting the alphavirus particles from the helper cells; and D) combining the first population of alphavirus particles produced from the first helper cell, the second population of alphavirus particles produced from the second helper cell and the third population of alphavirus particles produced from the third helper cell, thereby producing the population of alphavirus replicon particles.

Also provided is a method of making a population of alphavirus replicon particles, comprising:

A) (a) providing a first helper cell for producing a first population of infectious, replication defective alphavirus particles, comprising in an alphavirus-permissive cell:

(i) an alphavirus replicon RNA, wherein the replicon RNA comprises an alphavirus packaging signal and a nucleic acid encoding an env gene product or an immunogenic fragment thereof of a human immunodeficiency virus, and wherein the replicon RNA lacks sequences encoding alphavirus structural proteins;

(ii) a first helper RNA separate from said replicon RNA, said first helper RNA encoding at least one alphavirus structural protein and furthermore not encoding at least one other alphavirus structural protein; and (iii) one or more additional helper RNA(s) separate from said replicon RNA and separate from said first helper RNA, said additional helper RNA(s) encoding at least one other alphavirus structural protein not encoded by said first helper RNA;

and ticles containing the gag gene product or the immunogenic fragment thereof and their release from a cell, and an isolated nucleic acid encoding a pol gene product or an immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof.

In addition, the present invention provides a composition comprising a population of alphavirus replicon particles comprising two or more isolated nucleic acids selected from the group consisting of 1) an isolated nucleic acid encoding an env gene product or an immunogenic fragment thereof of a human immunodeficiency virus, 2) an isolated nucleic acid encoding a gag gene product or an immunogenic fragment thereof of a human immunodeficiency virus, wherein the gag gene product or immunogenic fragment thereof is modified to inhibit formation of virus-like particles containing the gag gene product or the immunogenic fragment thereof and their release from a cell, and 3) an isolated nucleic acid encoding a pol gene product or an immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof, and wherein the nucleic acids are each contained within a separate alphavirus replicon particle.

Also provided herein is a composition comprising a population of alphavirus replicon particles comprising two or more isolated nucleic acids selected from the group consisting of 1) an isolated nucleic acid encoding an env gene product or an immunogenic fragment thereof of a human immunodeficiency virus, 2) an isolated nucleic acid encoding a gag gene product or an immunogenic fragment thereof of a human immunodeficiency virus, wherein the gag gene product or immunogenic fragment thereof is modified to inhibit formation of virus-like particles containing the gag gene product or the immunogenic fragment thereof and their release from a cell, and 3) an isolated nucleic acid encoding a pol gene product or an immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof, and wherein the nucleic acids are each contained within a separate alphavirus replicon particle, and further wherein the alphavirus replicon particles comprise a replicon RNA or at least one structural protein which comprises one or more attenuating mutations.

In these embodiments, the gag gene product or immunogenic fragment thereof can be modified by mutation of the second codon, whereby a glycine is changed to an alanine and the pol gene product or immunogenic fragment thereof can be modified by mutation of the nucleotide sequence encoding the active site motif, whereby YMDD is changed to YMAA or HMAA. In addition, the pol gene product or immunogenic fragment thereof is modified to remove protease, integrase and RNase H regions and to produce only p51 of the pol gene product or immunogenic fragment thereof.

The present invention provides a method of making a population of alphavirus replicon particles, comprising:

A) (a) providing a first helper cell for producing a first population of infectious, replication defective alphavirus particles, comprising in an alphavirus-permissive cell:

(i) an alphavirus replicon RNA, wherein the replicon RNA comprises an alphavirus packaging signal and a nucleic acid encoding an env gene product or an immunogenic fragment thereof of a human immunodeficiency virus, and wherein the replicon RNA lacks sequences encoding alphavirus structural proteins;

(ii) a first helper RNA separate from said replicon RNA, said first helper RNA encoding at least one alphavirus structural protein and furthermore not encoding at least one other alphavirus structural protein; and (iii) one or more additional helper RNA(s) separate from said replicon RNA and separate from said first helper RNA, said additional helper RNA(s) encoding at least one other alphavirus structural protein not encoded by said first helper RNA;

and with at least one of said helper RNAs lacking an alphavirus packaging signal;

wherein the combined expression of the alphavirus replicon RNA and the helper RNAs produces an assembled alphavirus particle which is able to infect a cell, and is unable to complete viral replication, and further wherein the first population contains no detectable replication-competent alphavirus particles as determined by passage on permissive cells in culture;

(b) producing the alphavirus particles in the helper cell; and (c) collecting the alphavirus particles from the helper cells;

B) (a) providing a second helper cell for producing a second population of infectious, replication defective alphavirus particles, comprising in an alphavirus-permissive cell:

(i) an alphavirus replicon RNA, wherein the replicon RNA comprises an alphavirus packaging signal and a nucleic acid encoding a gag gene product or an immunogenic fragment thereof of a human immunodeficiency virus, wherein the gag gene product or immunogenic fragment thereof is modified to inhibit formation of virus-like particles containing the gag gene product or the immunogenic fragment thereof and their release from a cell, and wherein the replicon RNA lacks sequences encoding alphavirus structural proteins;

(ii) a first helper RNA separate from said replicon RNA, said first helper RNA encoding at least one alphavirus structural protein and furthermore not encoding at least one other alphavirus structural protein; and (iii) one or more additional helper RNA(s) separate from said replicon RNA and separate from said first helper RNA, said additional helper RNA(s) encoding at least one other alphavirus structural protein not encoded by said first helper RNA;

and with at least one of said helper RNAs lacking an alphavirus packaging signal;

wherein the combined expression of the alphavirus replicon RNA and the helper RNAs produces an assembled alphavirus particle which is able to infect a cell, and is unable to complete viral replication, and further wherein the second population contains no detectable replication-competent alphavirus particles as determined by passage on permissive cells in culture;

(b) producing the alphavirus particles in the helper cell; and (c) collecting the alphavirus particles from the helper cells;

C) (a) providing a third helper cell for producing a third population of infectious, replication defective alphavirus particles, comprising in an alphavirus-permissive cell:
  (i) an alphavirus replicon RNA, wherein the replicon RNA comprises an alphavirus packaging signal and a nucleic acid encoding a pol gene product or an immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof, and wherein the replicon RNA lacks sequences encoding alphavirus structural proteins;
  (ii) a first helper RNA separate from said replicon RNA, said first helper RNA encoding at least one alphavirus structural protein and furthermore not encoding at least one other alphavirus structural protein; and (iii) one or more additional helper RNA(s) separate from said replicon RNA and separate from said first helper RNA, said additional helper RNA(s) encoding at least one other alphavirus structural protein not encoded by said first helper RNA;

and with at least one of said helper RNAs lacking an alphavirus packaging signal;

wherein the combined expression of the alphavirus replicon RNA and the helper RNAs produces an assembled alphavirus particle which is able to infect a cell, and is unable to complete viral replication, and further wherein the third population contains no detectable replication-competent alphavirus particles as determined by passage on permissive cells in culture;

(b) producing the alphavirus particles in the helper cell; and (c) collecting the alphavirus particles from the helper cells; and D) combining the first population of alphavirus particles produced from the first helper cell, the second population of alphavirus particles produced from the second helper cell and the third population of alphavirus particles produced from the third helper cell, thereby producing the population of alphavirus replicon particles.

An additional method of making a population of alphavirus replicon particles is provided, comprising:

A) (a) providing a first helper cell for producing a first population of infectious, replication defective alphavirus particles, comprising in an alphavirus-permissive cell:

(i) an alphavirus replicon RNA, wherein the replicon RNA comprises an alphavirus packaging signal and a nucleic acid encoding an env gene product or an immunogenic fragment thereof of a human immunodeficiency virus, and wherein the replicon RNA lacks sequences encoding alphavirus structural proteins;

(ii) a first helper RNA separate from said replicon RNA, said first helper RNA encoding at least one alphavirus structural protein and furthermore not encoding at least one other alphavirus structural protein; and (iii) one or more additional helper RNA(s) separate from said replicon RNA and separate from said first helper RNA, said additional helper RNA(s) encoding at least one other alphavirus structural protein not encoded by said first helper RNA;

and with at least one of said helper RNAs lacking an alphavirus packaging signal;

wherein the combined expression of the alphavirus replicon RNA and the helper RNAs produces an assembled alphavirus particle which is able to infect a cell, and is unable to complete viral replication, and further wherein the first population contains no detectable replication-competent alphavirus particles as determined by passage on permissive cells in culture, and further wherein at least one of said replicon RNA, said first helper RNA, and said one or more additional helper RNA(s) comprises one or more attenuating mutations;

(b) producing the alphavirus particles in the helper cell; and (c) collecting the alphavirus particles from the helper cells;

B) (a) providing a second helper cell for producing a second population of infectious, replication defective alphavirus particle, comprising in an alphavirus-permissive cell:

(i) an alphavirus replicon RNA, wherein the replicon RNA comprises an alphavirus packaging signal and a nucleic acid encoding a gag gene product or an immunogenic fragment thereof of a human immunodeficiency virus, wherein the gag gene product or immunogenic fragment thereof is modified to inhibit formation of virus-like particles containing the gag gene product or the immunogenic fragment thereof and their release from a cell, and wherein the replicon RNA lacks sequences encoding alphavirus structural proteins;

(ii) a first helper RNA separate from said replicon RNA, said first helper RNA encoding at least one alphavirus structural protein and furthermore not encoding at least one other alphavirus structural protein; and (iii) one or more additional helper RNA(s) separate from said replicon RNA and separate from said first helper RNA, said additional helper RNA(s) encoding at least one other alphavirus structural protein not encoded by said first helper RNA, and with at least one of said helper RNAs lacking an alphavirus packaging signal;

wherein the combined expression of the alphavirus replicon RNA and the helper RNAs produces an assembled alphavirus particle which is able to infect a cell, and is unable to complete viral replication, and further wherein the second population contains no detectable replication-competent alphavirus particles as determined by passage on permissive cells in culture, and further wherein at least one of said replicon RNA, said first helper RNA, and said one or more additional helper RNA(s) comprises one or more attenuating mutations;

(b) producing the alphavirus particles in the helper cell; and (c) collecting the alphavirus particles from the helper cells;

C) (a) providing a third helper cell for producing a third population of infectious, replication defective alphavirus particles, comprising in an alphavirus-permissive cell:

(i) an alphavirus replicon RNA, wherein the replicon RNA comprises an alphavirus packaging signal and a nucleic acid encoding a pol gene product or an immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof, and wherein the replicon RNA lacks sequences encoding alphavirus structural proteins;

(ii) a first helper RNA separate from said replicon RNA, said first helper RNA encoding at least one alphavirus structural protein and furthermore not encoding at least one other alphavirus structural protein; and (iii) one or more additional helper RNA(s) separate from said replicon RNA and separate from said first helper RNA, said additional helper RNA(s) encoding at least one other alphavirus structural protein not encoded by said first helper RNA;

and with at least one of said helper RNAs lacking an alphavirus packaging signal;

wherein the combined expression of the alphavirus replicon RNA and the helper RNAs produces an assembled alphavirus particle which is able to infect a cell, and is unable to complete viral replication, and further wherein the third population contains no detectable replication-competent alphavirus particles as determined by passage on permissive cells in culture, and further wherein at least one of said replicon RNA, said first helper RNA, and said one or more additional helper RNA(s) comprises one or more attenuating mutations;

(b) producing the alphavirus particles in the helper cell; and (c) collecting the alphavirus particles from the helper cells; and D) combining the first population of alphavirus particles produced from the first helper cell, the second population of alphavirus particles produced from the second helper cell and the third population of alphavirus particles produced from the third helper cell, thereby producing the population of alphavirus replicon particles.

In each of the methods above, the alphavirus replicon RNA of at least one of the first helper cell, the second helper cell and the third helper cell can comprise sequence encoding at least one alphavirus structural protein and the first helper RNA and the one or more additional helper RNA(s) in the at least one of the first helper cell, the second helper cell and the third helper cell, can encode at least one other alphavirus structural protein not encoded by the replicon RNA.

Furthermore, in the methods above which recite attenuating mutations, only at least one of the first population of alphavirus particles, the second population of alphavirus particles and the third population of alphavirus particles can comprise particles wherein at least one of the replicon RNA, the first helper RNA, and the one or more additional helper RNA(s) comprises one or more attenuating mutations.

The present invention further provides alphavirus particles produced by any of the methods of this invention.

The present invention further provides a method of inducing an immune response to human immunodeficiency virus in a subject, comprising administering to the subject an immunogenic amount of the populations and/or compositions of this invention, in a pharmaceutically acceptable carrier.

Also provided herein is a method of treating or preventing infection by human immunodeficiency virus in a subject, comprising administering to the subject an immunogenic amount of the populations and/or compositions of this invention, in a pharmaceutically acceptable carrier.

Also provided by the present invention is an alphavirus replicon virosome comprising an alphavirus replicon RNA encapsidated by a lipid bilayer comprising alphavirus glycoproteins, E1 and E2, which in one embodiment, can be Venezuelan Equine Encephalitis glycoproteins E1 and E2.

A method of producing an alphavirus replicon virosome is further provided, comprising: a) combining alphavirus replicon RNA, alphavirus glycoproteins E1 and E2, non-cationic lipids and detergent; and b) gradually removing detergent, whereby alphavirus replicon virosomes are produced. Also provided is a virosome produced by this method.

Furthermore, the present invention provides a method of eliciting an immune response in a subject, comprising administering to the subject an immunogenic amount of the alphavirus replicon virosome of this invention in a pharmaceutically acceptable carrier.

The present invention additionally provides a method of treating or preventing infection by human immunodeficiency virus in a subject, comprising administering to the subject an immunogenic amount of the alphavirus replicon virosome of this invention, wherein the virosome comprises alphavirus replicon RNA encoding one or more HIV immunogens.

In further embodiments, the present invention provides a composition comprising a population of alphavirus replicon virosomes comprising two or more isolated nucleic acids selected from the group consisting of 1) an isolated nucleic acid encoding an env gene product or an immunogenic fragment thereof of a human immunodeficiency virus, 2) an isolated nucleic acid encoding a gag gene product or an immunogenic fragment thereof of a human immunodeficiency virus, wherein the gag gene product or immunogenic fragment thereof is modified to inhibit formation of virus-like particles containing the gag gene product or the immunogenic fragment thereof and their release from a cell, and 3) an isolated nucleic acid encoding a pol gene product or an immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof, and wherein the nucleic acids are each contained within a separate alphavirus replicon virosome.

Additionally provided herein is a composition comprising a population of alphavirus replicon virosomes comprising two or more isolated nucleic acids selected from the group consisting of 1) an isolated nucleic acid encoding an env gene product or an immunogenic fragment thereof of a human immunodeficiency virus, 2) an isolated nucleic acid encoding a gag gene product or an immunogenic fragment thereof of a human immunodeficiency virus, wherein the gag gene product or immunogenic fragment thereof is modified to inhibit formation of virus-like particles containing the gag gene product or the immunogenic fragment thereof and their release from a cell, and 3) an isolated nucleic acid encoding a pol gene product or an immunogenic fragment thereof of a human immunodeficiency virus, wherein the pol gene product or immunogenic fragment thereof comprises a modification resulting in inactivation of reverse transcriptase activity in the pol gene product or immunogenic fragment thereof, and wherein the nucleic acids are each contained within a separate alphavirus replicon virosome.

A method of producing a population of alphavirus replicon virosomes is provided herein, comprising:

A) (a) producing a first population of alphavirus replicon virosomes by combining alphavirus replicon RNA comprising nucleic acid encoding an env gene product or immunogenic fragment thereof, alphavirus glycoproteins E1 and E2, non-cationic lipids and detergent; and b) gradually removing detergent, whereby alphavirus replicon virosomes are produced;

B) (a) producing a second population of alphavirus replicon virosomes by combining alphavirus replicon RNA comprising nucleic acid encoding a gag gene product or immunogenic fragment thereof, wherein the gag gene product or immunogenic fragment thereof is modified to inhibit formation of virus-like particles containing the gag gene product or the immunogenic fragment thereof and their release from a cell, alphavirus glycoproteins E1 and E2, non-cationic lipids and detergent; and b) gradually removing detergent, whereby alphavirus replicon virosomes are produced;

C) (a) producing a third population of alphavirus replicon virosomes by combining alphavirus replicon RNA comprising nucleic acid encoding the pol gene product or immunogenic fragment thereof, wherein the pol gene product or immunogenic fragment thereof comprises a modification resulting in deletion or inactivation of protease, integrase, RNase H and reverse transcriptase functions in the pol gene product or immunogenic fragment thereof, alphavirus glycoproteins E1 and E2, non-cationic lipids and detergent; and b) gradually removing detergent, whereby alphavirus replicon virosomes are produced; and D) combining the first population of alphavirus replicon virosomes, the second population of alphavirus replicon virosomes and the third population of alphavirus replicon virosomes to produce the population of alphavirus replicon virosomes.

In addition, a method of producing a population of alphavirus replicon virosomes is provided, comprising:

A) (a) producing a first population of alphavirus replicon virosomes by combining alphavirus replicon RNA comprising nucleic acid encoding and env gene product or immunogenic fragment thereof, alphavirus glycoproteins E1 and E2, non-cationic lipids and detergent; and b) gradually removing detergent, whereby alphavirus replicon virosomes are produced;

B) (a) producing a second population of alphavirus replicon virosomes by combining alphavirus replicon RNA comprising nucleic acid encoding and gag gene product or immunogenic fragment thereof, wherein the gag gene product or immunogenic fragment thereof is modified to inhibit formation of virus-like particles containing the gag gene product or the immunogenic fragment thereof and their release from a cell, alphavirus glycoproteins E1 and E2, non-cationic lipids and detergent; and b) gradually removing detergent, whereby alphavirus replicon virosomes are produced;

C) (a) producing a third population of alphavirus replicon virosomes by combining alphavirus replicon RNA comprising nucleic acid encoding the pol gene product or immunogenic fragment thereof, wherein the pol gene product or immunogenic fragment thereof comprises a modification resulting in inactivation of reverse transcriptase activity in the pol gene product or immunogenic fragment thereof, alphavirus glycoproteins E1 and E2, non-cationic lipids and detergent; and b) gradually removing detergent, whereby alphavirus replicon virosomes are produced; and D) combining the first population of alphavirus replicon virosomes, the second population of alphavirus replicon virosomes and the third population of alphavirus replicon virosomes to produce the population of alphavirus replicon virosomes of claim 48.

Furthermore, the present invention provides a method of inducing an immune response in a subject, comprising administering to the subject an immunogenic amount of the virosomes of this invention, in a pharmaceutically acceptable carrier.

Also provided is a method of treating or preventing infection by human immunodeficiency virus in a subject, comprising administering to the subject an immunogenic amount of the virosomes of this invention, in a pharmaceutically acceptable carrier.

Additionally provided by this invention is a composition comprising heparin affinity-purified alphavirus replicon particles, wherein the alphavirus replicon particles comprise at least one structural protein which comprises one or more attenuating mutations, as well as a method of preparing heparin affinity-purified alphavirus particles, comprising:

a) producing alphavirus replicon particles, wherein the alphavirus replicon particles comprise at least one structural protein which comprises one or more attenuating mutations;

b) loading the alphavirus replicon particles of step (a) in a heparin affinity chromatography column;

c) eluting the particles from the column of step (b) with a salt gradient (e.g., NaCl gradient); and d) collecting the fraction from the column which contains the heparin affinity-purified alphavirus replicon particles.

In further embodiments, the present invention provides a method of producing VRP for use in a vaccine comprising:

a) producing a plasmid encoding the nucleotide sequence of an alphavirus replicon RNA;

b) producing a plasmid encoding the nucleotide sequence of one or more helper RNAs;

c) transcribing the plasmids of steps (a) and (b) into RNA in vitro;

d) electroporating the RNA of step (c) into a Vero cell line; and e) purifying VRP from the Vero cell line of step (d) by heparin affinity chromatography. By this method, VRPs can be produced in large-scale.

In additional embodiments, the present invention provides an isolated nucleic acid encoding a pol gene product or immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof. This nucleic acid can be present in a composition and in a vector. Such a vector can be present in a cell. This nucleic acid can also be present in an alphavirus replicon particle.

The present invention further provides a method of making an alphavirus replicon particle comprising nucleic acid encoding a pol gene product or immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof, comprising a) providing a helper cell for producing an infectious, defective alphavirus particle, comprising in an alphavirus-permissive cell:
   (i) an alphavirus replicon RNA, wherein the replicon RNA comprises an alphavirus packaging signal and a nucleic acid encoding a pol gene product or an immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof, and wherein the replicon RNA lacks sequences encoding alphavirus structural proteins;
   (ii) a first helper RNA separate from said replicon RNA, said first helper RNA encoding at least one alphavirus structural protein and furthermore not encoding at least one other alphavirus structural protein; and
   (iii) one or more additional helper RNA(s) separate from said replicon RNA and separate from said first helper RNA, said additional helper RNA(s) encoding at least one other alphavirus structural protein not encoded by said first helper RNA;

and with at least one of said helper RNAs lacking an alphavirus packaging signal;

wherein the combined expression of the alphavirus replicon RNA and the helper RNAs produces an assembled alphavirus particle which is able to infect a cell, and is unable to complete viral replication, and further wherein the population contains no detectable replication-competent alphavirus particles as determined by passage on permissive cells in culture;

(b) producing the alphavirus particles in the helper cell; and (c) collecting the alphavirus particles from the helper cell.

In the method described above, at least one of the replicon RNA, the first helper RNA, and the one or more additional helper RNA(s) can comprise one or more attenuating mutations. The present invention additionally provides alphavirus replicon particle produced according to the above methods.

Further provided is a method of inducing an immune response in a subject, comprising administering to the subject an immunogenic amount of a composition comprising alphavirus replicon particles encoding a pol gene product or an immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof in a pharmaceutically acceptable carrier.

BRIEF DESCRIPTION OF THE DRAWINGS

FIG. 12. Phylogenetic comparison of Du151 Clade C isolate Env isolate with referenced Clade C strains. Du151 the vaccine strain had 93% amino acid sequence homology to the South African consensus Clade C sequence.

DETAILED DESCRIPTION OF THE INVENTION

Figure 1:
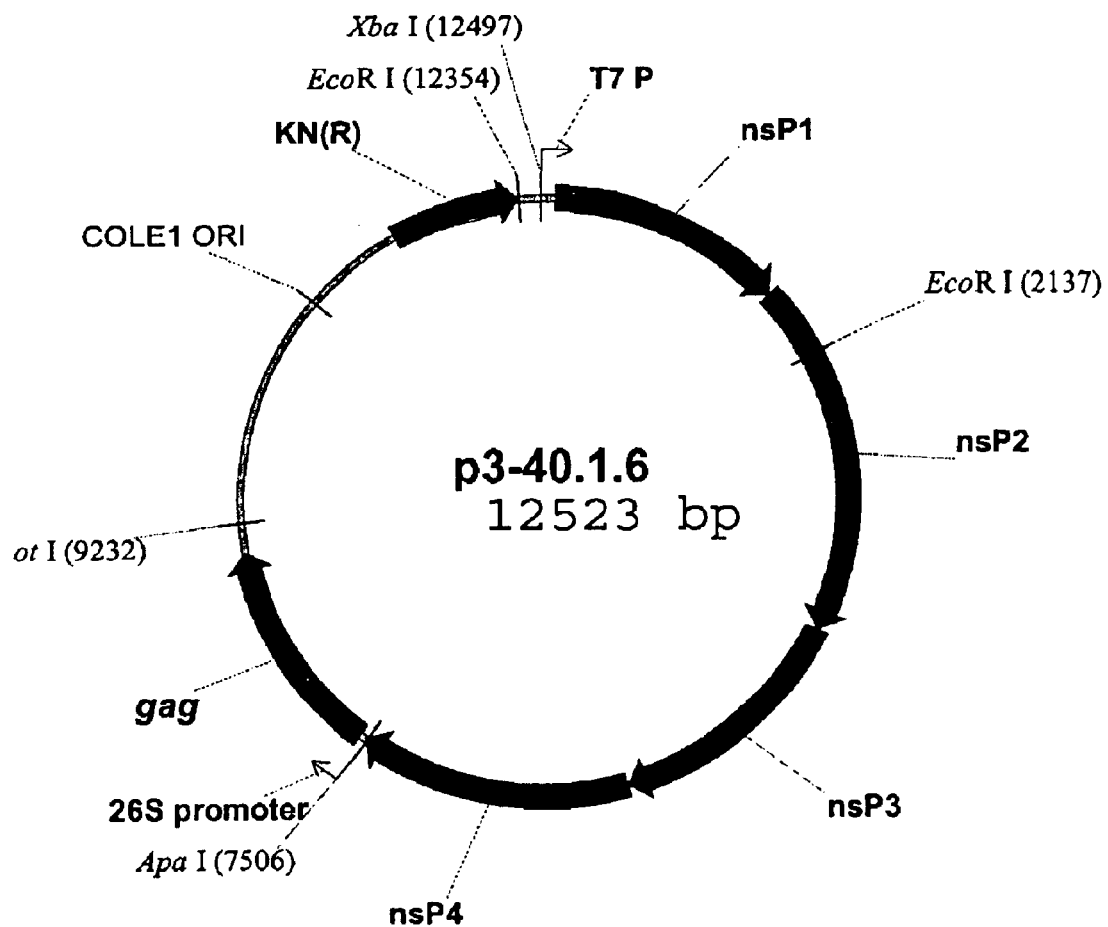
FIG. 1. DNA plasmid map of VEE replicon RNA encoding the HIV gag gene (p3–40.1.6). The plasmid is 12523 base pairs in length and encodes a single polyprotein encoding the four non-structural genes nsP1–4, the Clade C gag gene and antibiotic resistance marker, Kanamycin KN(R). The plasmid contains two promoter regions, the T7 polymerase promoter and the 26S RNA promoter. The unique NotI restriction enzyme site used to linearize prior to in vitro transcription is also noted.

As used in the specification and the appended claims, the singular forms "a," "an," and "the" include plural referents unless the context clearly dictates otherwise. Thus, for example, reference to "a pharmaceutical carrier" can mean a single pharmaceutical carrier or mixtures of two or more such carriers.

The present invention is based on the discovery of a vaccine for the treatment and/or prevention of infection by HIV, comprising novel combinations of isolated nucleic acids encoding two or more distinct antigens which elicit an immune response in a subject which is effective in treating and/or preventing infection by HIV. In a particular embodiment, the nucleic acids encoding the antigens of the vaccine are modified to enhance the immunogenicity of the antigen, improve the safety of the vaccine, or both.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can be accomplished by well known techniques such as cell lysis or disruption of virus particles, followed by phenol plus chloroform extraction, followed by ethanol precipitation of the nucleic acids (Sambrook et al., latest edition). The nucleic acids of this invention can be isolated according to methods well known in the art for isolating nucleic acids. Alternatively, the nucleic acids of the present invention can be synthesized according to standard protocols well described in the literature for synthesis, cloning and amplification of nucleic acids.

HIV-VRP Vaccines

The antigens of this invention can be gene products which are complete proteins or any fragment of a protein determined to be immunogenic by methods well known in the art. Modifications are made to the antigens of this invention to enhance immunogenicity and/or improve the safety of administration of a vaccine containing the antigen. Examples of such modifications are described in the Examples section herein. Furthermore, it is understood that, where desired, other modifications and changes (e.g., substitutions, deletions, additions) may be made in the amino acid sequence of the antigen of the present invention, which may not specifically impart enhanced immunogenicity or improved safety, yet still result in a protein or fragment which retains all of the functional characteristics by which the protein or fragment is defined. Such changes may occur in natural isolates, may be introduced by synthesis of the protein or fragment, or may be introduced into the amino acid sequence of the protein or fragment using site-specific mutagenesis of nucleic acid encoding the protein or fragment, the procedures for which, such as mis-match polymerase chain reaction (PCR), are well known in the art.

The nucleic acids of this invention can be present in a vector and the vector of this invention can be present in a cell. The vectors and cells of this invention can be in a composition comprising the cell or vector and a pharmaceutically acceptable carrier.

The vector of this invention can be an expression vector which contains all of the genetic components required for expression of the nucleic acids of this invention in cells into which the vector has been introduced, as are well known in the art. For example, the expression vector of this invention can be a vector comprising the helper RNAs of this invention. Such an expression vector can be a commercial expression vector or it can be constructed in the laboratory according to standard molecular biology protocols. The expression vector can comprise viral nucleic acid including, but not limited to, alphavirus, flavivirus, adenovirus, retrovirus and/or adeno-associated virus nucleic acid. The nucleic acid or vector of this invention can also be in a liposome or a delivery vehicle which can be taken up by a cell via receptor-mediated or other type of endocytosis.

In another embodiment, the nucleic acids of this invention can be present in a composition comprising a population of alphavirus replicon particles which comprise two or more distinct isolated nucleic acids of this invention and wherein the nucleic acids are each contained within a separate alphavirus replicon particle (herein referred to as a "VRP"). Thus, the expression vector of the present invention can be an alphavirus replicon particle comprising a nucleic acid encoding an antigen of this invention.

In a particular embodiment, the present invention provides a composition comprising two or more isolated nucleic acids selected from the group consisting of an isolated nucleic acid encoding an env gene product or an immunogenic fragment thereof of a human immunodeficiency virus, an isolated nucleic acid encoding a gag gene product or an immunogenic fragment thereof of a human immunodeficiency virus, wherein the gag gene product or immunogenic fragment thereof is modified to inhibit formation of particles, e.g., virus-like particles, containing the gag gene product or the immunogenic fragment thereof, and their release from a cell, and an isolated nucleic acid encoding a pol gene product or an immunogenic fragment thereof of a human immunodeficiency virus, wherein the pol gene product or immunogenic fragment thereof is modified to inhibit reverse transcriptase activity.

In a preferred embodiment, the invention provides alphavirus replicon particles (VRPs) that can be administered as an HIV vaccine. These HIV-VRPs are propagation defective, single cycle vector constructs that contain a self-amplifying RNA (replicon RNA), e.g., from VEE, in which the structural protein genes of the virus are replaced by a HIV-1 Clade C gag gene or any other HIV antigen to be expressed. Following introduction into packaging (or helper) cells in vitro, the replicon RNA is packaged into VRPs by supplying the viral structural proteins in trans (helper RNAs).

The present invention further provides a population of alphavirus replicon particles comprising two or more isolated nucleic acids selected from the group consisting of 1) an isolated nucleic acid encoding an env gene product or an immunogenic fragment thereof of a human immunodeficiency virus, 2) an isolated nucleic acid encoding a gag gene product or an immunogenic fragment thereof of a human immunodeficiency virus, wherein the gag gene product or immunogenic fragment thereof is modified to inhibit formation of particles, such as virus-like particles, containing the gag gene product or the immunogenic fragment thereof, from a cell, and 3) an isolated nucleic acid encoding a pol gene product or an immunogenic fragment thereof of a human immunodeficiency virus, wherein the pol gene product or immunogenic fragment thereof is modified to inhibit reverse transcriptase activity, and wherein the nucleic acids are each contained within a separate alphavirus replicon particle.

It is also contemplated that the compositions of this invention comprise alphavirus replicon particles in which either the replicon RNA or at least one structural protein comprises one or more attenuating mutations. Thus, the present invention additionally provides a population of alphavirus replicon particles comprising two or more distinct types of such particles selected from the group consisting of 1) particles expressing a nucleic acid encoding an env gene product or an immunogenic fragment thereof of a human immunodeficiency virus, 2) particles expressing a nucleic acid encoding a gag gene product or an immunogenic fragment thereof of a human immunodeficiency virus, wherein the gag gene product or immunogenic fragment thereof is modified to inhibit release of particles, such as virus-like particles, containing the gag gene product or the immunogenic fragment thereof, from a cell, and 3) particles expressing a nucleic acid encoding a pol gene product or an immunogenic fragment thereof of a human immunodeficiency virus, wherein the pol gene product or immunogenic fragment thereof is modified to inhibit reverse transcriptase activity; and wherein the nucleic acids are each contained within a separate alphavirus replicon particle and further wherein the alphavirus replicon particles comprise a replicon RNA or at least one structural protein which comprises one or more attenuating mutations.

In a preferred embodiment, the population of alphavirus replicon particles comprises particles expressing the nucleic acids encoding pol, env, and gag gene products. In this embodiment, vigorous antigen-specific cellular (e.g., CTL, NK cell and T-helper) and/or humoral (e.g., antibody) responses can be obtained when such particle populations are administered to a subject.

In the compositions described above, the gag gene product or immunogenic fragment thereof can be modified by mutation of the second codon, whereby a glycine is changed to an alanine. Alternatively, the gag gene product or immunogenic fragment thereof can be modified by any other means known in the art for inhibiting the release of particles containing the gag gene product or immunogenic fragment thereof from a cell.

Furthermore, in the compositions of this invention, the pol gene product or immunogenic fragment thereof can be modified by mutation of the nucleotide sequence encoding the active site motif, whereby YMDD is changed to YMAA or HMAA (the latter providing a convenient site for cloning, see SEQ ID NO:16). The pol gene product or immunogenic fragment thereof can also be modified by any means known in the art for inhibiting reverse transcriptase activity.

The pol gene product or immunogenic fragment thereof of this invention may be further modified such that the coding sequences for protease, integrase and RNase H are removed, inactivated and/or modified, e.g., by producing only the p51 region of the pol gene product. This modification has been shown in some studies to reduce the possibility of formation of replication competent alphavirus particles during production of alphavirus replicon particles comprising the pol gene product or immunogenic fragment thereof. This modification can be of the nucleic acid encoding the pol gene product or immunogenic fragment thereof according to methods known in the art. Thus, the particles and compositions of this invention can comprise nucleic acid encoding a pol gene product or an immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof.

In the compositions of this invention, the gag, env or pol gene products or immunogenic fragments thereof can be from any HIV isolate or consensus sequence derived from HIV primary isolates now known or later identified, the isolation and characterization of which are well known in the art. Also, in the compositions of this invention, the gag, env or pol gene products or immunogenic fragments thereof can be produced from the same HIV isolate or HIV consensus sequence or from any combination of HIV isolates or HIV consensus sequences. In the Examples provided herein, the nucleic acid sequences encoding the env, gag and pol gene products of this invention were selected based on a consensus sequence generated from primary isolates obtained from recent seroconvertors in KwaZulu/Natal Province in South Africa. Sequence analysis of these isolates identified them as subtype (or lade) C, and in preferred embodiments of the invention, the env, gag and pol genes are from Clade C isolates of HIV.

Figure 11:
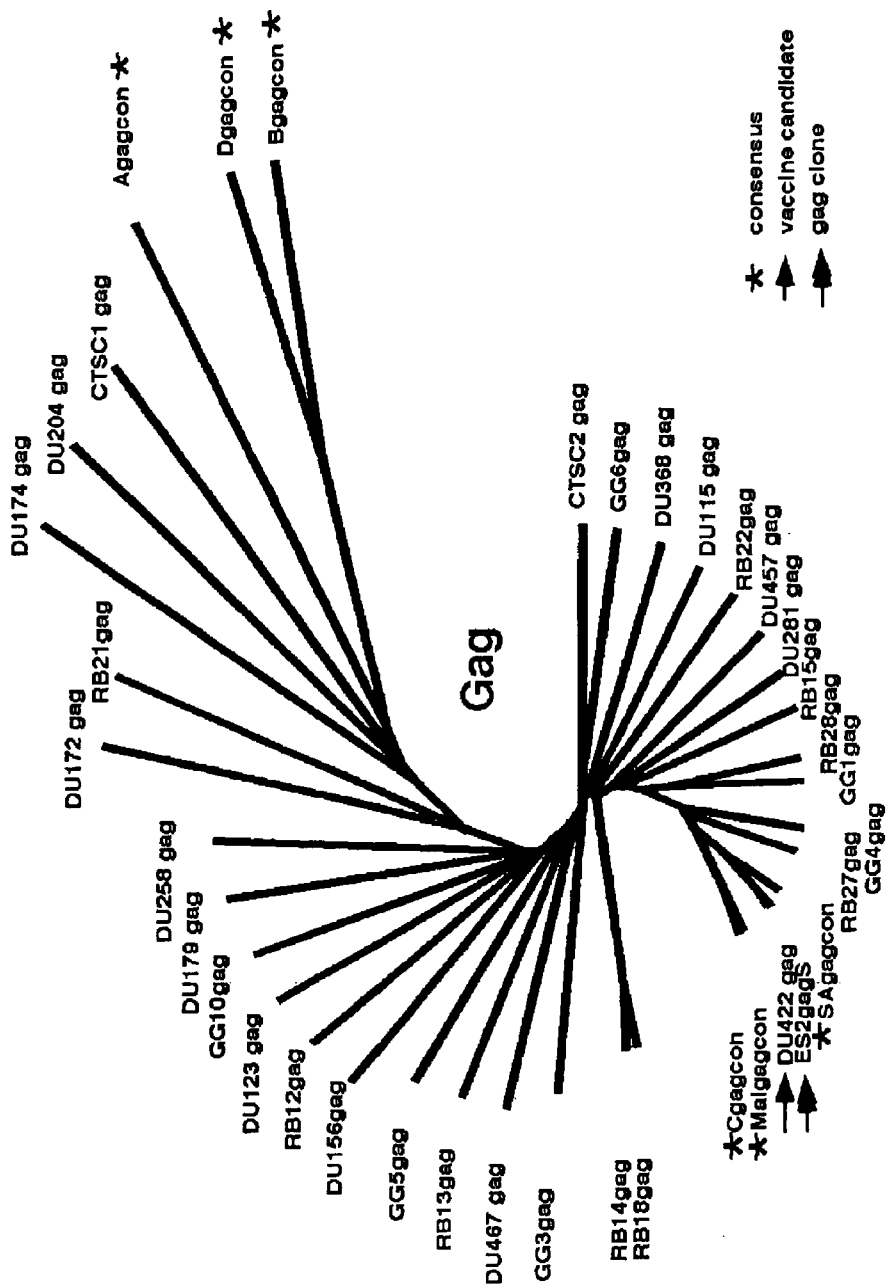
FIG. 11. Phylogenetic comparison of Du422 Clade C Gag isolate with referenced Clade C strains. Consensus lade A, B, D, Mal and SA strains are also shown. Du422 the vaccine strain had 95% amino acid sequence homology to the South African consensus Clade C sequence.
Figure 12:
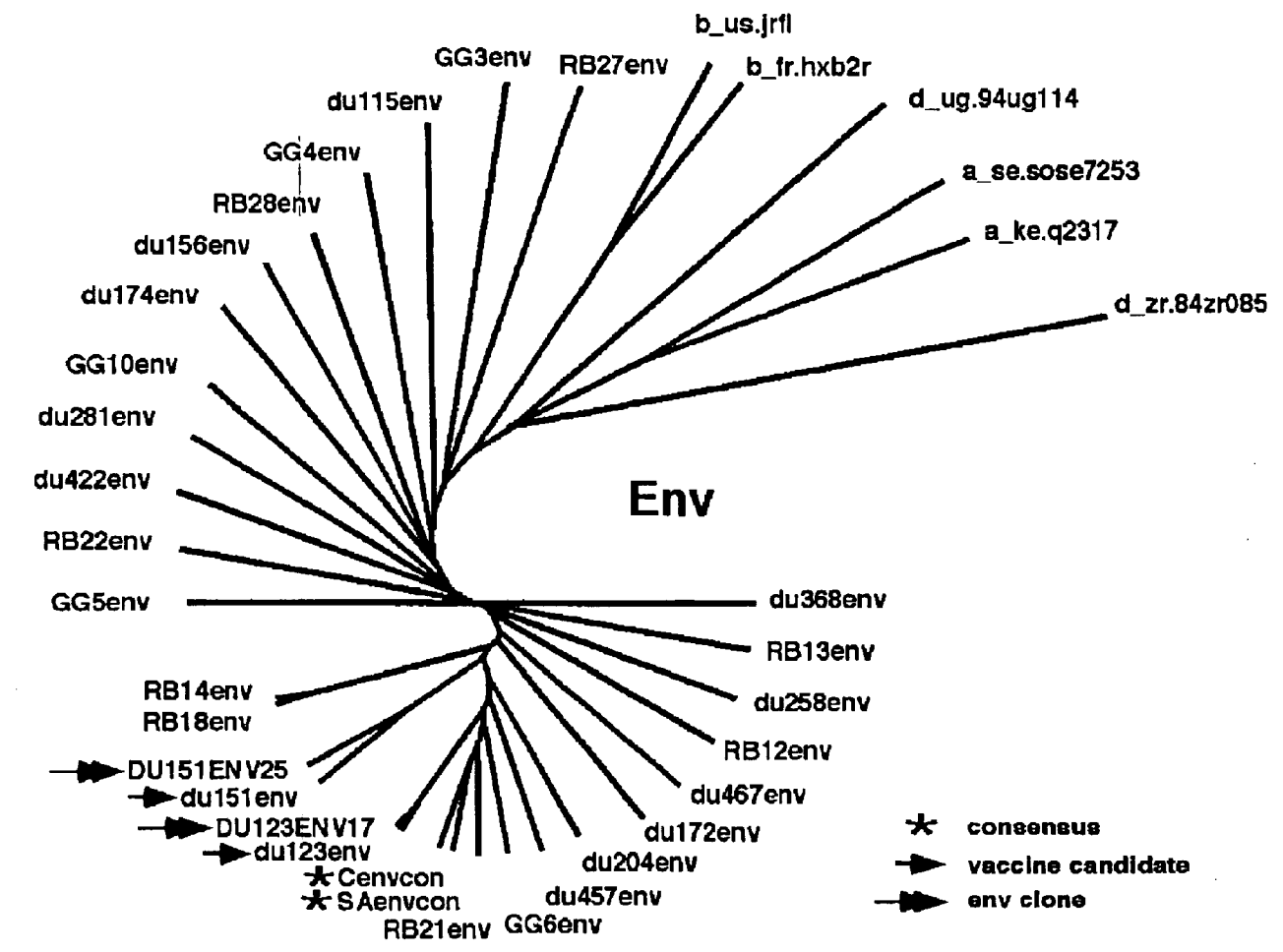
Figure 13:
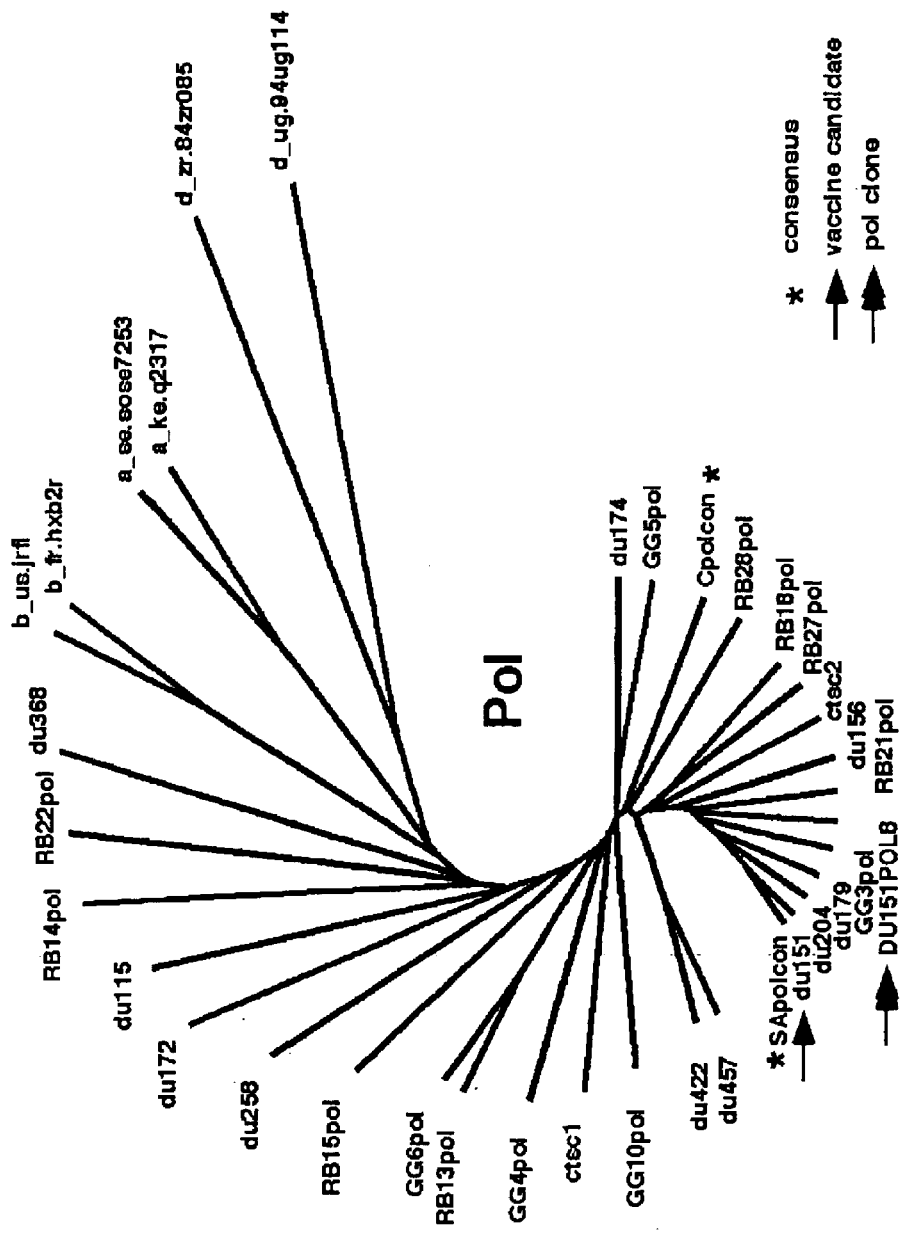
FIG. 13. Phylogenetic comparison of Du151 Clade C isolate Pol isolate with referenced Clade C strains. Du151 the vaccine strain had 99% amino acid sequence homology to the South African consensus Clade C sequence.
Figure 14:
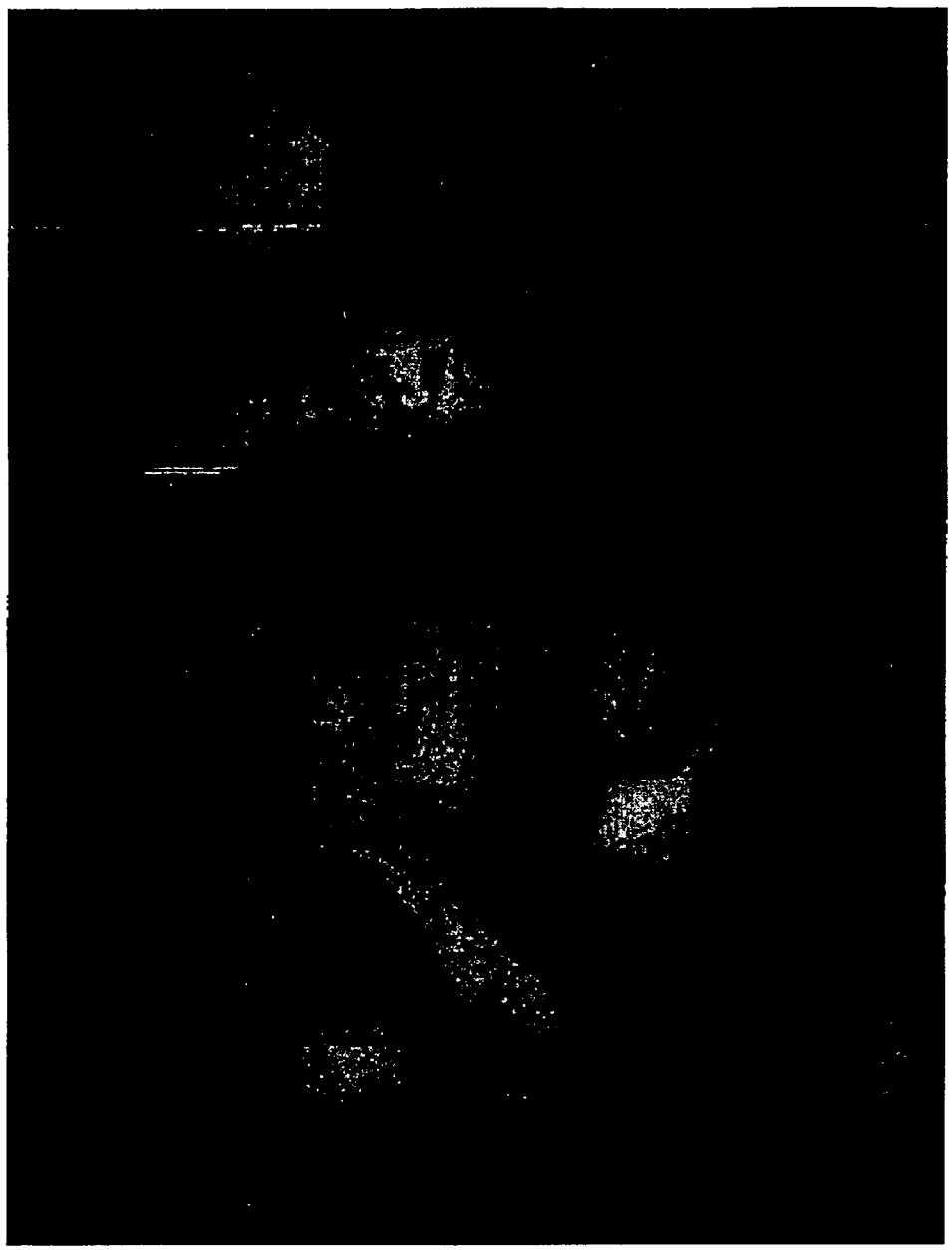
FIG. 14. Du422HIV Gag expression as detected by immunofluorescence following electroporation with Gag replicon RNA. BHK cells were electroporated and subjected to imunofluorescence staining with an anti-Gag monoclonal antibody at 24 hours post-electroporation, to demonstrate expression of the Clade C protein.

In preferred embodiments, each of the three HIV genes are derived from one or more of the South African isolates obtained from recent seroconverters in Kwazulu/Natal as described herein (see FIGS. 11–13 for isolate names). In a further embodiment, the gag gene or gene fragment is from a gag sequence having 95% or greater amino acid identity with the South African consensus sequence for the gag gene. In a specific embodiment, the gag gene or fragment thereof is derived from HIV Subtype Clade C isolate Du422 and the env and pol genes or fragments thereof are derived from HIV isolate Du151.

The term "alphavirus" has its conventional meaning in the art and includes the various species of the alphavirus genus, such as Eastern Equine Encephalitis virus (EEE), Venezuelan Equine Encephalitis virus (VEE), Western Equine Encephalitis virus (WEE), Everglades virus, Mucambo virus, Pixuna virus, Sindbis virus, Semliki Forest virus, South African Arbovirus No. 86, Middleburg virus, Chikungunya virus, O-Nyong-Nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, Buggy Creek virus, as well as any specific strains of these alphaviruses (e.g., TR339; Girdwood) and any other virus classified by the International Committee on Taxonomy of Viruses (ICTV) as an alphavirus.

An "alphavirus replicon particle" as used herein is an infectious, replication defective, alphavirus particle which comprises alphavirus structural proteins and further comprises a replicon RNA. The replicon RNA comprises nucleic acid encoding the alphavirus packaging segment, nucleic acid encoding alphavirus non-structural proteins and a heterologous nucleic acid sequence encoding an antigen of this invention. The non-structural proteins encoded by the replicon RNA may be such proteins as are required for replication and transcription. In a specific embodiment of this invention, the structure of the replicon RNA, starting at the 5' end, comprises the 5' untranslated region of the alphavirus RNA, the non-structural proteins (e.g., nsPs1–4) of the alphavirus, the 26S promoter (also known as the "subgenomic promoter"), the heterologous nucleic acid encoding an HIV antigen, and the 3' untranslated region of the alphavirus RNA. An example of a nucleic acid encoding alphavirus nonstructural proteins that can be incorporated into the embodiments of this invention is SEQ ID NO:2, which encodes the amino acid sequence of SEQ ID NO:3.

Although the alphavirus replicon RNA can comprise nucleic acid encoding one or two alphavirus structural proteins, the replicon RNA does not contain nucleic acid encoding all of the alphavirus structural proteins. The replicon RNA can lack nucleic acid encoding any alphavirus structural protein(s). Thus, the resulting alphavirus replicon particles of this invention are replication defective inasmuch as the replicon RNA does not encode all of the structural proteins required for encapsidation of the replicon RNA and assembly of an infectious virion.

As used herein, "alphavirus structural protein" or "structural protein" means the alphavirus proteins required for encapsidation of alphavirus replicon RNA and packaging of the encapsidated RNA into a virus particle. The alphavirus structural proteins include PE2, E2, E3, 6K and E1.

The alphavirus replicon particles of this invention can comprise replicon RNA from any of the alphaviruses of this invention. Furthermore, the alphavirus replicon particles of this invention can comprise alphavirus structural proteins from any of the alphaviruses of this invention. Thus, the replicon particles can be made up of replicon RNA and structural proteins from the same alphavirus or from different alphaviruses, the latter of which would be chimeric alphavirus replicon particles (e.g., a particle comprising Sindbis virus replicon RNA and VEE structural proteins).

The alphavirus replicon particles of this invention can be made by employing a helper cell for expressing an infectious, replication defective, alphavirus particle in an alphavirus-permissive cell. The helper cell includes (a) a first helper RNA encoding (i) at least one alphavirus structural protein, and (ii) not encoding at least one alphavirus structural protein; and (b) a second helper RNA separate from the first helper RNA, the second helper RNA (i) not encoding the at least one alphavirus structural protein encoded by the first helper RNA, and (ii) encoding at least one alphavirus structural protein not encoded by the first helper RNA, such that all of the alphavirus structural proteins assemble together into alphavirus particles in the cell.

The alphavirus structural protein genes can be present on the helper RNAs of this invention in any combination. For example, the helper RNA of this invention can encode the alphavirus capsid and E1, capsid and E2, E1 and E2, capsid only, E1 only, E2 only, etc. It is also contemplated that the alphavirus structural proteins are provided in trans from genes located on three separate RNA molecules within the helper cell.

Figure 3:
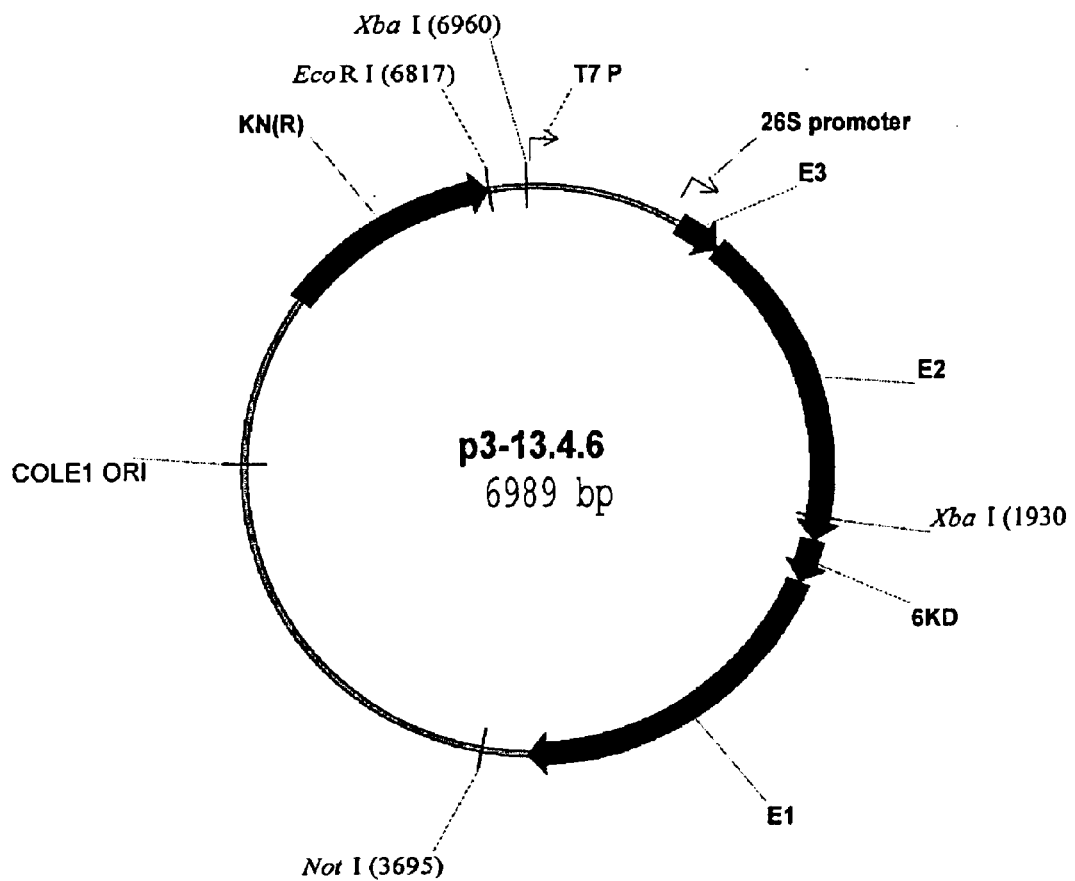
FIG. 3. DNA plasmid map of the glycoprotein helper construct (p3–13.4.6). The plasmid is 6989 base pairs in length and encodes the VEE glycoprotein genes (E3, E2, 6K and E1) and antibiotic resistance marker, Kanamycin KN(R). The plasm cells. The positions of molecular weight of markers run in the same gel are shown on the right, and the inferred positions of gp160, gp120 and gp41 are shown on the left.

In a preferred embodiment, the helper cell also includes a replicon RNA, which encodes the alphavirus packaging segment and an inserted heterologous RNA. In the embodiment wherein the helper cell also includes a replicon RNA, the alphavirus packaging segment may be, and preferably is, deleted from both the first helper RNA and the second helper RNA. For example, in an embodiment wherein the helper cell includes a replicon RNA encoding the alphavirus packaging segment and an inserted heterologous RNA, the first helper RNA encodes the alphavirus E1 glycoprotein and the alphavirus E2 glycoprotein, and the second helper RNA encodes the alphavirus capsid protein. In a preferred embodiment, the first helper RNA encodes the E3-E2-6k-E1 cassette from an alphavirus. In an alternative embodiment, the cassette encoded on the first helper RNA is referred to as the E3-E2-E1 cassette. A specific embodiment of this aspect of the invention is diagrammed in FIG. 3, and an exemplary nucleotide sequence is SEQ ID NO:11. The replicon RNA, first helper RNA, and second helper RNA are all on separate molecules and are cotransfected, e.g., by electroporation, into the helper cell, which can be any alphavirus permissive cell, as is well known in the art.

In an alternative embodiment, the helper cell includes a replicon RNA encoding the alphavirus packaging segment and an inserted heterologous RNA and also includes the alphavirus capsid protein otherwise encoded by the second helper RNA. The first helper RNA encodes the alphavirus E1 glycoprotein and the alphavirus E2 glycoprotein. Thus, the replicon RNA and the first helper RNA are on separate molecules, and the replicon RNA and the second helper RNA are on a single molecule.

The RNA encoding the structural proteins, i.e., the first helper RNA and the second helper RNA, can include one or more attenuating mutations. In a preferred embodiment, either one or both of the first helper RNA and the second helper RNA include at least one attenuating mutation. The attenuating mutations provide the advantage that in the event of RNA-RNA recombination the resulting recombinant RNA molecules encoding the alphavirus structural and non-structural genes will yield or produce virus of decreased virulence.

The alphavirus replicon particles of this invention can be made by a) transfecting a helper cell as given above with a replication defective replicon RNA, b) producing the alphavirus particles in the transfected cell, and c) collecting the alphavirus particles from the cell. The replicon RNA encodes the alphavirus packaging segment and a heterologous RNA. The transfected helper cell further includes the first helper RNA and second helper RNA as described above.

As described hereinabove, the structural proteins used to assemble the alphavirus replicon particles of this invention are distributed among one or more helper RNAs (i.e., a first helper RNA and a second helper RNA). As noted herein, one or more structural protein genes may be located on the replicon RNA, provided that at least one structural protein gene is deleted from the replicon RNA such that the replicon RNA and resulting alphavirus particle are replication defective. As used herein, the terms "deleted" or "deletion" mean either total deletion of the specified nucleic acid or the deletion of a sufficient portion of the specified nucleic acid to render the nucleic acid and/or its resultant gene product inoperative or nonfunctional, in accordance with standard usage. (See, e.g., U.S. Pat. No. 4,650,764 to Temin et al.) The term "replication defective" as used herein means that the replicon RNA cannot replicate in the host cell (i.e., produce progeny infectious viral particles) in the absence of the helper RNA. The replicon RNA is replication defective inasmuch as the replicon RNA does not include all of the alphavirus structural protein genes required for replication, at least one of the required structural protein genes being deleted therefrom.

Figure 2:
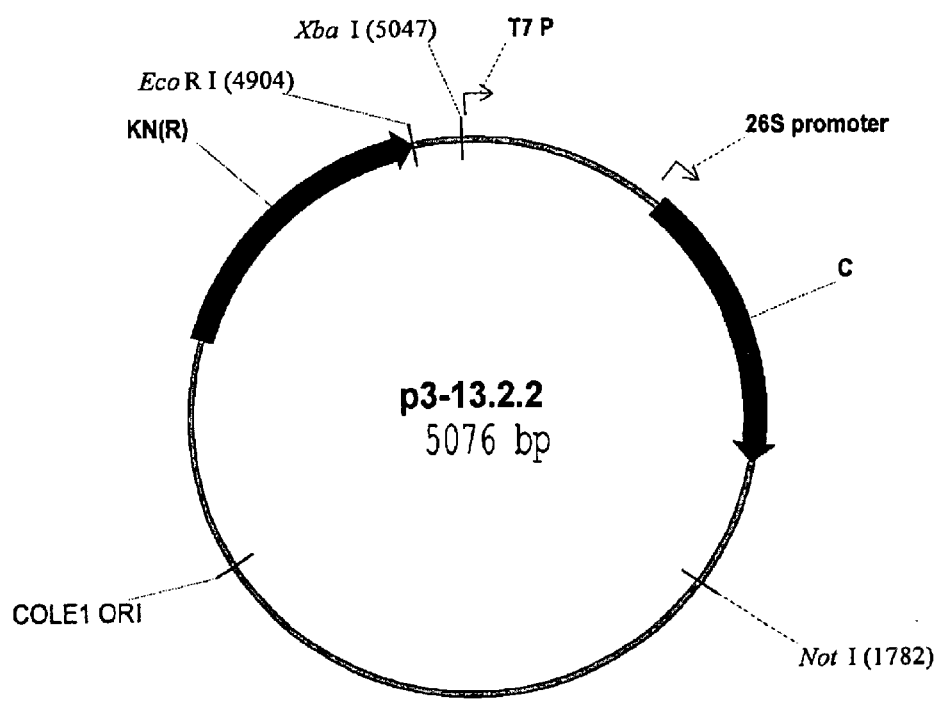
FIG. 2. DNA plasmid map of the capsid helper construct (p3–13.2.2). The plasmid is 5076 base pairs in length and encodes the VEE capsid gene (C) and antibiotic resistance marker, Kanamycin KN(R). The plasmid contains two promoter regions, the T7 polymerase promoter and the 26S RNA promoter. The unique NotI restriction enzyme site used to linearize DNA prior to in vitro transcription is also noted.

In one embodiment, the packaging segment or "encapsidation sequence" is deleted from at least the first helper RNA. In a preferred embodiment, the packaging segment is deleted from both the first helper RNA and the second helper RNA. In a specific embodiment, the second helper RNA is constructed from a VEE cDNA clone, deleting all of the non-structural proteins (i.e., nsPs1–4) except approximately 500 nucleotides at the 5' end of nsP 1, the packaging signal, and the glycoprotein cassette (E3-E2-E1). An example of a plasmid encoding such a second helper RNA is provided in FIG. 2, and an exemplary nucleotide sequence for such a second helper RNA is SEQ ID NO:8.

In the preferred embodiment wherein the packaging segment is deleted from both the first helper RNA and the second helper RNA, preferably the helper cell contains a replicon RNA in addition to the first helper RNA and the second helper RNA. The replicon RNA encodes the packaging segment and an inserted heterologous RNA encoding an HIV antigen or a fragment thereof. Typically, the inserted heterologous RNA encodes a gene product which is expressed in the target cell, and includes the promoter and regulatory segments necessary for the expression of that gene product in that cell.

In another preferred embodiment, the replicon RNA, the first helper RNA and the second helper RNA are provided on separate molecules such that a first molecule, i.e., the replicon RNA, encodes the packaging segment and the inserted heterologous RNA, a second molecule, i.e., the first helper RNA, encodes at least one but not all of the required alphavirus structural proteins, and a third molecule, i.e., the second helper RNA, encodes at least one but not all of the required alphavirus structural proteins. For example, in one preferred embodiment of the present invention, the helper cell includes a set of RNAs which include (a) a replicon RNA encoding an alphavirus packaging sequence and an inserted heterologous RNA, (b) a first helper RNA encoding the alphavirus E1 glycoprotein and the alphavirus E2 glycoprotein, and (c) a second helper RNA encoding the alphavirus capsid protein, so that the alphavirus E1 glycoprotein, the alphavirus E2 glycoprotein and the capsid protein assemble together into alphavirus particles containing the replicon RNA in the helper cell.

In an alternate embodiment, the replicon RNA and the first helper RNA are on separate molecules, and the replicon RNA and the second helper RNA are on a single molecule together, thereby providing a first molecule, i.e., the first helper RNA, encoding at least one but not all of the required alphavirus structural proteins, and a second molecule, i.e., the replicon RNA and second helper RNA, encoding the packaging segment, the inserted heterologous gene product and the structural protein(s) not encoded by the first helper. Thus, one or more structural protein(s) is encoded by the second helper RNA, but the second helper RNA is located on the second molecule together with the replicon RNA. For example, in one preferred embodiment of the present invention, the helper cell includes a set of RNAs including (a) a replicon RNA encoding an alphavirus packaging sequence, an inserted heterologous RNA, and an alphavirus capsid protein, and (b) a first helper RNA encoding the alphavirus E1 glycoprotein and the alphavirus E2 glycoprotein so that the alphavirus E1 glycoprotein, the alphavirus E2 glycoprotein and the capsid protein assemble together into alphavirus particles in the helper cell.

The present invention also contemplates alphavirus replicon particles which comprise replicon RNA encoding more than one heterologous gene product. For expression of more than one heterologous nucleic acid from a single replicon RNA, a promoter can be inserted upstream of each heterologous nucleic acid on the replicon RNA, such that the promoter regulates expression of the heterologous nucleic acid, resulting in the production of more than one antigen from a single replicon RNA Another embodiment contemplates the insertion of an IRES sequence, such as the one from the picornavirus, EMC virus, between the heterologous genes downstream from a 26S promoter of the replicon, thus leading to translation of multiple antigens from a single replicon.

In one preferred embodiment of the present invention, the RNA encoding the alphavirus structural proteins, i.e., the capsid, E1 glycoprotein and/or E2 glycoprotein, contains at least one attenuating mutation. It is further contemplated that the RNA encoding the non-structural proteins can contain at least one attenuating mutation. The phrases "attenuating mutation" and "attenuating amino acid," as used herein, mean a nucleotide mutation or an amino acid coded for in view of such a mutation which result in a decreased probability of causing disease in its host (i.e., a loss of virulence), in accordance with standard terminology in the art, See, e.g., Davis et el. (1980). The mutation can be, for example, a substitution mutation or an in-frame deletion mutation. The phrase "attenuating mutation" excludes mutations which would be lethal to the virus. Thus, according to this embodiment, the E1 RNA and/or the E2 RNA and/or the capsid RNA can include at least one attenuating mutation. In a more preferred embodiment, the E1 RNA and/or the E2 RNA and/or the capsid RNA includes at least two, or multiple, attenuating mutations. The multiple attenuating mutations may be positioned in either the first helper RNA or in the second helper RNA, or they may be distributed randomly with one or more attenuating mutations being positioned in the first helper RNA and one or more attenuating mutations positioned in the second helper RNA. Appropriate attenuating mutations will be dependent upon the alphavirus used, as is well known in the art.

For example, when the alphavirus is VEE, suitable attenuating mutations can be in codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine, or histidine as E2 amino acid 209; codons at E1 amino acid 272 which specify an attenuating mutation, preferably threonine or serine as E1 amino acid 272; codons at E1 amino acid 81 which specify an attenuating mutation, preferably isoleucine or leucine as E1 amino acid 81; and codons at E1 amino acid 253 which specify an attenuating mutation, preferably serine or threoinine as E1 amino acid 253; and the combination mutation of the deletion of E3 codons 56–59 together with codons at E1 amino acid 253 which specify an attenuating mutation, as provided herein. Other suitable attenuating mutations within the VEE genome will be known to those skilled in the art.

In an alternate embodiment, wherein the alphavirus is the South African Arbovirus No. 86 (S.A.A.R.86), suitable attenuating mutations can be, for example, in codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid 304; codons at E2 amino acid position 314 which specify an attenuating amino acid, preferably lysine as E2 amino acid 314; codons at E2 amino acid position 376 which specify an attenuating amino acid, preferably alanine as E2 amino acid 376; codons at E2 amino acid position 372 which specify an attenuating amino acid, preferably leucine as E2 amino acid 372; codons at nsP2 amino acid position 96 which specify an attenuating amino acid, preferably glycine as nsP2 amino acid 96; codons at nsP2 amino acid position 372 which specify an attenuating amino acid, preferably valine as nsP2 amino acid 372; in combination, codons at E2 amino acid residues 304, 314, 372 and 376; codons at E2 amino acid position 378 which specify an attenuating amino acid, preferably leucine as E2 amino acid 378; codons at nsP2 amino acid residue 372 which specify an attenuating mutation, preferably valine as nsP2 amino acid 372; in combination, codons at nsP2 amino acid residues 96 and 372 attenuating substitution mutations at nsP2 amino acid residues 96 and 372; codons at nsP2 amino acid residue 529 which specify an attenuating mutation, preferably leucine, at nsP2 amino acid residue 529; codons at nsP2 amino acid residue 571 which specify an attenuating mutation, preferably asparagine, at nsP2 amino acid residue 571; codons at nsP2 amino acid residue 682 which specify an attenuating mutation, preferably arginine, at nsP2 amino acid residue 682; codons at nsP2 amino acid residue 804 which specify an attenuating mutation, preferably arginine, at nsP2 amino acid residue 804; codons at nsP3 amino acid residue 22 which specify an attenuating mutation, preferably arginine, at nsP3 amino acid residue 22; and in combination, codons at nsP2 amino acid residues 529, 571, 682 and 804, and at nsP3 amino acid residue 22, specifying attenuating amino acids at nsP2 amino acid residues 529, 571, 682 and 804 and at nsP3 amino acid residue 22. Other suitable attenuating mutations within the S.A.A.R.86 genome will be known to those skilled in the art.

The alphavirus capsid gene used to make alphavirus replicon particles can also be subjected to site-directed mutagenesis. The altered capsid protein provides additional assurance that recombination to produce the virulent virus will not occur. The altered capsid protein gene which functions in particle assembly but not in autoproteolysis provides helper function for production of replicon particles, but does not allow for production of a viable recombinant. The capsid residues required for proteolytic function are known (Strauss et al., 1990).

Suitable attenuating mutations useful in embodiments wherein any of the alphaviruses of this invention are employed are known to or can be identified by those skilled in the art using routine protocols. Attenuating mutations may be introduced into the RNA by performing site-directed mutagenesis on the cDNA which encodes the RNA, in accordance with known procedures. See Kunkel (1985), the disclosure of which is incorporated herein by reference in its entirety. Alternatively, mutations may be introduced into the RNA by replacement of homologous restriction fragments in the cDNA which encodes for the RNA, in accordance with known procedures. The identification of a particular mutation in an alphavirus as attenuating is done using routine experimentation according to methods well known in the art.

Preferably, the helper RNA of this invention includes a promoter. It is also preferred that the replicon RNA includes a promoter. Suitable promoters for inclusion in the helper RNA and replicon RNA are well known in the art. One preferred promoter is the alphavirus 26S promoter, although many suitable promoters are available, as is well known in the art.

In the system wherein a first helper RNA, a second helper RNA, and a replicon RNA are all on separate molecules, if the same promoter is used for all three RNAs, then a homologous sequence between the three molecules is provided. Thus, it is advantageous to employ different promoters on the first and second helper RNAs to provide further impediment to RNA recombination that might produce virulent virus. It is preferred that the selected promoter is operative with the non-structural proteins encoded by the replicon RNA molecule.

The infectious, replication defective, alphavirus particles of this invention are prepared according to the methods disclosed herein in combination with techniques known to those skilled in the art. The methods include, for example, transfecting an alphavirus-permissive cell with a replication defective replicon RNA including the alphavirus packaging segment and an inserted heterologous RNA, a first helper RNA encoding at least one alphavirus structural protein, and a second helper RNA encoding at least one alphavirus structural protein which is different from that encoded by the first helper RNA; producing the alphavirus particles in the transfected cell; and collecting the alphavirus particles from the cell.

Methods for transfecting the alphavirus-permissive cell with the replicon RNA and helper RNAs can be achieved, for example, by (i) treating the cells with DEAE-dextran, (ii) by lipofection, by treating the cells with, for example, LIPOFECTIN, and (iii) by electroporation, with electroporation being a preferred means of achieving RNA uptake into the alphavirus-permissive cells. Examples of these techniques are well known in the art, see e.g., U.S. Pat. No. 5,185,440 to Davis et al., and PCT Publication No. WO 92/10578 to Bioption AB, the disclosures of which are incorporated herein by reference in their entirety.

The steps of producing the infectious viral particles in the cells may also be carried out using conventional techniques.

See e.g., U.S. Pat. No. 5,185,440 to Davis et al., PCT Publication No. WO 92/10578 to Bioption AB, and U.S. Pat. No. 4,650,764 to Temin et al. (although Temin et al., relates to retroviruses rather than alphaviruses). The infectious viral particles may be produced by standard cell culture growth techniques.

The steps of collecting the infectious alphavirus particles may also be carried out using conventional techniques. For example, the infectious particles may be collected by cell lysis, or collection of the supernatant of the cell culture, as is known in the art. See e.g., U.S. Pat. No. 5,185,440 to Davis et al., PCT Publication No. WO 92/10578 to Bioption AB, and U.S. Pat. No. 4,650,764 to Temin et al. (although Temin et al. relates to retroviruses rather than alphaviruses). Other suitable techniques will be known to those skilled in the art. Optionally, the collected infectious alphavirus particles may be purified, if desired. Purification techniques for viruses are well known to those skilled in the art, and these are suitable for the purification of small batches of infectious alphavirus particles.

Thus, the present invention provides a method of making the populations of alphavirus replicon particles of this invention comprising:

A) (a) providing a first helper cell for producing a first population of infectious, defective alphavirus particles, comprising in an alphavirus-permissive cell;
  (i) an alphavirus replicon RNA, wherein the replicon RNA comprises an alphavirus packaging signal and a nucleic acid encoding an env gene product or an immunogenic fragment thereof of a human immunodeficiency virus, and wherein the replicon RNA lacks sequences encoding alphavirus structural proteins;
  (ii) a first helper RNA separate from said replicon RNA, said first helper RNA encoding at least one alphavirus structural protein and furthermore not encoding at least one other alphavirus structural protein; and
  (iii) one or more additional helper RNA(s) separate from said replicon RNA and separate from said first helper RNA, said additional helper RNA(s) encoding at least one other alphavirus structural protein not encoded by said first helper RNA;
  and with at least one of said helper RNAs lacking an alphavirus packaging signal;
  wherein the combined expression of the alphavirus replicon RNA and the helper RNAs produces an assembled alphavirus particle which is able to infect a cell, and is unable to complete viral replication, and further wherein the first population contains no detectable replication-competent alphavirus particles as determined by passage on permissive cells in culture;
 (b) producing the alphavirus particles in the helper cell; and
 (c) collecting the alphavirus particles from the helper cells;

B) (a) providing a second helper cell for producing a second population of infectious, defective alphavirus particles, comprising in an alphavirus-permissive cell:
  (i) an alphavirus replicon RNA, wherein the replicon RNA comprises an alphavirus packaging signal and a nucleic acid encoding a gag gene product or an immunogenic fragment thereof of a human immunodeficiency virus, wherein the gag gene product or immunogenic fragment thereof is modified to inhibit formation of virus-like particles containing the gag gene product or the immunogenic fragment thereof and their release from a cell, and wherein the replicon RNA lacks sequences encoding alphavirus structural proteins;
  (ii) a first helper RNA separate from said replicon RNA, said first helper RNA encoding at least one alphavirus structural protein and furthermore not encoding at least one other alphavirus structural protein; and
  (iii) one or more additional helper RNA(s) separate from said replicon RNA and separate from said first helper RNA, said additional helper RNA(s) encoding at least one other alphavirus structural protein not encoded by said first helper RNA;
  and with at least one of said helper RNAs lacking an alphavirus packaging signal;
  wherein the combined expression of the alphavirus replicon RNA and the helper RNAs produces an assembled alphavirus particle which is able to infect a cell, and is unable to complete viral replication, and further wherein the second population contains no detectable replication-competent alphavirus particles as determined by passage on permissive cells in culture;
 (b) producing the alphavirus particles in the helper cell; and
 (c) collecting the alphavirus particles from the helper cells;

C) providing a third helper cell for producing a third population of infectious, defective alphavirus particles, comprising in an alphavirus-permissive cell:
  (i) an alphavirus replicon RNA, wherein the replicon RNA comprises an alphavirus packaging signal and a nucleic acid encoding a pol gene product or an immunogenic fragment thereof of a human immunodeficiency virus, wherein the pol gene product or immunogenic fragment thereof is modified to inhibit reverse transcriptase activity or is modified to inactivate or delete protease, integrase, RNase H and reverse transcriptase functions in the pol gene product or immunogenic fragment thereof, and wherein the replicon RNA lacks sequences encoding alphavirus structural proteins;
  (ii) a first helper RNA separate from said replicon RNA, said first helper RNA encoding at least one alphavirus structural protein and furthermore not encoding at least one other alphavirus structural protein; and
  (iii) one or more additional helper RNA(s) separate from said replicon RNA and separate from said first helper RNA, said additional helper RNA(s) encoding at least one other alphavirus structural protein not encoded by said first helper RNA;
  and with at least one of said helper RNAs lacking an alphavirus packaging signal;
  wherein the combined expression of the alphavirus replicon RNA and the helper RNAs produces an assembled alphavirus particle which is able to infect a cell, and unable to complete viral replication, and further wherein the third population contains no detectable replication-competent alphavirus particles as determined by passage on permissive cells in culture;
 (b) producing the alphavirus particles in the helper cell; and
 (c) collecting the alphavirus particles from the helper cells; and D) combining the first population of alphavirus particles produced from the first helper cell, the second population of alphavirus particles produced from the second helper cell and the third population of alphavirus particles produced from the third helper cell, thereby producing the populations of alphavirus replicon particles.

In a preferred embodiment, as noted above, the method provided also includes a mutation in the pot gene product or immunogenic fragment thereof resulting in inactivation or deletion of protease, integrase and RNase H functions of the pol gene product or immunogenic fragment thereof. In a specific embodiment of this method, the region of the pot gene encoding the protease, RNase H and integrase function of the pot gene product or immunogenic fragment thereof has been deleted.

A method of making the populations of alphavirus replicon particles of this invention, wherein the particles comprise at least one attenuating mutation, is also provided, comprising:

A) (a) providing a first helper cell for producing a first population of infectious, defective alphavirus particles, comprising in an alphavirus-permissive cell:
  (i) an alphavirus replicon RNA, wherein the replicon RNA comprises an alphavirus packaging signal and a nucleic acid encoding an env gene product or an immunogenic fragment thereof of a human immunodeficiency virus, and wherein the replicon RNA lacks sequences encoding alphavirus structural proteins;
  (ii) a first helper RNA separate from said replicon RNA, said first helper RNA encoding at least one alphavirus structural protein and furthermore not encoding at least one other alphavirus structural protein; and
  (iii) one or more additional helper RNA(s) separate from said replicon RNA and separate from said first helper RNA, said additional helper RNA(s) encoding at least one other alphavirus structural protein not encoded by said first helper RNA;

and with at least one of said helper RNAs lacking an alphavirus packaging signal;

wherein the combined expression of the alphavirus replicon RNA and the helper RNAs produces an assembled alphavirus particle which is able to infect a cell, and is unable to complete viral replication, and further wherein the first population contains no detectable replication-competent alphavirus particles as determined by passage on permissive cells in culture, and further wherein at least one of said replicon RNA, said first helper RNA, and said one or more additional helper RNA(s) comprises one or more attenuating mutations;

(b) producing the alphavirus particles in the helper cell; and (c) collecting the alphavirus particles from the helper cells;

B) (a) providing a second helper cell for producing a second population of infectious, defective alphavirus particles, comprising in an alphavirus-permissive cell:
  (i) an alphavirus replicon RNA, wherein the replicon RNA comprises an alphavirus packaging signal and a nucleic acid encoding a gag gene product or an immunogenic fragment thereof of a human immunodeficiency virus, wherein the gag gene product or immunogenic fragment thereof is modified to inhibit release of particles, such as virus-like particles, containing the gag gene product or the immunogenic fragment thereof from a cell, and wherein the replicon RNA lacks sequences encoding alphavirus structural proteins;
  (ii) a first helper RNA separate from said replicon RNA, said first helper RNA encoding at least one alphavirus structural protein and furthermore not encoding at least one other alphavirus structural protein; and
  (iii) one or more additional helper RNA(s) separate from said replicon RNA and separate from said first helper RNA, said additional helper RNA(s) encoding at least one other alphavirus structural protein not encoded by said first helper RNA;

and with at least one of said helper RNAs lacking an alphavirus packaging signal;

wherein the combined expression of the alphavirus replicon RNA and the helper RNAs produces an assembled alphavirus particle which is able to infect a cell, and is unable to complete viral replication, and further wherein the second population contains no detectable replication-competent alphavirus particles as determined by passage on permissive cells in culture, and further wherein at least one of said replicon RNA, said first helper RNA, and said one or more additional helper RNA(s) comprises one or more attenuating mutations;

(b) producing the alphavirus particles in the helper cell; and (c) collecting the alphavirus particles from the helper cells;

C) providing a third helper cell for producing a third population of infectious, defective alphavirus particles, comprising in an alphavirus-permissive cell:
  (i) an alphavirus replicon RNA, wherein the replicon RNA comprises an alphavirus packaging signal and a nucleic acid encoding a pol gene product or an immunogenic fragment thereof of a human immunodeficiency virus, wherein the pol gene product or immunogenic fragment thereof is modified to inhibit reverse transcriptase activity or is modified to inactivate or delete protease, integrase, RNase H and reverse transcriptase functions in the pol gene product or immunogenic fragment thereof, and wherein the replicon RNA lacks sequences encoding alphavirus structural proteins;
  (ii) a first helper RNA separate from said replicon RNA, said first helper RNA encoding at least one alphavirus structural protein and furthermore not encoding at least one other alphavirus structural protein; and
  (iii) one or more additional helper RNA(s) separate from said replicon RNA and separate from said first helper RNA, said additional helper RNA(s) encoding at least one other alphavirus structural protein not encoded by said first helper RNA;

and with at least one of said helper RNAs lacking an alphavirus packaging signal;

wherein the combined expression of the alphavirus replicon RNA and the helper RNAs produces an assembled alphavirus particle which is able to infect a cell, and is unable to complete viral replication, and further wherein the third population contains no detectable replication-competent alphavirus particles as determined by passage on permissive cells in culture, and further wherein at least one of said replicon RNA, said first helper RNA, and said one or more additional helper RNA(s) comprises one or more attenuating mutations;

(b) producing the alphavirus particles in the helper cell; and (c) collecting the alphavirus particles from the helper cells; and D) combining the first population of alphavirus particles produced from the first helper cell, the second population of alphavirus particles produced from the second helper cell and the third population of alphavirus particles produced from the third helper cell, thereby producing the populations of alphavirus replicon particles of the present invention comprising at least one attenuating mutation.

In a preferred embodiment, as noted above, the method provided above can include a further mutation in the pol gene product or immunogenic fragment thereof resulting in inactivation or deletion of protease, integrase and RNase H functions of the pol gene product or immunogenic fragment thereof. In a specific embodiment of this method, the region of the pol gene encoding the protease, RNase H and integrase function of the pol gene product or immunogenic fragment thereof has been deleted.

It is also contemplated regarding the method described above, that not all of the first, second and third populations of alphavirus particles do not all have to comprise an attenuating mutation. For example, the first population may comprise attenuating mutations, but the second and third populations may not, etc.

The present invention further provides the compositions of the present invention which are produced by the methods of this invention.

The compositions and methods of this invention which incorporate attenuating mutations into the alphavirus replicon particles forming the composition and/or produced by the methods include purified compositions and methods of purification based on the presence of the attenuating mutations. In particular, certain attenuating mutations in the alphavirus structural proteins introduce heparin binding sites into these proteins which are present on the surface of the alphavirus replicon particles. As an example, the V3014 E2 glycoprotein (SEQ ID NO:12 and SEQ ID NO:13) has a mutation in which a lysine is substituted for the glutamic acid at amino acid position 209. This mutation, which creates a more positively charged glycoprotein, increases the affinity of this protein for heparin. Thus, it is possible to purify such particles using heparin affinity chromatography. Such chromatography can be performed using any of several commercially available resins to which heparin has been bound. The source of heparin is variable; the commercially available resins currently use porcine heparin. The choice of resin will be based on its relative ease of use in a scaled-up, GMP-compliant process, e.g., price, column packing limitations, and potential for easy sanitization. The use of heparin affinity chromatography results in a substantial purification of the VRPs with very little loss of material, and it is a scalable purification step. In a preferred embodiment, a heparin affinity chromatography step results in between an 8- to 27-fold reduction in total protein per ml, or from a 300- to 1000-fold reduction in total protein per VRP. Thus, the present invention provides heparin affinity-purified alphavirus replicon particles containing attenuating mutations which are useful as clinical trial material and commercial product. The present invention also provides methods for preparing purified alphavirus replicon particles containing attenuating mutations comprising the use of heparin affinity chromatography, as described in the Examples provided herein. These particles can also be present in a composition of this invention.

The alphavirus replicon particles of this invention can also be made in a cell free system. Such replicon particles are herein referred to as virosomes. In a specific embodiment of the method, such particles are constructed from a mixture containing replicon RNA that does not encode all of the alphavirus structural proteins, purified glycoproteins E1 and E2, one or more non-cationic lipids, such as lecithin, and detergent. Detergent is slowly removed from the mixture to allow formation of lipid bilayers with incorporated RNA and glycoproteins.

In preferred embodiments of the methods of this invention, the glycoproteins E1 and E2 could be expressed in any recombinant protein expression system capable of glycosylation of mammalian proteins, such as stably transformed cell lines, for example CHO cells, or viral vector expression systems such as vaccinia, baculovirus, herpes virus, alphavirus or adenovirus. In a preferred embodiment, following expression of the proteins, the E1 and E2 glycoproteins are purified from contaminating cellular proteins in the expression supernatant. The purification of these glycoproteins can be achieved by affinity chromatographic column purification, for example using lectin-, heparin-, or antibody-affinity columns. This affinity purification step may be preceded by selective precipitation or selective extraction from the expression system supernatant by methods including, but not limited to, ammonium sulfate precipitation or detergent extraction respectively. Final polishing steps of purification may include ion-exchange chromatography or buffer exchange, for example, and tangential flow methods to generate purified glycoproteins suitable for virosome assembly.

Thus, the present invention provides a method of producing alphavirus replicon virosomes, comprising: a) combining alphavirus replicon RNA, alphavirus glycoproteins E1 and E2, non-cationic lipids and detergent; and b) gradually removing detergent, whereby alphavirus replicon virosomes are produced. This method is described in more detail in the Examples section herein.

The present invention also provides alphavirus replicon virosomes comprising an alphavirus replicon RNA encapsidated by a lipid bilayer in which alphavirus glycoproteins are embedded. The replicon RNA can be from any alphavirus and the glycoproteins can be from any alphavirus. In a specific embodiment, the alphavirus glycoproteins are VEE E1 and E2. The advantage of the alphavirus replicon virosomes is the ease of preparation, their stability, and their purity, since they are devoid of any cellular components being made in a cell free system.

The helper cells, RNAs and methods of the present invention are useful in in vitro expression systems, wherein the inserted heterologous RNA located on the replicon RNA encodes a protein or peptide which is desirably produced in vitro. The helper cells, RNAs, methods, compositions and pharmaceutical formulations of the present invention are additionally useful in a method of administering a protein or peptide to a subject in need of the desired protein or peptide, as a method of treatment or otherwise.

It is contemplated that the proteins, peptides, nucleic acids, vectors and alphavirus replicon particles of this invention can be administered to a subject to impart a therapeutic or beneficial effect. Therefore, the proteins, peptides, nucleic acids, vectors and particles of this invention can be present in a pharmaceutically acceptable carrier. By "pharmaceutically acceptable" is meant a material that is not biologically or otherwise undesirable, i.e., the material may be administered to a subject, along with the nucleic acid or vector of this invention, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art (see, e.g., *Remington's Pharmaceutical Science*; latest edition).

Pharmaceutical formulations of this invention, such as vaccines, of the present invention can comprise an immunogenic amount of the alphavirus replicon particles as disclosed herein in combination with a pharmaceutically acceptable carrier. An "immunogenic amount" is an amount of the infectious alphavirus particles which is sufficient to evoke an immune response (humoral and/or cellular immune response) in the subject to which the pharmaceutical formulation is administered. An amount of from about $10^3$ to about $10^7$ replicon-containing particles, and preferably, about $10^4$ to about $10^6$ replicon-containing particles per dose is believed suitable, depending upon the age and species of the subject being treated. Exemplary pharmaceutically acceptable carriers include, but are not limited to, sterile pyrogen-free water and sterile pyrogen-free physiological saline solution.

Subjects which may be administered immunogenic amounts of the infectious, replication defective alphavirus particles of the present invention include, but are not limited to, human and animal (e.g., horse, donkey, mouse, hamster, monkey) subjects. Administration may be by any suitable means, such as intraperitoneal or intramuscular injection.

Pharmaceutical formulations for the present invention can include those suitable for parenteral (e.g., subcutaneous, intradermal, intramuscular, intravenous and intraarticular) administration. Alternatively, pharmaceutical formulations of the present invention may be suitable for administration to the mucous membranes of a subject (e.g., intranasal administration). The formulations may be conveniently prepared in unit dosage form and may be prepared by any of the methods well known in the art.

Thus, the present invention provides a method for delivering nucleic acids and vectors (e.g., alphavirus replicon particles; virosomes) encoding the antigens of this invention to a cell, comprising administering the nucleic acids or vectors to a cell under conditions whereby the nucleic acids are expressed, thereby delivering the antigens of this invention to the cell. The nucleic acids can be delivered as naked DNA or in a vector (which can be a viral vector) or other delivery vehicles and can be delivered to cells in vivo and/or ex vivo by a variety of mechanisms well known in the art (e.g., uptake of naked DNA, viral infection, liposome fusion, endocytosis and the like). The cell can be any cell which can take up and express exogenous nucleic acids.

Further provided herein is a method of inducing an immune response to an HIV antigen of this invention in a subject, comprising administering to the subject an immunogenic amount of the particles, virosomes and/or composition of this invention, in a pharmaceutically acceptable carrier.

A method of treating and/or preventing infection by HIV in a subject is also provided herein, comprising administering to the subject an effective amount of the particles, virosomes and/or compositions of this invention, in a pharmaceutically acceptable carrier.

The subject of this invention can be any animal in which an immune response can be induced or in which an infection by HIV can be treated and/or prevented. In a preferred embodiment, the subject of this invention is a mammal and most preferably is a human.

Protocols and data regarding the testing of the compositions of this invention in animals and protocols for administration to humans are provided in the Examples herein.

In a particular embodiment, the present invention provides an isolated nucleic acid encoding a pol gene product or immunogenic fragment thereof of a human immunodeficiency virus, wherein the protease, integrase, RNase H and reverse transcriptase functions of the pol gene product or immunogenic fragment thereof have been inactivated or deleted. Such a modification has been shown in some studies to facilitate inhibition of the formation of replication competent alphavirus particles during production of alphavirus replicon particles comprising the pol gene product or immunogenic fragment thereof.

Also provided herein is a composition comprising the pol-expressing nucleic acid described above, a vector comprising the nucleic acid and a cell comprising the vector. The pol-expressing nucleic acid can also be present in an alphavirus replicon particle comprising the nucleic acid.

As noted above, the nucleic acid encoding the pol gene product or immunogenic fragment thereof comprises a modification resulting in the inhibition of reverse transcriptase activity. In a preferred embodiment, a mutation is introduced at the active site motif that results in inhibition of reverse transcriptase activity. Such a mutation may remove the DNA binding domain of the enzyme, for example. A mutation from YMDD to YMAA or HMAA at this motif is an example of such a mutation.

The present invention additionally provides a method of making an alphavirus replicon particle comprising nucleic acid encoding a pol gene product or immunogenic fragment thereof of a human immunodeficiency virus, wherein the pol gene product or immunogenic fragment thereof comprises a modification resulting in deletion or inactivation of protease, integrase, RNase H and reverse transcriptase functions from the pol gene product or immunogenic fragment thereof, comprising A) providing a helper cell for producing an infectious, defective alphavirus particle, comprising in an alphavirus-permissive cell:
  (i) an alphavirus replicon RNA, wherein the replicon RNA comprises an alphavirus packaging signal and a nucleic acid encoding a pol gene product or an immunogenic fragment thereof of a human immunodeficiency virus, wherein the pol gene product or immunogenic fragment thereof is modified to delete or inactivate protease, RNase H, integrase and reverse transcriptase functions in the pol gene product or immunogenic fragment thereof, and wherein the replicon RNA lacks sequences encoding alphavirus structural proteins;
  (ii) a first helper RNA separate from said replicon RNA, said first helper RNA encoding at least one alphavirus structural protein and furthermore not encoding at least one other alphavirus structural protein; and
  (iii) one or more additional helper RNA(s) separate from said replicon RNA and separate from said first helper RNA, said additional helper RNA(s) encoding at least one other alphavirus structural protein not encoded by said first helper RNA;
and with at least one of said helper RNAs lacking an alphavirus packaging signal;
wherein the combined expression of the alphavirus replicon RNA and the helper RNAs produces an assembled alphavirus particle which is able to infect a cell, and is unable to complete viral replication, and further wherein the population contains no detectable replication-competent alphavirus particles as determined by passage on permissive cells in culture;

(B) producing the alphavirus particles in the helper cell; and (C) collecting the alphavirus particles from the helper cell.

In the method provided above, at least one of the replicon RNA, the first helper RNA, and the one or more additional helper RNA(s) can comprise one or more attenuating mutations, as described herein.

In a specific embodiment of this method, a mutation is introduced at the active site motif in the pol gene product or immunogenic fragment thereof that results in inhibition of reverse transcriptase activity. Such a mutation may remove the DNA binding domain of the enzyme, for example. A mutation from YMDD to YMAA or HMAA at this motif is an example of such a mutation.

Also provided herein is an alphavirus replicon particle expressing the pol gene product or immunogenic fragment thereof, wherein the pol gene product or immunogenic fragment thereof comprises a modification resulting in deletion or inactivation of protease, integrase, RNase H and reverse transcriptase functions in the pol gene product or immunogenic fragment thereof, produced according to any of the above methods.

In a further embodiment, the present invention provides a method of inducing an immune response in a subject, comprising administering to the subject an immunogenic amount of a composition comprising an alphavirus particle comprising nucleic acid encoding a pol gene product or immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof, in a pharmaceutically acceptable carrier.

Furthermore, the present invention provides a method of treating or preventing infection by human immunodeficiency virus in a subject, comprising administering to the subject an effective amount of a composition comprising an alphavirus particle comprising nucleic acid encoding a pol gene product or immunogenic fragment thereof of a human immunodeficiency virus, wherein the pol gene product or immunogenic fragment thereof comprises a modification resulting in deletion or inactivation of protease, integrase, RNase H and reverse transcriptase functions in the pol gene product or immunogenic fragment thereof, in a pharmaceutically acceptable carrier.

In preferred embodiments of the methods of this invention, the subject is administered an effective amount of a population of alphavirus particles comprising particles expressing (1) nucleic acid encoding a pol gene product or immunogenic fragment thereof of a human immunodeficiency virus, wherein the pol gene product or immunogenic fragment thereof comprises a modification resulting in inactivation or deletion of protease, integrase, RNase H and reverse transcriptase functions in the pol gene product or immunogenic fragment thereof, (2) nucleic acid encoding a gag gene product or immunogenic fragment thereof of a human immunodeficiency virus, wherein the gag gene product or immunogenic fragment thereof is modified to inhibit release of gag gene product or the immunogenic fragment thereof from a cell, and (3) nucleic acid encoding an env gene product or an immunogenic fragment thereof of a human immunodeficiency virus in a pharmaceutically acceptable carrier.

In further preferred embodiments, the population of alphavirus particles comprises particles expressing (1) nucleic acid encoding a gag gene sequence that has at least 95% identity with SEQ ID NO:4; (2) nucleic acid encoding a pol gene sequence that has at least 99% identity with SEQ ID NO:15; and (3) nucleic acid encoding an env gene sequence with at least 92% identity with SEQ ID NO:18. In a specific embodiment, the population of alphavirus particles comprises particles expressing (1) nucleic acid of SEQ ID NO:4, (2) nucleic acid of SEQ ID NO:15, and (3) nucleic acid of SEQ ID NO:18.

EXAMPLES

The following examples are provided to illustrate the present invention, and should not be construed as limiting thereof. In these examples, nm means nanometer, mL means milliliter, pfu/mL means plaque forming units/milliliter, VEE means Venezuelan Equine Encephalitis virus, EMC means encephalomyocarditis virus, BHK means baby hamster kidney cells, HA means hemagglutinin gene, N means nucleocapsid, FACS means fluorescence activated cell sorter, and IRES means internal ribosome entry site. The expression "E2 amino acid (e.g., lys, thr, etc.) number" indicates the designated amino acid at the designated residue of the E2 gene, and is also used to refer to amino acids at specific residues in the E1 protein and in the E3 protein, respectively.

Example 1

VEE Replicon Particles as Vaccines

Replicon particles for use as a vaccine are produced using the VEE-based vector system, originally developed from a full-length, infectious cDNA clone of the RNA genome of VEE (FIG. 1 in Davis et al., 1989). In this Example, one or more attenuating mutations (Johnston and Smith, 1988; Davis et al., 1990) have been inserted into the clone to generate attenuated VEE vaccine vectors (Davis et al., 1991; 1995; Grieder et al., 1995).

As described herein, these constructs are genetically modified to create an RNA replicon (i.e., an RNA that self-amplifies and expresses), and one or more helper RNAs to allow packaging. The replicon RNA expresses an HIV gene, e.g., the Clade C HIV-1 gag gene. The replicon RNA is packaged into virus-like particles (herein referred to as "virus replicon particles" or "VRPs") that are infectious for only one cycle. During this cycle, the characteristics of the alphavirus-based vector result in very high levels of expression of the replicon RNA in cells to which the VRP is targeted, e.g., cells of the lymph node.

In the cytoplasm of the target cell, the replicon RNA is first translated to produce the viral replicase proteins necessary to initiate self-amplification and expression. In this Example, the HIV-1 Clade C gag gene is encoded by a subgenomic mRNA, abundantly transcribed from a negative-sense replicon RNA intermediate, leading to high-level expression of the HIV-1 Clade C gag gene product. Since the VEE structural protein genes are not encoded by the replicon RNA, progeny virion particles are not assembled, thus limiting the replication to a single cycle within the infected target cell.

Importantly, only the replicon RNA is packaged into VRPs, as the helper RNAs lack the cis-acting packaging sequence required for encapsidation. The "split helper" or bipartite system (see Example 4) greatly reduces the chance for an intact genome being assembled by recombination, and as a back-up safety feature, one or more highly attenuating mutations, such as those contained in the glycoprotein genes in V3014 (Grieder et al., 1995), are incorporated.

Overall, the design of the VRPs incorporates several layered and redundant safety features. In addition to the above-described split helper system and attenuating mutations, over one-third of the genome of the virus has been removed, creating a defective genome which prevents spread from the initially infected target cell. Nonetheless, if a statistically rare recombination event occurs to yield replication competent virus (RCV), the resulting virus would be a highly attenuated VEE strain.

Example 2

Construction of VEE Replicon

The VEE structural protein genes (C-PE2-6K-E1) are removed from a cDNA clone pV3014 which contained two attenuating mutations (E2 lys 209, E1 thr 272), and a duplication of the 26S subgenomic RNA promoter sequence immediately downstream from the 3'-end of the E1 glycoprotein gene, followed by a multiple cloning site as described in U.S. Pat. No. 5,505,947 to Johnston et al. The pV3014 plasmid DNA is digested to completion with ApaI restriction enzyme, which cuts the VEE genomic sequence at nucleotide 7505 (numbered from the 5'-end of the genome sequence). A second recognition site for this enzyme is found in the duplicate 26S subgenomic promoter. Therefore, digestion of pV3014 with ApaI produces two DNA fragments, one containing the VEE nonstructural genes (e.g., SEQ ID NO:2) and a single copy of the 26S subgenomic RNA promoter followed by a multiple cloning site, and a second smaller fragment containing a 26S subgenomic RNA promoter followed by the VEE structural genes. The large fragment is isolated and religated to produce the replicon, pVR2. A multiple cloning site (MCS) was inserted into pVR2 to generate pVERV. In this example, as well as in the construction of the helper plasmids (Example 3), the ampicillin resistance gene in each plasmid was replaced with a kanamycin resistance gene (SEQ ID NO:6; encoding amino acid sequence as in SEQ ID NO:7). The kanamycin resistance gene was obtained from the pET-9a plasmid, and was used to aid in the cloning manipulations and for regulatory compliance.

Example 3

Construction of Helper Plasmids

The starting materials for the helper plasmids are four full-length cDNA clones: V3000, the virulent Trinidad donkey strain of VEE, three clones with attenuating mutations, pV3014 (E2 lys 209, E1 thr 272), V3519 (E2 lys 76, E2 lys 209, E1 thr 272) and V3526 (deletion of E3 56–59, E1 ser 253), which are in the genetic background of Trinidad donkey strain VEE. Several different helper plasmids have been made by using unique or rare restriction sites in the full-length cDNA clone to delete portions of the nonstructural protein region. The full-length clone is digested with one or two restriction enzymes, the larger DNA fragment is isolated and then religated to form a functional plasmid. In vitro RNA transcripts from these plasmids upon transfection of tissue culture cells would not encode a functional RNA replication complex, and also would not include an encapsidation signal. The helper constructs differ in the size of the nonstructural gene deletion. The helper constructs are designated by the attenuated mutant clone used in their construction, and by the percentage of the nonstructural region deleted. The following helper constructs were generated:

V3014Δ520–7507(93%)
V3519Δ520–7507(93%)
V3526Δ520–7505(93%)
V3014Δ520–6965(87%)
V3519Δ1687–7507(78%)
V3014Δ2311–7505(70%)
V3519Δ3958–7507(47%)
V3526Δ520–7505(93%)
V3014Δ3958–7505(47%)
V3519Δ1955–3359(19%)
V3014Δ520–3954(46%)
V3014Δ1955–3359(19%)
V3014Δ1951–3359(19%)
V3014Δ2311–3055(10%)
V3014Δ2307–3055(10%)

Example 4

Construction of Bipartite RNA Helper Plasmids

A bipartite helper system is constructed as described herein. The V3014Δ520–7505(93%) helper is used to construct an additional deletion of the E2 and E1 glycoprotein genes by digestion with HpaI restriction enzyme and ligation, resulting in deletion of the sequence between nucleotide 8494 (in the E3 gene) and nucleotide 11,299 (near the 3'-end of the E1 gene). In vitro RNA transcripts of this glycoprotein helper plasmid (presented graphically in FIG. 2; an exemplary nucleotide sequence for such a plasmid is SEQ ID NO:8, including the nucleotide sequence (SEQ ID NO:9 and the amino acid sequence (SEQ ID NO:10 of the VEE capsid), when electroporated into BHK cells with a replicon RNA, are replicated and transcribed to give a mRNA encoding only the capsid protein of VEE.

The second member of the bipartite helper is constructed from the same original helper plasmid 3014Δ5207505(93%) by cleavage with Tth111I restriction enzyme (at nucleotide 7544) and SpeI restriction enzyme (at nucleotide 8389), resulting in deletion of the capsid gene, followed by insertion of a synthetic double-stranded oligonucleotide with Tth111I and SpeI termini. The inserted sequence restored the downstream portion of the 26S promoter and an ATG initiation codon followed by a Ser codon, such that the first amino acid residue of E3 (Ser) is the first codon following the inserted AUG. The resulting glycoprotein helper plasmid is presented graphically in FIG. 3, and an exemplary nucleic acid sequence for such a plasmid is SEQ ID NO:11, encoding the VEE glycoproteins (E3-E2-6 kD-E1), SEQ ID NO:12. The in vitro transcript of this plasmid, when transfected into a cell with replicon RNA, will produce the VEE glycoproteins (SEQ ID NO:13). Co-electroporation of both of these helper RNAs into a cell with replicon RNA results in production of infectious particles containing only replicon RNA.

Other than the 5' and 3' ends and the 26S promoters (40 nucleotides) of these helper RNAs, the only sequence in common between the capsid and glycoprotein helpers is the sequence from 8389 to 8494 (106 nucleotides)

Example 5

VEE Replicon Particles Expressing HIV Genes

Figure 10:
FIG. 10. Diagrammatic representation of the HIV-1 genome. Black bars indicate relative regions of the genome sequenced to generate phylogenetic sequence comparative data for Clade C gag, pol and env gene isolates.

The vaccines of this invention are exemplified by the use of a propagation defective, replicon particle vector system derived from an attenuated strain of Venezuelan equine encephalitis virus (VEE) to create a mixture of VEE replicon particles individually expressing HIV-1 gag, pol, or env genes. The three genes used in this Example were selected based on homology to consensus sequences generated from primary isolates obtained from recent seroconverters in KwaZulu/Natal Province, South Africa. Plasma samples from approximately 20 recent seroconverters in the Durban/Hlabisa cohort and a similar number of HIV-positive, asymptomatic individuals were collected. HIV viral RNA was isolated from the plasma, and the sequences of the gag, pol and env genes were analyzed. Two regions from each gene were amplified, and the resulting PCR products were sequenced (see FIG. 10 for regions analyzed). A consensus sequence was derived for each gene, and the sequences of each isolate were compared to the derived consensus. All isolates were found to be Subtype C of HIV, thus confirming the predominance of this subtype in South Africa.

A. Construction of the Gag-VRP Vaccine

Described herein is the design and manufacture of VEE replicon particles (VRPs) engineered to express the gag gene from a Subtype C isolate of HIV-1. The main purpose of this single antigen vaccine is to establish a safety profile for VRPs in healthy human subjects. Optimally, the HIV-Gag-VRPs will be formulated as a component of a trivalent vaccine, also containing HIV-Pol-VRP and HIV-gp160-VRP (env) made in analogous procedures to the one described herein for HIV-Gag-VRPs.

In this Example, the VEE particles are based on the V3014 glycoprotein helper plasmid (FIG. 3, SEQ ID NO:12 and SEQ ID NO:13), which harbors two highly attenuating mutations, one in E2 and the other in E1 (Grieder et al, 1995). The V3014 glycoprotein helper RNA is able to package VRPs with significantly greater efficiency than the glycoprotein helper RNA derived from V3526 (Pushko et al., 1997). Nonetheless, safety of the VRP vector system has not been compromised since detailed pathogenesis studies clearly have shown V3014 to be avirulent in adult mice by subcutaneous inoculation (Grieder et al., 1995). V3014 was found to be significantly impaired in its ability to reach and spread beyond the draining lymph node following subcutaneous inoculation. Unlike wild-type V3000, V3014 does not establish a viremia and does not reach the brain. In addition, on rare occasions when found, histopathological lesions in the periphery were much less severe than those induced by wild-type V3000 (Grieder et al., 1995). Following inoculation with V3014, adult mice are protected against lethal wild-type VEE infection.

The attenuated phenotype of V3014 also was observed in VEE challenge studies in horses. Animals inoculated subcutaneously with V3014 showed no significant leukopenia or febrile response compared to mock-vaccinated controls. In addition, results indicated that these animals were completely protected against virulent VEE (V3000) challenge.

Taken together, these data indicate that if the rare recombination event did occur during VRP assembly to yield RCV, the worst case scenario would be the generation of a highly attenuated strain of VEE.

B. Selection and Cloning of the Heterologous Antigen

The exemplary HIV genes used in this invention, gag, pol and env, are derived from Subtype C (Clade C) viruses isolated from likely Phase III clinical trial sites in South Africa. The HIV infection rate in South Africa and its long established virology and public health infrastructure make this country an attractive choice for clinical testing of HIV vaccines. Focused sequencing and phylogenetic analysis of the gag, pol, and env genes of these isolates has allowed the selection of genes representative of the Clade C isolates circulating in this region of Africa.

1. HIV-1 Clade C gag Gene

Two 400 bp regions of the gag gene were sequenced from approximately 30 plasma samples collected from HIV seropositive individuals in South Africa. A South African consensus sequence was then determined for the gag gene as well as a consensus sequence from the Los Alamos database for Subtype C virus. In addition, approximately 20 comparable sequences from Malawi were used, generated as part of another study, to confirm conclusions about sequence variation. Several isolates that were close to the South African consensus sequence were compared to other isolates in distance measurements. Among these 30 isolates, one was chosen as the source for the gag gene (SEQ ID NO:4; corresponding to the amino acid sequence in SEQ ID NO:5) for the following reasons.

This isolate had greater than 95% amino acid identity to the South African consensus sequence, representing the approximate middle of the sequence diversity of all isolates. This isolate, known as Du422, came from a recent seroconvertor, reflecting currently circulating strains and the transmitted phenotype. The phenotype of Du422 is NS1, CCR5(+), and CXCR4(−).

Prior to the insertion of the gag gene into the VEE replicon plasmid vector, the amino terminal myristylation ("myr") site of gag was removed to prevent the formation of Gag-containing virus-like particles. Restriction enzyme digests of the gag gene plasmid, the capsid helper plasmid, and the glycoprotein helper plasmid were performed to confirm the identity of the three vectors when compared to published maps of the parental plasmid pBR322, with the kanamycin resistance gene substituted for the ampicillin resistance gene. The confirmed plasmid maps of the VEE replicon plasmid containing the Du422 gag gene (p3–40.1.6), the capsid helper plasmid (p3–13.2.2), and the glycoprotein helper plasmid (p3–13.4.6) are presented in FIGS. 1, 2, and 3, respectively. The full nucleotide sequence of each of these plasmids is presented herein as SEQ ID NO:1, SEQ ID NO:8, and SEQ ID NO:11, respectively.

Figure 6:
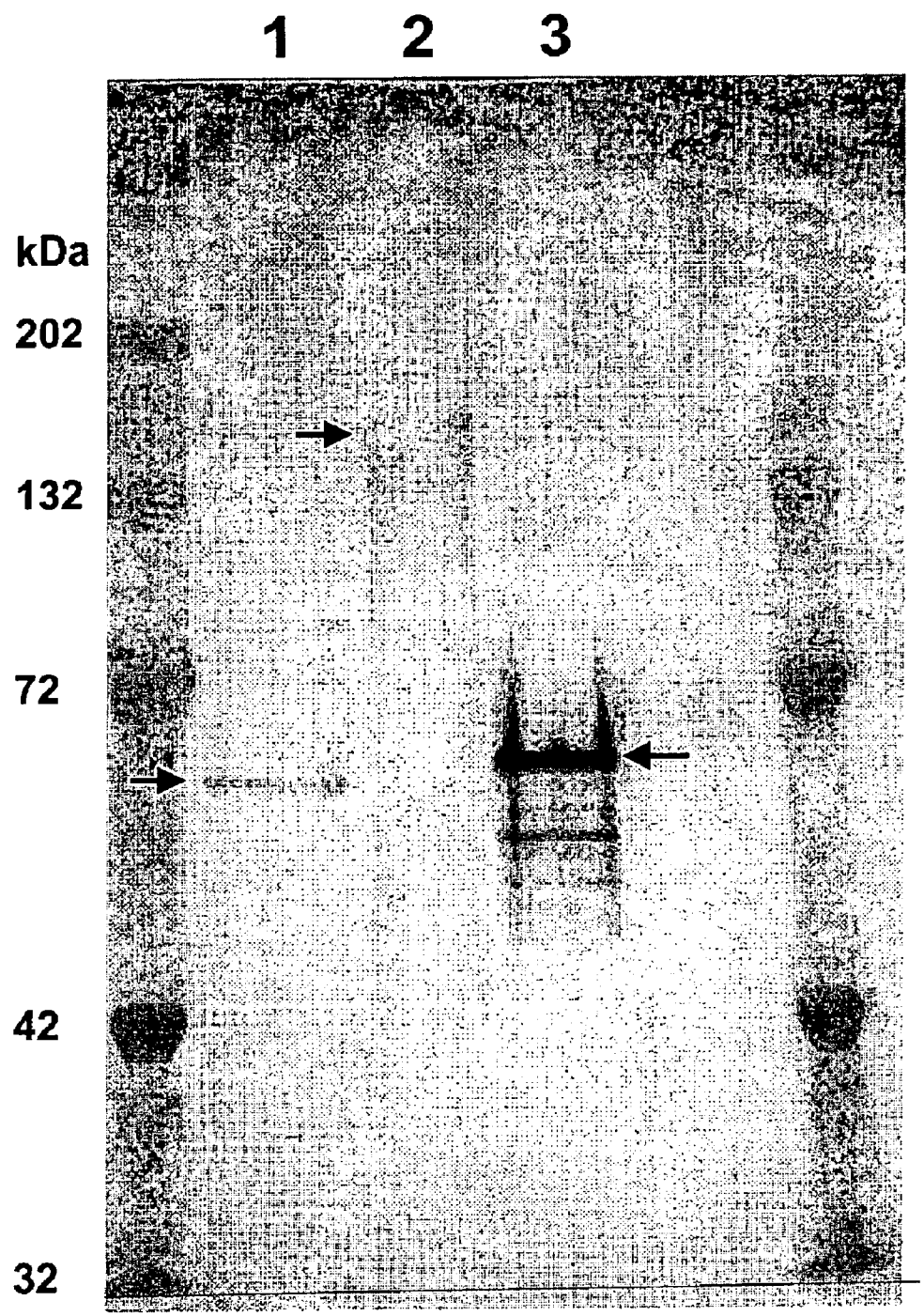
Figure 15:
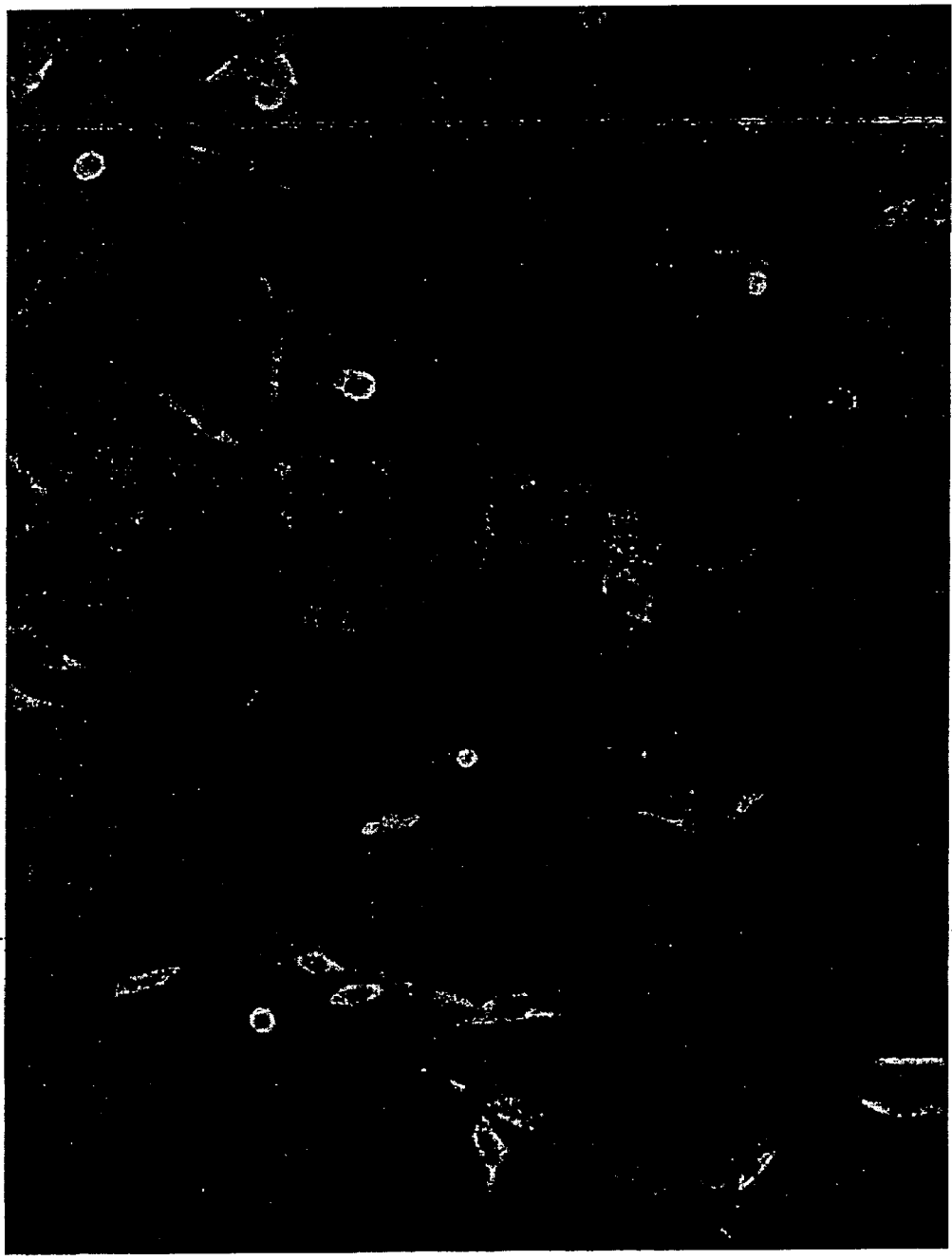
FIG. 15. Immunofluorescence detection of Du422 Gag protein expression in BHK cells. BHK cells were infected with VRP-Gag particles and subjected to immunfluorescence staining with an anti-Gag monoclonal antibody at 24 hours post-infection, to demonstrate expression of the Clade C protein.

In FIGS. 6 and 15, expression of this HIV-1 Gag protein in BHK cells infected with VRPs expressing such a gag construct is demonstrated (FIG. 6: Western blot, lane 3; FIG. 15, immunofluorescence detection). The cells were infected at a multiplicity of infection (m.o.i.) of 3.5 infectious units (i.u.) per cell, and expression was measured 18 hours post-infection (p.i.). Cell lysates (from approximately $2 \times 10^3$ cells) were collected and fractionated either by a 4–12% gradient SDS-PAGE or by 10% SDS-PAGE. The fractionated polypeptides were transferred to PVDF membranes and probed with human HIV-1 positive serum.

2. HIV-1 Clade C env Gene

Figure 5:
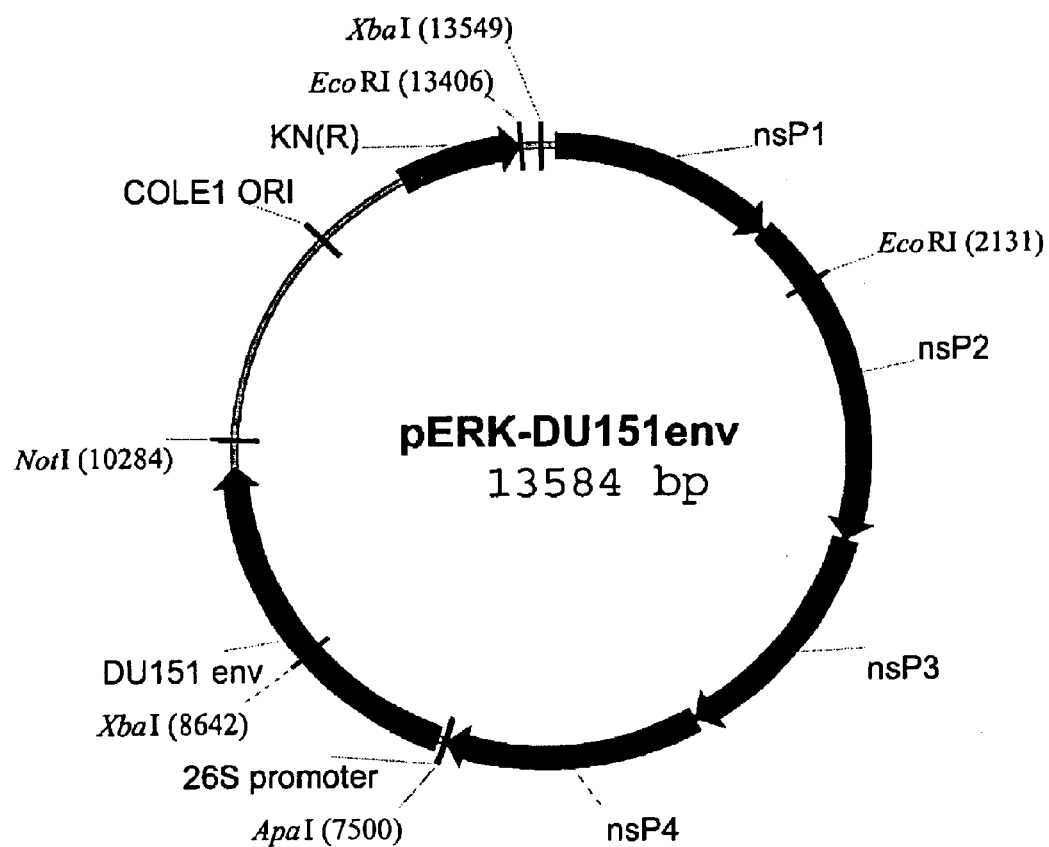

A Clade C env gene (aka "gp160") from another HIV isolate, Du151, from a recent seroconverter was chosen based on its 92% amino acid identity to the South African consensus sequence for this gene, determined in an analogous method to the one described for the gag gene in Example 5.A.1. The phenotype of the Du151 isolate is NS 1, CCR5(+), CXCR4(−). This gene was engineered into a VEE RNA replicon plasmid as shown in FIG. 5, and the entire sequence of the plasmid is given at SEQ ID NO:17. The env gene construct used in this Example is SEQ ID NO:18.

Figure 7:
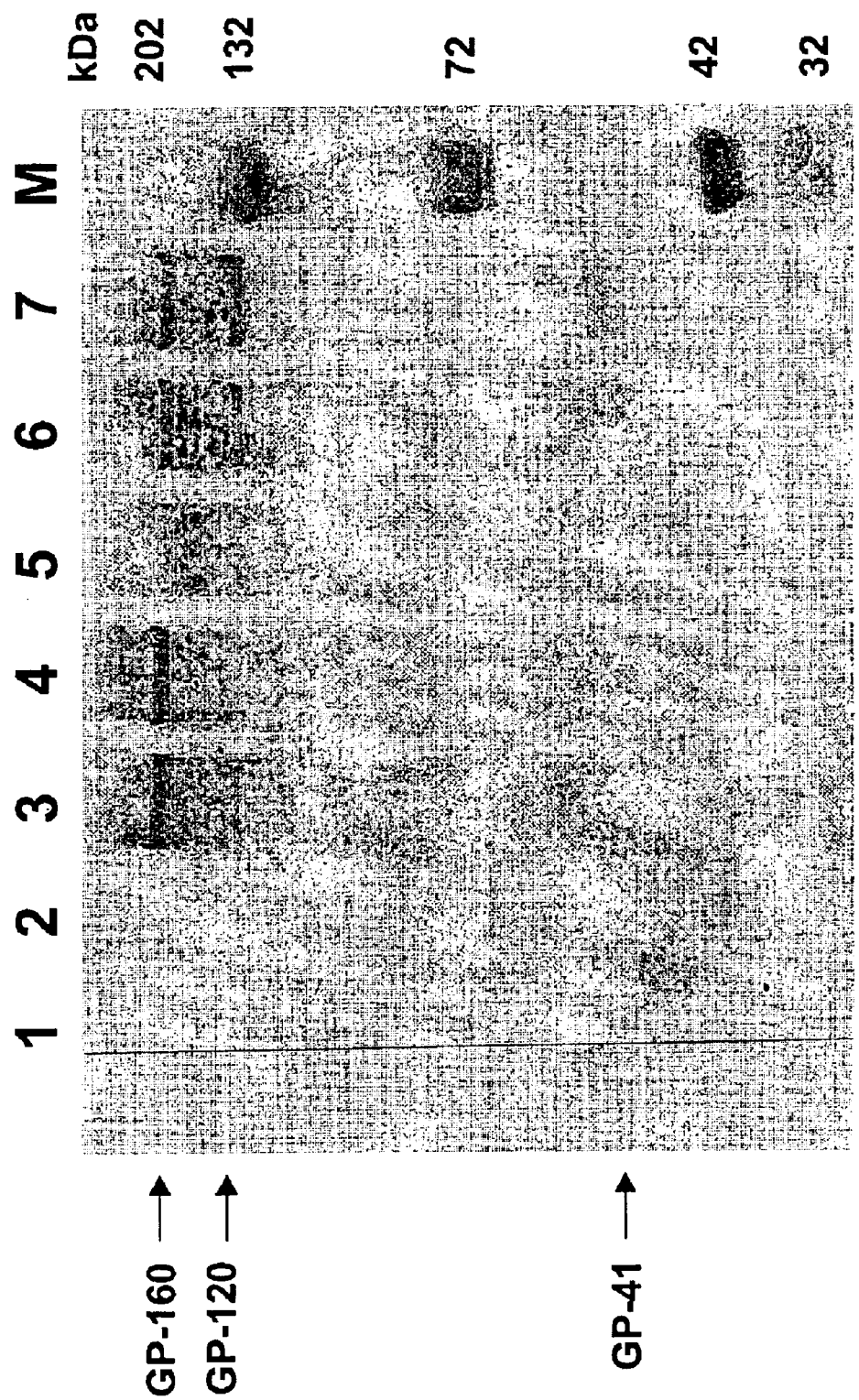
Figure 8:
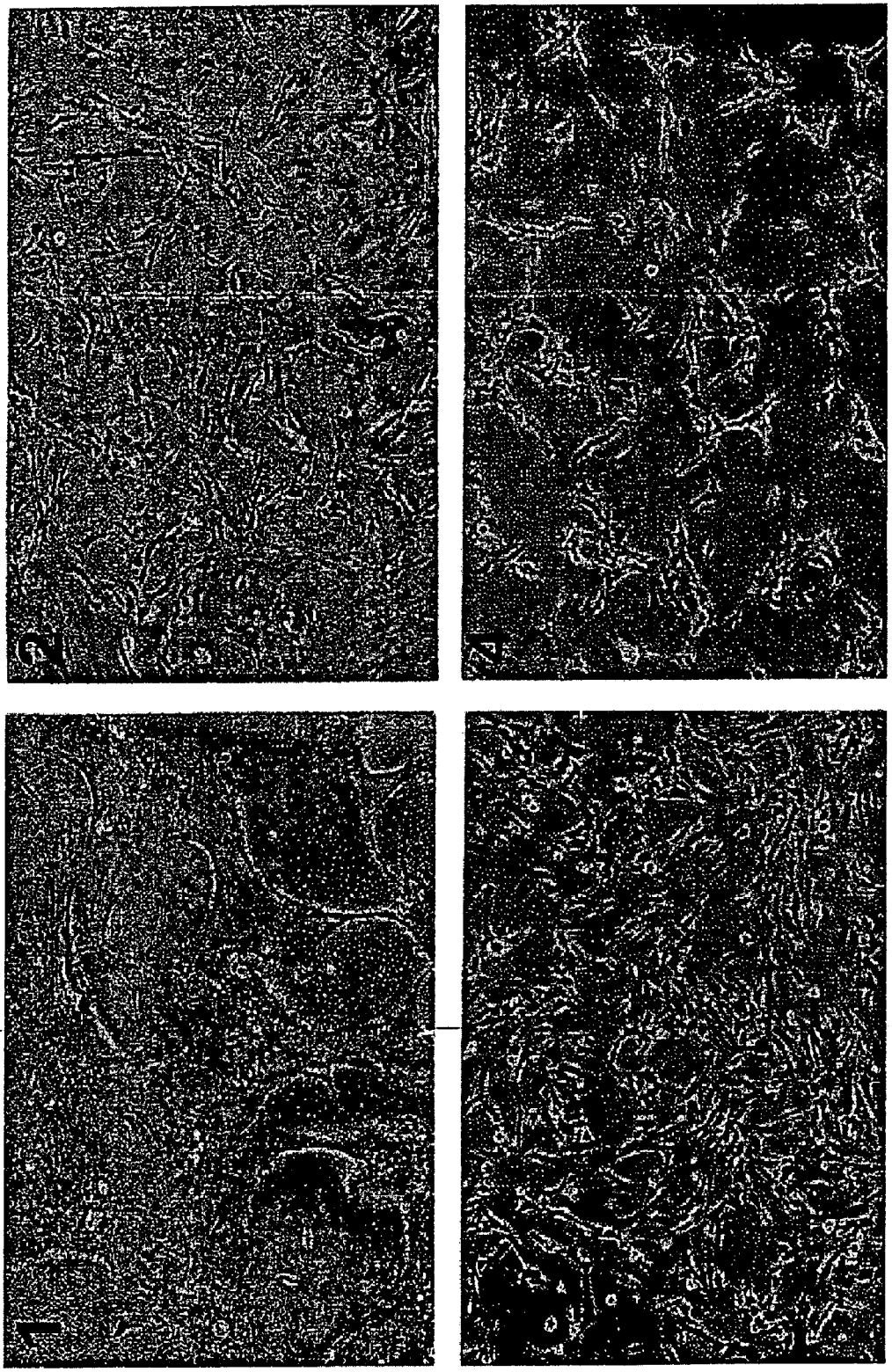
FIG. 8. Micrographs of U87.CD4-CCR and BHK cells used to examine expression and syncytium formation of Du151 envelope expressed from the VEE replicon. U87.CD4-CCR5 cells alone (Panel 1), or a mixture of U87.CD4-CCR5 and BHK cells (Panel 2), BHK cells alone (Panel 3) and U87.CD4-CXCR4 cells (Panel 4) were infected with Du151 env VRP at a multiplicity of infection of 3 i.u. per cell. At 18 hours post infection, the cells were examined using light microscopy for the presence of syncytia. The U87.CD4-CCR5 in Panel 1 and 2 show clear syncytia, which was absent in the control cell types in the lower panels. In addition, no syntycia were seen in uninfected control cells or VRP-GFP infected cells (data not shown).
Figure 9A:
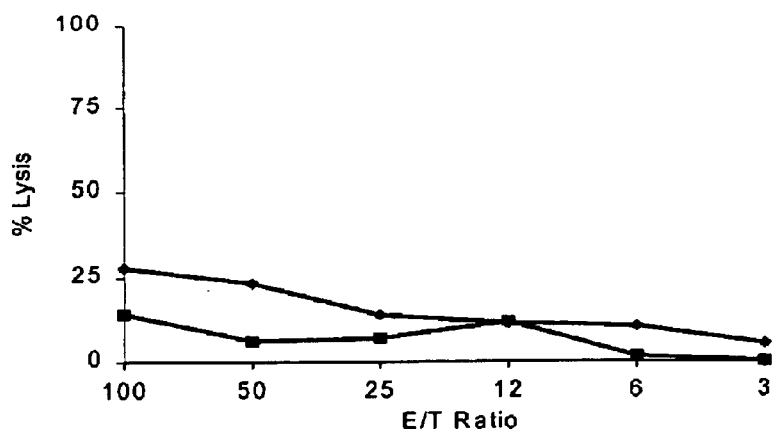
FIGS. 9A–C. Antigen-specific CTL response in mice to the HIV-1 Clade C VRP-Gag vaccine. Eight BALB/c mice were immunized twice, first at day 0 and again at day 28 with $10^3$ i.u. (Panel A) or $10^5$ i.u. (Panels B and C) VRP-Gag. Eight days (Panels A and B) or 49 days (Panel C) post-boost, spleen cells were isolated and stimulated in vitro with vaccinia virus expressing HIV Gag for 1 week. Chromium release assays were performed using vaccinia-Gag infected target cells (diamond symbols) or control vaccinia alone-infected sc11 target cells (square symbols). Clear HIV Gag-specific lysis was detected in animals vaccinated with the VRP-Gag vaccine.
Figure 9B:
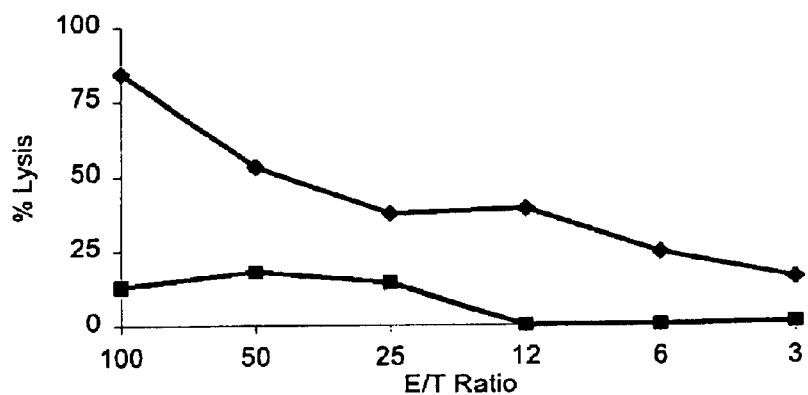
Figure 9C:
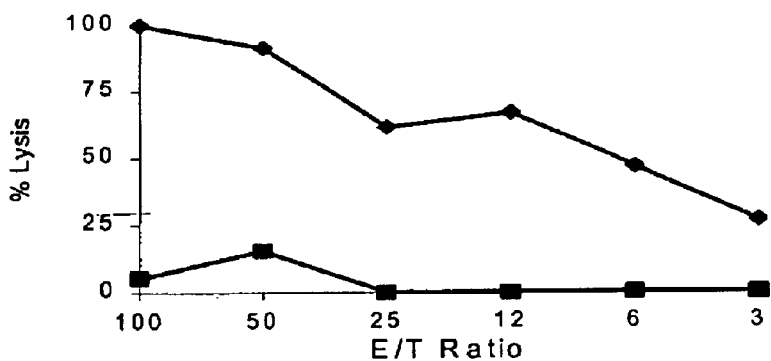

In FIG. 6, expression of this ENV protein (SEQ. ID. NO:19) in BHK cells infected with VRPs expressing this HIV env construct is demonstrated (Western blot, lane 2), showing that the protein expressed in the cells is of the correct size and is immunoreactive. In FIG. 7, expression of this ENV protein in U87.CD4.CCR5 cells is shown. These cells process the ENV protein into two components, gp120, gp41 and gp160. In these cells, the expressed gp160 is fusogenic (see FIG. 8).

3. HIV-1 Clade C pol Gene

Figure 4:
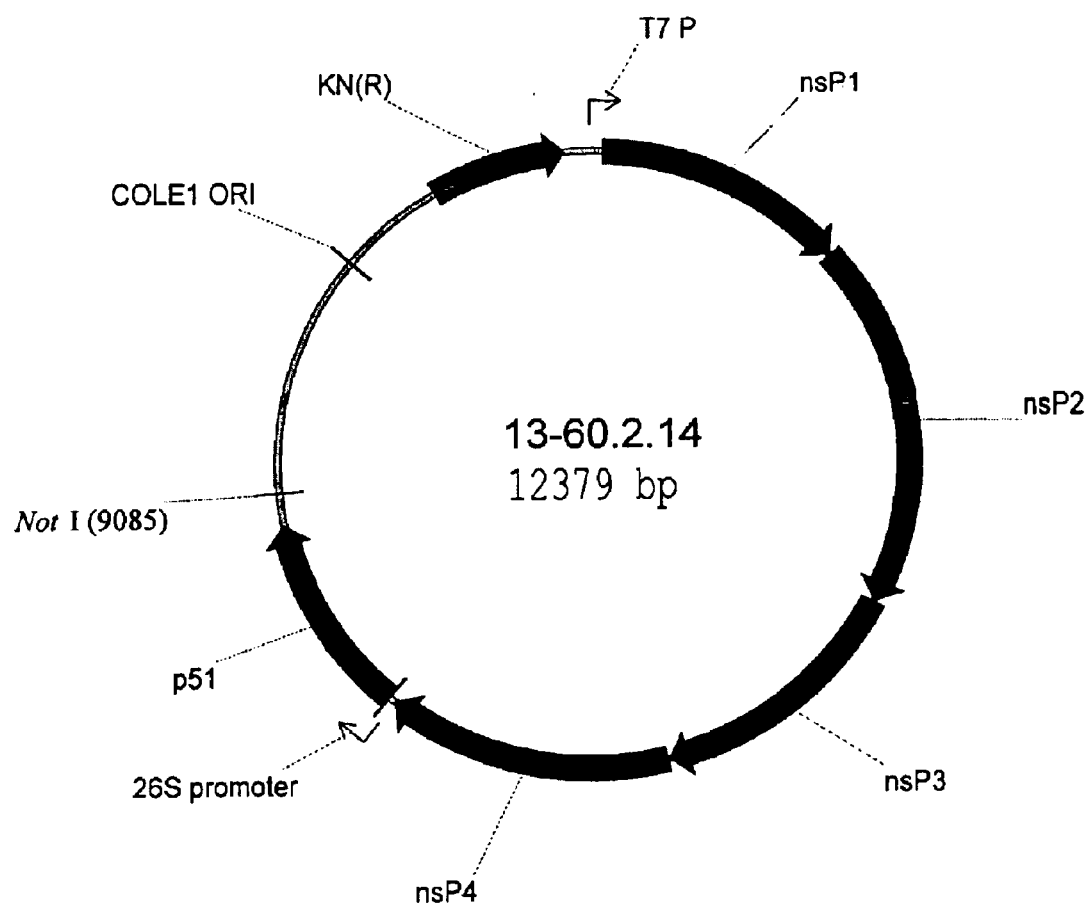

A Clade C pol gene from isolate Du151 was chosen based on its 99% amino acid identity with the South African consensus sequence. This gene was modified at the active site of the reverse transcriptase encoding sequence to inhibit its activity, and the p51 fragment of this modified gene (SEQ ID NO:15) was engineered into a VEE RNA replicon plasmid. The map of this pol plasmid is shown in FIG. 4, and the nucleotide sequence of the plasmid is provided as SEQ ID NO:14. In FIG. 6, expression of this POL p51 fragment (SEQ ID NO:16) in BHK cells is demonstrated (Western blot, lane 1), showing that the protein expressed in these cells is both the correct size and immunoreactive.

C. Immunological Response to VRP-Gag Vaccine

Mice were injected subcutaneously in two doses, with 8–9 mice in each group. The mice were immunized once, then immunized a second time, with the same dose, 28 days later. Serum was collected the day prior to the first immunization, then at day 27 ("after $1^{st}$ immunization) and at day 35 (after $2^{nd}$ immunization).

The vigorous, antigen-specific humoral response of mice to the HIV-1 Clade C VRP-Gag vaccine described in Example 5.A.1. is presented in Table 1. Details of this assay are described in Example 7A.1.

TABLE 1

Humoral Response to VRP-Gag Vaccine

| Dose: | Total Ab Titer ($log_{10}$) |
|---|---|
| $10^3$ i.u. dose: | |
| after $1^{st}$ immunization | 1.3 +/− 0.1 |
| after $2^{nd}$ immunization | 2.8 +/− 1.1 |
| $10^5$ i.u. dose | |
| after $1^{st}$ immunization | 2.1 +/− 0.5 |
| after $2^{nd}$ immunization | 4.1 +/− 0.6 |

A robust, Gag-specific response in mice was induced by the HIV-1 clade C VRP-Gag vaccine and is presented in FIG. 9. Details of this assay are described in Example 7A.3.

Example 6

Manufacturing Process for HIV VRP Vaccines

A. Manufacturing Process

Disclosed herein is a manufacturing process for VRP vaccines that is suitable for large-scale preparation of GMP-compliant (GMP=Good Manufacturing Practices) material for use in human clinical trials or for commercial manufacture. The process includes several steps and after each step (as appropriate), a set of "in process control" (IPC) assays or Release Tests (RT) is performed to confirm the successful completion of the step. The IPC/RT tests and process steps and the accompanying IPC assay(s) or RTs (described in more detail in Example 6D.1 and 6D.2) are as follows:

| Process Step | IPC/RT Tests and Process Steps |
|---|---|
| Linearize 3 DNA plasmids | IPC: Check for linearity |
| In vitro RNA transcription | IPC: Size, integrity and concentration |
| Electroporation of certified Vero cell line | |
| Harvest culture fluids | IPC:<br>Titration/Identity<br>Test for replication-competent virus (RCV) |
| Pool the culture fluid | RT:<br>Mycoplasma<br>Adventitious virus<br>PERT assay |
| Purification of bulk VRP by heparin affinity chromatography | IPCs:<br>Heparin residual assay<br>BSA assay<br>Bovine IgG assay |
| Filtration of bulk VRP | RT:<br>Test for RCV<br>Titration/Identity<br>Contaminating protein/DNA<br>Sterility<br>Endotoxin |
| Formulate, Fill, Release | RT:<br>Titration/Identity<br>Sterility<br>General Safety |

B. Preparation of plasmid DNAs

Stock solutions of replicon plasmid DNA, capsid helper plasmid DNA and glycoprotein helper plasmid DNA are produced in *Eschericia coli* XL2 Blue cells (Stratagene, cat# 200150). All plasmids harbor the kanamycin resistance gene marker. The three plasmid DNAs were manufactured and purified by PureSyn, Inc. (Malvern, Pa.) under appropriate GLP/GMP procedures, with a complete Batch Record with full traceability. Following fermentation and cell harvest, cell paste was lysed with base and plasmid DNAs were purified by ion pair chromatography on PolyFlo™ separation media.

Prior to release by appropriate quality assurance/quality control oversight, each lot of each plasmid DNA is analyzed to confirm identity, purity and quality (Table 2). An approved certificate of analysis for each DNA is then established for each plasmid DNA lot.

TABLE 2

Plasmid DNA Release Tests

| Test | Method | Specification |
|---|---|---|
| DNA homogeneity | Agarose gel electrophoresis | >90% supercoiled |
| *E. coli* genomic DNA | Southern Blot | <50 μg/mg plasmid |
| *E. coli* RNA | Agarose gel electrophoresis | No detectable bands |
| Endotoxin | Limulus Amoebocyte Lysate (LAL) | <0.1 EU/mg |
| Total protein | Abs 260/280 | 1.8–1.9 |
| Sterility | Bioburden assay, USP23 | <1 CFU |
| Identity | Restriction enzyme analysis | Matches map |

To produce HIV-VRP vaccine for clinical use, both replicon and helper plasmids are linearized by digestion at the unique Not I site and used as templates for synthesis of run-off transcripts. The quality of the transcription products (i.e., the replicon and the two helper RNAs) is evaluated by agarose gel electrophoresis.

C. Characterization of the Vero Cells

Vero cells are used in the production of HIV-VRPs (WHO Vero MCB P139, BioReliance Inc., Rockville, Md.). Vials contained approximately 1×10⁷ cells/mL in a cryoprotectant solution of 90% fetal bovine serum and 10% dimethyl sulfoxide. A Cell Certification Summary is provided with each lot. BioReliance Inc. has filed a Master File with the FDA regarding the WHO Vero MCB P139.

Vials of WHO Vero MCB P139 cells are expanded into flasks. Each of the flasks is then expanded again in order to prepare the Master Cell Bank (MCB). The Working Cell Bank (WCB) is prepared from the MCB. The MCB is tested for purity and identity. The WCB is tested for adventitious agents (detection of mycoplasma and viruses). Viability tests are performed on both the MCB and the WCB.

Tumorigenicity tests are performed once at the end of the production period.

D. Electroporation

Vero cells are cotransfected by electroporation with RNA mixtures comprising replicon RNA transcripts encoding HIV-gag, VEE capsid helper RNA transcripts, and VEE glycoprotein helper RNA transcripts. The transfected cells are transferred to tissue culture vessels and incubated in well-defined culture medium. Following harvest, the HIV-Gag-VRP is purified from pooled culture fluid supernatants by affinity column chromatography. Prior to formulation and filling, purified, bulk HIV-Gag-VRP is tested for the presence of RCV.

E. Final Formulated Product

The HIV-Gag-VRP vaccine is vialed at four different doses. The material is filtered (0.22 μm) and added to vials at the appropriate concentration and volume, stoppered, quick-frozen and stored at −20° C.

F. Control Tests of the Gag-VRP Vaccine

1. In-Process Controls

Table 3 below summarizes the In-Process Controls performed during the manufacturing process of the HIV-Gag-VRP Vaccine.

TABLE 3

IPCs during the manufacture of HIV-Gag-VRP Vaccine

| Test | Method | Target |
|---|---|---|
| Check for linearity | Agarose Gel electrophoresis | Report |
| Size, integrity and concentration of RNAs | Agarose Gel electrophoresis | Report |
| Titration/Identity | Indirect immunofluorescence assay(IFA), using standardized Gag-specific antibody preparation | Report |
| Test for RCV | CPE Assay | Report |
| Heparin Residual | Chromogenic Inhibitory Assay | Report |
| BSA residual | ELISA | Report |
| Bovine IgG Residual | ELISA | Report |

2. Release Tests

Tables 4 and 5 below summarize the release tests performed on the HIV-Gag-VRP Vaccine.

TABLE 4

Pool of the Culture Fluids

| Test | Method | Target |
|---|---|---|
| Adventitious Virus (in vivo) | European guidelines | Negative |
| Adventitious Virus (in vitro) | 5 cell lines | No growth |
| Mycoplasma | 21CFR 610.30 | No Growth |
| Reverse Transcriptase | PERT Assay | Negative |

TABLE 5

Bulk VRP and Final Vial testing

| Test | Method | Target Result |
|---|---|---|
| Replication competent virus (RCV) | Cytopathic effect (CPE) assay | Absence (in VERO cells, sensitivity is 1–10 pfu V3014) |
| VRP identity/potency | Indirect immunofluorescence assay (IFA) | $10^6$ to $10^8$ i.u. per mL |
| Cellular Protein Contaminant | Pierce BCA protein assay | Total protein content per dose |
| Cellular DNA Contaminant | Southern Blot or PCR | <10 ng per dose |
| Sterility | 21 CFR § 610.12 | Pass |
| Endotoxin | LAL | <5 EU/dose |
| General Safety | 21 CFR § 610.11 | Pass |
| Particulates | USP | Pass |
| Stability | IFA | $10^6$ to $10^8$ i.u. per mL |

Example 7

Preclinical Studies

Pilot lots are manufactured following written procedures (SOPs and STMs) and according to the manufacturing scheme described in Example 6. These pilot lots are prepared and used for two major tasks. The first one is a preclinical immunogenicity evaluation, which includes studies to assess the immune response and the cell-mediated immune response in vaccinated animals. The second major task is a preclinical safety evaluation, which includes evaluations of system toxicity, hematopoietic and immune system toxicity, and local reactogenicity.

A. Immunogenicity Studies

A.1 Humoral Immune Response in Mice

Three groups of five female BALB/c mice (4–6 weeks of age) are inoculated subcutaneously with $10^5$, $10^6$, or $10^7$ i.u. of the HIV-Gag-VRP at three time points: on day 0, and at weeks 4 and 8. The fourth group, Control Group, receives the vehicle only. Immediately prior to inoculation, and at weeks 3, 5, 8 and 10 post-inoculation, blood samples are collected for humoral immune response evaluations. Gag protein-specific serum antibody titers and seroconversion rates are measured by ELISA (Caley et al, 1997) against purified, recombinant Gag protein. The source of the antigen is the homologous Clade C gag gene expressed in insect or mammalian cells. Antigen specificity also is confirmed by immunoblot analysis. Anti-VEE responses are monitored by ELISA (Johnston and Smith, 1988).

A.2 Humoral Immune Response in Rabbits

Three groups of five female New Zealand white rabbits are inoculated subcutaneously with $10^5$, $10^6$, or $10^7$ i.u. of the HIV-Gag-VRP. The fourth group, Control Group, receives the vehicle only. Immediately prior to inoculation, and at weeks 3, 5, 8 and 10 post-inoculation, blood samples are collected for humoral immune response evaluations.

Humoral immune responses are evaluated as described in Section A.1.

A.3 Cell-Mediated Immune Response in Mice

Three groups of five female BALB/c mice are inoculated subcutaneously with $10^5$, $10^6$, or $10^7$ i.u. of the HIV-Gag-VRP at day 0 and day 28. The fourth group, Control Group, receives the vehicle only. Blood samples are collected at week 3 post-inoculation. Spleens are harvested for splenocyte collection on day 7 following the second inoculation for evaluation of cell-mediated immune responses.

The cell-mediated immune response is evaluated by determining the ability of splenic T cells from immunized mice to proliferate ex vivo in the presence of either Gag protein or Gag peptide(s). The ability of splenic T and CD4+ T cells to produce interferon-γ and interleukin-4 respectively, is determined. Finally, the ability of cytotoxic T lymphocytes to lyse target cells that present murine major histocompatibility complex class-I restricted epitopes for HIV-1 Clade C Gag protein is measured (see Betts et al., 1997 for methods).

B. Safety Study

Three groups of six male and six female New Zealand white rabbits are inoculated subcutaneously with $10^4$, $10^6$, or $3×10^7$ i.u. of the HIV-Gag-VRP. The fourth group, Control Group, receives the vehicle only. Animals receive four injections at week 0, week 3, week 6 and Week 9. Half of the animals are sacrificed two days after the last injection (week 9) and the other half at three weeks after the last injection (week 12). Similar studies are performed in mice with a high dose at $10^8$ i.u. This level is 10–100 times the likely primate dose, based on efficacy studies in rhesus macaques.

In addition to system toxicity (record of mortality/morbidity, body temperature, body weight, food consumption and ophthalmic examinations), hematopoietic toxicity is evaluated by quantitating cellular components of peripheral blood, and immune system toxicity is assessed by histopathologic evaluation of the lymphoid organs. Local reactogenicity is evaluated by examining the injection sites grossly and microscopically to determine irritation potential. Serum samples are also tested for the presence of replication competent virus by blind passage in cell culture.

C. In Situ Hybridization Study in Mice

Three groups of five female BALB/c mice are inoculated subcutaneously with $10^5$, $10^6$, or $10^7$ i.u. of the HIV-Gag-VRP. The fourth group, Control Group, receives the vehicle only. A single injection is performed in each group.

To verify expression of HIV-GAG-VRP in lymphoid tissue, the draining lymph nodes, spleen, and thymus of the mice are examined by in situ hybridization at 24 hours and 48 hours after the single inoculation.

Example 8

Heparin Affinity Chromatography of VRPs

Generally, the majority of contaminating protein is non-VEE protein from the conditioned media. Heparin column capacity requirements for GMP manufacturing runs are therefore based on the volume of conditioned media, rather than the concentration of VRPs. Column parameters are optimized at room temperature, but variations in temperature do not greatly affect performance. The expected yields of VRPs can range from 50% to >90%.

While only minimal leaching of heparin from the columns has been detected, GMP requirements stipulate that a residual heparin assay be performed as an IPC test following the chromatography step.

A. Pharmacia HiTrap® Heparin

Five mL columns of Pharmacia HiTrap® Heparin (cat no. 17-0407-01, Amersham Pharmacia Biotech), pre-equilibrated with 25 mM HEPES/0.25 M NaCl, pH 7.5, were loaded with HIV-Gag-VRPs produced in Vero cells. After column washing with the equilibration buffer, VRPs were eluted with a 15 column volume gradient from 0.25–1.0 M NaCl gradient in 25 mM HEPES, pH 7.5. The HIV-Gag-VRPs eluted at a conductivity of approximately 48 mS/cm. The wash step was optimized (based on the $A_{280}$ peak) at a NaCl concentration between 0.25 M and 0.3 M.

B. Heparin Sepharose 6 Fast Flow® Resin

Heparin Sepharose 6 Fast Flow® resin (catalog no. 90-1000-2; Amersham Pharmacia Biotech) is supplied as a bulk resin which allows various size columns to be packed as needed. Fast Flow® resins have the advantages of excellent flow characteristics and ability to be sanitized with sodium hydroxide solutions, which are particularly useful in a GMP manufacturing process. A 6 mL column was prepared by packing the Heparin Sepharose 6 Fast Flow® bulk resin in a BioRad® Econo-Column chromatography column, which was then pre-equilibrated with 25 mM HEPES/0.12 M NaCl, pH 7.5. VRPs were loaded onto the column, which was then washed with the equilibration buffer. Initial experiments indicated that the VRPs eluted at a lower conductivity (36 mS/cm) with this resin as compared to the HiTrap® Heparin, so the wash conditions were modified accordingly. The VRPs were eluted from the Fast Flow® resin with a 15 column volume gradient from 0.12 M to 1 M NaCl in 25 mM HEPES, pH 7.5.

Example 9

Virosome Formation

The feasibility of virosome formation is demonstrated in a series of experiments in which replicon RNA and RNA encoding the glycoprotein E1 and E2 genes (glycoprotein helper) were first transfected into BHK cells by electroporation. After 18–24 hours, cell supernatants were harvested and tested for the presence of virosomes as described briefly below.

Cell Culture

BHK cells were used as a cell substrate and were maintained in growth medium (alpha-MEM (Life Technologies), supplemented with 10% Fetal Bovine Serum (HyClone), 1× Glutamine (Life-Technologies)), in an atmosphere of 5% $CO_2$ at 37° C. Prior to electroporation, cells were detached from the cell culture vessel using 0.05% trypsin-0.53 mM EDTA solution (Life Technologies). Trypsin was neutralized with growth medium, and cells were washed twice with cold Phosphate-Buffered Saline (PBS, BioWhittaker) and resuspended at a concentration of $1.5×10^7$ cells/ml.

RNA Transcription, Electroporation and Virosome Harvest

Plasmid DNA pVR-GFP (green fluorescent protein) was linearized using restriction endonuclease NotI (New England Biolabs) as recommended by the manufacturer. DNA was extracted with phenol:chloroform:iso-amyl alcohol (25:24:1, Gibco BRL) and precipitated with ethanol, following the addition of $NH_4Ac$ to 2.5 M final concentration. RNA was synthesized in an in vitro transcription reaction using an Message mMachine® kit (Ambion) as recommended by the manufacturer. This RNA, without further purification, was used to transfect BHK cells. Helper RNA was prepared in a similar fashion. A BHK cell suspension in PBS (0.8 ML, $1.2×10^7$ cells) was mixed with 10 μg of each RNA, and the mixture was electroporated. Electroporation settings for Gene-Pulser® (Bio-Rad Laboratories) were: 850 V, 25 μF, 3 pulses. Culture supernatant was collected at 18–24 hr post-electroporation and clarified by centrifugation for 10 min at 1000 rpm.

Titration of Virosomes

The presence of infectious virosome particles was demonstrated using an immunofluorescence assay to titer the virosomes by detecting the fluorescence of the GFP encoded by the replicon RNA in the virosomes. Serial dilutions of the cell culture supernatant were added to 12-well plates of BHK cells. Following an 18–24 hour incubation in an atmosphere of 5% $CO_2$ at 37° C., the medium was removed from each plate. Virosome infectious titer was then determined by counting the number of green-fluorescent single cells at a particular dilution, followed by a back-calculation to determine total infectious units (i.u.) per mL. A final titer of 440 i.u./mL was collected.

Confirmation of Virosome Identity

Three independent experimental methods were used to determine that the infectious particles were in fact virosomes, rather than replication competent viral particles or naked RNA being carried over from the electroporated cells.

i) The virosome-containing supernatant was passaged a second time by removing the cell supernatant from the 12-well plate used for titration and placing this supernatant onto a fresh monolayer of BHK cells. At 18–24 hours post-passage, the monolayer was examined under U/V fluorescence and found to contain 0 (zero) GFP-positive cells, indicating the infectious particles produced using this method can undergo only a single round of replication, a critical characteristic of a virosome.

ii) To establish that the infectious titer detected following virosome packaging was not due to carry-over of RNA used in the electroporation, the supernatant was treated with RNase A (Invitrogen) at a concentration of 100 $\mu$g/mL for 15 minutes at 37° C. The treated and untreated control supernatants were titered according to the methods outlined above. The RNase-treated sample contained 400 i.u./mL and the control group had 440 i.u./mL, indicating that the RNAse treatment had no significant effect on virosome titer.

iii) To establish that the infectious particles were enveloped in the E1 and E2 glycoproteins, anti-VEE mouse serum was used to treat the cell supernatant in a neutralization assay. As a control, normal mouse serum was used to treat the virosome supernatant. In addition, VEE replicon particles expressing GFP were used in the assay, the infectivity of which is known to be inhibited by this serum.

|  | Particle Titer (i.u./mL) | | |
|---|---|---|---|
|  | Anti-VEE serum | Normal Mouse Serum | No serum |
| Virosome Supernatant | 20 | 440 | 530 |
| VRP-GFP | 0 | 530 | 890 |

The infectivity of the virosomes was inhibited similar to that of VRP-GFP, indicating that the virosome particles were enveloped by the E1 and E2 glycoproteins.

These examples clearly demonstrate the ability to produce infectious virosome particles comprising replicon RNA enveloped with only the alphavirus E1 and E2 glycoproteins. Testing confirmed that these virosomes are infectious agents, but that they undergo only a single round of replication, as indicated by the inability to passage the agent. In addition, the agents contained the E1 and E2 glycoproteins, as evidenced by the ability to block infection with only VEE specific serum. Finally, the infectious RNA is protected from RNase enzymatic digestion, indicating an enveloped particle.

The natural lipid content in BHK cells is primarily non-cationic. Virosomes made in a completely cell free system can be made by using one or more non-cationic lipids, such as lecithin (phosphatidylcholine).

Example 10

Phase I Clinical Protocol

Phase I Safety and Immunogenicity Trial of an HIV Subtype C Gag-VEE Replicon Particle Vaccine in HIV-1 Seronegative Human Subjects A Phase I trial is conducted to evaluate the safety and immunogenicity of the HIV Gag-VRP prototype vaccine component in healthy seronegative adult volunteers. The doses are selected based on preclinical studies in rodents and nonhuman primates. The schedule mimics previous preclinical efficacy studies with the SIV model that demonstrated the capacity of SIV-VRP to induce SIV specific neutralizing antibodies and CTL.

Purpose: To evaluate the candidate vaccine component in an open-labeled, placebo-controlled study.

Subjects: Healthy adult volunteers without a history of identifiable high-risk behavior for HIV-1 infection as determined by a comprehensive screening questionnaire.

No. Subjects: 40

Route: Subcutaneous injection

Scheme: The volunteers are arranged in four groups, ten subjects per group. In each group, two subjects receive a placebo, while the other eight subjects receive either $10^4$, $10^6$, $10^7$, or $10^8$ i.u. of HIV-Gag-VRPs. Subjects are vaccinated on day 0, day 30, and day 120.

Estimated Duration: Forty weeks

A. Selection of Subjects

Subjects are healthy HIV-1 seronegative adults who fully comprehend the purpose and details of the study as described in the informed consent. Subjects whom either themselves or whose sexual partners have identifiable higher risk behavior for HIV-1 infection are not eligible. Higher risk behavior is determined by a prescreen series of questions designed to identify risk factors for HIV-1 infection. An assessment of absolute exclusion criteria using the self-administered and interview questions is conducted. Subsequently, investigators proceed with phlebotomy, history and physical examination, and final questions regarding sexual behavior and other practices. Eligibility determinations for the trial depend on results of laboratory tests and answers to these self-administered and interview questions. The criteria used to define low risk behavior are as follows:

Either All of the Following
1. No newly acquired higher risk associated STD in the last six months
2. No possibly safe or unsafe sex with a known HIV+ individual or an active injection drug user in the past six months
3. No unsafe sexual activity
4. Possibly safe sexual activity with two or fewer partners within the last six months
5. No injection drug use Or Both of the Following
1. Mutually monogamous relationship with a known or presumed HIV seronegative partner for the last six months
2. No injection drug use A.1 Inclusion Criteria Age: 18–60

Sex: Male or Female [For females, negative pregnancy test at time of entry and assurance that adequate birth control measures will be used for one month prior to immunization and the duration of the study]

Normal history and physical examination

Lower risk sexual behavior as defined above.

Normal complete blood count and differential defined as:

Hematocrit 34% for women; 38% for men

White count 3500 cells/mm$^3$ with normal differential

Total lymphocyte count 800 cells/mm$^3$

Absolute CD4 count 400 cells/mm$^3$

Platelets (150,000–550,000)

Normal ALT (~1.5× institutional upper normal limit) and creatinine (1.6 mg/dl)

Normal urine dipstick with esterase and nitrite

Negative for hepatitis B surface antigen

Negative ELISA for HIV within eight weeks of immunization

Availability for follow-up for planned duration of the study (68 weeks)

A viable EBV transformed autologous B cell line

A.2 Exclusion Criteria

History of immunodeficiency, chronic illness, malignancy, autoimmune disease, or use of immunosuppressive medications Medical or psychiatric condition or occupational responsibilities which preclude subject compliance with the protocol Subjects with identifiable higher risk behavior for HIV infection as determined by screening questionnaire designed to identify risk factors for HIV infection; specific exclusions include:

History of injection drug use within the last 12 months prior to enrollment.

Higher risk sexual behavior defined as one or more of the following behaviors:

1. A newly acquired higher risk associated STD within the past six months
2. Possibly safe or unsafe sex with a known HIV+ individual in the past six months
3. Possibly safe sexual activity with twelve or more partners in the past six months
4. Unsafe sexual activity with four or more partners within the past six months.

Live attenuated vaccines within 60 days of study [NOTE: Medically indicated subunit or killed vaccines (e.g., influenza, pneumococcal) are not exclusionary, but should be given at least two weeks away from test article immunizations.]

Use of experimental agents within 30 days prior to study

Receipt of blood products or immunoglobulin in the past six months

Active syphilis [NOTE: If the serology is documented to be a false positive or due to a remote (>six months) treated infection, the volunteer is eligible]

Active tuberculosis [NOTE: Volunteers with a positive PPD and a normal chest X-ray showing no evidence of TB and not requiring INH therapy are eligible.]

History of anaphylaxis or other serious adverse reactions to vaccines

Prior receipt of HIV vaccines or a placebo recipient in an HIV vaccine trial

Pregnant or lactating women

B. Safety and Immunogenicity Monitoring

Safety is evaluated by monitoring volunteers for adverse reactions during the course of the trial. Volunteers are followed for a total of 26 weeks post-final inoculation. The main toxicity associated with the subcutaneous injection in this study is that associated with subcutaneous injection of any immunogen, i.e., pain, redness and swelling at the injection site, as well as the possibility of fever, chills, aches and pains and perhaps fatigue.

Safety monitoring includes periodic review of data from the trial with particular emphasis on monitoring for adverse reactions including the following evaluations:

Hematologic: CBC, differential, platelets

Hepatic/renal: ALT, creatinine, urinalysis

Neurologic: headache, paralysis, anxiety, confusion, weakness, tremors.

Systemic symptoms: fever, gastrointestinal complaints, myalgia, malaise, fatigue, headache, anaphylaxis, immune complex disease, and other hypersensitivity reactions Local toxicity at the site of injection: e.g., pain, tenderness, erythema, regional lymphadenopathy, limitation of limb movement The immunogenicity monitoring includes the following immunological assays, all utilizing HIV Subtype C based reagents:

Humoral Responses

HIV Subtype C Gag-specific ELISA

Anti-VEE ELISA

Cellular Immune Responses

Standard cell-killing assay (i.e., chromium release) to measure CD8+Gag-specific CTL activity ELISPOT assay to measure IFN-?

Mucosal Immune Responses

Standardized assay for assessment of Gag-specific IgA

Throughout this application, various publications are referenced. The disclosures of these publications in their entireties are hereby incorporated by reference into this application in order to more fully describe the state of the art to which this invention pertains.

REFERENCES

Barany F. 1985. Single-stranded hexameric linkers: a system for in-phase insertion mutagenesis and protein engineering. *Gene* 37(1–3):111–23.

Betts, M. R., J. Krowka, C. Santamaria, K. Balsamo, F. Gao, G. Mulundu, C. Luo, N. N'Gandu, H. Sheppard, B. H. Hahn, S. Allen and J. A. Frelinger. 1997. Cross-clade human immunodeficiency virus (HIV)-specific cytotoxic T-lymphocyte responses in HIV-infected Zambians. *J. Virol.* 71:8908–8911.

Caley, I. J., M. R. Betts, D. M. Irlbeck, N. L. Davis, R. Swanstrom, J. A. Frelinger and R. E. Johnston. 1997. Humoral, mucosal and cellular immunity in response to an HIV-1 vaccine candidate. *J. Virol.* 71:3031–3038.

Davis et al. 1980. In: *Microbiology*, 3d ed., p. 132.

Davis, N. L., L. V. Willis, J. F. Smith and R. E. Johnston. 1989. In vitro synthesis of infectious Venezuelan equine encephalitis virus RNA from a cDNA clone: Analysis of a viable deletion mutant. *Virology* 171:189–204.

Davis, N. L., L. V. Willis, J. F. Smith, G. Greenwald and R. E. Johnston. 1990. In vitro synthesis of infectious VEE virus RNA from a cDNA clone: Analysis of a viable deletion mutant and mutations affecting virulence. In: *Vaccines 90*, Cold Spring Harbor Press, Cold Spring Harbor, N.Y. pp. 109–113.

Davis, N. L., N. Powell, G. F. Greenwald, L. V. Willis, B. J. Johnson, J. F. Smith and R. E. Johnston. 1991. Attenuating mutations in the E2 glycoprotein gene of Venezuelan equine encephalitis virus: Construction of single and multiple mutants in a full-length cDNA clone. *Virology* 183:20–31.

Davis, N. L., K. W. Brown, G. F. Greenwald, A. J. Zajac, V. L. Zacny, J. F. Smith and R. E. Johnston. 1995. Attenuated mutants of Venezuelan equine encephalitis virus containing lethal mutations in the PE2 cleavage signal combined with a second-site suppressor mutation in E1. *Virology* 212:102–110.

Davis, N. L., K. W. Brown and R. E. Johnston. 1996a. A viral vaccine vector that expresses foreign genes in lymph nodes and protects against mucosal challenge. *J. Virol.* 70:3781–3787.

Davis, N. L., P. Pushko, K. W. Brown, P. C. Charles, I. J. Caley, M. Parker, G. Ludwig, J. F. Smith and R. E. Johnston. 1996b. Immunization against influenza with attenuated Venezuelan equine encephalitis virus vectors. In: *Options for the Control of Influenza III*, L. E. Brown and A. W. Hampson, eds. Elsevier, Amsterdam. pp.803–809.

Davis, N. L., I. J. Caley, K. W. Brown, M. R. Betts, D. L. Irlbeck, K. M. McGrath, M. J. Connell, D. C. Montefiori, J. A. Frelinger, R. Swanstrom, P. R. Johnson and R. E. Johnston. 2000. Vaccination of macaques against pathogenic simian immunodeficiency virus with Venezuelan equine encephalitis virus replicon particles. *J. Virol.* 74:371–378

Grieder, F. B., N. L. Davis, J. F. Aronson, P. C. Charles, D. C. Sellon, K. Suzuki and R. E. Johnston. 1995. Specific restrictions in the progression of Venezuelan equine encephalitis virus induced disease resulting from single amino acid changes in the glycoproteins. *Virology* 206:994–1006.

Hevey, M., D. Negley, P. Pushko, J. Smith and A. Schmaljohn. 1998. Marburg virus vaccines based upon alphavirus replicons protect guinea pigs and nonhuman primates. *Virology* 251:28–37.

Hirsch, V., T. R. Fuerst, G. Sutter, M. W. Carroll, L. C. Yang, S. Goldstein et al. 1996. Patterns of viral replication correlate with outcome in SIV-infected macaques: effect of prior immunization with a trivalent SIV vaccine in modified vaccinia virus Ankara. *J. Virol.* 70:3741–3752.

Johnston, Robert E. and Jonathan F. Smith. 1988. Selection for accelerated penetration in cell culture co-selects for attenuated mutants of Venezuelan equine encephalitis virus. *Virology* 162:437–443.

Johnston, R. E. and C. J. Peters. 1996. Alphaviruses. In: *Virology*, Third Edition, B. N. Fields, D. M. Knipe and P. M. Howley, eds., Raven Press, New York. pp. 843–898.

Kinney, R. M., B. J. B. Johnson, J. B. Welch, K. R. Tsuchiya and D. W. Trent. 1989. The full-length nucleotide sequences of the virulent Trinidad donkey strain of Venezuelan equine encephalitis virus and its attenuated vaccine derivative, strain TC-83. *Virology* 170:19–30.

Kinney, R. M., G-J. Chang, K. R. Tsuchiya, J. M. Sneider, J. T. Roehrig, T. M. Woodward and D. W. Trent. 1993. Attenuation of Venezuelan equine encephalitis virus strain TC-83 is encoded by the 5'-noncoding region and the E2 envelope glycoprotein. *J. Virol.* 67:1269–1277.

Kunkel. 1985. *Proc. Natl. Acad. Sci.* USA 82:488.

Paredes, A. M., D. T. Brown, R. Rothnagel, W. Chiu, R. J. Schoepp, R. E. Johnston and B. V. Prasad. 1993. Three-dimensional structure of a membrane-containing virus. *Proc. Natl. Acad. Sci.*, USA 90:9095–9099.

Pushko, P., M. Parker, G. V. Ludwig, N. L. Davis, R. E. Johnston and J. F. Smith. 1997. Replicon-helper systems from attenuated Venezuelan equine encephalitis virus: expression of heterologous genes in vitro and immunization against heterologous pathogens in vivo. *Virology* 239:389–401.

Rosenberg, A. H., et al 1987. Vectors for selective expression of cloned DNAs by T7 RNA polymerase. *Gene.* 56(1): p. 125–35.

Schlesinger, S. and M. J. Schlesinger. 1990. Replication of *Togaviridae and Flaviviridae*. In: *Virology*, Fields, B. N. and Knipe, D. M. (eds.) Raven Press. pp. 697–711.

Strauss et al. 1990. *Seminars in Virology* 1:347.

Strauss, J. H. and E. G. Strauss. 1994. The alphaviruses: Gene expression, replication, and evolution. *Micro. Rev.* 58:491–562.

Studier, F. W., et al. 1990. Use of T7 RNA polymerase to direct expression of cloned genes. 1990. *Methods Enzymol.* 185:60–89.

What is claimed is:

1. A composition comprising two or more isolated nucleic acids selected from the group consisting of an isolated nucleic acid encoding an env gene product or a fragment containing an epitope thereof of a human immunodeficiency virus, an isolated nucleic acid encoding a gag gene product or a fragment containing an epitope thereof of a human immunodeficiency virus, wherein the gag gene product or said fragment thereof is modified to inhibit formation of virus-like particles containing the gag gene product or said fragment thereof and their release from a cell, and an isolated nucleic acid encoding a pol gene product or a fragment containing an epitope thereof of a human immunodeficiency virus, wherein the pol gene product or said fragment thereof is modified to inhibit reverse transcriptase activity.

2. A composition comprising a population of alphavirus replicon particles comprising two or more isolated nucleic acids selected from the group consisting of 1) an isolated nucleic acid encoding an env gene product, or a fragment containing an epitope thereof, of a human immunodeficiency virus, 2) an isolated nucleic acid encoding a gag gene product, or a fragment containing an epitope thereof, of a human immunodeficiency virus, wherein the gag gene product or said fragment thereof is modified to inhibit formation of virus-like particles containing the gag gene product or said fragment thereof and their release from a cell, and 3) an isolated nucleic acid encoding a pol gene product, or a fragment containing an epitope thereof, of a human immunodeficiency virus, wherein the pal gene product or said fragment thereof is modified to inhibit reverse transcriptase activity.

3. A composition comprising a population of alphavirus replicon particles comprising two or more isolated nucleic acids selected from the group consisting of 1) an isolated nucleic acid encoding an env gene product or a fragment containing an epitope thereof, of a human immunodeficiency virus, 2) an isolated nucleic acid encoding a gag gene product, or a fragment containing an epitope thereof, of a human immunodeficiency virus, wherein the gag gene product or said fragment thereof is modified to inhibit formation of virus-like particles containing the gag gene product or said fragment thereof and their release from a cell, and 3) an isolated nucleic acid encoding a pol gene product, or a fragment containing an epitope thereof, of a human immunodeficiency virus, wherein the pol gene product or said fragment thereof is modified to inhibit reverse transcriptase activity, and wherein the alphavirus replicon particles comprise a replicon RNA or at least one structural protein which comprises one or more attenuating mutations.

4. A method of inducing an immune response to human immunodeficiency virus in a subject, comprising administering to the subject an immunogenic amount of the composition of claim 1 in a pharmaceutically acceptable carrier.

5. A method of inducing an immune response to human immnunodeficiency virus in a subject, comprising administering to the subject an immunogenic amount of the composition of claim 2 in a pharmaceutically acceptable carrier.

6. A method of inducing an immune response to human immunodeficiency virus in a subject, comprising administering to the subject an immunogenic amount of the composition of claim 3 in a pharmaceutically acceptable carrier.

7. A composition comprising two or more isolated nucleic acids selected from the group consisting of an isolated nucleic acid encoding an env gene product a fragment containing an epitope thereof of a human immunodeficiency virus, an isolated nucleic acid encoding a gag gene product a fragment containing an epitope thereof of a human immunodeficiency virus, wherein the gag gene product or said fragment thereof is modified to inhibit formation of virus-like particles containing the gag gene product or said fragment thereof and their release from a cell, and an isolated nucleic acid encoding a pol gene product or a fragment containing an epitope thereof of a human immunodeficiency virus, wherein the pol gene product or said fragment thereof comprises a modification resulting in deletion or inactivation of protease, integrase, RNase H and reverse transcriptase functions in the pol gene product or said fragment thereof.

8. A composition comprising a population of alphavirus replicon particles comprising two or more isolated nucleic acids selected from the group consisting of 1) an isolated nucleic acid encoding an env gene product, or a fragment containing an epitope thereof, of a human immunodeficiency virus, 2) an isolated nucleic acid encoding a gag gene product, or a fragment containing an epitope thereof, of a human immunodeficiency virus, wherein the gag gene product or said fragment thereof is modified to inhibit formation of virus-like particles containing the gag gene product or the said fragment thereof and their release from a cell, and 3) an isolated nucleic acid encoding a pol gene product, or a fragment containing an epitope thereof, of a human immunodeficiency virus, wherein the pol gene product or said fragment thereof comprises a modification resulting in deletion or inactivation of integrase, RNase H and reverse transcriptase functions in the pol gene product or said fragment thereof.

9. A composition comprising a population of alphavirus replicon particles comprising two or more isolated nucleic acids selected from the group consisting of 1) an isolated nucleic acid encoding an env gene product, or a fragment containing an epitope thereof, of a human immunodeficiency virus, 2) an isolated nucleic acid encoding a gag gene product, or a fragment containing an epitope thereof, of a human immunodeficiency virus, wherein the gag gene product or said fragment thereof is modified to inhibit formation of virus-like particles containing the gag gene product or said fragment thereof and their release from a cell, and 3) an isolated nucleic acid encoding a pol gene product, or a fragment containing an epitope thereof, of a human immunodeficiency virus, wherein the pol gene product or said fragment thereof comprises a modification resulting in deletion or inactivation of protease, integrase, RNase H and reverse transcriptase functions in the pol gene product or said fragment thereof, and wherein the alphavirus replicon particles comprise a replicon RNA or at least one structural protein which comprises one or more attenuating mutations.

10. A method of inducing an immune response to human immnunodeficiency virus in a subject, comprising administering to the subject an immunogenic amount of the composition of claim 7 in a pharmaceutically acceptable carrier.

11. A method of inducing an immune response to human immunodeficiency virus in a subject, comprising administering to the subject an immunogenic amount of the composition of claim 8 in a pharmaceutically acceptable carrier.

12. A method of inducing an immune response to human immunodeficiency virus in a subject, comprising administering to the subject an immunogenic amount of the composition of claim 9 in a pharmaceutically acceptable carrier.

13. An isolated nucleic acid encoding a pol gene product or a fragment containing an epitope thereof of a human immunodeficiency virus, wherein the pol gene product or said fragment thereof comprises a modification resulting in deletion or inactivation of integrase, RNase H and reverse transcriptase functions in the pol gene product or said fragment thereof.

14. A composition comprising the nucleic acid of claim 13.

15. A vector comprising the nucleic acid of claim 13.

16. A cell comprising the vector of claim 15.

17. An alphavirus replicon particle comprising the nucleic acid of claim 13.

18. A method of making the alphavirus replicon particle of claim 17, comprising
a) providing a helper cell for producing an infectious, defective alphavirus particle, comprising in an alphavirus-permissive cell:
   (i) an alphavirus replicon RNA, wherein the replicon RNA comprises an alphavirus packaging signal and a nucleic acid encoding a pol gene product, or a fragment containing an epitope thereof, of a human immnunodeficiency virus, wherein the pol gene product or said fragment thereof comprises a modification resulting in deletion or inactivation of protease, integrase, RNase H and reverse transcriptase functions in the pol gene product or said fragment thereof, and wherein the replicon RNA lacks sequences encoding alphavirus structural proteins;
   (ii) a first helper RNA separate from said replicon RNA, said first helper RNA encoding at least one alphavirus structural protein and furthermore not encoding at least one other alphavirus structural protein; and
   (iii) one or more additional helper RNA(s) separate from said replicon RNA and separate from said first helper RNA, said additional helper RNA(s) encoding at least one other alphavirus structural protein not encoded by said first helper RNA;
and with at least one of said helper RNAs lacking an alphavirus packaging signal;
wherein the combined expression of the alphavirus replicon RNA and the helper RNAs produces an assembled alphavirus replicon particle which is able to infect a cell, and is unable to complete viral propagation, and further wherein the population contains no detectable replication-competent alphavirus particles as determined by passage on permissive cells in culture;

(b) producing the alphavirus replicon particles in the helper cell; and (c) collecting the alphavirus replicon particles from the helper cell.

19. The method of claim 18, wherein at least one of said replicon RNA, said first helper RNA, and said one or more additional helper RNA(s) comprises one or more attenuating mutations.

20. An alphavirus replicon particle produced according to the method of claim 18.

21. An alphavirus replicon particle produced according to the method of claim 19.

22. A method of inducing an immune response in a subject, comprising administering to the subject an immunogenic amount of the composition of claim 14 in a pharmaceutically acceptable carrier.

23. A method of inducing an immune response in a subject, comprising administering to the subject an immunogenic amount of the alphavirus replicon particle of claim 17 in a pharmaceutically acceptable carrier.

24. A method of inducing an immune response in a subject, comprising administering to the subject an immunogenic amount of a composition comprising the alphavirus replicon particles of claim 20 in a pharmaceutically acceptable carrier.

25. A method of inducing an immune response in a subject, comprising administering to the subject an immunogenic amount of a composition comprising the alphavirus replicon particles of claim 21 in a pharmaceutically acceptable carrier.

* * * * *

UNITED STATES PATENT AND TRADEMARK OFFICE
CERTIFICATE OF CORRECTION

PATENT NO. : 6,783,939 B2
APPLICATION NO. : 09/991258
DATED : August 31, 2004
INVENTOR(S) : Olmsted et al.

It is certified that error appears in the above-identified patent and that said Letters Patent is hereby corrected as shown below:

In the Claims:

Column 167, claim 1 should read -- 1. A composition comprising two or more isolated nucleic acids selected from the group consisting of an isolated nucleic acid encoding an *env* gene product or a fragment containing an epitope thereof of a human immunodeficiency virus, an isolated nucleic acid encoding a *gag* gene product or a fragment containing an epitope thereof of a human immunodeficiency virus, wherein the *gag* gene product or said fragment thereof is modified to inhibit formation of virus-like particles containing the *gag* gene product or said fragment thereof and their release from a cell, and an isolated nucleic acid encoding a *pol* gene product or a fragment containing an epitope thereof of a human immunodeficiency virus, wherein the *pol* gene product or said fragment thereof is modified to inhibit reverse transcriptase activity. --

Column 167, claim 2 should read -- 2. A composition comprising a population of alphavirus replicon particles comprising two or more isolated nucleic acids selected from the group consisting of 1) an isolated nucleic acid encoding an *env* gene product, or a fragment containing an epitope thereof, of a human immunodeficiency virus, 2) an isolated nucleic acid encoding a *gag* gene product, or a fragment containing an epitope thereof, of a human immunodeficiency virus, wherein the *gag* gene product or said fragment thereof is modified to inhibit formation of virus-like particles containing the *gag* gene product or said fragment thereof and their release from a cell, and 3) an isolated nucleic acid encoding a *pol* gene product, or a fragment containing an epitope thereof, of a human immunodeficiency virus, wherein the *pol* gene product or said fragment thereof is modified to inhibit reverse transcriptase activity. --

Columns 167-168, claim 3 should read -- 3. A composition comprising a population of alphavirus replicon particles comprising two or more isolated nucleic acids selected from the group consisting of 1) an isolated nucleic acid encoding an *env* gene product or a fragment containing an epitope thereof, of a human immunodeficiency virus, 2) an isolated nucleic acid encoding a *gag* gene product, or a fragment containing an epitope thereof, of a human immunodeficiency virus, wherein the *gag* gene product or said fragment thereof is modified to inihibit formation of virus-like particles containing the *gag* gene product or said fragment thereof and their release from a cell, and 3) an isolated nucleic acid encoding a *pol* gene product, or a fragment containing an epitope thereof, of a human immunodeficiency virus, wherein the *pol* gene product or said fragment thereof is modified to inhibit reverse transcriptase activity, and wherein the alphavirus replicon particles comprise a replicon RNA or at least one structural protein which comprises one or more attenuating mutations. --

Column 168, claim 7 should read -- 7. A composition comprising two or more isolated

UNITED STATES PATENT AND TRADEMARK OFFICE
CERTIFICATE OF CORRECTION

PATENT NO. : 6,783,939 B2
APPLICATION NO. : 09/991258
DATED : August 31, 2004
INVENTOR(S) : Olmsted et al.

It is certified that error appears in the above-identified patent and that said Letters Patent is hereby corrected as shown below:

Column 168, (cont'd)
nucleic acids selected from the group consisting of an isolated nucleic acid encoding an *env* gene product a fragment containing an epitope thereof of a human immunodeficiency virus, an isolated nucleaic acid encoding a *gag* gene product a fragment containing an epitope thereof of a human immunodeficiency virus, wherein the *gag* gene product or said fragment thereof is modified to inhibit formation of virus-like particles containing the *gag* gene product or said fragment thereof and their release from a cell, and an isolated nucleic acid encoding a *pol* gene product or a fragment containing an epitope thereof of a human immunodeficiency virus, wherein the pol gene product or said fragment thereof comprises a modification resulting in deletion of inactivation of protease, integrase, RNase H and reverse transcriptase functions in the *pol* gene product or said fragment thereof. --

Column 169, claim 8 should read -- 8. A composition comprising a population of alphavirus replicon particles comprising two or more isolated nucleic acids selected from the group consisting of 1) an isolated nucleic acid encoding an *env* gene product, or a fragment containing an epitope thereof, of a human immunodeficiency virus, 2) an isolated nucleic acid encoding a *gag* gene product, or a fragment containing an epitope thereof, of a human immunodeficiency virus, wherein the *gag* gene product or said fragment thereof is modified to inhibit formation of virus-like particles containing the *gag* gene product or the said fragment thereof and their release from a cell, and 3) an isolated nucleic acid encoding a *pol* gene product, or a fragment containing an epitope thereof, of a human immunodeficiency virus, wherein the *pol* gene product or said fragment thereof comprises a modification resulting in deletion or inactivation of integrase, RNase H and reverse transcriptase function in the *pol* gene product or said fragment thereof. --

Column 169, claim 9 should read -- 9. A composition comprising a population of alphavirus replicon particles comprising two or more isolated nucleic acids selected from the group consisting of 1) an isolated nucleic acid encoding an *env* gene product, or a fragment containing an epitope thereof, of a human immunodeficiency virus, 2) an isolated nucleic acid encoding a *gag* gene product, or a fragment containing an epitope thereof, of a human immunodeficiency virus, wherein the *gag* gene product or said fragment thereof is modified to inhibit formation of virus-like particles containing the *gag* gene product or said fragment thereof and their release from a cell, and 3) an isolated nucleic acid encoding a *pol* gene product, or a fragment containing an epitope thereof, of a human immunodeficiency virus, wherein the *pol* gene product or said fragment thereof comprises a modification resulting in deletion or inactivation of protease, integrase, RNase H and reverse transcriptase functions in the *pol* gene product or said fragment thereof, and wherein the alphavirus replicon particles comprise a replicon RNA or at least one structural protein which comprises one or more attenuating

UNITED STATES PATENT AND TRADEMARK OFFICE
CERTIFICATE OF CORRECTION

PATENT NO. : 6,783,939 B2
APPLICATION NO. : 09/991258
DATED : August 31, 2004
INVENTOR(S) : Olmsted et al.

It is certified that error appears in the above-identified patent and that said Letters Patent is hereby corrected as shown below:

Column 169, claim 9 (cont'd)
mutations. --

Column 169, claim 13 should read -- 13. An isolated nucleic acid encoding a *pol* gene product or a fragment containing an epitope thereof of a human immunodeficiency virus, wherien the *pol* gene product or said fragment thereof comprises a modification resulting in deletion or inactivation of integrase, RNase H and reverse transcriptase functions in the *pol* gene product or said fragment thereof. --

Columns 169-170, claim 18 should read -- 18. A method of making the alphavirus replicon particle of claim 17, comprising
a) providing a helper cell for producing an infectious, defective alphavirus particle, comprising in an alphavirus-permissive cell:
(i) an alphavirus replicon RNA, wherein the replicon RNA comprises an alphavirus packaging signal and a nucleic acid encoding a *pol* gene product, or a fragment containing an epitope thereof, of a human immunodeficiency virus, wherein the *pol* gene product or said fragment thereof comprises a modification resulting in deletion or inactivation of protease, integrase, RNase H and reverse transcriptase functions in the *pol* gene product or said fragment thereof, and wherein the replicon RNA lacks sequences encoding alphavirus structural proteins;
(ii) a first helper RNA separate from said replicon RNA, said first helper RNA encoding at least one alphavirus structural protein and furthermore not encoding at least one other alphavirus structural protein;
and
(iii) one or more additional helper RNA(s) separate from said replicon RNA and

UNITED STATES PATENT AND TRADEMARK OFFICE
CERTIFICATE OF CORRECTION

PATENT NO. : 6,783,939 B2
APPLICATION NO. : 09/991258
DATED : August 31, 2004
INVENTOR(S) : Olmsted et al.

It is certified that error appears in the above-identified patent and that said Letters Patent is hereby corrected as shown below:

Columns 169-170, (cont'd)
other alphavirus structural protein not encoded by said first helper RNA;
and with at least one of said helper RNAs lacking an alphavirus packaging signal;
wherein the combined expression of the alphavirus replicon RNA and the helper RNAs produces an assembled alphavirus replicon particle which is able to infect a cell, and is unable to complete viral propagation, and further wherein the population contains no detectable replication-competent alphavirus particles as determined by passage on permissive cells in culture;
(b) producing the alphavirus replicon particles in the helper cell; and
(c) collecting the alphavirus replicon particles from the helper cell. --

Signed and Sealed this

Twenty-sixth Day of September, 2006

JON W. DUDAS
*Director of the United States Patent and Trademark Office*

UNITED STATES PATENT AND TRADEMARK OFFICE
CERTIFICATE OF CORRECTION

PATENT NO.         : 6,783,939 B2
APPLICATION NO. : 09/991258
DATED              : August 31, 2004
INVENTOR(S)      : Olmsted et al.

It is certified that error appears in the above-identified patent and that said Letters Patent is hereby corrected as shown below:

In the Claims:

Column 167, claim 1 should read -- 1. A composition comprising two or more isolated nucleic acids selected from the group consisting of an isolated nucleic acid encoding an *env* gene product or a fragment containing an epitope thereof of a human immunodeficiency virus, an isolated nucleic acid encoding a *gag* gene product or a fragment containing an epitope thereof of a human immunodeficiency virus, wherein the *gag* gene product or said fragment thereof is modified to inhibit formation of virus-like particles containing the *gag* gene product or said fragment thereof and their release from a cell, and an isolated nucleic acid encoding a *pol* gene product or a fragment containing an epitope thereof of a human immunodeficiency virus, wherein the *pol* gene product or said fragment thereof is modified to inhibit reverse transcriptase activity. --

Column 167, claim 2 should read -- 2. A composition comprising a population of alphavirus replicon particles comprising two or more isolated nucleic acids selected from the group consisting of 1) an isolated nucleic acid encoding an *env* gene product, or a fragment containing an epitope thereof, of a human immunodeficiency virus, 2) an isolated nucleic acid encoding a *gag* gene product, or a fragment containing an epitope thereof, of a human immunodeficiency virus, wherein the *gag* gene product or said fragment thereof is modified to inhibit formation of virus-like particles containing the *gag* gene product or said fragment thereof and their release from a cell, and 3) an isolated nucleic acid encoding a *pol* gene product, or a fragment containing an epitope thereof, of a human immunodeficiency virus, wherein the *pol* gene product or said fragment thereof is modified to inhibit reverse transcriptase activity. --

Columns 167-168, claim 3 should read -- 3. A composition comprising a population of alphavirus replicon particles comprising two or more isolated nucleic acids selected from the group consisting of 1) an isolated nucleic acid encoding an *env* gene product or a fragment containing an epitope thereof, of a human immunodeficiency virus, 2) an isolated nucleic acid encoding a *gag* gene product, or a fragment containing an epitope thereof, of a human immunodeficiency virus, wherein the *gag* gene product or said fragment thereof is modified to inihibit formation of virus-like particles containing the *gag* gene product or said fragment thereof and their release from a cell, and 3) an isolated nucleic acid encoding a *pol* gene product, or a fragment containing an epitope thereof, of a human immunodeficiency virus, wherein the *pol* gene product or said fragment thereof is modified to inhibit reverse transcriptase activity, and wherein the alphavirus replicon particles comprise a replicon RNA or at least one structural protein which comprises one or more attenuating mutations. --

Column 168, claim 7 should read -- 7. A composition comprising two or more isolated

UNITED STATES PATENT AND TRADEMARK OFFICE
CERTIFICATE OF CORRECTION

| | |
|---|---|
| PATENT NO. | : 6,783,939 B2 |
| APPLICATION NO. | : 09/991258 |
| DATED | : August 31, 2004 |
| INVENTOR(S) | : Olmsted et al. |

It is certified that error appears in the above-identified patent and that said Letters Patent is hereby corrected as shown below:

Column 168, (cont'd)
nucleic acids selected from the group consisting of an isolated nucleic acid encoding an *env* gene product a fragment containing an epitope thereof of a human immunodeficiency virus, an isolated nucleaic acid encoding a *gag* gene product a fragment containing an epitope thereof of a human immunodeficiency virus, wherein the *gag* gene product or said fragment thereof is modified to inhibit formation of virus-like particles containing the *gag* gene product or said fragment thereof and their release from a cell, and an isolated nucleic acid encoding a *pol* gene product or a fragment containing an epitope thereof of a human immunodeficiency virus, wherein the pol gene product or said fragment thereof comprises a modification resulting in deletion of inactivation of protease, integrase, RNase H and reverse transcriptase functions in the *pol* gene product or said fragment thereof. --

Column 169, claim 8 should read -- 8. A composition comprising a population of alphavirus replicon particles comprising two or more isolated nucleic acids selected from the group consisting of 1) an isolated nucleic acid encoding an *env* gene product, or a fragment containing an epitope thereof, of a human immunodeficiency virus, 2) an isolated nucleic acid encoding a *gag* gene product, or a fragment containing an epitope thereof, of a human immunodeficiency virus, wherein the *gag* gene product or said fragment thereof is modified to inhibit formation of virus-like particles containing the *gag* gene product or the said fragment thereof and their release from a cell, and 3) an isolated nucleic acid encoding a *pol* gene product, or a fragment containing an epitope thereof, of a human immunodeficiency virus, wherein the *pol* gene product or said fragment thereof comprises a modification resulting in deletion or inactivation of integrase, RNase H and reverse transcriptase function in the *pol* gene product or said fragment thereof. --

Column 169, claim 9 should read -- 9. A composition comprising a population of alphavirus replicon particles comprising two or more isolated nucleic acids selected from the group consisting of 1) an isolated nucleic acid encoding an *env* gene product, or a fragment containing an epitope thereof, of a human immunodeficiency virus, 2) an isolated nucleic acid encoding a *gag* gene product, or a fragment containing an epitope thereof, of a human immunodeficiency virus, wherein the *gag* gene product or said fragment thereof is modified to inhibit formation of virus-like particles containing the *gag* gene product or said fragment thereof and their release from a cell, and 3) an isolated nucleic acid encoding a *pol* gene product, or a fragment containing an epitope thereof, of a human immunodeficiency virus, wherein the *pol* gene product or said fragment thereof comprises a modification resulting in deletion or inactivation of protease, integrase, RNase H and reverse transcriptase functions in the *pol* gene product or said fragment thereof, and wherein the alphavirus replicon particles comprise a replicon RNA or at least one structural protein which comprises one or more attenuating

UNITED STATES PATENT AND TRADEMARK OFFICE
CERTIFICATE OF CORRECTION

PATENT NO. : 6,783,939 B2
APPLICATION NO. : 09/991258
DATED : August 31, 2004
INVENTOR(S) : Olmsted et al.

It is certified that error appears in the above-identified patent and that said Letters Patent is hereby corrected as shown below:

Column 169, claim 9 (cont'd)
mutations. --

Column 169, claim 13 should read -- 13. An isolated nucleic acid encoding a *pol* gene product or a fragment containing an epitope thereof of a human immunodeficiency virus, wherien the *pol* gene product or said fragment thereof comprises a modification resulting in deletion or inactivation of integrase, RNase H and reverse transcriptase functions in the *pol* gene product or said fragment thereof. --

Columns 169-170, claim 18 should read -- 18. A method of making the alphavirus replicon particle of claim 17, comprising
a) providing a helper cell for producing an infectious, defective alphavirus particle, comprising in an alphavirus-permissive cell:
(i)   an alphavirus replicon RNA, wherein the replicon RNA comprises an alphavirus packaging signal and a nucleic acid encoding a *pol* gene product, or a fragment containing an epitope thereof, of a human immunodeficiency virus, wherein the *pol* gene product or said fragment thereof comprises a modification resulting in deletion or inactivation of protease, integrase, RNase H and reverse transcriptase functions in the *pol* gene product or said fragment thereof, and wherein the replicon RNA lacks sequences encoding alphavirus structural proteins;
(ii)   a first helper RNA separate from said replicon RNA, said first helper RNA encoding at least one alphavirus structural protein and furthermore not encoding at least one other alphavirus structural protein;
and
(iii)   one or more additional helper RNA(s) separate from said replicon RNA and separate from said first helper RNA, said additional helper RNA(s) encoding at least one

UNITED STATES PATENT AND TRADEMARK OFFICE
CERTIFICATE OF CORRECTION

PATENT NO. : 6,783,939 B2
APPLICATION NO. : 09/991258
DATED : August 31, 2004
INVENTOR(S) : Olmsted et al.

It is certified that error appears in the above-identified patent and that said Letters Patent is hereby corrected as shown below:

Columns 169-170, claim 18 (cont'd)
other alphavirus structural protein not encoded by said first helper RNA;
and with at least one of said helper RNAs lacking an alphavirus packaging signal; wherein the combined expression of the alphavirus replicon RNA and the helper RNAs produces an assembled alphavirus replicon particle which is able to infect a cell, and is unable to complete viral propagation, and further wherein the population contains no detectable replication-competent alphavirus particles as determined by passage on permissive cells in culture;
(b) producing the alphavirus replicon particles in the helper cell; and
(c) collecting the alphavirus replicon particles from the helper cell. --

This certificate supersedes Certificate of Correction issued September 26, 2006.

Signed and Sealed this

Thirtieth Day of January, 2007

JON W. DUDAS
*Director of the United States Patent and Trademark Office*

SEQUENCE LISTING

<160> NUMBER OF SEQ ID NOS: 19

<210> SEQ ID NO 1
<211> LENGTH: 12523
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 1

```
atgggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
```

-continued

```
ccaataaggg agttagagtc gcctactgga taggctttga caccacccct tttatgttta      600
agaacttggc tggagcatat ccatcatact ctaccaactg ggccgacgaa accgtgttaa      660
cggctcgtaa cataggccta tgcagctctg acgttatgga gcggtcacgt agagggatgt      720
ccattcttag aaagaagtat tgaaaccat ccaacaatgt tctattctct gttggctcga       780
ccatctacca cgagaagagg gacttactga ggagctggca cctgccgtct gtatttcact      840
tacgtggcaa gcaaaattac acatgtcggt gtgagactat agttagttgc gacgggtacg      900
tcgttaaaag aatagctatc agtccaggcc tgtatgggaa gccttcaggc tatgctgcta      960
cgatgcaccg cgagggattc ttgtgctgca aagtgacaga cacattaaac ggggagaggg     1020
tctcttttcc cgtgtgcacg tatgtgccag ctacattgtg tgaccaaatg actggcatac     1080
tggcaacaga tgtcagtgcg gacgacgcgc aaaaactgct ggttgggctc aaccagcgta     1140
tagtcgtcaa cggtcgcacc cagagaaaca ccaataccat gaaaaattac cttttgcccg     1200
tagtggccca ggcatttgct aggtgggcaa aggaatataa ggaagatcaa gaagatgaaa     1260
ggccactagg actacgagat agacagttag tcatggggtg ttgttgggct tttagaaggc     1320
acaagataac atctatttat aagcgcccgg atacccaaac catcatcaaa gtgaacagcg     1380
atttccactc attcgtgctg cccaggatag gcagtaacac attggagatc gggctgagaa     1440
caagaatcag gaaaatgtta gaggagcaca aggagccgtc acctctcatt accgccgagg     1500
acgtacaaga agctaagtgc gcagccgatg aggctaagga ggtgcgtgaa gccgaggagt     1560
tgcgcgcagc tctaccacct ttggcagctg atgttgagga gcccactctg gaagccgatg     1620
tcgacttgat gttacaagag gctggggccg gctcagtgga gacacctcgt ggcttgataa     1680
aggttaccag ctacgctggc gaggacaaga tcggctctta cgctgtgctt tctccgcagg     1740
ctgtactcaa gagtgaaaaa ttatcttgca tccaccctct cgctgaacaa gtcatagtga     1800
taacacactc tggccgaaaa gggcgttatg ccgtggaacc ataccatggt aaagtagtgg     1860
tgccagaggg acatgcaata cccgtccagg actttcaagc tctgagtgaa agtgccacca     1920
ttgtgtacaa cgaacgtgag ttcgtaaaca ggtacctgca ccatattgcc acacatggag     1980
gagcgctgaa cactgatgaa gaatattaca aaactgtcaa gcccagcgag cacgacggcg     2040
aatacctgta cgacatcgac aggaaacagt gcgtcaagaa agaactagtc actgggctag     2100
ggctcacagg cgagctggtg gatcctccct tccatgaatt cgcctacgag agtctgagaa     2160
cacgaccagc cgctccttac caagtaccaa ccataggggt gtatggcgtg ccaggatcag     2220
gcaagtctgg catcattaaa agcgcagtca ccaaaaaaga tctagtggtg agcgccaaga     2280
aagaaaactg tgcagaaatt ataagggacg tcaagaaaat gaaagggctg gacgtcaatg     2340
ccagaactgt ggactcagtg ctcttgaatg gatgcaaaca ccccgtagag accctgtata     2400
ttgacgaagc ttttgcttgt catgcaggta ctctcagagc gctcatagcc attataagac     2460
ctaaaaaggc agtgctctgc ggggatcccc aacagtgcgg ttttttttaac atgatgtgcc     2520
tgaaagtgca ttttaaccac gagatttgca cacaagtctt ccacaaaagc atctctcgcc     2580
gttgcactaa atctgtgact tcggtcgtct caaccttgtt ttacgacaaa aaaatgagaa     2640
cgacgaatcc gaaagagact aagattgtga ttgacactac cggcagtacc aaacctaagc     2700
aggacgatct cattctcact tgtttcagag ggtgggtgaa gcagttgcaa atagattaca     2760
aaggcaacga ataatgacg gcagctgcct ctcaagggct gacccgtaaa ggtgtgtatg      2820
ccgttcggta caaggtgaat gaaaatcctc tgtacgcacc cacctcagaa catgtgaacg     2880
tcctactgac ccgcacggag gaccgcatcg tgtggaaaac actagccggc gacccatgga     2940
```

```
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcgaga ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag acaacctgg cggaggggtg tgcggagcgc    4140
tgtataagaa gttcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaacttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tccttttccat    4920 tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacacct ggagggagct agcgtgacca    5340
```

```
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccacccgc    5520 caggcgtgaa tagggtgatc actagagagg agctcgaggc gcttacccg tcacgcactc    5580 ctagcaggtc ggtctcgaga accagcctgg tctccaaccc gccaggcgta ataggggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaagaagaa ttactacgca agaaattaca gttaaatccc acacctgcta    5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca agctgcgca gctttccaaa gaaacactcc tatttggaac    6240
ccacaatacg atcggcagtg ccttcagcga tccagaacac gctccagaac gtcctggcag   6300
ctgccacaaa agaaattgc aatgtcacgc aaatgagaga attgcccgta ttggattcgg    6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcccta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatggctgcg agagcgtcaa tattaagagg ggaaaaatta gataaatggg aaaagattag   7620
gttaaggcca gggggaaaga aacattatat gttaaaacac atagtatggg cgagcaggga   7680
gctggaaaga tttgcactta accctggcct tttagaaaca tcagaaggat gtaaacaaat   7740
```

```
aatgaaacag ctacaaccag ctctccagac aggaacagag gaacttaaat cattatacaa    7800
cacagtagca actctctatt gtgtacatga aaagatagaa gtacgagaca ccaaggaagc    7860
cttagataag atagaggaag aacaaaacaa atgtcagcaa aaaacgcagc aggcaaaagc    7920
ggctgacggg aaagtcagtc aaaattatcc tatagtgcag aatctccaag ggcaaatggt    7980
acatcaagcc atatcaccta gaaccttgaa tgcatgggta aaagtaatag aagaaaggc    8040 ttttagccca gaggtaatac ccatgtttac agcattatca gaaggagcca ccccacaaga    8100
tttaaacacc atgttaaata cagtgggggg acaccaagca gccatgcaaa tgttaaaaga    8160
tactattaat gaagaggctg cagaatggga tagattacat ccagtccatg cggggcctat    8220
tgcaccaggc cagatgagag aaccaagggg aagtgacata gcaggaacta ctagtaccct    8280
tcaggaacaa atagcatgga tgacaagtaa cccacctatt ccagtgggag acatctataa    8340
aagatggata attctggggt taaataaaat agtgagaatg tatagccctg tcagcatttt    8400
ggacataaga caagggccaa aggaacccct tcgagactat gtagatcggt tctttaaaac    8460
tttaagagct gaacaagcta cacaagaagt aaaaaattgg atgacagaca ccttgttagt    8520
ccaaaatgcg aacccagatt gtaagaccat tttgagagca ttaggaccag ggctacatt    8580 agaagaaatg atgacagcat gtcaagggt gggaggacct ggccacaaag caagagtatt    8640
ggctgaggca atgagtcaaa caaacagtgg aaacataatg atgcagagaa gcaattttaa    8700
aggccctaga agaattgtta atgttttaa ctgtggcaag gaagggcaca tagccagaaa    8760
ttgcagagcc cctaggaaaa aaggctgttg gaaatgtgga aaagaaggac accaaatgaa    8820
agactgcact gagaggcagg ctaattttt agggaaaatt tggccttccc acaaggggag    8880
gccagggaat ttccttcaga acagaccaga gccaacagcc ccaccagcag agagcttcag    8940
gttcgaagag acaaccccg ctccgaaaca ggagccgata gaaagggaac ccttaacttc    9000
cctcaaatca ctctttggca gcgacccctt gtctcaataa gagtttaatt aagtaacgat    9060
acagcagcaa ttggcaagct gcttacatag aactcgcggc gattggcatg ccgctttaaa    9120 attttatt tattttcttt ttcttttccg aatcggattt tgttttaat atttcaaaaa    9180 aaaaaaaaa aaaaaaaa aaaaaaaaa aaaaaaaa gggaagagcg cggccgcgcg    9240
ctgggctacg ttttgctggc gttcgcgacg cgaggctgga tggccttccc cattatgatt    9300
cttctcgctt ccggcggcat cgggatgccc gcgttgcagg ccatgctgtc caggcaggta    9360
gatgacgacc atcagggaca gcttcaagga tcgctcgcgg ctcttaccag cctaacttcg    9420
atcattggac cgctgatcgt cacggcgatt tatgccgcct cggcgagcac atggaacggg    9480
ttggcatgga ttgtaggcgc cgccctatac cttgtctgcc tccccgcgtt gcgtcgcggt    9540
gcatggagcc gggccacctc gacctgaatg gaagccggcg gcacctcgct aacggattca    9600
ccactccaag aattggagcc aatcaattct tgcggagaac tgtgaatgcg caaaccaacc    9660
cttggcagaa catatccatc gcgtccgcca tctccagcag ccgcacgcgg cgcatctcgg    9720
gcagcgttgg gtcctggcca cgggtgcgca tgatcgtgct cctgtcgttg aggacccggc    9780
taggctggcg gggttgcctt actggttagc agaatgaatc accgatacgc gagcgaacgt    9840
gaagcgactg ctgctgcaaa acgtctgcga cctgagcaac aacatgaatg gtcttcggtt    9900
tccgtgtttc gtaaagtctg gaaacgcgga agtcagcgcc ctgcaccatt atgttccgga    9960
tctgcatcgc aggatgctgc tggctaccct gtggaacacc tacatctgta ttaacgaagc    10020
gctggcattg accctgagtg atttttctct ggtcccgccg catccatacc gccagttgtt    10080
taccctcaca acgttccagt aaccgggcat gttcatcatc agtaacccgt atcgtgagca    10140
```

```
tcctctctcg tttcatcggt atcattaccc ccatgaacag aaatccccct tacacggagg    10200
catcagtgac caaacaggaa aaaccgccc  ttaacatggc ccgctttatc agaagccaga    10260
cattaacgct tctggagaaa ctcaacgagc tggacgcgga tgaacaggca gacatctgtg    10320
aatcgcttca cgaccacgct gatgagcttt accgcagctg cctcgcgcgt ttcggtgatg    10380
acggtgaaaa cctctgacac atgcagctcc cggagacggt cacagcttgt ctgtaagcgg    10440
atgccgggag cagacaagcc cgtcagggcg cgtcagcggt gttggcggg  tgtcggggcg    10500 cagccatgac ccagtcacgt agcgatagcg gagtgtatac tggcttaact atgcggcatc    10560
agagcagatt gtactgagag tgcaccattg cggtgtgaaa taccgcacag atgcgtaagg    10620
agaaaatacc gcatcaggcg ctcttccgct tcctcgctca ctgactcgct gcgctcggtc    10680
gttcggctgc ggcgagcggt atcagctcac tcaaaggcgg taatacggtt atccacagaa    10740
tcagggnata acgcaggaaa gaacatgtga gcaaaaggcc agcaaaaggc caggaaccgt    10800
aaaaaggccg cgttgctggc gttttccat  aggctccgcc cccctgacga gcatcacaaa    10860
aatcgacgct caagtcagag gtggcgaaac ccgacaggac tataaagata ccaggcgttt    10920
ccccctggaa gctccctcgt gcgctctcct gttccgaccc tgccgcttac cggatacctg    10980
tccgcctttc tcccttcggg aagcgtggcg ctttctcata gctcacgctg taggtatctc    11040
agttcggtgt aggtcgttcg ctccaagctg ggctgtgtgc acgaaccccc cgttcagccc    11100
gaccgctgcg ccttatccgg taactatcgt cttgagtcca acccggtaag acacgactta    11160
tcgccactgg cagcagccac tggtaacagg attagcagag cgaggtatgt aggcggtgct    11220
acagagttct tgaagtggtg gcctaactac ggctacacta aaggacagt  atttggtatc    11280 tgcgctctgc tgaagccagt taccttcgga aaaagagttg gtagctcttg atccggcaaa    11340
caaaccaccg ctggtagcgg tggttttttt gtttgcaagc agcagattac gcgcagaaaa    11400
aaaggatctc aagaagatcc tttgatcttt tctacgggt  ctgacgctca gtggaacgaa    11460
aactcacgtt aagggatttt ggtcatgaac aataaaactg tctgcttaca taaacagtaa    11520
tacaaggggt gttatgagcc atattcaacg ggaaacgtct tgctcgaggc cgcgattaaa    11580
ttccaacatg gatgctgatt tatatgggta taaatgggct cgcgataatg tcgggcaatc    11640
aggtgcgaca atctatcgat tgtatgggaa gcccgatgcg ccagagttgt ttctgaaaca    11700
tggcaaaggt agcgttgcca atgatgttac agatgagatg gtcagactaa actggctgac    11760
ggaatttatg cctcttccga ccatcaagca ttttatccgt actcctgatg atgcatggtt    11820
actcaccact gcgatccccg ggaaaacagc attccaggta ttagaagaat atcctgattc    11880
aggtgaaaat attgttgatg cgctggcagt gttcctgcgc cggttgcatt cgattcctgt    11940
ttgtaattgt ccttttaaca gcgatcgcgt atttcgtctc gctcaggcgc aatcacgaat    12000
gaataacggt ttggttgatg cgagtgattt tgatgacgag cgtaatggct ggcctgttga    12060
acaagtctgg aaagaaatgc ataagctttt gccattctca ccggattcag tcgtcactca    12120
tggtgatttc tcacttgata accttatttt tgacgagggg aaattaatag gttgtattga    12180
tgttggacga gtcggaatcg cagaccgata ccaggatctt gccatcctat ggaactgcct    12240
cggtgagttt tctccttcat tacagaaacg ctttttcaa  aaatatggta ttgataatcc    12300
tgatatgaat aaattgcagt ttcatttgat gctcgatgag ttttttctaag aattctcatg    12360 tttgacagct tatcatcgat aagctttaat gcggtagttt atcacagtta aattgctaac    12420
gcagtcaggc accgtgtatg aaatctaaca atgcgctcat cgtcatcctc ggcaccgtca    12480
ccctggatgc tgtctagagg atccctaata cgactcacta tag                      12523
```

```
<210> SEQ ID NO 2
<211> LENGTH: 7479
<212> TYPE: DNA
<213> ORGANISM: Artificial Sequence
<220> FEATURE:
<223> OTHER INFORMATION: Description of Artificial Sequence; Note =
      synthetic construct
<221> NAME/KEY: CDS
<222> LOCATION: (1)...(7479)

<400> SEQUENCE: 2 atg gag aaa gtt cac gtt gac atc gag gaa gac agc cca ttc ctc aga      48
Met Glu Lys Val His Val Asp Ile Glu Glu Asp Ser Pro Phe Leu Arg
 1               5                  10                  15 gct ttg cag cgg agc ttc ccg cag ttt gag gta gaa gcc aag cag gtc      96
Ala Leu Gln Arg Ser Phe Pro Gln Phe Glu Val Glu Ala Lys Gln Val
             20                  25                  30 act gat aat gac cat gct aat gcc aga gcg ttt tcg cat ctg gct tca     144
Thr Asp Asn Asp His Ala Asn Ala Arg Ala Phe Ser His Leu Ala Ser
         35                  40                  45 aaa ctg atc gaa acg gag gtg gac cca tcc gac acg atc ctt gac att     192
Lys Leu Ile Glu Thr Glu Val Asp Pro Ser Asp Thr Ile Leu Asp Ile
     50                  55                  60 gga agt gcg ccc gcc cgc aga atg tat tct aag cac aag tat cat tgt     240
Gly Ser Ala Pro Ala Arg Arg Met Tyr Ser Lys His Lys Tyr His Cys
 65                  70                  75                  80 atc tgt ccg atg aga tgt gcg gaa gat ccg gac aga ttg tat aag tat     288
Ile Cys Pro Met Arg Cys Ala Glu Asp Pro Asp Arg Leu Tyr Lys Tyr
                 85                  90                  95 gca act aag ctg aag aaa aac tgt aag gaa ata act gat aag gaa ttg     336
Ala Thr Lys Leu Lys Lys Asn Cys Lys Glu Ile Thr Asp Lys Glu Leu
            100                 105                 110 gac aag aaa atg aag gag ctc gcc gcc gtc atg agc gac cct gac ctg     384
Asp Lys Lys Met Lys Glu Leu Ala Ala Val Met Ser Asp Pro Asp Leu
        115                 120                 125 gaa act gag act atg tgc ctc cac gac gac gag tcg tgt cgc tac gaa     432
Glu Thr Glu Thr Met Cys Leu His Asp Asp Glu Ser Cys Arg Tyr Glu
    130                 135                 140 ggg caa gtc gct gtt tac cag gat gta tac gcg gtt gac gga ccg aca     480
Gly Gln Val Ala Val Tyr Gln Asp Val Tyr Ala Val Asp Gly Pro Thr
145                 150                 155                 160 agt ctc tat cac caa gcc aat aag gga gtt aga gtc gcc tac tgg ata     528
Ser Leu Tyr His Gln Ala Asn Lys Gly Val Arg Val Ala Tyr Trp Ile
                165                 170                 175 ggc ttt gac acc acc cct ttt atg ttt aag aac ttg gct gga gca tat     576
Gly Phe Asp Thr Thr Pro Phe Met Phe Lys Asn Leu Ala Gly Ala Tyr
            180                 185                 190 cca tca tac tct acc aac tgg gcc gac gaa acc gtg tta acg gct cgt     624
Pro Ser Tyr Ser Thr Asn Trp Ala Asp Glu Thr Val Leu Thr Ala Arg
        195                 200                 205 aac ata ggc cta tgc agc tct gac gtt atg gag cgg tca cgt aga ggg     672
Asn Ile Gly Leu Cys Ser Ser Asp Val Met Glu Arg Ser Arg Arg Gly
    210                 215                 220 atg tcc att ctt aga aag aag tat ttg aaa cca tcc aac aat gtt cta     720
Met Ser Ile Leu Arg Lys Lys Tyr Leu Lys Pro Ser Asn Asn Val Leu
225                 230                 235                 240 ttc tct gtt ggc tcg acc atc tac cac gag aag agg gac tta ctg agg     768
Phe Ser Val Gly Ser Thr Ile Tyr His Glu Lys Arg Asp Leu Leu Arg
                245                 250                 255 agc tgg cac ctg ccg tct gta ttt cac tta cgt ggc aag caa aat tac     816
Ser Trp His Leu Pro Ser Val Phe His Leu Arg Gly Lys Gln Asn Tyr
            260                 265                 270
```

```
aca tgt cgg tgt gag act ata gtt agt tgc gac ggg tac gtc gtt aaa       864
Thr Cys Arg Cys Glu Thr Ile Val Ser Cys Asp Gly Tyr Val Val Lys
            275                 280                 285 aga ata gct atc agt cca ggc ctg tat ggg aag cct tca ggc tat gct       912
Arg Ile Ala Ile Ser Pro Gly Leu Tyr Gly Lys Pro Ser Gly Tyr Ala
    290                 295                 300 gct acg atg cac cgc gag gga ttc ttg tgc tgc aaa gtg aca gac aca       960
Ala Thr Met His Arg Glu Gly Phe Leu Cys Cys Lys Val Thr Asp Thr
305                 310                 315                 320 tta aac ggg gag agg gtc tct ttt ccc gtg tgc acg tat gtg cca gct      1008
Leu Asn Gly Glu Arg Val Ser Phe Pro Val Cys Thr Tyr Val Pro Ala
                325                 330                 335 aca ttg tgt gac caa atg act ggc ata ctg gca aca gat gtc agt gcg      1056
Thr Leu Cys Asp Gln Met Thr Gly Ile Leu Ala Thr Asp Val Ser Ala
        340                 345                 350 gac gac gcg caa aaa ctg ctg gtt ggg ctc aac cag cgt ata gtc gtc      1104
Asp Asp Ala Gln Lys Leu Leu Val Gly Leu Asn Gln Arg Ile Val Val
    355                 360                 365 aac ggt cgc acc cag aga aac acc aat acc atg aaa aat tac ctt ttg      1152
Asn Gly Arg Thr Gln Arg Asn Thr Asn Thr Met Lys Asn Tyr Leu Leu
370                 375                 380 ccc gta gtg gcc cag gca ttt gct agg tgg gca aag gaa tat aag gaa      1200
Pro Val Val Ala Gln Ala Phe Ala Arg Trp Ala Lys Glu Tyr Lys Glu
385                 390                 395                 400 gat caa gaa gat gaa agg cca cta gga cta cga gat aga cag tta gtc      1248
Asp Gln Glu Asp Glu Arg Pro Leu Gly Leu Arg Asp Arg Gln Leu Val
                405                 410                 415 atg ggg tgt tgt tgg gct ttt aga agg cac aag ata aca tct att tat      1296
Met Gly Cys Cys Trp Ala Phe Arg Arg His Lys Ile Thr Ser Ile Tyr
        420                 425                 430 aag cgc ccg gat acc caa acc atc atc aaa gtg aac agc gat ttc cac      1344
Lys Arg Pro Asp Thr Gln Thr Ile Ile Lys Val Asn Ser Asp Phe His
    435                 440                 445 tca ttc gtg ctg ccc agg ata ggc agt aac aca ttg gag atc ggg ctg      1392
Ser Phe Val Leu Pro Arg Ile Gly Ser Asn Thr Leu Glu Ile Gly Leu
450                 455                 460 aga aca aga atc agg aaa atg tta gag gag cac aag gag ccg tca cct      1440
Arg Thr Arg Ile Arg Lys Met Leu Glu Glu His Lys Glu Pro Ser Pro
465                 470                 475                 480 ctc att acc gcc gag gac gta caa gaa gct aag tgc gca gcc gat gag      1488
Leu Ile Thr Ala Glu Asp Val Gln Glu Ala Lys Cys Ala Ala Asp Glu
                485                 490                 495 gct aag gag gtg cgt gaa gcc gag gag ttg cgc gca gct cta cca cct      1536
Ala Lys Glu Val Arg Glu Ala Glu Glu Leu Arg Ala Ala Leu Pro Pro
        500                 505                 510 ttg gca gct gat gtt gag gag ccc act ctg gaa gcc gat gtc gac ttg      1584
Leu Ala Ala Asp Val Glu Glu Pro Thr Leu Glu Ala Asp Val Asp Leu
    515                 520                 525 atg tta caa gag gct ggg gcc ggc tca gtg gag aca cct cgt ggc ttg      1632
Met Leu Gln Glu Ala Gly Ala Gly Ser Val Glu Thr Pro Arg Gly Leu
530                 535                 540 ata aag gtt acc agc tac gct ggc gag gac aag atc ggc tct tac gct      1680
Ile Lys Val Thr Ser Tyr Ala Gly Glu Asp Lys Ile Gly Ser Tyr Ala
545                 550                 555                 560 gtg ctt tct ccg cag gct gta ctc aag agt gaa aaa tta tct tgc atc      1728
Val Leu Ser Pro Gln Ala Val Leu Lys Ser Glu Lys Leu Ser Cys Ile
                565                 570                 575 cac cct ctc gct gaa caa gtc ata gtg ata aca cac tct ggc cga aaa      1776
His Pro Leu Ala Glu Gln Val Ile Val Ile Thr His Ser Gly Arg Lys
        580                 585                 590
```

-continued

| | |
|---|---|
| ggg cgt tat gcc gtg gaa cca tac cat ggt aaa gta gtg gtg cca gag<br>Gly Arg Tyr Ala Val Glu Pro Tyr His Gly Lys Val Val Val Pro Glu<br>595                600                605 | 1824 |
| gga cat gca ata ccc gtc cag gac ttt caa gct ctg agt gaa agt gcc<br>Gly His Ala Ile Pro Val Gln Asp Phe Gln Ala Leu Ser Glu Ser Ala<br>610                615                620 | 1872 |
| acc att gtg tac aac gaa cgt gag ttc gta aac agg tac ctg cac cat<br>Thr Ile Val Tyr Asn Glu Arg Glu Phe Val Asn Arg Tyr Leu His His<br>625                630                635                640 | 1920 |
| att gcc aca cat gga gga gcg ctg aac act gat gaa gaa tat tac aaa<br>Ile Ala Thr His Gly Gly Ala Leu Asn Thr Asp Glu Glu Tyr Tyr Lys<br>                645                650                655 | 1968 |
| act gtc aag ccc agc gag cac gac ggc gaa tac ctg tac gac atc gac<br>Thr Val Lys Pro Ser Glu His Asp Gly Glu Tyr Leu Tyr Asp Ile Asp<br>660                665                670 | 2016 |
| agg aaa cag tgc gtc aag aaa gaa cta gtc act ggg cta ggg ctc aca<br>Arg Lys Gln Cys Val Lys Lys Glu Leu Val Thr Gly Leu Gly Leu Thr<br>                675                680                685 | 2064 |
| ggc gag ctg gtg gat cct ccc ttc cat gaa ttc gcc tac gag agt ctg<br>Gly Glu Leu Val Asp Pro Pro Phe His Glu Phe Ala Tyr Glu Ser Leu<br>690                695                700 | 2112 |
| aga aca cga cca gcc gct cct tac caa gta cca acc ata ggg gtg tat<br>Arg Thr Arg Pro Ala Ala Pro Tyr Gln Val Pro Thr Ile Gly Val Tyr<br>705                710                715                720 | 2160 |
| ggc gtg cca gga tca ggc aag tct ggc atc att aaa agc gca gtc acc<br>Gly Val Pro Gly Ser Gly Lys Ser Gly Ile Ile Lys Ser Ala Val Thr<br>                725                730                735 | 2208 |
| aaa aaa gat cta gtg gtg agc gcc aag aaa gaa aac tgt gca gaa att<br>Lys Lys Asp Leu Val Val Ser Ala Lys Lys Glu Asn Cys Ala Glu Ile<br>740                745                750 | 2256 |
| ata agg gac gtc aag aaa atg aaa ggg ctg gac gtc aat gcc aga act<br>Ile Arg Asp Val Lys Lys Met Lys Gly Leu Asp Val Asn Ala Arg Thr<br>                755                760                765 | 2304 |
| gtg gac tca gtg ctc ttg aat gga tgc aaa cac ccc gta gag acc ctg<br>Val Asp Ser Val Leu Leu Asn Gly Cys Lys His Pro Val Glu Thr Leu<br>770                775                780 | 2352 |
| tat att gac gaa gct ttt gct tgt cat gca ggt act ctc aga gcg ctc<br>Tyr Ile Asp Glu Ala Phe Ala Cys His Ala Gly Thr Leu Arg Ala Leu<br>785                790                795                800 | 2400 |
| ata gcc att ata aga cct aaa aag gca gtg ctc tgc ggg gat ccc aaa<br>Ile Ala Ile Ile Arg Pro Lys Lys Ala Val Leu Cys Gly Asp Pro Lys<br>                805                810                815 | 2448 |
| cag tgc ggt ttt ttt aac atg atg tgc ctg aaa gtg cat ttt aac cac<br>Gln Cys Gly Phe Phe Asn Met Met Cys Leu Lys Val His Phe Asn His<br>820                825                830 | 2496 |
| gag att tgc aca caa gtc ttc cac aaa agc atc tct cgc cgt tgc act<br>Glu Ile Cys Thr Gln Val Phe His Lys Ser Ile Ser Arg Arg Cys Thr<br>                835                840                845 | 2544 |
| aaa tct gtg act tcg gtc gtc tca acc ttg ttt tac gac aaa aaa atg<br>Lys Ser Val Thr Ser Val Val Ser Thr Leu Phe Tyr Asp Lys Lys Met<br>850                855                860 | 2592 |
| aga acg acg aat ccg aaa gag act aag att gtg att gac act acc ggc<br>Arg Thr Thr Asn Pro Lys Glu Thr Lys Ile Val Ile Asp Thr Thr Gly<br>865                870                875                880 | 2640 |
| agt acc aaa cct aag cag gac gat ctc att ctc act tgt ttc aga ggg<br>Ser Thr Lys Pro Lys Gln Asp Asp Leu Ile Leu Thr Cys Phe Arg Gly<br>                885                890                895 | 2688 |
| tgg gtg aag cag ttg caa ata gat tac aaa ggc aac gaa ata atg acg<br>Trp Val Lys Gln Leu Gln Ile Asp Tyr Lys Gly Asn Glu Ile Met Thr<br>900                905                910 | 2736 |

```
gca gct gcc tct caa ggg ctg acc cgt aaa ggt gtg tat gcc gtt cgg     2784
Ala Ala Ala Ser Gln Gly Leu Thr Arg Lys Gly Val Tyr Ala Val Arg
            915                 920                 925 tac aag gtg aat gaa aat cct ctg tac gca ccc acc tca gaa cat gtg     2832
Tyr Lys Val Asn Glu Asn Pro Leu Tyr Ala Pro Thr Ser Glu His Val
        930                 935                 940 aac gtc cta ctg acc cgc acg gag gac cgc atc gtg tgg aaa aca cta     2880
Asn Val Leu Leu Thr Arg Thr Glu Asp Arg Ile Val Trp Lys Thr Leu
945                 950                 955                 960 gcc ggc gac cca tgg ata aaa aca ctg act gcc aag tac cct ggg aat     2928
Ala Gly Asp Pro Trp Ile Lys Thr Leu Thr Ala Lys Tyr Pro Gly Asn
                965                 970                 975 ttc act gcc acg ata gag gag tgg caa gca gag cat gat gcc atc atg     2976
Phe Thr Ala Thr Ile Glu Glu Trp Gln Ala Glu His Asp Ala Ile Met
            980                 985                 990 agg cac atc ttg gag aga ccg gac cct acc gac gtc ttc cag aat aag     3024
Arg His Ile Leu Glu Arg Pro Asp Pro Thr Asp Val Phe Gln Asn Lys
        995                 1000                1005 gca aac gtg tgt tgg gcc aag gct tta gtg ccg gtg ctg aag acc gct     3072
Ala Asn Val Cys Trp Ala Lys Ala Leu Val Pro Val Leu Lys Thr Ala
    1010                1015                1020 ggc ata gac atg acc act gaa caa tgg aac act gtg gat tat ttt gaa     3120
Gly Ile Asp Met Thr Thr Glu Gln Trp Asn Thr Val Asp Tyr Phe Glu
1025                1030                1035                1040 acg gac aaa gct cac tca gca gag ata gta ttg aac caa cta tgc gtg     3168
Thr Asp Lys Ala His Ser Ala Glu Ile Val Leu Asn Gln Leu Cys Val
                1045                1050                1055 agg ttc ttt gga ctc gat ctg gac tcc ggt cta ttt tct gca ccc act     3216
Arg Phe Phe Gly Leu Asp Leu Asp Ser Gly Leu Phe Ser Ala Pro Thr
            1060                1065                1070 gtt ccg tta tcc att agg aat aat cac tgg gat aac tcc ccg tcg cct     3264
Val Pro Leu Ser Ile Arg Asn Asn His Trp Asp Asn Ser Pro Ser Pro
        1075                1080                1085 aac atg tac ggg ctg aat aaa gaa gtg gtc cgt cag ctc tct cgc agg     3312
Asn Met Tyr Gly Leu Asn Lys Glu Val Val Arg Gln Leu Ser Arg Arg
    1090                1095                1100 tac cca caa ctg cct cgg gca gtt gcc act gga aga gtc tat gac atg     3360
Tyr Pro Gln Leu Pro Arg Ala Val Ala Thr Gly Arg Val Tyr Asp Met
1105                1110                1115                1120 aac act ggt aca ctg cgc aat tat gat ccg cgc ata aac cta gta cct     3408
Asn Thr Gly Thr Leu Arg Asn Tyr Asp Pro Arg Ile Asn Leu Val Pro
                1125                1130                1135 gta aac aga aga ctg cct cat gct tta gtc ctc cac cat aat gaa cac     3456
Val Asn Arg Arg Leu Pro His Ala Leu Val Leu His His Asn Glu His
            1140                1145                1150 cca cag agt gac ttt tct tca ttc gtc agc aaa ttg aag ggc aga act     3504
Pro Gln Ser Asp Phe Ser Ser Phe Val Ser Lys Leu Lys Gly Arg Thr
        1155                1160                1165 gtc ctg gtg gtc ggg gaa aag ttg tcc gtc cca ggc aaa atg gtt gac     3552
Val Leu Val Val Gly Glu Lys Leu Ser Val Pro Gly Lys Met Val Asp
    1170                1175                1180 tgg ttg tca gac cgg cct gag gct acc ttc aga gct cgg ctg gat tta     3600
Trp Leu Ser Asp Arg Pro Glu Ala Thr Phe Arg Ala Arg Leu Asp Leu
1185                1190                1195                1200 ggc atc cca ggt gat gtg ccc aaa tat gac ata ata ttt gtt aat gtg     3648
Gly Ile Pro Gly Asp Val Pro Lys Tyr Asp Ile Ile Phe Val Asn Val
                1205                1210                1215 agg acc cca tat aaa tac cat cac tat cag cag tgt gaa gac cat gcc     3696
Arg Thr Pro Tyr Lys Tyr His His Tyr Gln Gln Cys Glu Asp His Ala
            1220                1225                1230
```

-continued

| | | |
|---|---|---|
| att aag ctt agc atg ttg acc aag aaa gct tgt ctg cat ctg aat ccc<br>Ile Lys Leu Ser Met Leu Thr Lys Lys Ala Cys Leu His Leu Asn Pro<br>1235                    1240                    1245 | | 3744 |
| ggc gga acc tgt gtc agc ata ggt tat ggt tac gct gac agg gcc agc<br>Gly Gly Thr Cys Val Ser Ile Gly Tyr Gly Tyr Ala Asp Arg Ala Ser<br>    1250                    1255                    1260 | | 3792 |
| gaa agc atc att ggt gct ata gcg cgg cag ttc aag ttt tcc cgg gta<br>Glu Ser Ile Ile Gly Ala Ile Ala Arg Gln Phe Lys Phe Ser Arg Val<br>1265                    1270                    1275                    1280 | | 3840 |
| tgc aaa ccg aaa tcc tca ctt gaa gag acg gaa gtt ctg ttt gta ttc<br>Cys Lys Pro Lys Ser Ser Leu Glu Glu Thr Glu Val Leu Phe Val Phe<br>                    1285                    1290                    1295 | | 3888 |
| att ggg tac gat cgc aag gcc cgt acg cac aat cct tac aag ctt tca<br>Ile Gly Tyr Asp Arg Lys Ala Arg Thr His Asn Pro Tyr Lys Leu Ser<br>1300                    1305                    1310 | | 3936 |
| tca acc ttg acc aac att tat aca ggt tcc aga ctc cac gaa gcc gga<br>Ser Thr Leu Thr Asn Ile Tyr Thr Gly Ser Arg Leu His Glu Ala Gly<br>    1315                    1320                    1325 | | 3984 |
| tgt gca ccc tca tat cat gtg gtg cga ggg gat att gcc acg gcc acc<br>Cys Ala Pro Ser Tyr His Val Val Arg Gly Asp Ile Ala Thr Ala Thr<br>        1330                    1335                    1340 | | 4032 |
| gaa gga gtg att ata aat gct gct aac agc aaa gga caa cct ggc gga<br>Glu Gly Val Ile Ile Asn Ala Ala Asn Ser Lys Gly Gln Pro Gly Gly<br>1345                    1350                    1355                    1360 | | 4080 |
| ggg gtg tgc gga gcg ctg tat aag aag ttc ccg gaa agc ttc gat tta<br>Gly Val Cys Gly Ala Leu Tyr Lys Lys Phe Pro Glu Ser Phe Asp Leu<br>                    1365                    1370                    1375 | | 4128 |
| cag ccg atc gaa gta gga aaa gcg cga ctg gtc aaa ggt gca gct aaa<br>Gln Pro Ile Glu Val Gly Lys Ala Arg Leu Val Lys Gly Ala Ala Lys<br>1380                    1385                    1390 | | 4176 |
| cat atc att cat gcc gta gga cca aac ttc aac aaa gtt tcg gag gtt<br>His Ile Ile His Ala Val Gly Pro Asn Phe Asn Lys Val Ser Glu Val<br>    1395                    1400                    1405 | | 4224 |
| gaa ggt gac aaa cag ttg gca gag gct tat gag tcc atc gct aag att<br>Glu Gly Asp Lys Gln Leu Ala Glu Ala Tyr Glu Ser Ile Ala Lys Ile<br>        1410                    1415                    1420 | | 4272 |
| gtc aac gat aac aat tac aag tca gta gcg att cca ctg ttg tcc acc<br>Val Asn Asp Asn Asn Tyr Lys Ser Val Ala Ile Pro Leu Leu Ser Thr<br>1425                    1430                    1435                    1440 | | 4320 |
| ggc atc ttt tcc ggg aac aaa gat cga cta acc caa tca ttg aac cat<br>Gly Ile Phe Ser Gly Asn Lys Asp Arg Leu Thr Gln Ser Leu Asn His<br>                    1445                    1450                    1455 | | 4368 |
| ttg ctg aca gct tta gac acc act gat gca gat gta gcc ata tac tgc<br>Leu Leu Thr Ala Leu Asp Thr Thr Asp Ala Asp Val Ala Ile Tyr Cys<br>1460                    1465                    1470 | | 4416 |
| agg gac aag aaa tgg gaa atg act ctc aag gaa gca gtg gct agg aga<br>Arg Asp Lys Lys Trp Glu Met Thr Leu Lys Glu Ala Val Ala Arg Arg<br>    1475                    1480                    1485 | | 4464 |
| gaa gca gtg gag gag ata tgc ata tcc gac gac tct tca gtg aca gaa<br>Glu Ala Val Glu Glu Ile Cys Ile Ser Asp Asp Ser Ser Val Thr Glu<br>        1490                    1495                    1500 | | 4512 |
| cct gat gca gag ctg gtg agg gtg cat ccg aag agt tct ttg gct gga<br>Pro Asp Ala Glu Leu Val Arg Val His Pro Lys Ser Ser Leu Ala Gly<br>1505                    1510                    1515                    1520 | | 4560 |
| agg aag ggc tac agc aca agc gat ggc aaa act ttc tca tat ttg gaa<br>Arg Lys Gly Tyr Ser Thr Ser Asp Gly Lys Thr Phe Ser Tyr Leu Glu<br>                    1525                    1530                    1535 | | 4608 |
| ggg acc aag ttt cac cag gcg gcc aag gat ata gca gaa att aat gcc<br>Gly Thr Lys Phe His Gln Ala Ala Lys Asp Ile Ala Glu Ile Asn Ala<br>1540                    1545                    1550 | | 4656 |

```
                                    -continued atg tgg ccc gtt gca acg gag gcc aat gag cag gta tgc atg tat atc       4704
Met Trp Pro Val Ala Thr Glu Ala Asn Glu Gln Val Cys Met Tyr Ile
        1555                1560                1565 ctc gga gaa agc atg agc agt att agg tcg aaa tgc ccc gtc gaa gag       4752
Leu Gly Glu Ser Met Ser Ser Ile Arg Ser Lys Cys Pro Val Glu Glu
    1570                1575                1580 tcg gaa gcc tcc aca cca cct agc acg ctg cct tgc ttg tgc atc cat       4800
Ser Glu Ala Ser Thr Pro Pro Ser Thr Leu Pro Cys Leu Cys Ile His
1585                1590                1595                1600 gcc atg act cca gaa aga gta cag cgc cta aaa gcc tca cgt cca gaa       4848
Ala Met Thr Pro Glu Arg Val Gln Arg Leu Lys Ala Ser Arg Pro Glu
                1605                1610                1615 caa att act gtg tgc tca tcc ttt cca ttg ccg aag tat aga atc act       4896
Gln Ile Thr Val Cys Ser Ser Phe Pro Leu Pro Lys Tyr Arg Ile Thr
            1620                1625                1630 ggt gtg cag aag atc caa tgc tcc cag cct ata ttg ttc tca ccg aaa       4944
Gly Val Gln Lys Ile Gln Cys Ser Gln Pro Ile Leu Phe Ser Pro Lys
        1635                1640                1645 gtg cct gcg tat att cat cca agg aag tat ctc gtg gaa aca cca ccg       4992
Val Pro Ala Tyr Ile His Pro Arg Lys Tyr Leu Val Glu Thr Pro Pro
    1650                1655                1660 gta gac gag act ccg gag cca tcg gca gag aac caa tcc aca gag ggg       5040
Val Asp Glu Thr Pro Glu Pro Ser Ala Glu Asn Gln Ser Thr Glu Gly
1665                1670                1675                1680 aca cct gaa caa cca cca ctt ata acc gag gat gag acc agg act aga       5088
Thr Pro Glu Gln Pro Pro Leu Ile Thr Glu Asp Glu Thr Arg Thr Arg
                1685                1690                1695 acg cct gag ccg atc atc atc gaa gag gaa gaa gag gat agc ata agt       5136
Thr Pro Glu Pro Ile Ile Ile Glu Glu Glu Glu Asp Ser Ile Ser
            1700                1705                1710 ttg ctg tca gat ggc ccg acc cac cag gtg ctg caa gtc gag gca gac       5184
Leu Leu Ser Asp Gly Pro Thr His Gln Val Leu Gln Val Glu Ala Asp
        1715                1720                1725 att cac ggg ccg ccc tct gta tct agc tca tcc tgg tcc att cct cat       5232
Ile His Gly Pro Pro Ser Val Ser Ser Ser Ser Trp Ser Ile Pro His
    1730                1735                1740 gca tcc gac ttt gat gtg gac agt tta tcc ata ctt gac acc ctg gag       5280
Ala Ser Asp Phe Asp Val Asp Ser Leu Ser Ile Leu Asp Thr Leu Glu
1745                1750                1755                1760 gga gct agc gtg acc agc ggg gca acg tca gcc gag act aac tct tac       5328
Gly Ala Ser Val Thr Ser Gly Ala Thr Ser Ala Glu Thr Asn Ser Tyr
                1765                1770                1775 ttc gca aag agt atg gag ttt ctg gcg cga ccg gtg cct gcg cct cga       5376
Phe Ala Lys Ser Met Glu Phe Leu Ala Arg Pro Val Pro Ala Pro Arg
            1780                1785                1790 aca gta ttc agg aac cct cca cat ccc gct ccg cgc aca aga aca ccg       5424
Thr Val Phe Arg Asn Pro Pro His Pro Ala Pro Arg Thr Arg Thr Pro
        1795                1800                1805 tca ctt gca ccc agc agg gcc tgc tcg aga acc agc cta gtt tcc acc       5472
Ser Leu Ala Pro Ser Arg Ala Cys Ser Arg Thr Ser Leu Val Ser Thr
    1810                1815                1820 ccg cca ggc gtg aat agg gtg atc act aga gag gag ctc gag gcg ctt       5520
Pro Pro Gly Val Asn Arg Val Ile Thr Arg Glu Glu Leu Glu Ala Leu
1825                1830                1835                1840 acc ccg tca cgc act cct agc agg tcg gtc tcg aga acc agc ctg gtc       5568
Thr Pro Ser Arg Thr Pro Ser Arg Ser Val Ser Arg Thr Ser Leu Val
                1845                1850                1855 tcc aac ccg cca ggc gta aat agg gtg att aca aga gag gag ttt gag       5616
Ser Asn Pro Pro Gly Val Asn Arg Val Ile Thr Arg Glu Glu Phe Glu
            1860                1865                1870
```

```
gcg ttc gta gca caa caa caa tga cgg ttt gat gcg ggt gca tac atc        5664
Ala Phe Val Ala Gln Gln Gln  *  Arg Phe Asp Ala Gly Ala Tyr Ile
    1875                1880                    1885 ttt tcc tcc gac acc ggt caa ggg cat tta caa caa aaa tca gta agg        5712
Phe Ser Ser Asp Thr Gly Gln Gly His Leu Gln Gln Lys Ser Val Arg
    1890                1895                    1900 caa acg gtg cta tcc gaa gtg gtg ttg gag agg acc gaa ttg gag att        5760
Gln Thr Val Leu Ser Glu Val Val Leu Glu Arg Thr Glu Leu Glu Ile
1905                1910                    1915 tcg tat gcc ccg cgc ctc gac caa gaa aaa gaa gaa tta cta cgc aag        5808
Ser Tyr Ala Pro Arg Leu Asp Gln Glu Lys Glu Glu Leu Leu Arg Lys
1920                1925                    1930                1935 aaa tta cag tta aat ccc aca cct gct aac aga agc aga tac cag tcc        5856
Lys Leu Gln Leu Asn Pro Thr Pro Ala Asn Arg Ser Arg Tyr Gln Ser
                1940                1945                    1950 agg aag gtg gag aac atg aaa gcc ata aca gct aga cgt att ctg caa        5904
Arg Lys Val Glu Asn Met Lys Ala Ile Thr Ala Arg Arg Ile Leu Gln
            1955                1960                    1965 ggc cta ggg cat tat ttg aag gca gaa gga aaa gtg gag tgc tac cga        5952
Gly Leu Gly His Tyr Leu Lys Ala Glu Gly Lys Val Glu Cys Tyr Arg
        1970                1975                    1980 acc ctg cat cct gtt cct ttg tat tca tct agt gtg aac cgt gcc ttt        6000
Thr Leu His Pro Val Pro Leu Tyr Ser Ser Ser Val Asn Arg Ala Phe
    1985                1990                    1995 tca agc ccc aag gtc gca gtg gaa gcc tgt aac gcc atg ttg aaa gag        6048
Ser Ser Pro Lys Val Ala Val Glu Ala Cys Asn Ala Met Leu Lys Glu
2000                2005                    2010                2015 aac ttt ccg act gtg gct tct tac tgt att att cca gag tac gat gcc        6096
Asn Phe Pro Thr Val Ala Ser Tyr Cys Ile Ile Pro Glu Tyr Asp Ala
                2020                2025                    2030 tat ttg gac atg gtt gac gga gct tca tgc tgc tta gac act gcc agt        6144
Tyr Leu Asp Met Val Asp Gly Ala Ser Cys Cys Leu Asp Thr Ala Ser
            2035                2040                    2045 ttt tgc cct gca aag ctg cgc agc ttt cca aag aaa cac tcc tat ttg        6192
Phe Cys Pro Ala Lys Leu Arg Ser Phe Pro Lys Lys His Ser Tyr Leu
        2050                2055                    2060 gaa ccc aca ata cga tcg gca gtg cct tca gcg atc cag aac acg ctc        6240
Glu Pro Thr Ile Arg Ser Ala Val Pro Ser Ala Ile Gln Asn Thr Leu
    2065                2070                    2075 cag aac gtc ctg gca gct gcc aca aaa aga aat tgc aat gtc acg caa        6288
Gln Asn Val Leu Ala Ala Ala Thr Lys Arg Asn Cys Asn Val Thr Gln
2080                2085                    2090                2095 atg aga gaa ttg ccc gta ttg gat tcg gcg gcc ttt aat gtg gaa tgc        6336
Met Arg Glu Leu Pro Val Leu Asp Ser Ala Ala Phe Asn Val Glu Cys
                2100                2105                    2110 ttc aag aaa tat gcg tgt aat aat gaa tat tgg gaa acg ttt aaa gaa        6384
Phe Lys Lys Tyr Ala Cys Asn Asn Glu Tyr Trp Glu Thr Phe Lys Glu
            2115                2120                    2125 aac ccc atc agg ctt act gaa gaa aac gtg gta aat tac att acc aaa        6432
Asn Pro Ile Arg Leu Thr Glu Glu Asn Val Val Asn Tyr Ile Thr Lys
        2130                2135                    2140 tta aaa gga cca aaa gct gct gct ctt ttt gcg aag aca cat aat ttg        6480
Leu Lys Gly Pro Lys Ala Ala Ala Leu Phe Ala Lys Thr His Asn Leu
    2145                2150                    2155 aat atg ttg cag gac ata cca atg gac agg ttt gta atg gac tta aag        6528
Asn Met Leu Gln Asp Ile Pro Met Asp Arg Phe Val Met Asp Leu Lys
2160                2165                    2170                2175 aga gac gtg aaa gtg act cca gga aca aaa cat act gaa gaa cgg ccc        6576
Arg Asp Val Lys Val Thr Pro Gly Thr Lys His Thr Glu Glu Arg Pro
                2180                2185                    2190
```

```
                                                       -continued aag gta cag gtg atc cag gct gcc gat ccg cta gca aca gcg tat ctg      6624
Lys Val Gln Val Ile Gln Ala Ala Asp Pro Leu Ala Thr Ala Tyr Leu
        2195                2200                2205 tgc gga atc cac cga gag ctg gtt agg aga tta aat gcg gtc ctg ctt      6672
Cys Gly Ile His Arg Glu Leu Val Arg Arg Leu Asn Ala Val Leu Leu
2210                2215                2220 ccg aac att cat aca ctg ttt gat atg tcg gct gaa gac ttt gac gct      6720
Pro Asn Ile His Thr Leu Phe Asp Met Ser Ala Glu Asp Phe Asp Ala
    2225                2230                2235 att ata gcc gag cac ttc cag cct ggg gat tgt gtt ctg gaa act gac      6768
Ile Ile Ala Glu His Phe Gln Pro Gly Asp Cys Val Leu Glu Thr Asp
2240                2245                2250                2255 atc gcg tcg ttt gat aaa agt gag gac gac gcc atg gct ctg acc gcg      6816
Ile Ala Ser Phe Asp Lys Ser Glu Asp Asp Ala Met Ala Leu Thr Ala
            2260                2265                2270 tta atg att ctg gaa gac tta ggt gtg gac gca gag ctg ttg acg ctg      6864
Leu Met Ile Leu Glu Asp Leu Gly Val Asp Ala Glu Leu Leu Thr Leu
        2275                2280                2285 att gag gcg gct ttc ggc gaa att tca tca ata cat ttg ccc act aaa      6912
Ile Glu Ala Ala Phe Gly Glu Ile Ser Ser Ile His Leu Pro Thr Lys
    2290                2295                2300 act aaa ttt aaa ttc gga gcc atg atg aaa tct gga atg ttc ctc aca      6960
Thr Lys Phe Lys Phe Gly Ala Met Met Lys Ser Gly Met Phe Leu Thr
2305                2310                2315 ctg ttt gtg aac aca gtc att aac att gta atc gca agc aga gtg ttg      7008
Leu Phe Val Asn Thr Val Ile Asn Ile Val Ile Ala Ser Arg Val Leu
2320                2325                2330                2335 aga gaa cgg cta acc gga tca cca tgt gca gca ttc att gga gat gac      7056
Arg Glu Arg Leu Thr Gly Ser Pro Cys Ala Ala Phe Ile Gly Asp Asp
            2340                2345                2350 aat atc gtg aaa gga gtc aaa tcg gac aaa tta atg gca gac agg tgc      7104
Asn Ile Val Lys Gly Val Lys Ser Asp Lys Leu Met Ala Asp Arg Cys
        2355                2360                2365 gcc acc tgg ttg aat atg gaa gtc aag att ata gat gct gtg gtg ggc      7152
Ala Thr Trp Leu Asn Met Glu Val Lys Ile Ile Asp Ala Val Val Gly
    2370                2375                2380 gag aaa gcg ccc tat ttc tgt gga ggg ttt att ttg tgt gac tcc gtg      7200
Glu Lys Ala Pro Tyr Phe Cys Gly Gly Phe Ile Leu Cys Asp Ser Val
2385                2390                2395 acc ggc aca gcg tgc cgt gtg gca gac ccc cta aaa agg ctg ttt aag      7248
Thr Gly Thr Ala Cys Arg Val Ala Asp Pro Leu Lys Arg Leu Phe Lys
2400                2405                2410                2415 ctt ggc aaa cct ctg gca gca gac gat gaa cat gat gat gac agg aga      7296
Leu Gly Lys Pro Leu Ala Ala Asp Asp Glu His Asp Asp Asp Arg Arg
            2420                2425                2430 agg gca ttg cat gaa gag tca aca cgc tgg aac cga gtg ggt att ctt      7344
Arg Ala Leu His Glu Glu Ser Thr Arg Trp Asn Arg Val Gly Ile Leu
        2435                2440                2445 tca gag ctg tgc aag gca gta gaa tca agg tat gaa acc gta gga act      7392
Ser Glu Leu Cys Lys Ala Val Glu Ser Arg Tyr Glu Thr Val Gly Thr
    2450                2455                2460 tcc atc ata gtt atg gcc atg act act cta gct agc agt gtt aaa tca      7440
Ser Ile Ile Val Met Ala Met Thr Thr Leu Ala Ser Ser Val Lys Ser
2465                2470                2475 ttc agc tac ctg aga ggg gcc cct ata act ctc tac ggc                  7479
Phe Ser Tyr Leu Arg Gly Ala Pro Ile Thr Leu Tyr Gly
2480                2485                2490
```

<210> SEQ ID NO 3
<211> LENGTH: 2492
<212> TYPE: PRT
<213> ORGANISM: Artificial Sequence
<220> FEATURE:
<223> OTHER INFORMATION: Description of Artificial Sequence; Note = synthetic construct

<400> SEQUENCE: 3

```
Met Glu Lys Val His Val Asp Ile Glu Asp Ser Pro Phe Leu Arg
 1               5                  10                  15

Ala Leu Gln Arg Ser Phe Pro Gln Phe Glu Val Glu Ala Lys Gln Val
                20                  25                  30

Thr Asp Asn Asp His Ala Asn Ala Arg Ala Phe Ser His Leu Ala Ser
            35                  40                  45

Lys Leu Ile Glu Thr Glu Val Asp Pro Ser Asp Thr Ile Leu Asp Ile
    50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
               100                 105                 110

Asp Lys Lys Met Lys Glu Leu Ala Ala Val Met Ser Asp Pro Asp Leu
           115                 120                 125

Glu Thr Glu Thr Met Cys Leu His Asp Asp Glu Ser Cys Arg Tyr Glu
       130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190

Pro Ser Tyr Ser Thr Asn Trp Ala Asp Glu Thr Val Leu Thr Ala Arg
        195                 200                 205

Asn Ile Gly Leu Cys Ser Ser Asp Val Met Glu Arg Ser Arg Arg Gly
    210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365
```

-continued

```
Asn Gly Arg Thr Gln Arg Asn Thr Asn Thr Met Lys Asn Tyr Leu Leu
    370                 375                 380
Pro Val Ala Gln Ala Phe Ala Arg Trp Ala Lys Glu Tyr Lys Glu
385                 390                 395                 400
Asp Gln Glu Asp Glu Arg Pro Leu Gly Leu Arg Asp Arg Gln Leu Val
                    405                 410                 415
Met Gly Cys Cys Trp Ala Phe Arg Arg His Lys Ile Thr Ser Ile Tyr
                420                 425                 430
Lys Arg Pro Asp Thr Gln Thr Ile Ile Lys Val Asn Ser Asp Phe His
            435                 440                 445
Ser Phe Val Leu Pro Arg Ile Gly Ser Asn Thr Leu Glu Ile Gly Leu
        450                 455                 460
Arg Thr Arg Ile Arg Lys Met Leu Glu Glu His Lys Glu Pro Ser Pro
465                 470                 475                 480
Leu Ile Thr Ala Glu Asp Val Gln Glu Ala Lys Cys Ala Ala Asp Glu
                    485                 490                 495
Ala Lys Glu Val Arg Glu Ala Glu Glu Leu Arg Ala Ala Leu Pro Pro
                500                 505                 510
Leu Ala Ala Asp Val Glu Glu Pro Thr Leu Glu Ala Asp Val Asp Leu
            515                 520                 525
Met Leu Gln Glu Ala Gly Ala Gly Ser Val Glu Thr Pro Arg Gly Leu
        530                 535                 540
Ile Lys Val Thr Ser Tyr Ala Gly Glu Asp Lys Ile Gly Ser Tyr Ala
545                 550                 555                 560
Val Leu Ser Pro Gln Ala Val Leu Lys Ser Glu Lys Leu Ser Cys Ile
                    565                 570                 575
His Pro Leu Ala Glu Gln Val Ile Val Ile Thr His Ser Gly Arg Lys
                580                 585                 590
Gly Arg Tyr Ala Val Glu Pro Tyr His Gly Lys Val Val Pro Glu
            595                 600                 605
Gly His Ala Ile Pro Val Gln Asp Phe Gln Ala Leu Ser Glu Ser Ala
        610                 615                 620
Thr Ile Val Tyr Asn Glu Arg Glu Phe Val Asn Arg Tyr Leu His His
625                 630                 635                 640
Ile Ala Thr His Gly Gly Ala Leu Asn Thr Asp Glu Glu Tyr Tyr Lys
                    645                 650                 655
Thr Val Lys Pro Ser Glu His Asp Gly Glu Tyr Leu Tyr Asp Ile Asp
                660                 665                 670
Arg Lys Gln Cys Val Lys Lys Glu Leu Val Thr Gly Leu Gly Leu Thr
            675                 680                 685
Gly Glu Leu Val Asp Pro Pro Phe His Glu Phe Ala Tyr Glu Ser Leu
        690                 695                 700
Arg Thr Arg Pro Ala Ala Pro Tyr Gln Val Pro Thr Ile Gly Val Tyr
705                 710                 715                 720
Gly Val Pro Gly Ser Gly Lys Ser Gly Ile Ile Lys Ser Ala Val Thr
                    725                 730                 735
Lys Lys Asp Leu Val Val Ser Ala Lys Lys Glu Asn Cys Ala Glu Ile
                740                 745                 750
Ile Arg Asp Val Lys Lys Met Lys Gly Leu Asp Val Asn Ala Arg Thr
            755                 760                 765
Val Asp Ser Val Leu Leu Asn Gly Cys Lys His Pro Val Glu Thr Leu
        770                 775                 780
```

-continued

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
            805                 810                 815

Gln Cys Gly Phe Asn Met Met Cys Leu Lys Val His Phe Asn His
        820                 825                 830

Glu Ile Cys Thr Gln Val Phe His Lys Ser Ile Ser Arg Arg Cys Thr
        835                 840                 845

Lys Ser Val Thr Ser Val Val Ser Thr Leu Phe Tyr Asp Lys Lys Met
        850                 855                 860

Arg Thr Thr Asn Pro Lys Glu Thr Lys Ile Val Ile Asp Thr Thr Gly
865                 870                 875                 880

Ser Thr Lys Pro Lys Gln Asp Asp Leu Ile Leu Thr Cys Phe Arg Gly
                885                 890                 895

Trp Val Lys Gln Leu Gln Ile Asp Tyr Lys Gly Asn Glu Ile Met Thr
            900                 905                 910

Ala Ala Ala Ser Gln Gly Leu Thr Arg Lys Gly Val Tyr Ala Val Arg
            915                 920                 925

Tyr Lys Val Asn Glu Asn Pro Leu Tyr Ala Pro Thr Ser Glu His Val
    930                 935                 940

Asn Val Leu Leu Thr Arg Thr Glu Asp Arg Ile Val Trp Lys Thr Leu
945                 950                 955                 960

Ala Gly Asp Pro Trp Ile Lys Thr Leu Thr Ala Lys Tyr Pro Gly Asn
                965                 970                 975

Phe Thr Ala Thr Ile Glu Glu Trp Gln Ala Glu His Asp Ala Ile Met
            980                 985                 990

Arg His Ile Leu Glu Arg Pro Asp Pro Thr Asp Val Phe Gln Asn Lys
        995                 1000                1005

Ala Asn Val Cys Trp Ala Lys Ala Leu Val Pro Val Leu Lys Thr Ala
    1010                1015                1020

Gly Ile Asp Met Thr Thr Glu Gln Trp Asn Thr Val Asp Tyr Phe Glu
1025                1030                1035                1040

Thr Asp Lys Ala His Ser Ala Glu Ile Val Leu Asn Gln Leu Cys Val
                1045                1050                1055

Arg Phe Phe Gly Leu Asp Leu Asp Ser Gly Leu Phe Ser Ala Pro Thr
            1060                1065                1070

Val Pro Leu Ser Ile Arg Asn Asn His Trp Asp Asn Ser Pro Ser Pro
        1075                1080                1085

Asn Met Tyr Gly Leu Asn Lys Glu Val Val Arg Gln Leu Ser Arg Arg
    1090                1095                1100

Tyr Pro Gln Leu Pro Arg Ala Val Ala Thr Gly Arg Val Tyr Asp Met
1105                1110                1115                1120

Asn Thr Gly Thr Leu Arg Asn Tyr Asp Pro Arg Ile Asn Leu Val Pro
                1125                1130                1135

Val Asn Arg Arg Leu Pro His Ala Leu Val Leu His His Asn Glu His
            1140                1145                1150

Pro Gln Ser Asp Phe Ser Ser Phe Val Ser Lys Leu Lys Gly Arg Thr
        1155                1160                1165

Val Leu Val Val Gly Glu Lys Leu Ser Val Pro Gly Lys Met Val Asp
    1170                1175                1180

Trp Leu Ser Asp Arg Pro Glu Ala Thr Phe Arg Ala Arg Leu Asp Leu
1185                1190                1195                1200

-continued

```
Gly Ile Pro Gly Asp Val Pro Lys Tyr Asp Ile Ile Phe Val Asn Val
            1205                1210                1215

Arg Thr Pro Tyr Lys Tyr His His Tyr Gln Cys Glu Asp His Ala
            1220                1225                1230

Ile Lys Leu Ser Met Leu Thr Lys Lys Ala Cys Leu His Leu Asn Pro
            1235                1240                1245

Gly Gly Thr Cys Val Ser Ile Gly Tyr Gly Tyr Ala Asp Arg Ala Ser
            1250                1255                1260

Glu Ser Ile Ile Gly Ala Ile Ala Arg Gln Phe Lys Phe Ser Arg Val
1265                1270                1275                1280

Cys Lys Pro Lys Ser Ser Leu Glu Glu Thr Glu Val Leu Phe Val Phe
            1285                1290                1295

Ile Gly Tyr Asp Arg Lys Ala Arg Thr His Asn Pro Tyr Lys Leu Ser
            1300                1305                1310

Ser Thr Leu Thr Asn Ile Tyr Thr Gly Ser Arg Leu His Glu Ala Gly
            1315                1320                1325

Cys Ala Pro Ser Tyr His Val Val Arg Gly Asp Ile Ala Thr Ala Thr
            1330                1335                1340

Glu Gly Val Ile Ile Asn Ala Ala Asn Ser Lys Gly Gln Pro Gly Gly
1345                1350                1355                1360

Gly Val Cys Gly Ala Leu Tyr Lys Lys Phe Pro Glu Ser Phe Asp Leu
            1365                1370                1375

Gln Pro Ile Glu Val Gly Lys Ala Arg Leu Val Lys Gly Ala Ala Lys
            1380                1385                1390

His Ile Ile His Ala Val Gly Pro Asn Phe Asn Lys Val Ser Glu Val
            1395                1400                1405

Glu Gly Asp Lys Gln Leu Ala Glu Ala Tyr Glu Ser Ile Ala Lys Ile
            1410                1415                1420

Val Asn Asp Asn Asn Tyr Lys Ser Val Ala Ile Pro Leu Leu Ser Thr
1425                1430                1435                1440

Gly Ile Phe Ser Gly Asn Lys Asp Arg Leu Thr Gln Ser Leu Asn His
            1445                1450                1455

Leu Leu Thr Ala Leu Asp Thr Thr Asp Ala Asp Val Ala Ile Tyr Cys
            1460                1465                1470

Arg Asp Lys Lys Trp Glu Met Thr Leu Lys Glu Ala Val Ala Arg Arg
            1475                1480                1485

Glu Ala Val Glu Glu Ile Cys Ile Ser Asp Asp Ser Ser Val Thr Glu
            1490                1495                1500

Pro Asp Ala Glu Leu Val Arg Val His Pro Lys Ser Ser Leu Ala Gly
1505                1510                1515                1520

Arg Lys Gly Tyr Ser Thr Ser Asp Gly Lys Thr Phe Ser Tyr Leu Glu
            1525                1530                1535

Gly Thr Lys Phe His Gln Ala Ala Lys Asp Ile Ala Glu Ile Asn Ala
            1540                1545                1550

Met Trp Pro Val Ala Thr Glu Ala Asn Glu Gln Val Cys Met Tyr Ile
            1555                1560                1565

Leu Gly Glu Ser Met Ser Ser Ile Arg Ser Lys Cys Pro Val Glu Glu
            1570                1575                1580

Ser Glu Ala Ser Thr Pro Pro Ser Thr Leu Pro Cys Leu Cys Ile His
1585                1590                1595                1600

Ala Met Thr Pro Glu Arg Val Gln Arg Leu Lys Ala Ser Arg Pro Glu
            1605                1610                1615
```

-continued

Gln Ile Thr Val Cys Ser Ser Phe Pro Leu Pro Lys Tyr Arg Ile Thr
                1620                1625                1630

Gly Val Gln Lys Ile Gln Cys Ser Gln Pro Ile Leu Phe Ser Pro Lys
                1635                1640                1645

Val Pro Ala Tyr Ile His Pro Arg Lys Tyr Leu Val Glu Thr Pro Pro
            1650                1655                1660

Val Asp Glu Thr Pro Glu Pro Ser Ala Glu Asn Gln Ser Thr Glu Gly
1665                1670                1675                1680

Thr Pro Glu Gln Pro Pro Leu Ile Thr Glu Asp Glu Thr Arg Thr Arg
                1685                1690                1695

Thr Pro Glu Pro Ile Ile Ile Glu Glu Glu Glu Asp Ser Ile Ser
                1700                1705                1710

Leu Leu Ser Asp Gly Pro Thr His Gln Val Leu Gln Val Glu Ala Asp
                1715                1720                1725

Ile His Gly Pro Pro Ser Val Ser Ser Ser Trp Ser Ile Pro His
            1730                1735                1740

Ala Ser Asp Phe Asp Val Asp Ser Leu Ser Ile Leu Asp Thr Leu Glu
1745                1750                1755                1760

Gly Ala Ser Val Thr Ser Gly Ala Thr Ser Ala Glu Thr Asn Ser Tyr
                1765                1770                1775

Phe Ala Lys Ser Met Glu Phe Leu Ala Arg Pro Val Pro Ala Pro Arg
                1780                1785                1790

Thr Val Phe Arg Asn Pro Pro His Pro Ala Pro Arg Thr Arg Thr Pro
                1795                1800                1805

Ser Leu Ala Pro Ser Arg Ala Cys Ser Arg Thr Ser Leu Val Ser Thr
                1810                1815                1820

Pro Pro Gly Val Asn Arg Val Ile Thr Arg Glu Glu Leu Glu Ala Leu
1825                1830                1835                1840

Thr Pro Ser Arg Thr Pro Ser Arg Ser Val Ser Arg Thr Ser Leu Val
                1845                1850                1855

Ser Asn Pro Pro Gly Val Asn Arg Val Ile Thr Arg Glu Glu Phe Glu
                1860                1865                1870

Ala Phe Val Ala Gln Gln Gln Arg Phe Asp Ala Gly Ala Tyr Ile Phe
                1875                1880                1885

Ser Ser Asp Thr Gly Gln Gly His Leu Gln Gln Lys Ser Val Arg Gln
                1890                1895                1900

Thr Val Leu Ser Glu Val Val Leu Glu Arg Thr Glu Leu Glu Ile Ser
1905                1910                1915                1920

Tyr Ala Pro Arg Leu Asp Gln Glu Lys Glu Glu Leu Leu Arg Lys Lys
                1925                1930                1935

Leu Gln Leu Asn Pro Thr Pro Ala Asn Arg Ser Arg Tyr Gln Ser Arg
                1940                1945                1950

Lys Val Glu Asn Met Lys Ala Ile Thr Ala Arg Arg Ile Leu Gln Gly
                1955                1960                1965

Leu Gly His Tyr Leu Lys Ala Glu Gly Lys Val Glu Cys Tyr Arg Thr
            1970                1975                1980

Leu His Pro Val Pro Leu Tyr Ser Ser Ser Val Asn Arg Ala Phe Ser
1985                1990                1995                2000

Ser Pro Lys Val Ala Val Glu Ala Cys Asn Ala Met Leu Lys Glu Asn
                2005                2010                2015

Phe Pro Thr Val Ala Ser Tyr Cys Ile Ile Pro Glu Tyr Asp Ala Tyr
                2020                2025                2030

```
Leu Asp Met Val Asp Gly Ala Ser Cys Cys Leu Asp Thr Ala Ser Phe
                2035                2040                2045
Cys Pro Ala Lys Leu Arg Ser Phe Pro Lys Lys His Ser Tyr Leu Glu
                2050                2055                2060
Pro Thr Ile Arg Ser Ala Val Pro Ser Ala Ile Gln Asn Thr Leu Gln
2065                2070                2075                2080
Asn Val Leu Ala Ala Ala Thr Lys Arg Asn Cys Asn Val Thr Gln Met
                2085                2090                2095
Arg Glu Leu Pro Val Leu Asp Ser Ala Ala Phe Asn Val Glu Cys Phe
                2100                2105                2110
Lys Lys Tyr Ala Cys Asn Asn Glu Tyr Trp Glu Thr Phe Lys Glu Asn
                2115                2120                2125
Pro Ile Arg Leu Thr Glu Glu Asn Val Val Asn Tyr Ile Thr Lys Leu
                2130                2135                2140
Lys Gly Pro Lys Ala Ala Ala Leu Phe Ala Lys Thr His Asn Leu Asn
2145                2150                2155                2160
Met Leu Gln Asp Ile Pro Met Asp Arg Phe Val Met Asp Leu Lys Arg
                2165                2170                2175
Asp Val Lys Val Thr Pro Gly Thr Lys His Thr Glu Glu Arg Pro Lys
                2180                2185                2190
Val Gln Val Ile Gln Ala Ala Asp Pro Leu Ala Thr Ala Tyr Leu Cys
                2195                2200                2205
Gly Ile His Arg Glu Leu Val Arg Arg Leu Asn Ala Val Leu Leu Pro
                2210                2215                2220
Asn Ile His Thr Leu Phe Asp Met Ser Ala Glu Asp Phe Asp Ala Ile
2225                2230                2235                2240
Ile Ala Glu His Phe Gln Pro Gly Asp Cys Val Leu Glu Thr Asp Ile
                2245                2250                2255
Ala Ser Phe Asp Lys Ser Glu Asp Asp Ala Met Ala Leu Thr Ala Leu
                2260                2265                2270
Met Ile Leu Glu Asp Leu Gly Val Asp Ala Glu Leu Leu Thr Leu Ile
                2275                2280                2285
Glu Ala Ala Phe Gly Glu Ile Ser Ser Ile His Leu Pro Thr Lys Thr
                2290                2295                2300
Lys Phe Lys Phe Gly Ala Met Met Lys Ser Gly Met Phe Leu Thr Leu
2305                2310                2315                2320
Phe Val Asn Thr Val Ile Asn Ile Val Ile Ala Ser Arg Val Leu Arg
                2325                2330                2335
Glu Arg Leu Thr Gly Ser Pro Cys Ala Ala Phe Ile Gly Asp Asp Asn
                2340                2345                2350
Ile Val Lys Gly Val Lys Ser Asp Lys Leu Met Ala Asp Arg Cys Ala
                2355                2360                2365
Thr Trp Leu Asn Met Glu Val Lys Ile Ile Asp Ala Val Val Gly Glu
                2370                2375                2380
Lys Ala Pro Tyr Phe Cys Gly Gly Phe Ile Leu Cys Asp Ser Val Thr
2385                2390                2395                2400
Gly Thr Ala Cys Arg Val Ala Asp Pro Leu Lys Arg Leu Phe Lys Leu
                2405                2410                2415
Gly Lys Pro Leu Ala Ala Asp Asp Glu His Asp Asp Asp Arg Arg Arg
                2420                2425                2430
Ala Leu His Glu Glu Ser Thr Arg Trp Asn Arg Val Gly Ile Leu Ser
                2435                2440                2445
```

```
Glu Leu Cys Lys Ala Val Glu Ser Arg Tyr Glu Thr Val Gly Thr Ser
    2450                2455                2460
Ile Ile Val Met Ala Met Thr Thr Leu Ala Ser Ser Val Lys Ser Phe
2465                2470                2475                2480
Ser Tyr Leu Arg Gly Ala Pro Ile Thr Leu Tyr Gly
            2485                2490

<210> SEQ ID NO 4
<211> LENGTH: 1476
<212> TYPE: DNA
<213> ORGANISM: Artificial Sequence
<220> FEATURE:
<223> OTHER INFORMATION: Description of Artificial Sequence; Note =
      synthetic construct
<221> NAME/KEY: CDS
<222> LOCATION: (1)...(1476)

<400> SEQUENCE: 4 atg gct gcg aga gcg tca ata tta aga ggg gaa aaa tta gat aaa tgg      48
Met Ala Ala Arg Ala Ser Ile Leu Arg Gly Glu Lys Leu Asp Lys Trp
 1               5                  10                  15 gaa aag att agg tta agg cca ggg gga aag aaa cat tat atg tta aaa      96
Glu Lys Ile Arg Leu Arg Pro Gly Gly Lys Lys His Tyr Met Leu Lys
             20                  25                  30 cac ata gta tgg gcg agc agg gag ctg gaa aga ttt gca ctt aac cct     144
His Ile Val Trp Ala Ser Arg Glu Leu Glu Arg Phe Ala Leu Asn Pro
         35                  40                  45 ggc ctt tta gaa aca tca gaa gga tgt aaa caa ata atg aaa cag cta     192
Gly Leu Leu Glu Thr Ser Glu Gly Cys Lys Gln Ile Met Lys Gln Leu
     50                  55                  60 caa cca gct ctc cag aca gga aca gag gaa ctt aaa tca tta tac aac     240
Gln Pro Ala Leu Gln Thr Gly Thr Glu Glu Leu Lys Ser Leu Tyr Asn
 65                  70                  75                  80 aca gta gca act ctc tat tgt gta cat gaa aag ata gaa gta cga gac     288
Thr Val Ala Thr Leu Tyr Cys Val His Glu Lys Ile Glu Val Arg Asp
                 85                  90                  95 acc aag gaa gcc tta gat aag ata gag gaa gaa caa aac aaa tgt cag     336
Thr Lys Glu Ala Leu Asp Lys Ile Glu Glu Glu Gln Asn Lys Cys Gln
            100                 105                 110 caa aaa acg cag cag gca aaa gcg gct gac ggg aaa gtc agt caa aat     384
Gln Lys Thr Gln Gln Ala Lys Ala Ala Asp Gly Lys Val Ser Gln Asn
        115                 120                 125 tat cct ata gtg cag aat ctc caa ggg caa atg gta cat caa gcc ata     432
Tyr Pro Ile Val Gln Asn Leu Gln Gly Gln Met Val His Gln Ala Ile
    130                 135                 140 tca cct aga acc ttg aat gca tgg gta aaa gta ata gaa gaa aag gct     480
Ser Pro Arg Thr Leu Asn Ala Trp Val Lys Val Ile Glu Glu Lys Ala
145                 150                 155                 160 ttt agc cca gag gta ata ccc atg ttt aca gca tta tca gaa gga gcc     528
Phe Ser Pro Glu Val Ile Pro Met Phe Thr Ala Leu Ser Glu Gly Ala
                165                 170                 175 acc cca caa gat tta aac acc atg tta aat aca gtg ggg gga cac caa     576
Thr Pro Gln Asp Leu Asn Thr Met Leu Asn Thr Val Gly Gly His Gln
            180                 185                 190 gca gcc atg caa atg tta aaa gat act att aat gaa gag gct gca gaa     624
Ala Ala Met Gln Met Leu Lys Asp Thr Ile Asn Glu Glu Ala Ala Glu
        195                 200                 205 tgg gat aga tta cat cca gtc cat gcg ggg cct att gca cca ggc cag     672
Trp Asp Arg Leu His Pro Val His Ala Gly Pro Ile Ala Pro Gly Gln
    210                 215                 220
```

```
atg aga gaa cca agg gga agt gac ata gca gga act act agt acc ctt    720
Met Arg Glu Pro Arg Gly Ser Asp Ile Ala Gly Thr Thr Ser Thr Leu
225                 230                 235                 240 cag gaa caa ata gca tgg atg aca agt aac cca cct att cca gtg gga    768
Gln Glu Gln Ile Ala Trp Met Thr Ser Asn Pro Pro Ile Pro Val Gly
            245                 250                 255 gac atc tat aaa aga tgg ata att ctg ggg tta aat aaa ata gtg aga    816
Asp Ile Tyr Lys Arg Trp Ile Ile Leu Gly Leu Asn Lys Ile Val Arg
        260                 265                 270 atg tat agc ccg gtc agc att ttg gac ata aga caa ggg cca aag gaa    864
Met Tyr Ser Pro Val Ser Ile Leu Asp Ile Arg Gln Gly Pro Lys Glu
    275                 280                 285 ccc ttt cga gac tat gta gat cgg ttc ttt aaa act tta aga gct gaa    912
Pro Phe Arg Asp Tyr Val Asp Arg Phe Phe Lys Thr Leu Arg Ala Glu
290                 295                 300 caa gct aca caa gaa gta aaa aat tgg atg aca gac acc ttg tta gtc    960
Gln Ala Thr Gln Glu Val Lys Asn Trp Met Thr Asp Thr Leu Leu Val
305                 310                 315                 320 caa aat gcg aac cca gat tgt aag acc att ttg aga gca tta gga cca   1008
Gln Asn Ala Asn Pro Asp Cys Lys Thr Ile Leu Arg Ala Leu Gly Pro
            325                 330                 335 ggg gct aca tta gaa gaa atg atg aca gca tgt cag ggg gtg gga gga   1056
Gly Ala Thr Leu Glu Glu Met Met Thr Ala Cys Gln Gly Val Gly Gly
        340                 345                 350 cct ggc cac aaa gca aga gta ttg gct gag gca atg agt caa aca aac   1104
Pro Gly His Lys Ala Arg Val Leu Ala Glu Ala Met Ser Gln Thr Asn
    355                 360                 365 agt gga aac ata atg atg cag aga agc aat ttt aaa ggc cct aga aga   1152
Ser Gly Asn Ile Met Met Gln Arg Ser Asn Phe Lys Gly Pro Arg Arg
370                 375                 380 att gtt aaa tgt ttt aac tgt ggc aag gaa ggg cac ata gcc aga aat   1200
Ile Val Lys Cys Phe Asn Cys Gly Lys Glu Gly His Ile Ala Arg Asn
385                 390                 395                 400 tgc aga gcc cct agg aaa aaa ggc tgt tgg aaa tgt gga aaa gaa gga   1248
Cys Arg Ala Pro Arg Lys Lys Gly Cys Trp Lys Cys Gly Lys Glu Gly
            405                 410                 415 cac caa atg aaa gac tgc act gag agg cag gct aat ttt tta ggg aaa   1296
His Gln Met Lys Asp Cys Thr Glu Arg Gln Ala Asn Phe Leu Gly Lys
        420                 425                 430 att tgg cct tcc cac aag ggg agg cca ggg aat ttc ctt cag aac aga   1344
Ile Trp Pro Ser His Lys Gly Arg Pro Gly Asn Phe Leu Gln Asn Arg
    435                 440                 445 cca gag cca aca gcc cca cca gca gag agc ttc agg ttc gaa gag aca   1392
Pro Glu Pro Thr Ala Pro Pro Ala Glu Ser Phe Arg Phe Glu Glu Thr
450                 455                 460 acc ccc gct ccg aaa cag gag ccg ata gaa agg gaa ccc tta act tcc   1440
Thr Pro Ala Pro Lys Gln Glu Pro Ile Glu Arg Glu Pro Leu Thr Ser
465                 470                 475                 480 ctc aaa tca ctc ttt ggc agc gac ccc ttg tct caa                   1476
Leu Lys Ser Leu Phe Gly Ser Asp Pro Leu Ser Gln
                485                 490
```

<210> SEQ ID NO 5
<211> LENGTH: 492
<212> TYPE: PRT
<213> ORGANISM: Artificial Sequence
<220> FEATURE:
<223> OTHER INFORMATION: Description of Artificial Sequence; Note = synthetic construct

<400> SEQUENCE: 5

```
Met Ala Ala Arg Ala Ser Ile Leu Arg Gly Glu Lys Leu Asp Lys Trp
  1               5                  10                  15
Glu Lys Ile Arg Leu Arg Pro Gly Gly Lys Lys His Tyr Met Leu Lys
             20                  25                  30
His Ile Val Trp Ala Ser Arg Glu Leu Glu Arg Phe Ala Leu Asn Pro
         35                  40                  45
Gly Leu Leu Glu Thr Ser Glu Gly Cys Lys Gln Ile Met Lys Gln Leu
     50                  55                  60
Gln Pro Ala Leu Gln Thr Gly Thr Glu Glu Leu Lys Ser Leu Tyr Asn
 65                  70                  75                  80
Thr Val Ala Thr Leu Tyr Cys Val His Glu Lys Ile Glu Val Arg Asp
                 85                  90                  95
Thr Lys Glu Ala Leu Asp Lys Ile Glu Glu Gln Asn Lys Cys Gln
            100                 105                 110
Gln Lys Thr Gln Gln Ala Lys Ala Ala Asp Gly Lys Val Ser Gln Asn
            115                 120                 125
Tyr Pro Ile Val Gln Asn Leu Gln Gly Gln Met Val His Gln Ala Ile
130                 135                 140
Ser Pro Arg Thr Leu Asn Ala Trp Val Lys Val Ile Glu Glu Lys Ala
145                 150                 155                 160
Phe Ser Pro Glu Val Ile Pro Met Phe Thr Ala Leu Ser Glu Gly Ala
                165                 170                 175
Thr Pro Gln Asp Leu Asn Thr Met Leu Asn Thr Val Gly Gly His Gln
            180                 185                 190
Ala Ala Met Gln Met Leu Lys Asp Thr Ile Asn Glu Glu Ala Ala Glu
            195                 200                 205
Trp Asp Arg Leu His Pro Val His Ala Gly Pro Ile Ala Pro Gly Gln
210                 215                 220
Met Arg Glu Pro Arg Gly Ser Asp Ile Ala Gly Thr Thr Ser Thr Leu
225                 230                 235                 240
Gln Glu Gln Ile Ala Trp Met Thr Ser Asn Pro Pro Ile Pro Val Gly
                245                 250                 255
Asp Ile Tyr Lys Arg Trp Ile Ile Leu Gly Leu Asn Lys Ile Val Arg
            260                 265                 270
Met Tyr Ser Pro Val Ser Ile Leu Asp Ile Arg Gln Gly Pro Lys Glu
            275                 280                 285
Pro Phe Arg Asp Tyr Val Asp Arg Phe Phe Lys Thr Leu Arg Ala Glu
290                 295                 300
Gln Ala Thr Gln Glu Val Lys Asn Trp Met Thr Asp Thr Leu Leu Val
305                 310                 315                 320
Gln Asn Ala Asn Pro Asp Cys Lys Thr Ile Leu Arg Ala Leu Gly Pro
                325                 330                 335
Gly Ala Thr Leu Glu Glu Met Met Thr Ala Cys Gln Gly Val Gly Gly
            340                 345                 350
Pro Gly His Lys Ala Arg Val Leu Ala Glu Ala Met Ser Gln Thr Asn
            355                 360                 365
Ser Gly Asn Ile Met Met Gln Arg Ser Asn Phe Lys Gly Pro Arg Arg
370                 375                 380
Ile Val Lys Cys Phe Asn Cys Gly Lys Glu Gly His Ile Ala Arg Asn
385                 390                 395                 400
Cys Arg Ala Pro Arg Lys Lys Gly Cys Trp Lys Cys Gly Lys Glu Gly
                405                 410                 415
```

```
His Gln Met Lys Asp Cys Thr Glu Arg Gln Ala Asn Phe Leu Gly Lys
            420                 425                 430

Ile Trp Pro Ser His Lys Gly Arg Pro Gly Asn Phe Leu Gln Asn Arg
            435                 440                 445

Pro Glu Pro Thr Ala Pro Ala Glu Ser Phe Arg Phe Glu Glu Thr
        450                 455                 460

Thr Pro Ala Pro Lys Gln Glu Pro Ile Glu Arg Glu Pro Leu Thr Ser
465                 470                 475                 480

Leu Lys Ser Leu Phe Gly Ser Asp Pro Leu Ser Gln
                485                 490

<210> SEQ ID NO 6
<211> LENGTH: 813
<212> TYPE: DNA
<213> ORGANISM: Artificial Sequence
<220> FEATURE:
<223> OTHER INFORMATION: Description of Artificial Sequence; Note =
      synthetic construct
<221> NAME/KEY: CDS
<222> LOCATION: (1)...(813)

<400> SEQUENCE: 6 atg agc cat att caa cgg gaa acg tct tgc tcg agg ccg cga tta aat      48
Met Ser His Ile Gln Arg Glu Thr Ser Cys Ser Arg Pro Arg Leu Asn
1               5                   10                  15 tcc aac atg gat gct gat tta tat ggg tat aaa tgg gct cgc gat aat      96
Ser Asn Met Asp Ala Asp Leu Tyr Gly Tyr Lys Trp Ala Arg Asp Asn
                20                  25                  30 gtc ggg caa tca ggt gcg aca atc tat cga ttg tat ggg aag ccc gat     144
Val Gly Gln Ser Gly Ala Thr Ile Tyr Arg Leu Tyr Gly Lys Pro Asp
            35                  40                  45 gcg cca gag ttg ttt ctg aaa cat ggc aaa ggt agc gtt gcc aat gat     192
Ala Pro Glu Leu Phe Leu Lys His Gly Lys Gly Ser Val Ala Asn Asp
        50                  55                  60 gtt aca gat gag atg gtc aga cta aac tgg ctg acg gaa ttt atg cct     240
Val Thr Asp Glu Met Val Arg Leu Asn Trp Leu Thr Glu Phe Met Pro
65                  70                  75                  80 ctt ccg acc atc aag cat ttt atc cgt act cct gat gat gca tgg tta     288
Leu Pro Thr Ile Lys His Phe Ile Arg Thr Pro Asp Asp Ala Trp Leu
                85                  90                  95 ctc acc act gcg atc ccc ggg aaa aca gca ttc cag gta tta gaa gaa     336
Leu Thr Thr Ala Ile Pro Gly Lys Thr Ala Phe Gln Val Leu Glu Glu
            100                 105                 110 tat cct gat tca ggt gaa aat att gtt gat gcg ctg gca gtg ttc ctg     384
Tyr Pro Asp Ser Gly Glu Asn Ile Val Asp Ala Leu Ala Val Phe Leu
        115                 120                 125 cgc cgg ttg cat tcg att cct gtt tgt aat tgt cct ttt aac agc gat     432
Arg Arg Leu His Ser Ile Pro Val Cys Asn Cys Pro Phe Asn Ser Asp
130                 135                 140 cgc gta ttt cgt ctc gct cag gcg caa tca cga atg aat aac ggt ttg     480
Arg Val Phe Arg Leu Ala Gln Ala Gln Ser Arg Met Asn Asn Gly Leu
145                 150                 155                 160 gtt gat gcg agt gat ttt gat gac gag cgt aat ggc tgg cct gtt gaa     528
Val Asp Ala Ser Asp Phe Asp Asp Glu Arg Asn Gly Trp Pro Val Glu
                165                 170                 175 caa gtc tgg aaa gaa atg cat aag ctt ttg cca ttc tca ccg gat tca     576
Gln Val Trp Lys Glu Met His Lys Leu Leu Pro Phe Ser Pro Asp Ser
            180                 185                 190 gtc gtc act cat ggt gat ttc tca ctt gat aac ctt att ttt gac gag     624
Val Val Thr His Gly Asp Phe Ser Leu Asp Asn Leu Ile Phe Asp Glu
        195                 200                 205
```

```
ggg aaa tta ata ggt tgt att gat gtt gga cga gtc gga atc gca gac    672
Gly Lys Leu Ile Gly Cys Ile Asp Val Gly Arg Val Gly Ile Ala Asp
    210                 215                 220 cga tac cag gat ctt gcc atc cta tgg aac tgc ctc ggt gag ttt tct    720
Arg Tyr Gln Asp Leu Ala Ile Leu Trp Asn Cys Leu Gly Glu Phe Ser
225                 230                 235                 240 cct tca tta cag aaa cgg ctt ttt caa aaa tat ggt att gat aat cct    768
Pro Ser Leu Gln Lys Arg Leu Phe Gln Lys Tyr Gly Ile Asp Asn Pro
                245                 250                 255 gat atg aat aaa ttg cag ttt cat ttg atg ctc gat gag ttt ttc        813
Asp Met Asn Lys Leu Gln Phe His Leu Met Leu Asp Glu Phe Phe
            260                 265                 270
```

<210> SEQ ID NO 7
<211> LENGTH: 271
<212> TYPE: PRT
<213> ORGANISM: Artificial Sequence
<220> FEATURE:
<223> OTHER INFORMATION: Description of Artificial Sequence; Note = synthetic construct

<400> SEQUENCE: 7

```
Met Ser His Ile Gln Arg Glu Thr Ser Cys Ser Arg Pro Arg Leu Asn
 1               5                  10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270
```

-continued

```
<210> SEQ ID NO 8
<211> LENGTH: 5076
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 8
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa actgtaagg     360 aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacgacc ctataactct ctacggctaa     540
cctgaatgga ctacgacata gtctagtccg ccaagatgtt cccgttccag ccaatgtatc     600
cgatgcagcc aatgccctat cgcaacccgt tcgcggcccc cgcaggccc tggttcccca     660 gaaccgaccc ttttctggcg atgcaggtgc aggaattaac ccgctcgatg gctaacctga     720
cgttcaagca acgccgggac gcgccacctg aggggccatc cgctaagaaa ccgaagaagg     780
aggcctcgca aaacagaaa gggggaggcc aagggaagaa gaagaagaac caagggaaga     840
agaaggctaa gacagggccg cctaatccga aggcacagaa tggaaacaag aagaagacca     900
acaagaaacc aggcaagaga cagcgcatgg tcatgaaatt ggaatctgac aagacgttcc     960
caatcatgtt ggaagggaag ataaacggct acgcttgtgt ggtcggaggg aagttattca    1020
ggccgatgca tgtggaaggc aagatcgaca acgacgttct ggccgcgctt aagacgaaga    1080
aagcatccaa atacgatctt gagtatgcag atgtgccaca gaacatgcgg gccgatacat    1140
tcaaatacac ccatgagaaa cccccaaggct attacagctg gcatcatgga gcagtccaat    1200
atgaaaatgg gcgttccacg gtgccgaaag gagttgggc caaggagac agcggacgac    1260 ccattctgga taaccaggga cgggtggtcg ctattgtgct gggaggtgtg aatgaaggat    1320
ctaggacagc cctttcagtc gtcatgtgga acgagaaggg agttaccgtg aagtatactc    1380
cggagaactg cgagcaatgg tcactagtga ccaccatgtg tctgctcgcc aatgtgacgt    1440
tcccatgtgc tcaaccacca atttgctacg acagaaaacc agcagagact ttggccatgc    1500
tcagcgttaa catccctgct gggaggatca gccgtaatta ttataattgg cttgtgctg    1560 gctactattg tggccatgta cgtgctgacc aaccagaaac ataattgaat acagcagcaa    1620
ttggcaagct gcttacatag aactcgcggc gattggcatg ccgctttaaa attttttattt    1680 tattttttctt ttcttttccg aatcggattt tgttttttaat atttcaaaaa aaaaaaaaaa    1740
aaaaaaaaaa aaaaaaaaaa aaaaaaaaaa gggaagagcg cggccgcgcg ctgggctacg    1800
tcttgctggc gttcgcgacg cgaggctgga tggccttccc cattatgatt cttctcgctt    1860
ccggcggcat cgggatgccc gcgttgcagg ccatgctgtc caggcaggta gatgacgacc    1920
atcagggaca gcttcaagga tcgctcgcgg ctcttaccag cctaacttcg atcactggac    1980
cgctgatcgt cacggcgatt tatgccgcct cggcgagcac atggaacggg ttggcatgga    2040
ttgtaggcgc cgccctatac cttgtctgcc tccccgcgtt gcgtcgcggt gcatggagcc    2100
```

```
gggccacctc gacctgaatg gaagccggcg gcacctcgct aacggattca ccactccaag    2160
aattggagcc aatcaattct tgcggagaac tgtgaatgcg caaaccaacc cttggcagaa    2220
catatccatc gcgtccgcca tctccagcag ccgcacgcgg cgcatctcgg gcagcgttgg    2280
gtcctggcca cgggtgcgca tgatcgtgct cctgtcgttg aggacccggc taggctggcg    2340
gggttgcctt actggttagc agaatgaatc accgatacgc gagcgaacgt gaagcgactg    2400
ctgctgcaaa acgtctgcga cctgagcaac aacatgaatg gtcttcggtt tccgtgtttc    2460
gtaaagtctg gaaacgcgga agtcagcgcc ctgcaccatt atgttccgga tctgcatcgc    2520
aggatgctgc tggctaccct gtggaacacc tacatctgta ttaacgaagc gctggcattg    2580
accctgagtg attttctct ggtcccgccg catccatacc gccagttgtt taccctcaca    2640
acgttccagt aaccgggcat gttcatcatc agtaacccgt atcgtgagca tcctctctcg    2700
tttcatcggt atcattaccc ccatgaacag aaatccccct tacacggagg catcagtgac    2760
caaacaggaa aaaccgccc ttaacatggc ccgctttatc agaagccaga cattaacgct    2820
tctggagaaa ctcaacgagc tggacgcgga tgaacaggca gacatctgtg aatcgcttca    2880
cgaccacgct gatgagcttt accgcagctg cctcgcgcgt ttcggtgatg acggtgaaaa    2940
cctctgacac atgcagctcc cggagacggt cacagcttgt ctgtaagcgg atgccgggag    3000
cagacaagcc cgtcagggcg cgtcagcggg tgttggcggg tgtcggggcg cagccatgac    3060
ccagtcacgt agcgatagcg gagtgtatac tggcttaact atgcggcatc agagcagatt    3120
gtactgagag tgcaccatat atgcggtgtg aaataccgca cagatgcgta aggagaaaat    3180
accgcatcag gcgctcttcc gcttcctcgc tcactgactc gctgcgctcg gtcgttcggc    3240
tgcggcgagc ggtatcagct cactcaaagg cggtaatacg gttatccaca gaatcagggg    3300
ataacgcagg aaagaacatg tgagcaaaag gccagcaaaa ggccaggaac cgtaaaaagg    3360
ccgcgttgct ggcgtttttc cataggctcc gcccccctga cgagcatcac aaaaatcgac    3420
gctcaagtca gaggtggcga aacccgacag gactataaag ataccaggcg tttccccctg    3480
gaagctccct cgtgcgctct cctgttccga ccctgccgct taccggatac ctgtccgcct    3540
ttctcccttc gggaagcgtg gcgctttctc atagctcacg ctgtaggtat ctcagttcgg    3600
tgtaggtcgt tcgctccaag ctgggctgtg tgcacgaacc ccccgttcag cccgaccgct    3660
gcgccttatc cggtaactat cgtcttgagt ccaacccggt aagacacgac ttatcgccac    3720
tggcagcagc cactggtaac aggattagca gagcgaggta tgtaggcggt gctacagagt    3780
tcttgaagtg gtggcctaac tacggctaca ctagaaggac agtatttggt atctgcgctc    3840
tgctgaagcc agttaccttc ggaaaaagag ttggtagctc ttgatccggc aaacaaacca    3900
ccgctggtag cggtggtttt tttgtttgca agcagcagat tacgcgcaga aaaaaggat    3960 ctcaagaaga tcctttgatc ttttctacgg ggtctgacgc tcagtggaac gaaaactcac    4020
gttaagggat tttggtcatg aacaataaaa ctgtctgctt acataaacag taatacaagg    4080
ggtgttatga gccatattca acgggaaacg tcttgctcga ggccgcgatt aaattccaac    4140
atggatgctg atttatatgg gtataaatgg ctcgcgata atgtcgggca atcaggtgcg    4200
acaatctatc gattgtatgg gaagcccgat gcgccagagt tgtttctgaa acatggcaaa    4260
ggtagcgttg ccaatgatgt tacagatgag atggtcagac taaactggct gacggaattt    4320
atgcctcttc cgaccatcaa gcattttatc cgtactcctg atgatgcatg gttactcacc    4380
actgcgatcc ccgggaaaac agcattccag gtattagaag aatatcctga ttcaggtgaa    4440
aatattgttg atgcgctggc agtgttcctg cgccggttgc attcgattcc tgtttgtaat    4500
```

-continued

```
tgtccttta  acagcgatcg  cgtatttcgt  ctcgctcagg  cgcaatcacg  aatgaataac    4560
ggtttggttg  atgcgagtga  ttttgatgac  gagcgtaatg  gctggcctgt  tgaacaagtc    4620
tggaaagaaa  tgcataagct  tttgccattc  tcaccggatt  cagtcgtcac  tcatggtgat    4680
ttctcacttg  ataaccttat  ttttgacgag  gggaaattaa  taggttgtat  tgatgttgga    4740
cgagtcggaa  tcgcagaccg  ataccaggat  cttgccatcc  tatggaactg  cctcggtgag    4800
ttttctcctt  cattacagaa  acggctttt  caaaaatatg  gtattgataa  tcctgatatg    4860
aataaattgc  agtttcattt  gatgctcgat  gagtttttct  aagaattctc  atgtttgaca    4920
gcttatcatc  gataagcttt  aatgcggtag  tttatcacag  ttaaattgct  aacgcagtca    4980
ggcaccgtgt  atgaaatcta  acaatgcgct  catcgtcatc  ctcggcaccg  tcaccctgga    5040
tgctgtctag  aggatcccta  atacgactca  ctatag                              5076
```

<210> SEQ ID NO 9
<211> LENGTH: 1026
<212> TYPE: DNA
<213> ORGANISM: Artificial Sequence
<220> FEATURE:
<223> OTHER INFORMATION: Description of Artificial Sequence; Note = synthetic construct
<221> NAME/KEY: CDS
<222> LOCATION: (1)...(1026)

<400> SEQUENCE: 9

```
atg ttc ccg ttc cag cca atg tat ccg atg cag cca atg ccc tat cgc        48
Met Phe Pro Phe Gln Pro Met Tyr Pro Met Gln Pro Met Pro Tyr Arg
 1               5                  10                  15 aac ccg ttc gcg gcc ccg cgc agg ccc tgg ttc ccc aga acc gac cct        96
Asn Pro Phe Ala Ala Pro Arg Arg Pro Trp Phe Pro Arg Thr Asp Pro
             20                  25                  30 ttt ctg gcg atg cag gtg cag gaa tta acc cgc tcg atg gct aac ctg       144
Phe Leu Ala Met Gln Val Gln Glu Leu Thr Arg Ser Met Ala Asn Leu
         35                  40                  45 acg ttc aag caa cgc cgg gac gcg cca cct gag ggg cca tcc gct aag       192
Thr Phe Lys Gln Arg Arg Asp Ala Pro Pro Glu Gly Pro Ser Ala Lys
     50                  55                  60 aaa ccg aag aag gag gcc tcg caa aaa cag aaa ggg gga ggc caa ggg       240
Lys Pro Lys Lys Glu Ala Ser Gln Lys Gln Lys Gly Gly Gly Gln Gly
 65                  70                  75                  80 aag aag aag aag aac caa ggg aag aag aag gct aag aca ggg ccg cct       288
Lys Lys Lys Lys Asn Gln Gly Lys Lys Lys Ala Lys Thr Gly Pro Pro
                 85                  90                  95 aat ccg aag gca cag aat gga aac aag aag aag acc aac aag aaa cca       336
Asn Pro Lys Ala Gln Asn Gly Asn Lys Lys Lys Thr Asn Lys Lys Pro
            100                 105                 110 ggc aag aga cag cgc atg gtc atg aaa ttg gaa tct gac aag acg ttc       384
Gly Lys Arg Gln Arg Met Val Met Lys Leu Glu Ser Asp Lys Thr Phe
        115                 120                 125 cca atc atg ttg gaa ggg aag ata aac ggc tac gct tgt gtg gtc gga       432
Pro Ile Met Leu Glu Gly Lys Ile Asn Gly Tyr Ala Cys Val Val Gly
    130                 135                 140 ggg aag tta ttc agg ccg atg cat gtg gaa ggc aag atc gac aac gac       480
Gly Lys Leu Phe Arg Pro Met His Val Glu Gly Lys Ile Asp Asn Asp
145                 150                 155                 160 gtt ctg gcc gcg ctt aag acg aag aaa gca tcc aaa tac gat ctt gag       528
Val Leu Ala Ala Leu Lys Thr Lys Lys Ala Ser Lys Tyr Asp Leu Glu
                165                 170                 175
```

```
tat gca gat gtg cca cag aac atg cgg gcc gat aca ttc aaa tac acc    576
Tyr Ala Asp Val Pro Gln Asn Met Arg Ala Asp Thr Phe Lys Tyr Thr
            180                 185                 190 cat gag aaa ccc caa ggc tat tac agc tgg cat cat gga gca gtc caa    624
His Glu Lys Pro Gln Gly Tyr Tyr Ser Trp His His Gly Ala Val Gln
        195                 200                 205 tat gaa aat ggg cgt ttc acg gtg ccg aaa gga gtt ggg gcc aag gga    672
Tyr Glu Asn Gly Arg Phe Thr Val Pro Lys Gly Val Gly Ala Lys Gly
    210                 215                 220 gac agc gga cga ccc att ctg gat aac cag gga cgg gtg gtc gct att    720
Asp Ser Gly Arg Pro Ile Leu Asp Asn Gln Gly Arg Val Val Ala Ile
225                 230                 235                 240 gtg ctg gga ggt gtg aat gaa gga tct agg aca gcc ctt tca gtc gtc    768
Val Leu Gly Gly Val Asn Glu Gly Ser Arg Thr Ala Leu Ser Val Val
                245                 250                 255 atg tgg aac gag aag gga gtt acc gtg aag tat act ccg gag aac tgc    816
Met Trp Asn Glu Lys Gly Val Thr Val Lys Tyr Thr Pro Glu Asn Cys
            260                 265                 270 gag caa tgg tca cta gtg acc acc atg tgt ctg ctc gcc aat gtg acg    864
Glu Gln Trp Ser Leu Val Thr Thr Met Cys Leu Leu Ala Asn Val Thr
        275                 280                 285 ttc cca tgt gct caa cca cca att tgc tac gac aga aaa cca gca gag    912
Phe Pro Cys Ala Gln Pro Pro Ile Cys Tyr Asp Arg Lys Pro Ala Glu
    290                 295                 300 act ttg gcc atg ctc agc gtt aac atc cct gct ggg agg atc agc cgt    960
Thr Leu Ala Met Leu Ser Val Asn Ile Pro Ala Gly Arg Ile Ser Arg
305                 310                 315                 320 aat tat tat aat tgg ctt ggt gct ggc tac tat tgt ggc cat gta cgt   1008
Asn Tyr Tyr Asn Trp Leu Gly Ala Gly Tyr Tyr Cys Gly His Val Arg
                325                 330                 335 gct gac caa cca gaa aca                                           1026
Ala Asp Gln Pro Glu Thr
        340

<210> SEQ ID NO 10
<211> LENGTH: 342
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 10

Met Phe Pro Phe Gln Pro Met Tyr Pro Met Gln Pro Met Pro Tyr Arg
 1               5                  10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Glu Gly Pro Ser Ala Lys
    50                  55                  60

Lys Pro Lys Lys Glu Ala Ser Gln Lys Gln Lys Gly Gly Gln Gly
65                  70                  75                  80

Lys Lys Lys Lys Asn Gln Gly Lys Lys Ala Lys Thr Gly Pro Pro
                85                  90                  95

Asn Pro Lys Ala Gln Asn Gly Asn Lys Lys Thr Asn Lys Lys Pro
            100                 105                 110

Gly Lys Arg Gln Arg Met Val Met Lys Leu Glu Ser Asp Lys Thr Phe
        115                 120                 125
```

-continued

```
Pro Ile Met Leu Glu Gly Lys Ile Asn Gly Tyr Ala Cys Val Val Gly
    130                 135                 140
Gly Lys Leu Phe Arg Pro Met His Val Glu Gly Lys Ile Asp Asn Asp
145                 150                 155                 160
Val Leu Ala Ala Leu Lys Thr Lys Lys Ala Ser Lys Tyr Asp Leu Glu
                165                 170                 175
Tyr Ala Asp Val Pro Gln Asn Met Arg Ala Asp Thr Phe Lys Tyr Thr
            180                 185                 190
His Glu Lys Pro Gln Gly Tyr Tyr Ser Trp His His Gly Ala Val Gln
        195                 200                 205
Tyr Glu Asn Gly Arg Phe Thr Val Pro Lys Gly Val Gly Ala Lys Gly
    210                 215                 220
Asp Ser Gly Arg Pro Ile Leu Asp Asn Gln Gly Arg Val Val Ala Ile
225                 230                 235                 240
Val Leu Gly Gly Val Asn Glu Gly Ser Arg Thr Ala Leu Ser Val Val
                245                 250                 255
Met Trp Asn Glu Lys Gly Val Thr Val Lys Tyr Thr Pro Glu Asn Cys
            260                 265                 270
Glu Gln Trp Ser Leu Val Thr Thr Met Cys Leu Leu Ala Asn Val Thr
        275                 280                 285
Phe Pro Cys Ala Gln Pro Pro Ile Cys Tyr Asp Arg Lys Pro Ala Glu
    290                 295                 300
Thr Leu Ala Met Leu Ser Val Asn Ile Pro Ala Gly Arg Ile Ser Arg
305                 310                 315                 320
Asn Tyr Tyr Asn Trp Leu Gly Ala Gly Tyr Tyr Cys Gly His Val Arg
                325                 330                 335
Ala Asp Gln Pro Glu Thr
            340
```

<210> SEQ ID NO 11
<211> LENGTH: 6989
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 11

| | | | | | |
|---|---|---|---|---|---|
| ataggcggcg | catgagagaa | gcccagacca | attacctacc | caaaatggag | aaagttcacg | 60 |
| ttgacatcga | ggaagacagc | ccattcctca | gagctttgca | gcggagcttc | ccgcagtttg | 120 |
| aggtagaagc | caagcaggtc | actgataatg | accatgctaa | tgccagagcg | ttttcgcatc | 180 |
| tggcttcaaa | actgatcgaa | acggaggtgg | acccatccga | cacgatcctt | gacattggaa | 240 |
| gtgcgcccgc | ccgcagaatg | tattctaagc | acaagtatca | ttgtatctgt | ccgatgagat | 300 |
| gtgcggaaga | tccggacaga | ttgtataagt | atgcaactaa | gctgaagaaa | aactgtaagg | 360 |
| aaataactga | taaggaattg | acaagaaaaa | tgaaggagct | cgccgccgtc | atgagcgacc | 420 |
| ctgacctgga | aactgagact | atgtgcctcc | acgacgacga | gtcgtgtcgc | tacgaagggc | 480 |
| aagtcgctgt | ttaccaggat | gtatacgcgg | ttgacggacc | ctataactct | ctacggctaa | 540 |
| cctgaatgga | ctacgacata | gtctagtccg | ccaagatgtc | actagtgacc | accatgtgtc | 600 |
| tgctcgccaa | tgtgacgttc | ccatgtgctc | aaccaccaat | ttgctacgac | agaaaaccag | 660 |
| cagagacttt | ggccatgctc | agcgttaacg | ttgacaaccc | gggctacgat | gagctgctgg | 720 |
| aagcagctgt | taagtgcccc | ggaaggaaaa | ggagatccac | cgaggagctg | tttaaggagt | 780 |

-continued

```
ataagctaac gcgcccttac atggccagat gcatcagatg tgcagttggg agctgccata      840
gtccaatagc aatcgaggca gtaaagagcg acgggcacga cggttatgtt agacttcaga      900
cttcctcgca gtatggcctg gattcctccg gcaacttaaa gggcaggacc atgcggtatg      960
acatgcacgg gaccattaaa gagataccac tacatcaagt gtcactccat acatctcgcc     1020
cgtgtcacat tgtggatggg cacggttatt tcctgcttgc caggtgcccg gcagggact      1080 ccatcaccat ggaatttaag aaagattccg tcacacactc ctgctcggtg ccgtatgaag     1140
tgaaatttaa tcctgtaggc agagaactct atactcatcc cccagaacac ggagtagagc     1200
aagcgtgcca agtctacgca catgatgcac agaacagagg agcttatgtc gagatgcacc     1260
tcccaggctc agaagtggac agcagtttgg tttccttgag cggcagttca gtcaccgtga     1320
cacctcctgt tgggactagc gccctggtgg aatgcgagtg tggcggcaca aagatctcca     1380
agaccatcaa caagacaaaa cagttcagcc agtgcacaaa gaaggagcag tgcagagcat     1440
atcggctgca gaacgataag tgggtgtata attctgacaa actgcccaaa gcagcgggag     1500
ccaccttaaa aggaaaactg catgtcccat tcttgctggc agacggcaaa tgcaccgtgc     1560
ctctagcacc agaacctatg ataaccttcg gtttcagatc agtgtcactg aaactgcacc     1620
ctaagaatcc cacatatcta accacccgcc aacttgctga tgagcctcac tacacgcatg     1680
agctcatatc tgaaccagct gttaggaatt ttaccgtcac cggaaaaggg tgggagtttg     1740
tatggggaaa ccacccgccg aaaaggtttt gggcacagga acagcacccc ggaaatccac     1800
atgggctacc gcacgaggtg ataactcatt attaccacag atacctatg tccaccatcc      1860 tgggtttgtc aatttgtgcc gccattgcaa ccgtttccgt tgcagcgtct acctggctgt     1920
tttgcagatc tagagttgcg tgcctaactc cttaccggct aacacctaac gctaggatac     1980
cattttgtct ggctgtgctt tgctgcgccc gcactgcccg ggccgagacc acctgggagt     2040
ccttggatca cctatggaac aataaccaac agatgttctg gattcaattg ctgatccctc     2100
tggccgcctt gatcgtagtg actcgcctgc tcaggtgcgt gtgctgtgtc gtgcctttt      2160 tagtcatggc cggcgccgca ggcgccggcg cctacgagca cgcgaccacg atgccgagcc     2220
aagcgggaat ctcgtataac actatagtca acagagcagg ctacgcacca ctccctatca     2280
gcataacacc aacaaagatc aagctgtatac ctacagtgaa cttggagtac gtcacctgcc     2340
actacaaaac aggaatggat tcaccagcca tcaaatgctg cggatctcag gaatgcactc     2400
caacttacag gcctgatgaa cagtgcaaag tcttcacagg ggtttacccg ttcatgtggg     2460
gtggtgcata ttgcttttgc gacactgaga cacccaagt cagcaaggcc tacgtaatga     2520
aatctgacga ctgccttgcg gatcatgctg aagcatataa agcgcacaca gcctcagtgc     2580
aggcgttcct caacatcaca gtgggagaac actctattgt gactaccgtg tatgtgaatg     2640
gagaaactcc tgtgaatttc aatggggtca aattaactgc aggtccgctt ccacagctt     2700 ggacacccctt tgatcgcaaa atcgtgcagt atgccgggga gatctataat tatgattttc     2760
ctgagtatgg ggcaggacaa ccaggagcat ttggagatat acaatccaga acagtctcaa     2820
gctcagatct gtatgccaat accaacctag tgctgcagag acccaaagca ggagcgatcc     2880
acgtgccata cactcaggca ccttcgggtt ttgagcaatg gaagaaagat aaagctccat     2940
cattgaaatt taccgcccct ttcggatgcg aaatatatac aaacccatt cgcgccgaaa      3000 actgtactgt agggtcaatt ccattagcct ttgacattcc cgacgccttg ttcaccaggg     3060
tgtcagaaac accgacactt tcagcggccg aatgcactct taacgagtgc gtgtattctt     3120
ccgactttgg tgggatcgcc acggtcaagt actcggccag caagtcaggc aagtgcgcag     3180
```

-continued

```
tccatgtgcc atcagggact gctaccctaa aagaagcagc agtcgagcta accgagcaag      3240
ggtcggcgac tatccatttc tcgaccgcaa atatccaccc ggagttcagg ctccaaatat      3300
gcacatcata tgttacgtgc aaaggtgatt gtcacccccc gaaagaccat attgtgacac      3360
accctcagta tcacgcccaa acatttacag ccgcggtgtc aaaaaccgcg tggacgtggt      3420
taacatccct gctgggagga tcagccgtaa ttattataat tggcttggtg ctggctacta      3480
ttgtggccat gtacgtgctg accaaccaga acataattg aatacagcag caattggcaa      3540
gctgcttaca tagaactcgc ggcgattggc atgccgcttt aaaatttta ttttatttt       3600 cttttctttt ccgaatcgga ttttgttttt aatatttcaa aaaaaaaaaa aaaaaaaaa      3660 aaaaaaaaaa aaaaaaaaaa aaagggaaga gcgcggccgc gcgctgggct acgtcttgct      3720
ggcgttcgcg acgcgaggct ggatggcctt ccccattatg attcttctcg cttccggcgg      3780
catcgggatg cccgcgttgc aggccatgct gtccaggcag gtagatgacg accatcaggg      3840
acagcttcaa ggatcgctcg cggctcttac cagcctaact tcgatcactg gaccgctgat      3900
cgtcacggcg atttatgccg cctcggcgag cacatggaac gggttggcat ggattgtagg      3960
cgccgcccta taccttgtct gcctcccgc gttgcgtcgc ggtgcatgga gccgggccac       4020
ctcgacctga atggaagccg gcggcacctc gctaacggat tcaccactcc aagaattgga      4080
gccaatcaat tcttgcggag aactgtgaat gcgcaaacca accttggca gaacatatcc       4140 atcgcgtccg ccatctccag cagccgcacg cggcgcatct cgggcagcgt gggtcctgg       4200 ccacgggtgc gcatgatcgt gctcctgtcg ttgaggaccc ggctaggctg gcggggttgc      4260
cttactggtt agcagaatga atcaccgata cgcgagcgaa cgtgaagcga ctgctgctgc      4320
aaaacgtctg cgacctgagc aacaacatga atggtcttcg gtttccgtgt ttcgtaaagt      4380
ctggaaacgc ggaagtcagc gccctgcacc attatgttcc ggatctgcat cgcaggatgc      4440
tgctggctac cctgtggaac acctacatct gtattaacga agcgctggca ttgaccctga      4500 gtgattttc tctggtcccg ccgcatccat accgccagtt gtttaccctc acaacgttcc       4560
agtaaccggg catgttcatc atcagtaacc cgtatcgtga gcatcctctc tcgtttcatc     4620
ggtatcatta cccccatgaa cagaaatccc ccttacacgg aggcatcagt gaccaaacag     4680
gaaaaaaccg cccttaacat ggcccgcttt atcagaagcc agacattaac gcttctggag     4740
aaactcaacg agctggacgc ggatgaacag gcagacatct gtgaatcgct tcacgaccac     4800
gctgatgagc tttaccgcag ctgcctcgcg cgtttcggtg atgacggtga aaacctctga     4860
cacatgcagc tcccggagac ggtcacagct tgtctgtaag cggatgccgg gagcagacaa     4920
gcccgtcagg gcgcgtcagc gggtgttggc gggtgtcggg gcgcagccat gacccagtca     4980
cgtagcgata gcggagtgta tactggctta actatgcggc atcagagcag attgtactga     5040
gagtgcacca tatatgcggt gtgaaatacc gcacagatgc gtaaggagaa aataccgcat     5100
caggcgctct tccgcttcct cgctcactga ctcgctgcgc tcggtcgttc ggctgcggcg     5160
agcggtatca gctcactcaa aggcggtaat acggttatcc acagaatcag gggataacgc     5220
aggaaagaac atgtgagcaa aaggccagca aaaggccagg aaccgtaaaa aggccgcgtt     5280
gctggcgttt ttccataggc tccgcccccc tgacgagcat cacaaaaatc gacgctcaag     5340
tcagaggtgg cgaaacccga caggactata aagataccag gcgtttcccc ctggaagctc     5400
cctcgtgcgc tctcctgttc cgaccctgcc gcttaccgga tacctgtccg cctttctccc     5460
ttcgggaagc gtggcgcttt ctcatagctc acgctgtagg tatctcagtt cggtgtaggt     5520
cgttcgctcc aagctgggct gtgtgcacga acccccgtt cagcccgacc gctgcgcctt      5580
```

-continued

```
atccggtaac tatcgtcttg agtccaaccc ggtaagacac gacttatcgc cactggcagc    5640
agccactggt aacaggatta gcagagcgag gtatgtaggc ggtgctacag agttcttgaa    5700
gtggtggcct aactacggct acactagaag gacagtattt ggtatctgcg ctctgctgaa    5760
gccagttacc ttcggaaaaa gagttggtag ctcttgatcc ggcaaacaaa ccaccgctgg    5820
tagcggtggt ttttttgttt gcaagcagca gattacgcgc agaaaaaaag gatctcaaga    5880
agatcctttg atcttttcta cggggtctga cgctcagtgg aacgaaaact cacgttaagg    5940
gattttggtc atgaacaata aaactgtctg cttacataaa cagtaataca agggtgtta    6000 tgagccatat tcaacgggaa acgtcttgct cgaggccgcg attaaattcc aacatggatg    6060
ctgatttata tgggtataaa tgggctcgcg ataatgtcgg gcaatcaggt gcgacaatct    6120
atcgattgta tgggaagccc gatgcgccag agttgtttct gaaacatggc aaaggtagcg    6180
ttgccaatga tgttacagat gagatggtca gactaaactg gctgacggaa tttatgcctc    6240
ttccgaccat caagcatttt atccgtactc ctgatgatgc atggttactc accactgcga    6300
tccccgggaa aacagcattc caggtattag aagaatatcc tgattcaggt gaaaatattg    6360
ttgatgcgct ggcagtgttc ctgcgccggt tgcattcgat tcctgtttgt aattgtcctt    6420
ttaacagcga tcgcgtattt cgtctcgctc aggcgcaatc acgaatgaat aacggtttgg    6480
ttgatgcgag tgattttgat gacgagcgta atggctggcc tgttaacaa gtctggaaag    6540 aaatgcataa gcttttgcca ttctcaccgg attcagtcgt cactcatggt gatttctcac    6600
ttgataacct tattttgac gaggggaaat taataggttg tattgatgtt ggacgagtcg    6660
gaatcgcaga ccgataccag gatcttgcca tcctatggaa ctgcctcggt gagttttctc    6720
cttcattaca gaaacggctt tttcaaaaat atggtattga taatcctgat atgaataaat    6780
tgcagtttca tttgatgctc gatgagtttt tctaagaatt ctcatgtttg acagcttatc    6840
atcgataagc tttaatgcgg tagtttatca cagttaaatt gctaacgcag tcaggcaccg    6900
tgtatgaaat ctaacaatgc gctcatcgtc atcctcggca ccgtcaccct ggatgctgtc    6960
tagaggatcc ctaatacgac tcactatag                                      6989
```

<210> SEQ ID NO 12
<211> LENGTH: 2943
<212> TYPE: DNA
<213> ORGANISM: Artificial Sequence
<220> FEATURE:
<223> OTHER INFORMATION: Description of Artificial Sequence; Note = synthetic construct
<221> NAME/KEY: CDS
<222> LOCATION: (1)...(2943)

<400> SEQUENCE: 12

```
atg tca cta gtg acc acc atg tgt ctg ctc gcc aat gtg acg ttc cca        48
Met Ser Leu Val Thr Thr Met Cys Leu Leu Ala Asn Val Thr Phe Pro
  1               5                  10                  15 tgt gct caa cca cca att tgc tac gac aga aaa cca gca gag act ttg        96
Cys Ala Gln Pro Pro Ile Cys Tyr Asp Arg Lys Pro Ala Glu Thr Leu
                 20                  25                  30 gcc atg ctc agc gtt aac gtt gac aac ccg ggc tac gat gag ctg ctg       144
Ala Met Leu Ser Val Asn Val Asp Asn Pro Gly Tyr Asp Glu Leu Leu
             35                  40                  45 gaa gca gct gtt aag tgc ccc gga agg aaa agg aga tcc acc gag gag       192
Glu Ala Ala Val Lys Cys Pro Gly Arg Lys Arg Arg Ser Thr Glu Glu
         50                  55                  60
```

-continued

| | | |
|---|---|---|
| ctg ttt aag gag tat aag cta acg cgc cct tac atg gcc aga tgc atc<br>Leu Phe Lys Glu Tyr Lys Leu Thr Arg Pro Tyr Met Ala Arg Cys Ile<br>65                     70                   75                 80 | 240 |
| aga tgt gca gtt ggg agc tgc cat agt cca ata gca atc gag gca gta<br>Arg Cys Ala Val Gly Ser Cys His Ser Pro Ile Ala Ile Glu Ala Val<br>                   85                   90                   95 | 288 |
| aag agc gac ggg cac gac ggt tat gtt aga ctt cag act tcc tcg cag<br>Lys Ser Asp Gly His Asp Gly Tyr Val Arg Leu Gln Thr Ser Ser Gln<br>                100                  105                  110 | 336 |
| tat ggc ctg gat tcc tcc ggc aac tta aag ggc agg acc atg cgg tat<br>Tyr Gly Leu Asp Ser Ser Gly Asn Leu Lys Gly Arg Thr Met Arg Tyr<br>115                     120                  125 | 384 |
| gac atg cac ggg acc att aaa gag ata cca cta cat caa gtg tca ctc<br>Asp Met His Gly Thr Ile Lys Glu Ile Pro Leu His Gln Val Ser Leu<br>130                     135                  140 | 432 |
| cat aca tct cgc ccg tgt cac att gtg gat ggg cac ggt tat ttc ctg<br>His Thr Ser Arg Pro Cys His Ile Val Asp Gly His Gly Tyr Phe Leu<br>145                     150                  155                  160 | 480 |
| ctt gcc agg tgc ccg gca ggg gac tcc atc acc atg gaa ttt aag aaa<br>Leu Ala Arg Cys Pro Ala Gly Asp Ser Ile Thr Met Glu Phe Lys Lys<br>                     165                  170                  175 | 528 |
| gat tcc gtc aca cac tcc tgc tcg gtg ccg tat gaa gtg aaa ttt aat<br>Asp Ser Val Thr His Ser Cys Ser Val Pro Tyr Glu Val Lys Phe Asn<br>                     180                  185                  190 | 576 |
| cct gta ggc aga gaa ctc tat act cat ccc cca gaa cac gga gta gag<br>Pro Val Gly Arg Glu Leu Tyr Thr His Pro Pro Glu His Gly Val Glu<br>                     195                  200                  205 | 624 |
| caa gcg tgc caa gtc tac gca cat gat gca cag aac aga gga gct tat<br>Gln Ala Cys Gln Val Tyr Ala His Asp Ala Gln Asn Arg Gly Ala Tyr<br>210                     215                  220 | 672 |
| gtc gag atg cac ctc cca ggc tca gaa gtg gac agc agt ttg gtt tcc<br>Val Glu Met His Leu Pro Gly Ser Glu Val Asp Ser Ser Leu Val Ser<br>225                     230                  235                  240 | 720 |
| ttg agc ggc agt tca gtc acc gtg aca cct cct gtt ggg act agc gcc<br>Leu Ser Gly Ser Ser Val Thr Val Thr Pro Pro Val Gly Thr Ser Ala<br>                     245                  250                  255 | 768 |
| ctg gtg gaa tgc gag tgt ggc ggc aca aag atc tcc aag acc atc aac<br>Leu Val Glu Cys Glu Cys Gly Gly Thr Lys Ile Ser Lys Thr Ile Asn<br>                     260                  265                  270 | 816 |
| aag aca aaa cag ttc agc cag tgc aca aag aag gag cag tgc aga gca<br>Lys Thr Lys Gln Phe Ser Gln Cys Thr Lys Lys Glu Gln Cys Arg Ala<br>275                     280                  285 | 864 |
| tat cgg ctg cag aac gat aag tgg gtg tat aat tct gac aaa ctg ccc<br>Tyr Arg Leu Gln Asn Asp Lys Trp Val Tyr Asn Ser Asp Lys Leu Pro<br>290                     295                  300 | 912 |
| aaa gca gcg gga gcc acc tta aaa gga aaa ctg cat gtc cca ttc ttg<br>Lys Ala Ala Gly Ala Thr Leu Lys Gly Lys Leu His Val Pro Phe Leu<br>305                     310                  315                  320 | 960 |
| ctg gca gac ggc aaa tgc acc gtg cct cta gca cca gaa cct atg ata<br>Leu Ala Asp Gly Lys Cys Thr Val Pro Leu Ala Pro Glu Pro Met Ile<br>                     325                  330                  335 | 1008 |
| acc ttc ggt ttc aga tca gtg tca ctg aaa ctg cac cct aag aat ccc<br>Thr Phe Gly Phe Arg Ser Val Ser Leu Lys Leu His Pro Lys Asn Pro<br>                     340                  345                  350 | 1056 |
| aca tat cta acc acc cgc caa ctt gct gat gag cct cac tac acg cat<br>Thr Tyr Leu Thr Thr Arg Gln Leu Ala Asp Glu Pro His Tyr Thr His<br>                     355                  360                  365 | 1104 |
| gag ctc ata tct gaa cca gct gtt agg aat ttt acc gtc acc gga aaa<br>Glu Leu Ile Ser Glu Pro Ala Val Arg Asn Phe Thr Val Thr Gly Lys<br>370                     375                  380 | 1152 |

```
ggg tgg gag ttt gta tgg gga aac cac ccg ccg aaa agg ttt tgg gca    1200
Gly Trp Glu Phe Val Trp Gly Asn His Pro Pro Lys Arg Phe Trp Ala
385                 390                 395                 400 cag gaa aca gca ccc gga aat cca cat ggg cta ccg cac gag gtg ata    1248
Gln Glu Thr Ala Pro Gly Asn Pro His Gly Leu Pro His Glu Val Ile
            405                 410                 415 act cat tat tac cac aga tac cct atg tcc acc atc ctg ggt ttg tca    1296
Thr His Tyr Tyr His Arg Tyr Pro Met Ser Thr Ile Leu Gly Leu Ser
        420                 425                 430 att tgt gcc gcc att gca acc gtt tcc gtt gca gcg tct acc tgg ctg    1344
Ile Cys Ala Ala Ile Ala Thr Val Ser Val Ala Ala Ser Thr Trp Leu
    435                 440                 445 ttt tgc aga tct aga gtt gcg tgc cta act cct tac cgg cta aca cct    1392
Phe Cys Arg Ser Arg Val Ala Cys Leu Thr Pro Tyr Arg Leu Thr Pro
450                 455                 460 aac gct agg ata cca ttt tgt ctg gct gtg ctt tgc tgc gcc cgc act    1440
Asn Ala Arg Ile Pro Phe Cys Leu Ala Val Leu Cys Cys Ala Arg Thr
465                 470                 475                 480 gcc cgg gcc gag acc acc tgg gag tcc ttg gat cac cta tgg aac aat    1488
Ala Arg Ala Glu Thr Thr Trp Glu Ser Leu Asp His Leu Trp Asn Asn
            485                 490                 495 aac caa cag atg ttc tgg att caa ttg ctg atc cct ctg gcc gcc ttg    1536
Asn Gln Gln Met Phe Trp Ile Gln Leu Leu Ile Pro Leu Ala Ala Leu
        500                 505                 510 atc gta gtg act cgc ctg ctc agg tgc gtg tgc tgt gtc gtg cct ttt    1584
Ile Val Val Thr Arg Leu Leu Arg Cys Val Cys Cys Val Val Pro Phe
    515                 520                 525 tta gtc atg gcc ggc gcc gca ggc gcc ggc gcc tac gag cac gcg acc    1632
Leu Val Met Ala Gly Ala Ala Gly Ala Gly Ala Tyr Glu His Ala Thr
530                 535                 540 acg atg ccg agc caa gcg gga atc tcg tat aac act ata gtc aac aga    1680
Thr Met Pro Ser Gln Ala Gly Ile Ser Tyr Asn Thr Ile Val Asn Arg
545                 550                 555                 560 gca ggc tac gca cca ctc cct atc agc ata aca cca aca aag atc aag    1728
Ala Gly Tyr Ala Pro Leu Pro Ile Ser Ile Thr Pro Thr Lys Ile Lys
            565                 570                 575 ctg ata cct aca gtg aac ttg gag tac gtc acc tgc cac tac aaa aca    1776
Leu Ile Pro Thr Val Asn Leu Glu Tyr Val Thr Cys His Tyr Lys Thr
        580                 585                 590 gga atg gat tca cca gcc atc aaa tgc tgc gga tct cag gaa tgc act    1824
Gly Met Asp Ser Pro Ala Ile Lys Cys Cys Gly Ser Gln Glu Cys Thr
    595                 600                 605 cca act tac agg cct gat gaa cag tgc aaa gtc ttc aca ggg gtt tac    1872
Pro Thr Tyr Arg Pro Asp Glu Gln Cys Lys Val Phe Thr Gly Val Tyr
610                 615                 620 ccg ttc atg tgg ggt ggt gca tat tgc ttt tgc gac act gag aac acc    1920
Pro Phe Met Trp Gly Gly Ala Tyr Cys Phe Cys Asp Thr Glu Asn Thr
625                 630                 635                 640 caa gtc agc aag gcc tac gta atg aaa tct gac gac tgc ctt gcg gat    1968
Gln Val Ser Lys Ala Tyr Val Met Lys Ser Asp Asp Cys Leu Ala Asp
            645                 650                 655 cat gct gaa gca tat aaa gcg cac aca gcc tca gtg cag gcg ttc ctc    2016
His Ala Glu Ala Tyr Lys Ala His Thr Ala Ser Val Gln Ala Phe Leu
        660                 665                 670 aac atc aca gtg gga gaa cac tct att gtg act acc gtg tat gtg aat    2064
Asn Ile Thr Val Gly Glu His Ser Ile Val Thr Thr Val Tyr Val Asn
    675                 680                 685 gga gaa act cct gtg aat ttc aat ggg gtc aaa tta act gca ggt ccg    2112
Gly Glu Thr Pro Val Asn Phe Asn Gly Val Lys Leu Thr Ala Gly Pro
690                 695                 700
```

```
ctt tcc aca gct tgg aca ccc ttt gat cgc aaa atc gtg cag tat gcc      2160
Leu Ser Thr Ala Trp Thr Pro Phe Asp Arg Lys Ile Val Gln Tyr Ala
705                 710                 715                 720 ggg gag atc tat aat tat gat ttt cct gag tat ggg gca gga caa cca      2208
Gly Glu Ile Tyr Asn Tyr Asp Phe Pro Glu Tyr Gly Ala Gly Gln Pro
                725                 730                 735 gga gca ttt gga gat ata caa tcc aga aca gtc tca agc tca gat ctg      2256
Gly Ala Phe Gly Asp Ile Gln Ser Arg Thr Val Ser Ser Ser Asp Leu
            740                 745                 750 tat gcc aat acc aac cta gtg ctg cag aga ccc aaa gca gga gcg atc      2304
Tyr Ala Asn Thr Asn Leu Val Leu Gln Arg Pro Lys Ala Gly Ala Ile
        755                 760                 765 cac gtg cca tac act cag gca cct tcg ggt ttt gag caa tgg aag aaa      2352
His Val Pro Tyr Thr Gln Ala Pro Ser Gly Phe Glu Gln Trp Lys Lys
    770                 775                 780 gat aaa gct cca tca ttg aaa ttt acc gcc cct ttc gga tgc gaa ata      2400
Asp Lys Ala Pro Ser Leu Lys Phe Thr Ala Pro Phe Gly Cys Glu Ile
785                 790                 795                 800 tat aca aac ccc att cgc gcc gaa aac tgt act gta ggg tca att cca      2448
Tyr Thr Asn Pro Ile Arg Ala Glu Asn Cys Thr Val Gly Ser Ile Pro
                805                 810                 815 tta gcc ttt gac att ccc gac gcc ttg ttc acc agg gtg tca gaa aca      2496
Leu Ala Phe Asp Ile Pro Asp Ala Leu Phe Thr Arg Val Ser Glu Thr
            820                 825                 830 ccg aca ctt tca gcg gcc gaa tgc act ctt aac gag tgc gtg tat tct      2544
Pro Thr Leu Ser Ala Ala Glu Cys Thr Leu Asn Glu Cys Val Tyr Ser
        835                 840                 845 tcc gac ttt ggt ggg atc gcc acg gtc aag tac tcg gcc agc aag tca      2592
Ser Asp Phe Gly Gly Ile Ala Thr Val Lys Tyr Ser Ala Ser Lys Ser
    850                 855                 860 ggc aag tgc gca gtc cat gtg cca tca ggg act gct acc cta aaa gaa      2640
Gly Lys Cys Ala Val His Val Pro Ser Gly Thr Ala Thr Leu Lys Glu
865                 870                 875                 880 gca gca gtc gag cta acc gag caa ggg tcg gcg act atc cat ttc tcg      2688
Ala Ala Val Glu Leu Thr Glu Gln Gly Ser Ala Thr Ile His Phe Ser
                885                 890                 895 acc gca aat atc cac ccg gag ttc agg ctc caa ata tgc aca tca tat      2736
Thr Ala Asn Ile His Pro Glu Phe Arg Leu Gln Ile Cys Thr Ser Tyr
            900                 905                 910 gtt acg tgc aaa ggt gat tgt cac ccc ccg aaa gac cat att gtg aca      2784
Val Thr Cys Lys Gly Asp Cys His Pro Pro Lys Asp His Ile Val Thr
        915                 920                 925 cac cct cag tat cac gcc caa aca ttt aca gcc gcg gtg tca aaa acc      2832
His Pro Gln Tyr His Ala Gln Thr Phe Thr Ala Ala Val Ser Lys Thr
    930                 935                 940 gcg tgg acg tgg tta aca tcc ctg ctg gga gga tca gcc gta att att      2880
Ala Trp Thr Trp Leu Thr Ser Leu Leu Gly Gly Ser Ala Val Ile Ile
945                 950                 955                 960 ata att ggc ttg gtg ctg gct act att gtg gcc atg tac gtg ctg acc      2928
Ile Ile Gly Leu Val Leu Ala Thr Ile Val Ala Met Tyr Val Leu Thr
                965                 970                 975 aac cag aaa cat aat                                                  2943
Asn Gln Lys His Asn
            980

<210> SEQ ID NO 13
<211> LENGTH: 981
<212> TYPE: PRT
<213> ORGANISM: Artificial Sequence
```

```
<220> FEATURE:
<223> OTHER INFORMATION: Description of Artificial Sequence; Note =
      synthetic construct

<400> SEQUENCE: 13

Met Ser Leu Val Thr Thr Met Cys Leu Leu Ala Asn Val Thr Phe Pro
 1               5                  10                  15

Cys Ala Gln Pro Pro Ile Cys Tyr Asp Arg Lys Pro Ala Glu Thr Leu
            20                  25                  30

Ala Met Leu Ser Val Asn Val Asp Asn Pro Gly Tyr Asp Glu Leu Leu
        35                  40                  45

Glu Ala Ala Val Lys Cys Pro Gly Arg Lys Arg Ser Thr Glu Glu
    50                  55                  60

Leu Phe Lys Glu Tyr Lys Leu Thr Arg Pro Tyr Met Ala Arg Cys Ile
65                  70                  75                  80

Arg Cys Ala Val Gly Ser Cys His Ser Pro Ile Ala Ile Glu Ala Val
                85                  90                  95

Lys Ser Asp Gly His Asp Gly Tyr Val Arg Leu Gln Thr Ser Ser Gln
               100                 105                 110

Tyr Gly Leu Asp Ser Ser Gly Asn Leu Lys Gly Arg Thr Met Arg Tyr
               115                 120                 125

Asp Met His Gly Thr Ile Lys Glu Ile Pro Leu His Gln Val Ser Leu
           130                 135                 140

His Thr Ser Arg Pro Cys His Ile Val Asp Gly His Gly Tyr Phe Leu
145                 150                 155                 160

Leu Ala Arg Cys Pro Ala Gly Asp Ser Ile Thr Met Glu Phe Lys Lys
                165                 170                 175

Asp Ser Val Thr His Ser Cys Ser Val Pro Tyr Glu Val Lys Phe Asn
            180                 185                 190

Pro Val Gly Arg Glu Leu Tyr Thr His Pro Pro Glu His Gly Val Glu
        195                 200                 205

Gln Ala Cys Gln Val Tyr Ala His Asp Ala Gln Asn Arg Gly Ala Tyr
    210                 215                 220

Val Glu Met His Leu Pro Gly Ser Glu Val Asp Ser Ser Leu Val Ser
225                 230                 235                 240

Leu Ser Gly Ser Ser Val Thr Val Thr Pro Pro Val Gly Thr Ser Ala
                245                 250                 255

Leu Val Glu Cys Glu Cys Gly Gly Thr Lys Ile Ser Lys Thr Ile Asn
            260                 265                 270

Lys Thr Lys Gln Phe Ser Gln Cys Thr Lys Lys Glu Gln Cys Arg Ala
        275                 280                 285

Tyr Arg Leu Gln Asn Asp Lys Trp Val Tyr Asn Ser Asp Lys Leu Pro
    290                 295                 300

Lys Ala Ala Gly Ala Thr Leu Lys Gly Lys Leu His Val Pro Phe Leu
305                 310                 315                 320

Leu Ala Asp Gly Lys Cys Thr Val Pro Leu Ala Pro Glu Pro Met Ile
                325                 330                 335

Thr Phe Gly Phe Arg Ser Val Ser Leu Lys Leu His Pro Lys Asn Pro
            340                 345                 350

Thr Tyr Leu Thr Thr Arg Gln Leu Ala Asp Glu Pro His Tyr Thr His
        355                 360                 365

Glu Leu Ile Ser Glu Pro Ala Val Arg Asn Phe Thr Val Thr Gly Lys
    370                 375                 380
```

-continued

```
Gly Trp Glu Phe Val Trp Gly Asn His Pro Pro Lys Arg Phe Trp Ala
385                 390                 395                 400

Gln Glu Thr Ala Pro Gly Asn Pro His Gly Leu Pro His Glu Val Ile
                405                 410                 415

Thr His Tyr Tyr His Arg Tyr Pro Met Ser Thr Ile Leu Gly Leu Ser
            420                 425                 430

Ile Cys Ala Ala Ile Ala Thr Val Ser Val Ala Ala Ser Thr Trp Leu
        435                 440                 445

Phe Cys Arg Ser Arg Val Ala Cys Leu Thr Pro Tyr Arg Leu Thr Pro
    450                 455                 460

Asn Ala Arg Ile Pro Phe Cys Leu Ala Val Leu Cys Cys Ala Arg Thr
465                 470                 475                 480

Ala Arg Ala Glu Thr Thr Trp Glu Ser Leu Asp His Leu Trp Asn Asn
                485                 490                 495

Asn Gln Gln Met Phe Trp Ile Gln Leu Leu Ile Pro Leu Ala Ala Leu
                500                 505                 510

Ile Val Val Thr Arg Leu Leu Arg Cys Val Cys Val Val Pro Phe
            515                 520                 525

Leu Val Met Ala Gly Ala Gly Ala Gly Ala Tyr Glu His Ala Thr
            530                 535                 540

Thr Met Pro Ser Gln Ala Gly Ile Ser Tyr Asn Thr Ile Val Asn Arg
545                 550                 555                 560

Ala Gly Tyr Ala Pro Leu Pro Ile Ser Ile Thr Pro Thr Lys Ile Lys
                565                 570                 575

Leu Ile Pro Thr Val Asn Leu Glu Tyr Val Thr Cys His Tyr Lys Thr
            580                 585                 590

Gly Met Asp Ser Pro Ala Ile Lys Cys Cys Gly Ser Gln Glu Cys Thr
            595                 600                 605

Pro Thr Tyr Arg Pro Asp Glu Gln Cys Lys Val Phe Thr Gly Val Tyr
        610                 615                 620

Pro Phe Met Trp Gly Gly Ala Tyr Cys Phe Cys Asp Thr Glu Asn Thr
625                 630                 635                 640

Gln Val Ser Lys Ala Tyr Val Met Lys Ser Asp Asp Cys Leu Ala Asp
                645                 650                 655

His Ala Glu Ala Tyr Lys Ala His Thr Ala Ser Val Gln Ala Phe Leu
                660                 665                 670

Asn Ile Thr Val Gly Glu His Ser Ile Val Thr Thr Val Tyr Val Asn
            675                 680                 685

Gly Glu Thr Pro Val Asn Phe Asn Gly Val Lys Leu Thr Ala Gly Pro
            690                 695                 700

Leu Ser Thr Ala Trp Thr Pro Phe Asp Arg Lys Ile Val Gln Tyr Ala
705                 710                 715                 720

Gly Glu Ile Tyr Asn Tyr Asp Phe Pro Glu Tyr Gly Ala Gly Gln Pro
                725                 730                 735

Gly Ala Phe Gly Asp Ile Gln Ser Arg Thr Val Ser Ser Ser Asp Leu
            740                 745                 750

Tyr Ala Asn Thr Asn Leu Val Leu Gln Arg Pro Lys Ala Gly Ala Ile
            755                 760                 765

His Val Pro Tyr Thr Gln Ala Pro Ser Gly Phe Glu Gln Trp Lys Lys
    770                 775                 780

Asp Lys Ala Pro Ser Leu Lys Phe Thr Ala Pro Phe Gly Cys Glu Ile
785                 790                 795                 800
```

```
Tyr Thr Asn Pro Ile Arg Ala Glu Asn Cys Thr Val Gly Ser Ile Pro
                805                 810                 815
Leu Ala Phe Asp Ile Pro Asp Ala Leu Phe Thr Arg Val Ser Glu Thr
            820                 825                 830
Pro Thr Leu Ser Ala Ala Glu Cys Thr Leu Asn Glu Cys Val Tyr Ser
        835                 840                 845
Ser Asp Phe Gly Gly Ile Ala Thr Val Lys Tyr Ser Ala Ser Lys Ser
    850                 855                 860
Gly Lys Cys Ala Val His Val Pro Ser Gly Thr Ala Thr Leu Lys Glu
865                 870                 875                 880
Ala Ala Val Glu Leu Thr Glu Gln Gly Ser Ala Thr Ile His Phe Ser
                885                 890                 895
Thr Ala Asn Ile His Pro Glu Phe Arg Leu Gln Ile Cys Thr Ser Tyr
            900                 905                 910
Val Thr Cys Lys Gly Asp Cys His Pro Pro Lys Asp His Ile Val Thr
        915                 920                 925
His Pro Gln Tyr His Ala Gln Thr Phe Thr Ala Ala Val Ser Lys Thr
    930                 935                 940
Ala Trp Thr Trp Leu Thr Ser Leu Leu Gly Gly Ser Ala Val Ile Ile
945                 950                 955                 960
Ile Ile Gly Leu Val Leu Ala Thr Ile Val Ala Met Tyr Val Leu Thr
                965                 970                 975
Asn Gln Lys His Asn
            980

<210> SEQ ID NO 14
<211> LENGTH: 12379
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 14
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa actgtaagg    360 aaataactga taaggaattg acaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
```

-continued

```
cgatgcaccg cgagggattc ttgtgctgca aagtgacaga cacattcaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg agcgtaagga ggtgcgtgaa gccgaggagt    1560
tgcgcgcagc tctaccacct ttggcagctg atgttgagga gcccactctg gaagccgatg    1620
tcgacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg    2340 ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttttaac atgatgtgcc    2520 tgaaagtgca ttttaaccac gagatttgca cacaagtctt ccacaaaagc atctctcgcc    2580
gttgcactaa atctgtgact tcggtcgtct caaccttgtt ttacgacaaa aaatgagaa    2640 cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct ggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
```

-continued

```
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctcctc accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggaggagct agcgtgacca    5340 gcgggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa taggtgatc actagagagg agctcgaggc gcttacccg tcacgcactc    5580 ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
```

```
cggtgctatc cgaagtggtg ttggagagga ccgaattgga gatttcgtat gccccgcgcc      5820
tcgaccaaga aaagaagaa ttactacgca agaaattaca gttaaatccc acacctgcta      5880
acagaagcag ataccagtcc aggaaggtgg agaacatgaa agccataaca gctagacgta      5940
ttctgcaagg cctagggcat tatttgaagg cagaaggaaa agtggagtgc taccgaaccc      6000
tgcatcctgt tcctttgtat tcatctagtg tgaaccgtgc cttttcaagc cccaaggtcg      6060
cagtggaagc ctgtaacgcc atgttgaaag gaactttcc gactgtggct tcttactgta      6120
ttattccaga gtacgatgcc tatttggaca tggttgacgg agcttcatgc tgcttagaca      6180
ctgccagttt ttgccctgca aagctgcgca gctttccaaa gaaacactcc tatttggaac      6240
ccacaatacg atcggcagtg ccttcagcga tccagaacac gctccagaac gtcctggcag      6300
ctgccacaaa aagaaattgc aatgtcacgc aaatgagaga attgcccgta ttggattcgg      6360
cggcctttaa tgtggaatgc ttcaagaaat atgcgtgtaa taatgaatat tgggaaacgt      6420
ttaaagaaaa ccccatcagg cttactgaag aaaacgtggt aaattacatt accaaattaa      6480
aaggaccaaa agctgctgct cttttttgcga agacacataa tttgaatatg ttgcaggaca      6540
taccaatgga caggttttgta atggacttaa agagagacgt gaaagtgact ccaggaacaa      6600
aacatactga agaacggccc aaggtacagg tgatccaggc tgccgatccg ctagcaacag      6660
cgtatctgtg cggaatccac cgagagctgg ttaggagatt aaatgcggtc ctgcttccga      6720
acattcatac actgtttgat atgtcggctg aagactttga cgctattata gccgagcact      6780
tccagcctgg ggattgtgtt ctggaaactg acatcgcgtc gtttgataaa agtgaggacg      6840
acgccatggc tctgaccgcg ttaatgattc tggaagactt aggtgtggac gcagagctgt      6900
tgacgctgat tgaggcggct ttcggcgaaa tttcatcaat acatttgccc actaaaacta      6960
aatttaaatt cggagccatg atgaaatctg gaatgttcct cacactgttt gtgaacacag      7020
tcattaacat tgtaatcgca agcagagtgt tgagagaacg gctaaccgga tcaccatgtg      7080
cagcattcat tggagatgac aatatcgtga aaggagtcaa atcggacaaa ttaatggcag      7140
acaggtgcgc cacctggttg aatatggaag tcaagattat agatgctgtg gtgggcgaga      7200
aagcgcctta tttctgtgga gggtttattt tgtgtgactc cgtgaccggc acagcgtgcc      7260
gtgtggcaga cccctaaaa aggctgtttta agcttggcaa acctctggca gcagacgatg      7320
aacatgatga tgacaggaga agggcattgc atgaagagtc aacacgctgg aaccgagtgg      7380
gtattctttc agagctgtgc aaggcagtag aatcaaggta tgaaaccgta ggaacttcca      7440
tcatagttat ggccatgact actctagcta gcagtgttaa atcattcagc tacctgagag      7500
gggcccctat aactctctac ggctaacctg aatggactac gacatagtct agtccgccaa      7560
gatgccaatc agtcccattg aaactgtacc agtaaaactg aagccaggaa tggatggccc      7620
aaaggttaaa caatggccgt taacagaagt gaaaataaaa gcattaacag caatttgtga      7680
agaaatggaa aaggaaggaa aaattacaaa aattgggcct gaaaatccat ataacactcc      7740
aatattcgcc ataaaaaagg aagacagcac taagtggaga aaattagtag atttcaggga      7800
actcaataaa agaactcaag acttttggga ggttcaatta ggaataccac acccagcagg      7860
gttaaaaaag aaaaaatcag tgacagtact ggatgtggga gatgcatatt tttcagttcc      7920
tttagatgaa ggcttcagga aatatactgc attcaccata cctagtataa acaatgaaac      7980
accagggatt agatatcaat ataatgtgct tccacaagga tggaaagggt caccagcaat      8040
attccaggct agcatgacaa aaatcctaga gccctttaga gctaaaaatc cagaaatagt      8100
catctatcaa catatggcgg cattgtatgt aggatctgac ttagaaatag ggcaacatag      8160
```

```
agcaaaaata gaagagttaa gagaacatct attaaagtgg ggatttacca caccagacaa   8220
aaaacatcag aaagaacccc catttctttg gatgggtat gaactccatc ctgacaaatg    8280
gacagtacag cctatacagc tgccagaaaa agatagctgg actgtcaatg acatacagaa   8340
gttagtggga aaattaaact ggacaagtca gatttaccca gggattaaag taaggcaact   8400
ttgtaagctc cttaggggga ccaaagcact aacagacata gtaccactaa ctgaagaagc   8460
agaattagaa ttggcagaga acagggaaat tctaaaagaa ccagtgcatg gagtatatta   8520
tgacccatca aaagacttga tagctgaaat acagaaacag ggggatgacc aatggacata   8580
tcaaatttac caagaaccat tcaaaaacct gaagacagga agtatgcaa aaaggaggac     8640
tacccacact aatgatgtaa aacagttaac agaggcagtg caaaaaatat ccttggaaag   8700
catagtaaca tggggaaaga ctcctaaatt tagactaccc atccaaaaag aaacatggga   8760
aatatggtgg acagactatt ggcaagccac atggattcct gagtgggagt ttgttaatac   8820
ccctccccta gtaaaactat ggtaccagct agaaaaagaa cccatagcag gagcagaaac   8880
tttctgaagg ccggccttaa ttaagtaacg atacagcagc aattggcaag ctgcttacat   8940
agaactcgcg gcgattggca tgccgcttta aaattttat tttatttttc ttttcttttc    9000
cgaatcggat tttgttttta atatttcaaa aaaaaaaaa aaaaaaaaa aaaaaaaaa      9060
aaaaaaaaa aaagggaaga gcgcggccgc gcgctgggct acgtcttgct ggcgttcgcg    9120
acgcgaggct ggatggcctt ccccattatg attcttctcg cttccggcgg catcgggatg   9180
cccgcgttgc aggccatgct gtccaggcag gtagatgacg accatcaggg acagcttcaa   9240
ggatcgctcg cggctcttac cagcctaact tcgatcactg gaccgctgat cgtcacggcg   9300
atttatgccg cctcggcgag cacatggaac ggggttggcat ggattgtagg cgccgcccta   9360
taccttgtct gcctccccgc gttgcgtcgc ggtgcatgga gccgggccac ctcgacctga   9420
atggaagccg gcggcacctc gctaacggat tcaccactcc aagaattgga gccaatcaat   9480
tcttgcggag aactgtgaat gcgcaaacca acccttggca gaacatatcc atcgcgtccg   9540
ccatctccag cagccgcacg cggcgcatct cgggcagcgt tgggtcctgg ccacgggtgc   9600
gcatgatcgt gctcctgtcg ttgaggaccc ggctaggctg gcggggttgc cttactggtt   9660
agcagaatga atcaccgata cgcgagcgaa cgtgaagcga ctgctgctgc aaaacgtctg   9720
cgacctgagc aacaacatga atggtcttcg gtttccgtgt ttcgtaaagt ctggaaacgc   9780
ggaagtcagc gccctgcacc attatgttcc ggatctgcat cgcaggatgc tgctggctac   9840
cctgtggaac acctacatct gtattaacga agcgctggca ttgaccctga gtgatttttc   9900
tctggtcccg ccgcatccat accgccagtt gtttaccctc acaacgttcc agtaaccggg   9960
catgttcatc atcagtaacc cgtatcgtga gcatcctctc tcgtttcatc ggtatcatta  10020
cccccatgaa cagaaatccc ccttacacgg aggcatcagt gaccaaacag gaaaaaaccg  10080
cccttaacat ggcccgcttt atcagaagcc agacattaac gcttctggag aaactcaacg  10140
agctggacgc ggatgaacag gcagacatct gtgaatcgct tcacgaccac gctgatgagc  10200
tttaccgcag ctgcctcgcg cgtttcggtg atgacggtga aacctctgac acatgcagc   10260
tcccggagac ggtcacagct tgtctgtaag cggatgccgg gagcagacaa gcccgtcagg  10320
gcgcgtcagc gggtgttggc gggtgtcggg gcgcagccat gacccagtca cgtagcgata  10380
gcggagtgta tactggctta actatgcggc atcagagcag attgtactga gagtgcacca  10440
tatatgcggt gtgaaatacc gcacagatgc gtaaggagaa ataccgcat caggcgctct   10500
tccgcttcct cgctcactga ctcgctgcgc tcggtcgttc ggctgcggcg agcggtatca  10560
```

-continued

```
gctcactcaa aggcggtaat acggttatcc acagaatcag gggataacgc aggaaagaac    10620
atgtgagcaa aaggccagca aaaggccagg aaccgtaaaa aggccgcgtt gctggcgttt    10680
ttccataggc tccgcccccc tgacgagcat cacaaaaatc gacgctcaag tcagaggtgg    10740
cgaaacccga caggactata agataccag gcgtttcccc ctggaagctc cctcgtgcgc     10800
tctcctgttc cgaccctgcc gcttaccgga tacctgtccg cctttctccc ttcgggaagc    10860
gtggcgcttt ctcatagctc acgctgtagg tatctcagtt cggtgtaggt cgttcgctcc    10920
aagctgggct gtgtgcacga acccccgtt cagcccgacc gctgcgcctt atccggtaac     10980
tatcgtcttg agtccaaccc ggtaagacac gacttatcgc cactggcagc agccactggt    11040
aacaggatta gcagagcgag gtatgtaggc ggtgctacag agttcttgaa gtggtggcct    11100
aactacggct acactagaag gacagtattt ggtatctgcg ctctgctgaa gccagttacc    11160
ttcggaaaaa gagttggtag ctcttgatcc ggcaaacaaa ccaccgctgg tagcggtggt    11220
tttttttgttt gcaagcagca gattacgcgc agaaaaaaag gatctcaaga agatcctttg   11280
atcttttcta cggggtctga cgctcagtgg aacgaaaact cacgttaagg gattttggtc    11340
atgaacaata aaactgtctg cttacataaa cagtaataca agggggtgtta tgagccatat   11400
tcaacgggaa acgtcttgct cgaggccgcg attaaattcc aacatggatg ctgatttata   11460
tgggtataaa tgggctcgcg ataatgtcgg gcaatcaggt gcgacaatct atcgattgta   11520
tgggaagccc gatgcgccag agttgtttct gaaacatggc aaaggtagcg ttgccaatga   11580
tgttacagat gagatggtca gactaaactg gctgacggaa tttatgcctc ttccgaccat   11640
caagcatttt atccgtactc ctgatgatgc atggttactc accactgcga tccccgggaa   11700
aacagcattc caggtattag aagaatatcc tgattcaggt gaaaatattg ttgatgcgct   11760
ggcagtgttc ctgcgccggt tgcattcgat tcctgtttgt aattgtcctt ttaacagcga   11820
tcgcgtattt cgtctcgctc aggcgcaatc acgaatgaat aacggtttgg ttgatgcgag   11880
tgatttttgat gacgagcgta atggctggcc tgttgaacaa gtctggaaag aaatgcataa   11940
gcttttgcca ttctcaccgg attcagtcgt cactcatggt gatttctcac ttgataaccct  12000
tattttttgac gaggggaaat taataggttg tattgatgtt ggacgagtcg gaatcgcaga   12060
ccgataccag gatcttgcca tcctatggaa ctgcctcggt gagttttctc cttcattaca   12120
gaaacggctt tttcaaaaat atggtattga taatcctgat atgaataaat tgcagtttca   12180
tttgatgctc gatgagtttt tctaagaatt ctcatgtttg acagcttatc atcgataagc   12240
tttaatgcgg tagtttatca cagttaaatt gctaacgcag tcaggcaccg tgtatgaaat   12300
ctaacaatgc gctcatcgtc atcctcggca ccgtcaccct ggatgctgtc tagaggatcc   12360
ctaatacgac tcactatag                                                12379
```

<210> SEQ ID NO 15
<211> LENGTH: 1323
<212> TYPE: DNA
<213> ORGANISM: Artificial Sequence
<220> FEATURE:
<223> OTHER INFORMATION: Description of Artificial Sequence; Note = synthetic construct
<221> NAME/KEY: CDS
<222> LOCATION: (1)...(1323)

<400> SEQUENCE: 15

```
atg cca atc agt ccc att gaa act gta cca gta aaa ctg aag cca gga    48
Met Pro Ile Ser Pro Ile Glu Thr Val Pro Val Lys Leu Lys Pro Gly
 1               5                  10                  15
```

-continued

| | |
|---|---|
| atg gat ggc cca aag gtt aaa caa tgg ccg tta aca gaa gtg aaa ata<br>Met Asp Gly Pro Lys Val Lys Gln Trp Pro Leu Thr Glu Val Lys Ile<br>20　　　　　　　25　　　　　　　30 | 96 |
| aaa gca tta aca gca att tgt gaa gaa atg gaa aag gaa gga aaa att<br>Lys Ala Leu Thr Ala Ile Cys Glu Glu Met Glu Lys Glu Gly Lys Ile<br>　　35　　　　　　　40　　　　　　　45 | 144 |
| aca aaa att ggg cct gaa aat cca tat aac act cca ata ttc gcc ata<br>Thr Lys Ile Gly Pro Glu Asn Pro Tyr Asn Thr Pro Ile Phe Ala Ile<br>50　　　　　　　55　　　　　　　60 | 192 |
| aaa aag gaa gac agc act aag tgg aga aaa tta gta gat ttc agg gaa<br>Lys Lys Glu Asp Ser Thr Lys Trp Arg Lys Leu Val Asp Phe Arg Glu<br>65　　　　　　　70　　　　　　　75　　　　　　　80 | 240 |
| ctc aat aaa aga act caa gac ttt tgg gag gtt caa tta gga ata cca<br>Leu Asn Lys Arg Thr Gln Asp Phe Trp Glu Val Gln Leu Gly Ile Pro<br>　　　　85　　　　　　　90　　　　　　　95 | 288 |
| cac cca gca ggg tta aaa aag aaa aaa tca gtg aca gta ctg gat gtg<br>His Pro Ala Gly Leu Lys Lys Lys Lys Ser Val Thr Val Leu Asp Val<br>　　　100　　　　　　　105　　　　　　　110 | 336 |
| gga gat gca tat ttt tca gtt cct tta gat gaa ggc ttc agg aaa tat<br>Gly Asp Ala Tyr Phe Ser Val Pro Leu Asp Glu Gly Phe Arg Lys Tyr<br>　　　115　　　　　　　120　　　　　　　125 | 384 |
| act gca ttc acc ata cct agt ata aac aat gaa aca cca ggg att aga<br>Thr Ala Phe Thr Ile Pro Ser Ile Asn Asn Glu Thr Pro Gly Ile Arg<br>130　　　　　　　135　　　　　　　140 | 432 |
| tat caa tat aat gtg ctt cca caa gga tgg aaa ggg tca cca gca ata<br>Tyr Gln Tyr Asn Val Leu Pro Gln Gly Trp Lys Gly Ser Pro Ala Ile<br>145　　　　　　　150　　　　　　　155　　　　　　　160 | 480 |
| ttc cag gct agc atg aca aaa atc cta gag ccc ttt aga gct aaa aat<br>Phe Gln Ala Ser Met Thr Lys Ile Leu Glu Pro Phe Arg Ala Lys Asn<br>　　　　165　　　　　　　170　　　　　　　175 | 528 |
| cca gaa ata gtc atc tat caa cat atg gcg gca ttg tat gta gga tct<br>Pro Glu Ile Val Ile Tyr Gln His Met Ala Ala Leu Tyr Val Gly Ser<br>　　　180　　　　　　　185　　　　　　　190 | 576 |
| gac tta gaa ata ggg caa cat aga gca aaa ata gaa gag tta aga gaa<br>Asp Leu Glu Ile Gly Gln His Arg Ala Lys Ile Glu Glu Leu Arg Glu<br>　　　195　　　　　　　200　　　　　　　205 | 624 |
| cat cta tta aag tgg gga ttt acc aca cca gac aaa aaa cat cag aaa<br>His Leu Leu Lys Trp Gly Phe Thr Thr Pro Asp Lys Lys His Gln Lys<br>210　　　　　　　215　　　　　　　220 | 672 |
| gaa ccc cca ttt ctt tgg atg ggg tat gaa ctc cat cct gac aaa tgg<br>Glu Pro Pro Phe Leu Trp Met Gly Tyr Glu Leu His Pro Asp Lys Trp<br>225　　　　　　　230　　　　　　　235　　　　　　　240 | 720 |
| aca gta cag cct ata cag ctg cca gaa aaa gat agc tgg act gtc aat<br>Thr Val Gln Pro Ile Gln Leu Pro Glu Lys Asp Ser Trp Thr Val Asn<br>　　　　245　　　　　　　250　　　　　　　255 | 768 |
| gac ata cag aag tta gtg gga aaa tta aac tgg aca agt cag att tac<br>Asp Ile Gln Lys Leu Val Gly Lys Leu Asn Trp Thr Ser Gln Ile Tyr<br>　　　260　　　　　　　265　　　　　　　270 | 816 |
| cca ggg att aaa gta agg caa ctt tgt aag ctc ctt agg ggg acc aaa<br>Pro Gly Ile Lys Val Arg Gln Leu Cys Lys Leu Leu Arg Gly Thr Lys<br>　　　275　　　　　　　280　　　　　　　285 | 864 |
| gca cta aca gac ata gta cca cta act gaa gaa gca gaa tta gaa ttg<br>Ala Leu Thr Asp Ile Val Pro Leu Thr Glu Glu Ala Glu Leu Glu Leu<br>290　　　　　　　295　　　　　　　300 | 912 |
| gca gag aac agg gaa att cta aaa gaa cca gtg cat gga gta tat tat<br>Ala Glu Asn Arg Glu Ile Leu Lys Glu Pro Val His Gly Val Tyr Tyr<br>305　　　　　　　310　　　　　　　315　　　　　　　320 | 960 |
| gac cca tca aaa gac ttg ata gct gaa ata cag aaa cag ggg gat gac<br>Asp Pro Ser Lys Asp Leu Ile Ala Glu Ile Gln Lys Gln Gly Asp Asp<br>　　　　325　　　　　　　330　　　　　　　335 | 1008 |

```
caa tgg aca tat caa att tac caa gaa cca ttc aaa aac ctg aag aca      1056
Gln Trp Thr Tyr Gln Ile Tyr Gln Glu Pro Phe Lys Asn Leu Lys Thr
            340                 345                 350 gga aag tat gca aaa agg agg act acc cac act aat gat gta aaa cag      1104
Gly Lys Tyr Ala Lys Arg Arg Thr Thr His Thr Asn Asp Val Lys Gln
        355                 360                 365 tta aca gag gca gtg caa aaa ata tcc ttg gaa agc ata gta aca tgg      1152
Leu Thr Glu Ala Val Gln Lys Ile Ser Leu Glu Ser Ile Val Thr Trp
370                 375                 380 gga aag act cct aaa ttt aga cta ccc atc caa aaa gaa aca tgg gaa      1200
Gly Lys Thr Pro Lys Phe Arg Leu Pro Ile Gln Lys Glu Thr Trp Glu
385                 390                 395                 400 ata tgg tgg aca gac tat tgg caa gcc aca tgg att cct gag tgg gag      1248
Ile Trp Trp Thr Asp Tyr Trp Gln Ala Thr Trp Ile Pro Glu Trp Glu
            405                 410                 415 ttt gtt aat acc cct ccc cta gta aaa cta tgg tac cag cta gaa aaa      1296
Phe Val Asn Thr Pro Pro Leu Val Lys Leu Trp Tyr Gln Leu Glu Lys
            420                 425                 430 gaa ccc ata gca gga gca gaa act ttc                                  1323
Glu Pro Ile Ala Gly Ala Glu Thr Phe
            435                 440

<210> SEQ ID NO 16
<211> LENGTH: 441
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 16

Met Pro Ile Ser Pro Ile Glu Thr Val Pro Val Lys Leu Lys Pro Gly
1               5                   10                  15

Met Asp Gly Pro Lys Val Lys Gln Trp Pro Leu Thr Glu Val Lys Ile
            20                  25                  30

Lys Ala Leu Thr Ala Ile Cys Glu Glu Met Glu Lys Glu Gly Lys Ile
        35                  40                  45

Thr Lys Ile Gly Pro Glu Asn Pro Tyr Asn Thr Pro Ile Phe Ala Ile
    50                  55                  60

Lys Lys Glu Asp Ser Thr Lys Trp Arg Lys Leu Val Asp Phe Arg Glu
65                  70                  75                  80

Leu Asn Lys Arg Thr Gln Asp Phe Trp Glu Val Gln Leu Gly Ile Pro
                85                  90                  95

His Pro Ala Gly Leu Lys Lys Lys Ser Val Thr Val Leu Asp Val
            100                 105                 110

Gly Asp Ala Tyr Phe Ser Val Pro Leu Asp Glu Gly Phe Arg Lys Tyr
        115                 120                 125

Thr Ala Phe Thr Ile Pro Ser Ile Asn Asn Glu Thr Pro Gly Ile Arg
    130                 135                 140

Tyr Gln Tyr Asn Val Leu Pro Gln Gly Trp Lys Gly Ser Pro Ala Ile
145                 150                 155                 160

Phe Gln Ala Ser Met Thr Lys Ile Leu Glu Pro Phe Arg Ala Lys Asn
                165                 170                 175

Pro Glu Ile Val Ile Tyr Gln His Met Ala Ala Leu Tyr Val Gly Ser
            180                 185                 190

Asp Leu Glu Ile Gly Gln His Arg Ala Lys Ile Glu Glu Leu Arg Glu
        195                 200                 205
```

```
His Leu Leu Lys Trp Gly Phe Thr Thr Pro Asp Lys Lys His Gln Lys
    210                 215                 220
Glu Pro Pro Phe Leu Trp Met Gly Tyr Glu Leu His Pro Asp Lys Trp
225                 230                 235                 240
Thr Val Gln Pro Ile Gln Leu Pro Glu Lys Asp Ser Trp Thr Val Asn
                245                 250                 255
Asp Ile Gln Lys Leu Val Gly Lys Leu Asn Trp Thr Ser Gln Ile Tyr
            260                 265                 270
Pro Gly Ile Lys Val Arg Gln Leu Cys Lys Leu Leu Arg Gly Thr Lys
        275                 280                 285
Ala Leu Thr Asp Ile Val Pro Leu Thr Glu Glu Ala Glu Leu Glu Leu
    290                 295                 300
Ala Glu Asn Arg Glu Ile Leu Lys Glu Pro Val His Gly Val Tyr Tyr
305                 310                 315                 320
Asp Pro Ser Lys Asp Leu Ile Ala Glu Ile Gln Lys Gln Gly Asp Asp
                325                 330                 335
Gln Trp Thr Tyr Gln Ile Tyr Gln Glu Pro Phe Lys Asn Leu Lys Thr
            340                 345                 350
Gly Lys Tyr Ala Lys Arg Arg Thr Thr His Thr Asn Asp Val Lys Gln
        355                 360                 365
Leu Thr Glu Ala Val Gln Lys Ile Ser Leu Glu Ser Ile Val Thr Trp
    370                 375                 380
Gly Lys Thr Pro Lys Phe Arg Leu Pro Ile Gln Lys Glu Thr Trp Glu
385                 390                 395                 400
Ile Trp Trp Thr Asp Tyr Trp Gln Ala Thr Trp Ile Pro Glu Trp Glu
                405                 410                 415
Phe Val Asn Thr Pro Pro Leu Val Lys Leu Trp Tyr Gln Leu Glu Lys
            420                 425                 430
Glu Pro Ile Ala Gly Ala Glu Thr Phe
        435                 440

<210> SEQ ID NO 17
<211> LENGTH: 13584
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 17
atgggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccatgagat      300 gtgcggaaga tccggacaga ttgtataagt atgcaactaa gctgaagaaa actgtaagg      360 aaataactga taaggaattg acaagaaaa tgaaggagct cgccgccgtc atgagcgacc      420
ctgacctgga aactgagact atgtgcctcc acgacgacga tcgtgtcgc tacgaagggc      480 aagtcgctgt ttaccaggat gtatacgcgg ttgacggacc gacaagtctc tatcaccaag     540
ccaataaggg agttagagtc gcctactgga taggctttga caccaccct tttatgttta      600 agaacttggc tggagcatat ccatcatact ctaccaactg ggccgacgaa accgtgttaa     660
cggctcgtaa cataggccta tgcagctctg acgttatgga gcggtcacgt agagggatgt    720
```

-continued

```
ccattcttag aaagaagtat ttgaaaccat ccaacaatgt tctattctct gttggctcga       780
ccatctacca cgagaagagg gacttactga ggagctggca cctgccgtct gtatttcact       840
tacgtggcaa gcaaaattac acatgtcggt gtgagactat agttagttgc gacgggtacg       900
tcgttaaaag aatagctatc agtccaggcc tgtatgggaa gccttcaggc tatgctgcta       960
cgatgcaccg cgagggattc ttgtgctgca aagtgacaga cacattcaac ggggagaggg      1020
tctcttttcc cgtgtgcacg tatgtgccag ctacattgtg tgaccaaatg actggcatac      1080
tggcaacaga tgtcagtgcg gacgacgcgc aaaaactgct ggttgggctc aaccagcgta      1140
tagtcgtcaa cggtcgcacc cagagaaaca ccaataccat gaaaaattac cttttgcccg      1200
tagtggccca ggcatttgct aggtgggcaa aggaatataa ggaagatcaa gaagatgaaa      1260
ggccactagg actacgagat agacagttag tcatggggtg ttgttgggct tttagaaggc      1320
acaagataac atctatttat aagcgcccgg atacccaaac catcatcaaa gtgaacagcg      1380
atttccactc attcgtgctg cccaggatag gcagtaacac attggagatc gggctgagaa      1440
caagaatcag gaaaatgtta gaggagcaca aggagccgtc acctctcatt accgccgagg      1500
acgtacaaga agctaagtgc gcagccgatg agcgtaagga ggtgcgtgaa gccgaggagt      1560
tgcgcgcagc tctaccacct ttggcagctg atgttgagga gcccactctg gaagccgatg      1620
tcgacttgat gttacaagag gctggggccg gctcagtgga gacacctcgt ggcttgataa      1680
aggttaccag ctacgatggc gaggacaaga tcggctctta cgctgtgctt tctccgcagg      1740
ctgtactcaa gagtgaaaaa ttatcttgca tccaccctct cgctgaacaa gtcatagtga      1800
taacacactc tggccgaaaa gggcgttatg ccgtggaacc ataccatggt aaagtagtgg      1860
tgccagaggg acatgcaata cccgtccagg actttcaagc tctgagtgaa agtgccacca      1920
ttgtgtacaa cgaacgtgag ttcgtaaaca ggtacctgca ccatattgcc acacatggag      1980
gagcgctgaa cactgatgaa gaatattaca aaactgtcaa gcccagcgag cacgacggcg      2040
aatacctgta cgacatcgac aggaaacagt gcgtcaagaa agaactagtc actgggctag      2100
ggctcacagg cgagctggtg gatcctccct tccatgaatt cgcctacgag agtctgagaa      2160
cacgaccagc cgctccttac caagtaccaa ccatagggt gtatggcgtg ccaggatcag      2220
gcaagtctgg catcattaaa agcgcagtca ccaaaaaaga tctagtggtg agcgccaaga      2280
aagaaaactg tgcagaaatt ataagggacg tcaagaaaat gaaagggctg acgtcaatg      2340 ccagaactgt ggactcagtg ctcttgaatg gatgcaaaca ccccgtagag accctgtata      2400
ttgacgaagc ttttgcttgt catgcaggta ctctcagagc gctcatagcc attataagac      2460
ctaaaaaggc agtgctctgc ggggatcca aacagtgcgg ttttttttaac atgatgtgcc      2520 tgaaagtgca ttttaaccac gagatttgca cacaagtctt ccacaaaagc atctctcgcc      2580
gttgcactaa atctgtgact tcggtcgtct caaccttgtt ttacgacaaa aaaatgagaa      2640
cgacgaatcc gaaagagact aagattgtga ttgacactac cggcagtacc aaacctaagc      2700
aggacgatct cattctcact tgtttcagag ggtgggtgaa gcagttgcaa atagattaca      2760
aaggcaacga aataatgacg gcagctgcct ctcaagggct gacccgtaaa ggtgtgtatg      2820
ccgttcggta caaggtgaat gaaaatcctc tgtacgcacc cacctcagaa catgtgaacg      2880
tcctactgac ccgcacggag gaccgcatcg tgtggaaaac actagccggc gacccatgga      2940
taaaaacact gactgccaag taccctggga atttcactgc cacgatagag gagtggcaag      3000
cagagcatga tgccatcatg aggcacatct tggagagacc ggaccctacc gacgtcttcc      3060
agaataaggc aaacgtgtgt tgggccaagg ctttagtgcc ggtgctgaag accgctggca      3120
```

```
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg ccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg ccaccgaag    4080
gagtgattat aaatgctgct aacagcaaag acaacctgg cggagggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctcctc accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacccct ggaggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccacccgc    5520
```

```
caggcgtgaa tagggtgatc actagagagg agctcgaggc gcttaccccg tcacgcactc      5580
ctagcaggtc ggtctcgaga accagcctgg tctccaaccc gccaggcgta aatagggtga      5640
ttacaagaga ggagtttgag gcgttcgtag cacaacaaca atgacggttt gatgcgggtg      5700
catacatctt ttcctccgac accggtcaag ggcatttaca acaaaaatca gtaaggcaaa      5760
cggtgctatc cgaagtggtg ttggagagga ccgaattgga gatttcgtat gccccgcgcc      5820
tcgaccaaga aaagaagaa ttactacgca agaaattaca gttaaatccc acacctgcta      5880
acagaagcag ataccagtcc aggaaggtgg agaacatgaa agccataaca gctagacgta      5940
ttctgcaagg cctagggcat tatttgaagg cagaaggaaa agtggagtgc taccgaaccc      6000
tgcatcctgt tcctttgtat tcatctagtg tgaaccgtgc cttttcaagc cccaaggtcg      6060
cagtggaagc ctgtaacgcc atgttgaaag gaactttcc gactgtggct tcttactgta      6120
ttattccaga gtacgatgcc tatttggaca tggttgacgg agcttcatgc tgcttagaca      6180
ctgccagttt ttgccctgca aagctgcgca gcttccaaa gaaacactcc tatttggaac      6240
ccacaatacg atcggcagtg ccttcagcga tccagaacac gctccagaac gtcctggcag      6300
ctgccacaaa aagaaattgc aatgtcacgc aaatgagaga attgcccgta ttggattcgg      6360
cggcctttaa tgtggaatgc ttcaagaaat atgcgtgtaa taatgaatat gggaaacgt      6420 ttaaagaaaa ccccatcagg cttactgaag aaaacgtggt aaattacatt accaaattaa      6480
aaggaccaaa agctgctgct cttttttgcga agacacataa tttgaatatg ttgcaggaca      6540
taccaatgga caggttttgta atggacttaa agagagacgt gaaagtgact ccaggaacaa      6600
aacatactga agaacggccc aaggtacagg tgatccaggc tgccgatccg ctagcaacag      6660
cgtatctgtg cggaatccac cgagagctgg ttaggagatt aaatgcggtc ctgcttccga      6720
acattcatac actgtttgat atgtcggctg aagactttga cgctattata gccgagcact      6780
tccagcctgg ggattgtgtt ctggaaactg acatcgcgtc gtttgataaa agtgaggacg      6840
acgccatggc tctgaccgcg ttaatgattc tggaagactt aggtgtggac gcagagctgt      6900
tgacgctgat tgaggcggct ttcggcgaaa tttcatcaat acatttgccc actaaaacta      6960
aatttaaatt cggagccatg atgaaatctg gaatgttcct cacactgttt gtgaacacag      7020
tcattaacat tgtaatcgca agcagagtgt tgagagaacg gctaaccgga tcaccatgtg      7080
cagcattcat tggagatgac aatatcgtga aaggagtcaa atcggacaaa ttaatggcag      7140
acaggtgcgc cacctggttg aatatggaag tcaagattat agatgctgtg gtgggcgaga      7200
aagcgcctta tttctgtgga gggtttattt tgtgtgactc cgtgaccggc acagcgtgcc      7260
gtgtggcaga ccccctaaaa aggctgtttta agcttggcaa acctctggca gcagacgatg      7320
aacatgatga tgacaggaga agggcattgc atgaagagtc aacacgctgg aaccgagtgg      7380
gtattctttc agagctgtgc aaggcagtag aatcaaggta tgaaccgta ggaacttcca      7440 tcatagttat ggccatgact actctagcta gcagtgttaa atcattcagc tacctgagag      7500 ggccctat aactctctac ggctaacctg aatggactac gacatagtct agtccgccaa      7560
gatgagagtg atgggatac agaggaattg gccacaatgg tggatatggg gcaccttagg      7620
cttttggatg ataataattt gtagggtggt ggggaacttg aacttgtggg tcacagtcta      7680 ttatgggta cctgtgtgga aagaagcaaa aactactcta ttctgtgcat cagatgctaa      7740
agcatatgat aaagaagtac ataatgtctg ggctacacat gcctgtgtac ccacagaccc      7800
caacccacga gaaatagttt tggaaaatgt aacagaaaat tttaacatgt ggaaaaatga      7860
catggtggat cagatgcatg aggatataat cagtttatgg gatcaaagcc taaaaccatg      7920
```

```
                                -continued
tgtaaagttg accccactct gtgtcacttt aaattgtaca aatgcacctg cctacaataa    7980
tagcatgcat ggagaaatga aaaattgctc tttcaataca accacagaga taagagatag    8040
gaaacagaaa gcgtatgcac ttttttataa acctgatgta gtgccactta ataggagaga    8100
agagaataat gggacaggag agtatatatt aataaattgc aattcctcaa ccataacaca    8160
agcctgtcca aaggtcactt ttgacccaat tcctatacat tattgtgctc cagctggtta    8220
tgcgattcta aagtgtaata ataagacatt caatgggaca ggaccatgca ataatgtcag    8280
cacagtacaa tgtacacatg gaattatgcc agtggtatca actcaattac tgttaaatgg    8340
tagcctagca gaagaagaga taataattag atctgaaaat ctgacaaaca atatcaaaac    8400
aataatagtc caccttaata aatctgtaga aattgtgtgt acaagaccca acaataatac    8460
aagaaaaagt ataaggatag gaccaggaca acattctat gcaacaggtg aaataatagg    8520
aaacataaga gaagcacatt gtaacattag taaaagtaac tggaccagta ctttagaaca    8580
ggtaaagaaa aaattaaaag aacactacaa taagacaata gaatttaacc cacc ctcagg    8640 aggggatcta gaagttacaa cacatagctt taattgtaga ggagaatttt tctattgcaa    8700
tacaacaaaa ctgttttcaa acaacagtga ttcaaacaac gaaaccatca cactcccatg    8760
caagataaaa caaattataa acatgtggca gaaggtagga cgagcaatgt atgcccctcc    8820
cattgaagga aacataacat gtaaatcaaa tatcacagga ctactattga cacgtgatgg    8880
aggaaagaat acaacaaatg agatattcag accgggagga ggaaatatga aggacaattg    8940
gagaagtgaa ttatataaat ataaagtggt agaaattgag ccattgggag tagcacccac    9000
taaatcaaaa aggagagtgg tggagagaga aaaaagagca gtgggactag gagctgtact    9060
ccttgggttc ttgggagcag caggaagcac tatgggcgcg gcgtcaataa cgctgacggt    9120
acaggccaga caactgttgt ctggtatagt gcaacagcaa agcaatttgc tgagagctat    9180
agaggcgcaa cagcatatgt tgcaactcac ggtctggggc attaagcagc tccagacaag    9240
agtcttggct atagagagat acctaaagga tcaacagctc ctagggcttt ggggctgctc    9300
tggaaaaatc atctgcacca ctgctgtgcc ttggaactcc agttggagta ataaatctca    9360
agaagatatt tgggataaca tgacctggat gcagtgggat agagaaatta gtaattacac    9420
aggcacaata tataggttac ttgaagactc gcaaaaccag caggagaaaa atgaaaaaga    9480
tttattagca ttggacagtt ggaaaaactt gtggaattgg tttaacataa caaattggct    9540
gtggtatata aaaatattca tcatgatagt aggaggcttg ataggtttga gaataatttt    9600
tggtgtactc gctatagtga aaagagttag gcagggatac tcacctttgt cgtttcagac    9660
ccttacccca gcccgagggg gtcccgacag gctcggaaga atcgaagaag aaggtggaga    9720
gcaagacaaa gacagatcca ttcgattagt gagcggattc ttagcacttg cctgggacga    9780
tctgcggagc ctgtgcctct tcagctacca ccacttgaga gacttcatat tgattgcagc    9840
gagagcagcg gaacttctgg gacgcagcag tctcagggga ctgcagagag ggtgggaagc    9900
ccttaagtat ctgggaaatc ttgtgcagta tgggggtctg gagctaaaaa gaagtgctat    9960
taaactgttt gataccatag caatagcagt agctgaagga acagatagga ttcttgaagt    10020
aatacagaga atttgtagag ctatccgcca catacctata agaataagac agggctttga    10080
agcagctttg caataattaa ttaagtaacc gatacagcag caattggcaa gctgcttaca    10140
tagaactcgc ggcgattggc atgccgcctt aaaatttta ttttattttt tcttttcttt    10200
tccgaatcgg attttgtttt taatatttca aaaaaaaaa aaaaaaaaa aaaaaaaaaa    10260 aaaaaaaaaa aaaaaaaaag gaagagcgcg gccgcgcgct gggctacgtc ttgctggcgt    10320
```

```
tcgcgacgcg aggctggatg gccttcccca ttatgattct tctcgcttcc ggcggcatcg    10380
ggatgcccgc gttgcaggcc atgctgtcca ggcaggtaga tgacgaccat cagggacagc    10440
ttcaaggatc gctcgcggct cttaccagcc taacttcgat cactggaccg ctgatcgtca    10500
cggcgattta tgccgcctcg gcgagcacat ggaacgggtt ggcatggatt gtaggcgccg    10560
ccctatacct tgtctgcctc cccgcgttgc gtcgcggtgc atggagccgg gccacctcga    10620
cctgaatgga agccggcggc acctcgctaa cggattcacc actccaagaa ttggagccaa    10680
tcaattcttg cggagaactg tgaatgcgca accaaccct tggcagaaca tatccatcgc     10740
gtccgccatc tccagcagcc gcacgcggcg catctcgggc agcgttgggt cctggccacg    10800
ggtgcgcatg atcgtgctcc tgtcgttgag gacccggcta ggctggcggg gttgccttac    10860
tggttagcag aatgaatcac cgatacgcga gcgaacgtga agcgactgct gctgcaaaac    10920
gtctgcgacc tgagcaacaa catgaatggt cttcggtttc cgtgtttcgt aaagtctgga    10980
aacgcggaag tcagcgccct gcaccattat gttccggatc tgcatcgcag gatgctgctg    11040
gctaccctgt ggaacaccta catctgtatt aacgaagcgc tggcattgac cctgagtgat    11100
ttttctctgg tccgccgca tccataccgc cagttgttta ccctcacaac gttccagtaa     11160
ccgggcatgt tcatcatcag taacccgtat cgtgagcatc ctctctcgtt tcatcggtat    11220
cattaccccc atgaacagaa atccccctta cacggaggca tcagtgacca aacaggaaaa    11280
aaccgcccct taacatggccc gctttatcag aagccagaca ttaacgcttc tggagaaact    11340
caacgagctg gacgcggatg aacaggcaga catctgtgaa tcgcttcacg accacgctga    11400
tgagctttac cgcagctgcc tcgcgcgttt cggtgatgac ggtgaaaacc tctgacacat    11460
gcagctcccg gagacggtca cagcttgtct gtaagcggat gccgggagca gacaagcccg    11520
tcagggcgcg tcagcgggtg ttggcgggtg tcgggcgca gccatgaccc agtcacgtag      11580
cgatagcgga gtgtatactg gcttaactat gcggcatcag agcagattgt actgagagtg    11640
caccatatat gcggtgtgaa ataccgcaca gatgcgtaag gagaaaatac cgcatcaggc    11700
gctcttccgc ttcctcgctc actgactcgc tgcgctcggt cgttcggctg cggcgagcgg    11760
tatcagctca ctcaaaggcg gtaatacggt tatccacaga atcaggggat aacgcaggaa    11820
agaacatgtg agcaaaaggc cagcaaaagg ccaggaaccg taaaaaggcc gcgttgctgg    11880
cgtttttcca taggctccgc ccccctgacg agcatcacaa aaatcgacgc tcaagtcaga    11940
ggtggcgaaa cccgacagga ctataaagat accaggcgtt tccccctgga agctccctcg    12000
tgcgctctcc tgttccgacc ctgccgctta ccggatacct gtccgccttt ctcccttcgg    12060
gaagcgtggc gctttctcat agctcacgct gtaggtatct cagttcggtg taggtcgttc    12120
gctccaagct gggctgtgtg cacgaacccc cgttcagccc gaccgctgcg ccttatccg     12180
gtaactatcg tcttgagtcc aacccggtaa gacacgactt atcgccactg gcagcagcca    12240
ctggtaacag gattagcaga gcgaggtatg taggcggtgc tacagagttc ttgaagtggt    12300
ggcctaacta cggctacact agaaggacag tatttggtat ctgcgctctg ctgaagccag    12360
ttaccttcgg aaaaagagtt ggtagctctt gatccggcaa acaaaccacc gctggtagcg    12420
gtggtttttt tgtttgcaag cagcagatta cgcgcagaaa aaaggatctc aagaagatc     12480
ctttgatctt ttctacgggg tctgacgctc agtggaacga aaactcacgt taagggattt    12540
tggtcatgaa caataaaact gtctgcttac ataaacagta atacaagggg tgttatgagc    12600
catattcaac gggaaacgtc ttgctcgagg ccgcgattaa attccaacat ggatgctgat    12660
ttatatgggt ataaatgggc tcgcgataat gtcgggcaat caggtgcgac aatctatcga    12720
```

-continued

```
ttgtatggga agcccgatgc gccagagttg tttctgaaac atggcaaagg tagcgttgcc     12780
aatgatgtta cagatgagat ggtcagacta aactggctga cggaatttat gcctcttccg     12840
accatcaagc attttatccg tactcctgat gatgcatggt tactcaccac tgcgatcccc     12900
gggaaaacag cattccaggt attagaagaa tatcctgatt caggtgaaaa tattgttgat     12960
gcgctggcag tgttcctgcg ccggttgcat tcgattcctg tttgtaattg tccttttaac     13020
agcgatcgcg tatttcgtct cgctcaggcg caatcacgaa tgaataacgg tttgttgat     13080 gcgagtgatt tgatgacga gcgtaatggc tggcctgttg aacaagtctg gaaagaaatg     13140
cataagcttt tgccattctc accggattca gtcgtcactc atggtgattt ctcacttgat     13200
aaccttattt ttgacgaggg gaaattaata ggttgtattg atgttggacg agtcggaatc     13260
gcagaccgat accaggatct tgccatccta tggaactgcc tcggtgagtt ttctccttca     13320
ttacagaaac ggcttttca aaaatatggt attgataatc ctgatatgaa taaattgcag     13380
tttcatttga tgctcgatga gttttctaa gaattctcat gtttgacagc ttatcatcga     13440
taagctttaa tgcggtagtt tatcacagtt aaattgctaa cgcagtcagg caccgtgtat     13500
gaaatctaac aatgcgctca tcgtcatcct cggcaccgtc accctggatg ctgtctagag     13560
gatccctaat acgactcact atag                                            13584
```

<210> SEQ ID NO 18
<211> LENGTH: 2532
<212> TYPE: DNA
<213> ORGANISM: Artificial Sequence
<220> FEATURE:
<223> OTHER INFORMATION: Description of Artificial Sequence; Note = synthetic construct
<221> NAME/KEY: CDS
<222> LOCATION: (1)...(2532)

<400> SEQUENCE: 18

```
atg aga gtg atg ggg ata cag agg aat tgg cca caa tgg tgg ata tgg           48
Met Arg Val Met Gly Ile Gln Arg Asn Trp Pro Gln Trp Trp Ile Trp
1               5                   10                  15 ggc acc tta ggc ttt tgg atg ata ata att tgt agg gtg gtg ggg aac           96
Gly Thr Leu Gly Phe Trp Met Ile Ile Ile Cys Arg Val Val Gly Asn
            20                  25                  30 ttg aac ttg tgg gtc aca gtc tat tat ggg gta cct gtg tgg aaa gaa          144
Leu Asn Leu Trp Val Thr Val Tyr Tyr Gly Val Pro Val Trp Lys Glu
        35                  40                  45 gca aaa act act cta ttc tgt gca tca gat gct aaa gca tat gat aaa          192
Ala Lys Thr Thr Leu Phe Cys Ala Ser Asp Ala Lys Ala Tyr Asp Lys
    50                  55                  60 gaa gta cat aat gtc tgg gct aca cat gcc tgt gta ccc aca gac ccc          240
Glu Val His Asn Val Trp Ala Thr His Ala Cys Val Pro Thr Asp Pro
65                  70                  75                  80 aac cca cga gaa ata gtt ttg gaa aat gta aca gaa aat ttt aac atg          288
Asn Pro Arg Glu Ile Val Leu Glu Asn Val Thr Glu Asn Phe Asn Met
                85                  90                  95 tgg aaa aat gac atg gtg gat cag atg cat gag gat ata atc agt tta          336
Trp Lys Asn Asp Met Val Asp Gln Met His Glu Asp Ile Ile Ser Leu
            100                 105                 110 tgg gat caa agc cta aaa cca tgt gta aag ttg acc cca ctc tgt gtc          384
Trp Asp Gln Ser Leu Lys Pro Cys Val Lys Leu Thr Pro Leu Cys Val
        115                 120                 125 act tta aat tgt aca aat gca cct gcc tac aat aat agc atg cat gga          432
Thr Leu Asn Cys Thr Asn Ala Pro Ala Tyr Asn Asn Ser Met His Gly
    130                 135                 140
```

-continued

| | |
|---|---|
| gaa atg aaa aat tgc tct ttc aat aca acc aca gag ata aga gat agg<br>Glu Met Lys Asn Cys Ser Phe Asn Thr Thr Thr Glu Ile Arg Asp Arg<br>145                    150                    155                    160 | 480 |
| aaa cag aaa gcg tat gca ctt ttt tat aaa cct gat gta gtg cca ctt<br>Lys Gln Lys Ala Tyr Ala Leu Phe Tyr Lys Pro Asp Val Val Pro Leu<br>                  165                    170                    175 | 528 |
| aat agg aga gaa gag aat aat ggg aca gga gag tat ata tta ata aat<br>Asn Arg Arg Glu Glu Asn Asn Gly Thr Gly Glu Tyr Ile Leu Ile Asn<br>        180                    185                    190 | 576 |
| tgc aat tcc tca acc ata aca caa gcc tgt cca aag gtc act ttt gac<br>Cys Asn Ser Ser Thr Ile Thr Gln Ala Cys Pro Lys Val Thr Phe Asp<br>195                    200                    205 | 624 |
| cca att cct ata cat tat tgt gct cca gct ggt tat gcg att cta aag<br>Pro Ile Pro Ile His Tyr Cys Ala Pro Ala Gly Tyr Ala Ile Leu Lys<br>        210                    215                    220 | 672 |
| tgt aat aat aag aca ttc aat ggg aca gga cca tgc aat aat gtc agc<br>Cys Asn Asn Lys Thr Phe Asn Gly Thr Gly Pro Cys Asn Asn Val Ser<br>225                    230                    235                    240 | 720 |
| aca gta caa tgt aca cat gga att atg cca gtg gta tca act caa tta<br>Thr Val Gln Cys Thr His Gly Ile Met Pro Val Val Ser Thr Gln Leu<br>                  245                    250                    255 | 768 |
| ctg tta aat ggt agc cta gca gaa gaa gag ata ata att aga tct gaa<br>Leu Leu Asn Gly Ser Leu Ala Glu Glu Glu Ile Ile Ile Arg Ser Glu<br>        260                    265                    270 | 816 |
| aat ctg aca aac aat atc aaa aca ata ata gtc cac ctt aat aaa tct<br>Asn Leu Thr Asn Asn Ile Lys Thr Ile Ile Val His Leu Asn Lys Ser<br>275                    280                    285 | 864 |
| gta gaa att gtg tgt aca aga ccc aac aat aat aca aga aaa agt ata<br>Val Glu Ile Val Cys Thr Arg Pro Asn Asn Asn Thr Arg Lys Ser Ile<br>        290                    295                    300 | 912 |
| agg ata gga cca gga caa aca ttc tat gca aca ggt gaa ata ata gga<br>Arg Ile Gly Pro Gly Gln Thr Phe Tyr Ala Thr Gly Glu Ile Ile Gly<br>305                    310                    315                    320 | 960 |
| aac ata aga gaa gca cat tgt aac att agt aaa agt aac tgg acc agt<br>Asn Ile Arg Glu Ala His Cys Asn Ile Ser Lys Ser Asn Trp Thr Ser<br>                  325                    330                    335 | 1008 |
| act tta gaa cag gta aag aaa aaa tta aaa gaa cac tac aat aag aca<br>Thr Leu Glu Gln Val Lys Lys Lys Leu Lys Glu His Tyr Asn Lys Thr<br>        340                    345                    350 | 1056 |
| ata gaa ttt aac cca ccc tca gga ggg gat cta gaa gtt aca aca cat<br>Ile Glu Phe Asn Pro Pro Ser Gly Gly Asp Leu Glu Val Thr Thr His<br>355                    360                    365 | 1104 |
| agc ttt aat tgt aga gga gaa ttt ttc tat tgc aat aca aca aaa ctg<br>Ser Phe Asn Cys Arg Gly Glu Phe Phe Tyr Cys Asn Thr Thr Lys Leu<br>370                    375                    380 | 1152 |
| ttt tca aac aac agt gat tca aac aac gaa acc atc aca ctc cca tgc<br>Phe Ser Asn Asn Ser Asp Ser Asn Asn Glu Thr Ile Thr Leu Pro Cys<br>385                    390                    395                    400 | 1200 |
| aag ata aaa caa att ata aac atg tgg cag aag gta gga cga gca atg<br>Lys Ile Lys Gln Ile Ile Asn Met Trp Gln Lys Val Gly Arg Ala Met<br>                  405                    410                    415 | 1248 |
| tat gcc cct ccc att gaa gga aac ata aca tgt aaa tca aat atc aca<br>Tyr Ala Pro Pro Ile Glu Gly Asn Ile Thr Cys Lys Ser Asn Ile Thr<br>        420                    425                    430 | 1296 |
| gga cta cta ttg aca cgt gat gga gga aag aat aca aca aat gag ata<br>Gly Leu Leu Leu Thr Arg Asp Gly Gly Lys Asn Thr Thr Asn Glu Ile<br>435                    440                    445 | 1344 |
| ttc aga ccg gga gga gga aat atg aag gac aat tgg aga agt gaa tta<br>Phe Arg Pro Gly Gly Gly Asn Met Lys Asp Asn Trp Arg Ser Glu Leu<br>450                    455                    460 | 1392 |

```
                                                                -continued tat aaa tat aaa gtg gta gaa att gag cca ttg gga gta gca ccc act       1440
Tyr Lys Tyr Lys Val Val Glu Ile Glu Pro Leu Gly Val Ala Pro Thr
465             470                 475                 480 aaa tca aaa agg aga gtg gtg gag aga gaa aaa aga gca gtg gga cta       1488
Lys Ser Lys Arg Arg Val Val Glu Arg Glu Lys Arg Ala Val Gly Leu
                    485                 490                 495 gga gct gta ctc ctt ggg ttc ttg gga gca gca gga agc act atg ggc       1536
Gly Ala Val Leu Leu Gly Phe Leu Gly Ala Ala Gly Ser Thr Met Gly
                500                 505                 510 gcg gcg tca ata acg ctg acg gta cag gcc aga caa ctg ttg tct ggt       1584
Ala Ala Ser Ile Thr Leu Thr Val Gln Ala Arg Gln Leu Leu Ser Gly
            515                 520                 525 ata gtg caa cag caa agc aat ttg ctg aga gct ata gag gcg caa cag       1632
Ile Val Gln Gln Gln Ser Asn Leu Leu Arg Ala Ile Glu Ala Gln Gln
530                 535                 540 cat atg ttg caa ctc acg gtc tgg ggc att aag cag ctc cag aca aga       1680
His Met Leu Gln Leu Thr Val Trp Gly Ile Lys Gln Leu Gln Thr Arg
545                 550                 555                 560 gtc ttg gct ata gag aga tac cta aag gat caa cag ctc cta ggg ctt       1728
Val Leu Ala Ile Glu Arg Tyr Leu Lys Asp Gln Gln Leu Leu Gly Leu
                565                 570                 575 tgg ggc tgc tct gga aaa atc atc tgc acc act gct gtg cct tgg aac       1776
Trp Gly Cys Ser Gly Lys Ile Ile Cys Thr Thr Ala Val Pro Trp Asn
            580                 585                 590 tcc agt tgg agt aat aaa tct caa gaa gat att tgg gat aac atg acc       1824
Ser Ser Trp Ser Asn Lys Ser Gln Glu Asp Ile Trp Asp Asn Met Thr
        595                 600                 605 tgg atg cag tgg gat aga gaa att agt aat tac aca ggc aca ata tat       1872
Trp Met Gln Trp Asp Arg Glu Ile Ser Asn Tyr Thr Gly Thr Ile Tyr
610                 615                 620 agg tta ctt gaa gac tcg caa aac cag cag gag aaa aat gaa aaa gat       1920
Arg Leu Leu Glu Asp Ser Gln Asn Gln Gln Glu Lys Asn Glu Lys Asp
625                 630                 635                 640 tta tta gca ttg gac agt tgg aaa aac ttg tgg aat tgg ttt aac ata       1968
Leu Leu Ala Leu Asp Ser Trp Lys Asn Leu Trp Asn Trp Phe Asn Ile
                645                 650                 655 aca aat tgg ctg tgg tat ata aaa ata ttc atc atg ata gta gga ggc       2016
Thr Asn Trp Leu Trp Tyr Ile Lys Ile Phe Ile Met Ile Val Gly Gly
            660                 665                 670 ttg ata ggt ttg aga ata att ttt ggt gta ctc gct ata gtg aaa aga       2064
Leu Ile Gly Leu Arg Ile Ile Phe Gly Val Leu Ala Ile Val Lys Arg
        675                 680                 685 gtt agg cag gga tac tca cct ttg tcg ttt cag acc ctt acc cca agc       2112
Val Arg Gln Gly Tyr Ser Pro Leu Ser Phe Gln Thr Leu Thr Pro Ser
690                 695                 700 ccg agg ggt ccc gac agg ctc gga aga atc gaa gaa gaa ggt gga gag       2160
Pro Arg Gly Pro Asp Arg Leu Gly Arg Ile Glu Glu Glu Gly Gly Glu
705                 710                 715                 720 caa gac aaa gac aga tcc att cga tta gtg agc gga ttc tta gca ctt       2208
Gln Asp Lys Asp Arg Ser Ile Arg Leu Val Ser Gly Phe Leu Ala Leu
                725                 730                 735 gcc tgg gac gat ctg cgg agc ctg tgc ctc ttc agc tac cac cac ttg       2256
Ala Trp Asp Asp Leu Arg Ser Leu Cys Leu Phe Ser Tyr His His Leu
            740                 745                 750 aga gac ttc ata ttg att gca gcg aga gca gcg gaa ctt ctg gga cgc       2304
Arg Asp Phe Ile Leu Ile Ala Ala Arg Ala Ala Glu Leu Leu Gly Arg
        755                 760                 765 agc agt ctc agg gga ctg cag aga ggg tgg gaa gcc ctt aag tat ctg       2352
Ser Ser Leu Arg Gly Leu Gln Arg Gly Trp Glu Ala Leu Lys Tyr Leu
770                 775                 780
```

-continued

```
gga aat ctt gtg cag tat ggg ggt ctg gag cta aaa aga agt gct att    2400
Gly Asn Leu Val Gln Tyr Gly Gly Leu Glu Leu Lys Arg Ser Ala Ile
785                 790                 795                 800 aaa ctg ttt gat acc ata gca ata gca gta gct gaa gga aca gat agg    2448
Lys Leu Phe Asp Thr Ile Ala Ile Ala Val Ala Glu Gly Thr Asp Arg
                805                 810                 815 att ctt gaa gta ata cag aga att tgt aga gct atc cgc cac ata cct    2496
Ile Leu Glu Val Ile Gln Arg Ile Cys Arg Ala Ile Arg His Ile Pro
            820                 825                 830 ata aga ata aga cag ggc ttt gaa gca gct ttg caa                    2532
Ile Arg Ile Arg Gln Gly Phe Glu Ala Ala Leu Gln
        835                 840

<210> SEQ ID NO 19
<211> LENGTH: 844
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 19

Met Arg Val Met Gly Ile Gln Arg Asn Trp Pro Gln Trp Trp Ile Trp
 1               5                  10                  15

Gly Thr Leu Gly Phe Trp Met Ile Ile Cys Arg Val Val Gly Asn
                20                  25                  30

Leu Asn Leu Trp Val Thr Val Tyr Tyr Gly Val Pro Val Trp Lys Glu
            35                  40                  45

Ala Lys Thr Thr Leu Phe Cys Ala Ser Asp Ala Lys Ala Tyr Asp Lys
        50                  55                  60

Glu Val His Asn Val Trp Ala Thr His Ala Cys Val Pro Thr Asp Pro
65                  70                  75                  80

Asn Pro Arg Glu Ile Val Leu Glu Asn Val Thr Glu Asn Phe Asn Met
                85                  90                  95

Trp Lys Asn Asp Met Val Asp Gln Met His Glu Asp Ile Ile Ser Leu
               100                 105                 110

Trp Asp Gln Ser Leu Lys Pro Cys Val Lys Leu Thr Pro Leu Cys Val
            115                 120                 125

Thr Leu Asn Cys Thr Asn Ala Pro Ala Tyr Asn Asn Ser Met His Gly
        130                 135                 140

Glu Met Lys Asn Cys Ser Phe Asn Thr Thr Glu Ile Arg Asp Arg
145                 150                 155                 160

Lys Gln Lys Ala Tyr Ala Leu Phe Tyr Lys Pro Asp Val Val Pro Leu
                165                 170                 175

Asn Arg Arg Glu Glu Asn Gly Thr Gly Glu Tyr Ile Leu Ile Asn
               180                 185                 190

Cys Asn Ser Ser Thr Ile Thr Gln Ala Cys Pro Lys Val Thr Phe Asp
            195                 200                 205

Pro Ile Pro Ile His Tyr Cys Ala Pro Ala Gly Tyr Ala Ile Leu Lys
        210                 215                 220

Cys Asn Asn Lys Thr Phe Asn Gly Thr Gly Pro Cys Asn Asn Val Ser
225                 230                 235                 240

Thr Val Gln Cys Thr His Gly Ile Met Pro Val Val Ser Thr Gln Leu
                245                 250                 255

Leu Leu Asn Gly Ser Leu Ala Glu Glu Glu Ile Ile Ile Arg Ser Glu
               260                 265                 270
```

```
Asn Leu Thr Asn Asn Ile Lys Thr Ile Ile Val His Leu Asn Lys Ser
            275                 280                 285

Val Glu Ile Val Cys Thr Arg Pro Asn Asn Thr Arg Lys Ser Ile
    290                 295                 300

Arg Ile Gly Pro Gly Gln Thr Phe Tyr Ala Thr Gly Glu Ile Ile Gly
305                 310                 315                 320

Asn Ile Arg Glu Ala His Cys Asn Ile Ser Lys Ser Asn Trp Thr Ser
                325                 330                 335

Thr Leu Glu Gln Val Lys Lys Leu Lys Glu His Tyr Asn Lys Thr
            340                 345                 350

Ile Glu Phe Asn Pro Pro Ser Gly Gly Asp Leu Glu Val Thr Thr His
            355                 360                 365

Ser Phe Asn Cys Arg Gly Glu Phe Phe Tyr Cys Asn Thr Thr Lys Leu
    370                 375                 380

Phe Ser Asn Asn Ser Asp Ser Asn Asn Glu Thr Ile Thr Leu Pro Cys
385                 390                 395                 400

Lys Ile Lys Gln Ile Ile Asn Met Trp Gln Lys Val Gly Arg Ala Met
                405                 410                 415

Tyr Ala Pro Pro Ile Glu Gly Asn Ile Thr Cys Lys Ser Asn Ile Thr
            420                 425                 430

Gly Leu Leu Leu Thr Arg Asp Gly Gly Lys Asn Thr Thr Asn Glu Ile
            435                 440                 445

Phe Arg Pro Gly Gly Gly Asn Met Lys Asp Asn Trp Arg Ser Glu Leu
450                 455                 460

Tyr Lys Tyr Lys Val Val Glu Ile Glu Pro Leu Gly Val Ala Pro Thr
465                 470                 475                 480

Lys Ser Lys Arg Arg Val Val Glu Arg Glu Lys Arg Ala Val Gly Leu
                485                 490                 495

Gly Ala Val Leu Leu Gly Phe Leu Gly Ala Ala Gly Ser Thr Met Gly
            500                 505                 510

Ala Ala Ser Ile Thr Leu Thr Val Gln Ala Arg Gln Leu Leu Ser Gly
            515                 520                 525

Ile Val Gln Gln Gln Ser Asn Leu Leu Arg Ala Ile Glu Ala Gln Gln
530                 535                 540

His Met Leu Gln Leu Thr Val Trp Gly Ile Lys Gln Leu Gln Thr Arg
545                 550                 555                 560

Val Leu Ala Ile Glu Arg Tyr Leu Lys Asp Gln Gln Leu Leu Gly Leu
                565                 570                 575

Trp Gly Cys Ser Gly Lys Ile Ile Cys Thr Thr Ala Val Pro Trp Asn
            580                 585                 590

Ser Ser Trp Ser Asn Lys Ser Gln Glu Asp Ile Trp Asp Asn Met Thr
            595                 600                 605

Trp Met Gln Trp Asp Arg Glu Ile Ser Asn Tyr Thr Gly Thr Ile Tyr
            610                 615                 620

Arg Leu Leu Glu Asp Ser Gln Asn Gln Gln Glu Lys Asn Glu Lys Asp
625                 630                 635                 640

Leu Leu Ala Leu Asp Ser Trp Lys Asn Leu Trp Asn Trp Phe Asn Ile
                645                 650                 655

Thr Asn Trp Leu Trp Tyr Ile Lys Ile Phe Ile Met Ile Val Gly Gly
            660                 665                 670

Leu Ile Gly Leu Arg Ile Ile Phe Gly Val Leu Ala Ile Val Lys Arg
            675                 680                 685
```

-continued

```
Val Arg Gln Gly Tyr Ser Pro Leu Ser Phe Gln Thr Leu Thr Pro Ser
    690                 695             700

Pro Arg Gly Pro Asp Arg Leu Gly Arg Ile Glu Glu Glu Gly Gly Glu
705              710             715                 720

Gln Asp Lys Asp Arg Ser Ile Arg Leu Val Ser Gly Phe Leu Ala Leu
                725             730                 735

Ala Trp Asp Asp Leu Arg Ser Leu Cys Leu Phe Ser Tyr His His Leu
            740             745             750

Arg Asp Phe Ile Leu Ile Ala Ala Arg Ala Ala Glu Leu Leu Gly Arg
        755             760             765

Ser Ser Leu Arg Gly Leu Gln Arg Gly Trp Glu Ala Leu Lys Tyr Leu
    770             775             780

Gly Asn Leu Val Gln Tyr Gly Gly Leu Glu Leu Lys Arg Ser Ala Ile
785             790             795                 800

Lys Leu Phe Asp Thr Ile Ala Ile Ala Val Ala Glu Gly Thr Asp Arg
            805             810             815

Ile Leu Glu Val Ile Gln Arg Ile Cys Arg Ala Ile Arg His Ile Pro
            820             825             830

Ile Arg Ile Arg Gln Gly Phe Glu Ala Ala Leu Gln
        835             840
```